US012790293B2

(12) United States Patent
Fujiwara et al.

(10) Patent No.: US 12,790,293 B2
(45) Date of Patent: Nov. 10, 2026

(54) ONIUM SALT COMPOUND, CHEMICALLY AMPLIFIED RESIST COMPOSITION AND PATTERNING PROCESS

(71) Applicant: Shin-Etsu Chemical Co., Ltd., Tokyo (JP)

(72) Inventors: Takayuki Fujiwara, Joetsu (JP); Kenichi Oikawa, Joetsu (JP); Tomohiro Kobayashi, Joetsu (JP); Masahiro Fukushima, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 17/108,223

(22) Filed: Dec. 1, 2020

(65) Prior Publication Data

US 2021/0188770 A1 Jun. 24, 2021

(30) Foreign Application Priority Data

Dec. 11, 2019 (JP) ................................. 2019-223621

(51) Int. Cl.

| | |
|---|---|
| ***G03F 7/20*** | (2006.01) |
| ***C07C 69/76*** | (2006.01) |
| ***C07C 381/12*** | (2006.01) |
| ***G03F 7/004*** | (2006.01) |
| ***G03F 7/028*** | (2006.01) |
| ***G03F 7/038*** | (2006.01) |
| ***G03F 7/32*** | (2006.01) |

(52) U.S. Cl.

CPC ............ *C07C 381/12* (2013.01); *C07C 69/76* (2013.01); *G03F 7/0045* (2013.01); *G03F 7/028* (2013.01); *G03F 7/0382* (2013.01); *G03F 7/20* (2013.01); *G03F 7/32* (2013.01)

(58) Field of Classification Search

CPC ........ G03F 7/0045; C07C 69/63; C07C 69/76

See application file for complete search history.

(56) References Cited

U.S. PATENT DOCUMENTS

| | | | |
|---|---|---|---|
| 9,221,742 | B2 | 12/2015 | Ohashi et al. |
| 10,248,020 | B2 | 4/2019 | Thackeray et al. |
| 2002/0051933 | A1 | 5/2002 | Kodama et al. |
| 2002/0098443 | A1 | 7/2002 | Hatakeyama et al. |
| 2004/0106063 | A1 | 6/2004 | Hatakeyama et al. |
| 2008/0085469 | A1 | 4/2008 | Ohsawa et al. |
| 2008/0118860 | A1 | 5/2008 | Harada et al. |
| 2008/0318160 | A1 | 12/2008 | Ohsawa et al. |
| 2009/0246694 | A1 | 10/2009 | Ohsawa et al. |
| 2010/0035185 | A1 | 2/2010 | Hagiwara et al. |
| 2010/0119970 | A1 | 5/2010 | Ohsawa et al. |
| 2010/0209827 | A1 | 8/2010 | Ohashi et al. |
| 2011/0008735 | A1 | 1/2011 | Ohsawa et al. |
| 2012/0045724 | A1 | 2/2012 | Ohsawa et al. |
| 2012/0100486 | A1 | 4/2012 | Sagehashi et al. |
| 2012/0225386 | A1 | 9/2012 | Watanabe et al. |
| 2013/0337378 | A1 | 12/2013 | Ohashi et al. |
| 2014/0199629 | A1 | 7/2014 | Ohashi et al. |
| 2015/0253664 | A1* | 9/2015 | Domon ................ G03F 7/0045 430/326 |
| 2015/0268556 | A1* | 9/2015 | Domon ..................... G03F 7/30 430/296 |
| 2015/0323865 | A1 | 11/2015 | Sagehashi et al. |
| 2016/0004155 | A1 | 1/2016 | Ohashi et al. |
| 2016/0299428 | A1 | 10/2016 | Masunaga et al. |
| 2017/0315442 | A1 | 11/2017 | Fukushima et al. |
| 2017/0351177 | A1* | 12/2017 | Hatakeyama ......... G03F 7/0048 |
| 2017/0369616 | A1* | 12/2017 | Hatakeyama ......... C08F 220/22 |
| 2018/0275512 | A1 | 9/2018 | Hatakeyama et al. |
| 2019/0155152 | A1* | 5/2019 | Aqad ...................... G03F 7/039 |
| 2019/0155155 | A1 | 5/2019 | Hatakeyama et al. |
| 2020/0301274 | A1* | 9/2020 | Taniguchi ............. C08F 220/20 |
| 2021/0149301 | A1 | 5/2021 | Fujiwara et al. |

FOREIGN PATENT DOCUMENTS

| | | | |
|---|---|---|---|
| JP | 2001-194776 | A | 7/2001 |
| JP | 2002-226470 | A | 8/2002 |
| JP | 2002-363148 | A | 12/2002 |
| JP | 2004-115630 | A | 4/2004 |
| JP | 2007-145797 | A | 6/2007 |
| JP | 2008-106045 | A | 5/2008 |
| JP | 2008-111103 | A | 5/2008 |
| JP | 2009-007327 | A | 1/2009 |
| JP | 4226803 | B2 | 2/2009 |
| JP | 2009-258695 | A | 11/2009 |
| JP | 2010-113209 | A | 5/2010 |
| JP | 2010-215608 | A | 9/2010 |
| JP | 2011-016746 | A | 1/2011 |
| JP | 2012-041320 | A | 3/2012 |
| JP | 2012-106986 | A | 6/2012 |
| JP | 2012-153644 | A | 8/2012 |
| JP | 2012-181306 | A | 9/2012 |

(Continued)

OTHER PUBLICATIONS

Oct. 20, 2021, Office Action issued in Korean Patent Application No. 10-2020-0034504.

Non-Final Office Action dated Apr. 5, 2022, issued in U.S. Appl. No. 16/798,842.

Office Action dated Oct. 17, 2023, issued in counterpart JP application No. 2020-194996, with English translation. (6 pages).

*Primary Examiner* — Keith Walker

*Assistant Examiner* — Anna Malloy

(74) *Attorney, Agent, or Firm* — WHDA, LLP

(57) ABSTRACT

The onium salt having formula (1) serves as an acid diffusion inhibitor. The chemically amplified resist composition includes the acid diffusion inhibitor are provided. When processed by lithography, the resist composition exhibits a high sensitivity, and excellent lithography performance factors such as CDU and LWR.

(1)

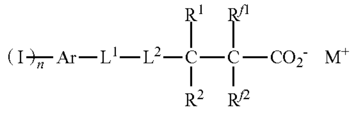

7 Claims, No Drawings

(56) References Cited

FOREIGN PATENT DOCUMENTS

| | | | |
|---|---|---|---|
| JP | 2014-001259 | A | 1/2014 |
| JP | 2014-133723 | A | 7/2014 |
| JP | 2014-142620 | A | 8/2014 |
| JP | 2015-214634 | A | 12/2015 |
| JP | 2016-018007 | A | 2/2016 |
| JP | 5904180 | B2 | 4/2016 |
| JP | 2021-080245 | A | 5/2021 |
| JP | 7096189 | B2 | 7/2022 |
| KR | 20160122085 | A | 10/2016 |
| KR | 20170138355 | A | 12/2017 |
| TW | 201701065 | A | 1/2017 |
| TW | 201812447 | A | 4/2018 |
| TW | 201838972 | A | 11/2018 |
| WO | 2016/063764 | A1 | 4/2016 |

* cited by examiner

ONIUM SALT COMPOUND, CHEMICALLY AMPLIFIED RESIST COMPOSITION AND PATTERNING PROCESS

CROSS-REFERENCE TO RELATED APPLICATION

This non-provisional application claims priority under 35 U.S.C. § 119(a) on Patent Application No. 2019-223621 filed in Japan on Dec. 11, 2019, the entire contents of which are hereby incorporated by reference.

TECHNICAL FIELD

This invention relates to an onium salt compound, a chemically amplified resist composition, and a pattern forming process.

BACKGROUND ART

To meet the demand for higher integration and operating speeds in LSIs, further miniaturization of the pattern rule is desired. The requirement to form resist patterns of high resolution necessitates not only to improve lithography properties as typified by pattern profile, contrast, mask error factor (MEF), depth of focus (DOF), critical dimension uniformity (CDU), and line width roughness (LWR), but also to minimize defects on the resist pattern after development.

As the pattern feature size is reduced, LWR becomes more noticeable. It is pointed out that LWR is affected by the segregation and agglomeration of a base polymer and an acid generator and acid diffusion. There is a propensity that LWR is degraded as the resist film becomes thinner. The degradation of LWR caused by resist film thinning to comply with further miniaturization becomes a serious problem.

For the EUV resist composition, it is necessary to achieve a high sensitivity, high resolution and low LWR at the same time. As the acid diffusion distance is shortened, the outcome is a smaller LWR, but a lower sensitivity. For example, when the PEB temperature is lowered, LWR becomes smaller, but sensitivity becomes lower. When the amount of an acid diffusion inhibitor or quencher added is increased, LWR becomes smaller, but sensitivity becomes lower. It is necessary to overcome the tradeoff relationship between sensitivity and LWR.

Studies have been made on various additives in order to overcome the tradeoff relationship between sensitivity and LWR. Means for enhancing sensitivity include the structural optimization of photoacid generators and acid diffusion inhibitors such as amines and weak acid onium salts and the addition of acid amplifiers. Patent Document 1 discloses an acid diffusion inhibitor of onium salt type having incorporated the mechanism that basicity is reduced by an acid. Yet a resist composition capable of meeting both sensitivity and LWR has not been developed.

Another means for enhancing sensitivity is the introduction of an element having high EUV absorption. The EUV absorption of a molecule largely depends on the type and number of elements of the molecule. Since halogen atoms, especially iodine atoms show higher absorption than carbon, hydrogen and oxygen atoms, studies are made on the introduction of halogen atoms and the optimization of the halogen-introduced structure.

As the acid diffusion inhibitor featuring minimal defects and improved LWR, Patent Document 2 discloses onium salts of the following formulae.

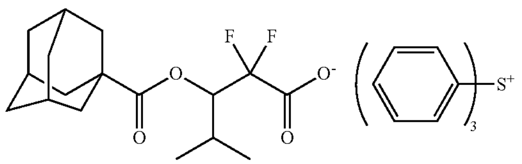

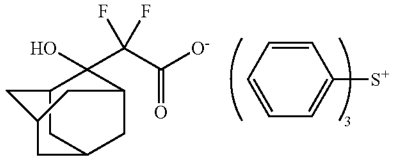

When these onium salts are used as an acid diffusion inhibitor, there are obtained no results satisfying various lithography factors for the current generation where ultrafine processing using ArF or EUV lithography is required.

CITATION LIST

Patent Document 1: JP-A 2014-142620 (U.S. Pat. No. 10,248,020)

Patent Document 2: JP 5904180 (U.S. Pat. No. 9,221,742)

DISCLOSURE OF INVENTION

While resist patterns of high resolution are recently required, resist compositions comprising conventional acid diffusion inhibitors do not always meet lithography performance factors such as sensitivity, CDU, and LWR.

An object of the invention is to provide a chemically amplified resist composition which when processed by lithography using high-energy radiation such as KrF or ArF excimer laser, EB or EUV, exhibits a high sensitivity and is improved in lithography performance factors such as CDU and LWR. Another object is to provide an acid diffusion inhibitor used in the resist composition and a pattern forming process using the resist composition.

The inventors have found that a chemically amplified resist composition comprising an onium salt compound of carboxylic acid having a specific iodized structure as an acid diffusion inhibitor exhibits a high sensitivity and improved lithography performance factors such as CDU and LWR, and is suited for high accuracy micropatterning.

In one aspect, the invention provides an onium salt compound having the formula (1).

(1)

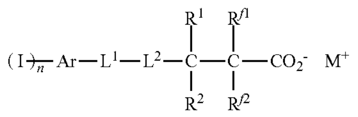

Herein $R^1$ and $R^2$ are each independently hydrogen, hydroxyl or a $C_1$-$C_{12}$ hydrocarbyl group, some hydrogen in the hydrocarbyl group may be substituted by a heteroatom-containing moiety, $-CH_2-$ in the hydrocarbyl group may be replaced by $-O-$ or $-C(=O)-$, $R^1$ and $R^2$ may bond together to form a ring with the carbon atom to which they are attached. $R^{f1}$ and $R^{f2}$ are each independently hydrogen, fluorine or trifluoromethyl, at least one thereof being fluorine or trifluoromethyl. $L^1$ is a single bond or $C_1$-$C_{15}$ hydrocarbylene group, some hydrogen in the hydrocarbylene group may be substituted by a heteroatom-containing moiety, —$CH_2$— in the hydrocarbylene group may be replaced by —O— or —C(=O)—. $L^2$ is a single bond, ether bond or ester bond. Ar is a (n+1)-valent $C_3$-$C_{15}$ aromatic group in which some or all of the hydrogen atoms may be substituted by substituents, n is an integer of 1 to 5. $M^+$ is a sulfonium or iodonium cation.

In a preferred embodiment, the onium salt compound has the formula (2).

(2)

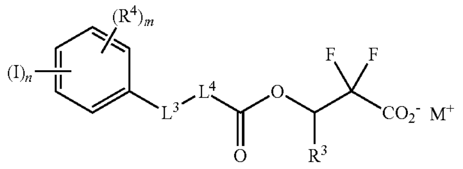

Herein $M^+$ is as defined above, n is an integer of 1 to 5, m is an integer of 0 to 4, n+m is from 1 to 5. $R^3$ is hydrogen or a $C_1$-$C_{10}$ hydrocarbyl group which may contain a heteroatom. $R^4$ is fluorine, hydroxyl, or a $C_1$-$C_{15}$ hydrocarbyl group, some hydrogen in the hydrocarbyl group may be substituted by a heteroatom-containing moiety, —$CH_2$— in the hydrocarbyl group may be replaced by —O—, —C(=O)—, or —N($R^N$)—, $R^N$ is hydrogen or a $C_1$-$C_{10}$ hydrocarbyl group, some hydrogen in the hydrocarbyl group $R^N$ may be substituted by a heteroatom-containing moiety, —$CH_2$— in the hydrocarbyl group $R^N$ may be replaced by —O—, —C(=O)—, or —S(=O)$_2$—, with the proviso that when m is 2 or more, a plurality of $R^4$ may be the same or different, or two $R^4$ may bond together to form a ring with the carbon atoms on the benzene ring to which they are attached. $L^3$ is a single bond, ether bond or ester bond. $L^4$ is a single bond or a $C_1$-$C_{10}$ hydrocarbylene group which may contain a heteroatom.

More preferably, $R^3$ is hydrogen, isopropyl, adamantyl or optionally substituted phenyl; and $L^3$ and $L^4$ each are a single bond.

Also preferably, $M^+$ is a cation having any one of the following formulae (M-1) to (M-4).

(M-1)

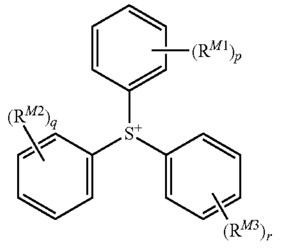

(M-2)

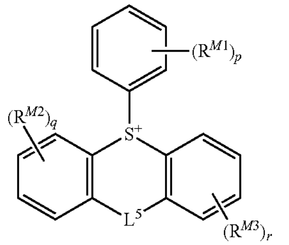

-continued (M-3)

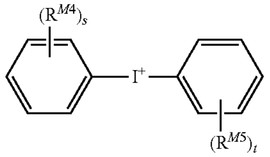

(M-4)

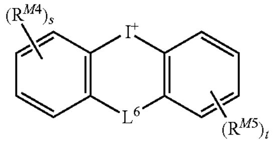

Herein $R^{M1}$, $R^{M2}$. $R^{M3}$, $R^{M4}$, and $R^{M5}$ are each independently halogen, hydroxyl, or a $C_1$-$C_{15}$ hydrocarbyl group, some hydrogen in the hydrocarbyl group may be substituted by a heteroatom-containing moiety, —$CH_2$— in the hydrocarbyl group may be replaced by —O—, —C(=O)—, —S—, —S(=O)—, —S(=O)$_2$— or —N($R^N$)—. $L^5$ and $L^6$ are each independently a single bond, —$CH_2$—, —O—, —C(=O)—, —S—, —S(=O)—, —S(=O)$_2$— or —N($R^N$)—. $R^N$ is hydrogen or a $C_1$-$C_{10}$ hydrocarbyl group, some hydrogen in the hydrocarbyl group may be substituted by a heteroatom-containing moiety, —$CH_2$— in the hydrocarbyl group may be replaced by —O—, —C(=O)— or —S(=O)$_2$—; p, q, r, s and t are each independently an integer of 0 to 5; when p is 2 or more, a plurality of $R^{M1}$ may be the same or different, and two $R^{M1}$ may bond together to form a ring with the carbon atoms on the benzene ring to which they are attached, when q is 2 or more, a plurality of $R^{M2}$ may be the same or different, and two $R^{M2}$ may bond together to form a ring with the carbon atoms on the benzene ring to which they are attached, when r is 2 or more, a plurality of $R^{M3}$ may be the same or different, and two $R^{M3}$ may bond together to form a ring with the carbon atoms on the benzene ring to which they are attached, when s is 2 or more, a plurality of $R^{M4}$ may be the same or different, and two $R^{M4}$ may bond together to form a ring with the carbon atoms on the benzene ring to which they are attached, when t is 2 or more, a plurality of $R^{M5}$ may be the same or different, and two $R^{M5}$ may bond together to form a ring with the carbon atoms on the benzene ring to which they are attached.

In a preferred embodiment, the onium salt compound has the following formula (3) or (4).

(3)

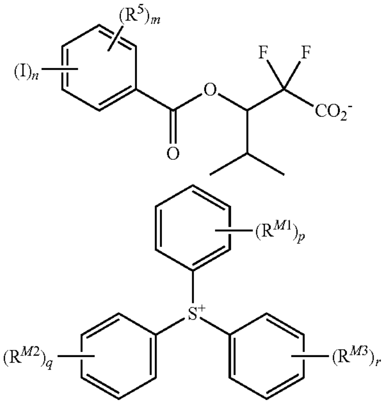

-continued (4)

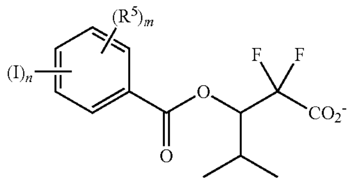

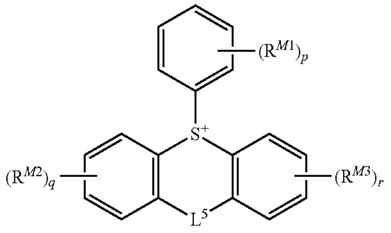

Herein $R^{M1}$, $R^{M2}$, $R^{M3}$, $L^5$, m, n, p, q, and r are as defined above. $R^5$ is fluorine, hydroxyl, or a $C_1$-$C_{10}$ hydrocarbyl group, some hydrogen in the hydrocarbyl group may be substituted by a heteroatom-containing moiety, —$CH_2$— in the hydrocarbyl group may be replaced by —O— or —C(═O)—, and when m is 2 or more, a plurality of $R^5$ may be the same or different, and two $R^5$ may bond together to form a ring with the carbon atoms to which they are attached. Preferably n is 2 or 3.

In another aspect, the invention provides an acid diffusion inhibitor comprising the onium salt compound defined above.

In a further aspect, the invention provides a chemically amplified resist composition comprising (A) a base polymer adapted to change its solubility in a developer under the action of an acid, (B) a photoacid generator, (C) an acid diffusion inhibitor comprising the onium salt compound defined above, and (D) an organic solvent; or a chemically amplified resist composition comprising (A') a base polymer adapted to change its solubility in a developer under the action of an acid, the base polymer comprising recurring units having a function of generating an acid upon exposure to light, (C) an acid diffusion inhibitor comprising the onium salt compound defined above, and (D) an organic solvent.

In a preferred embodiment, the base polymer comprises recurring units having the formula (a) or recurring units having the formula (b).

(a)

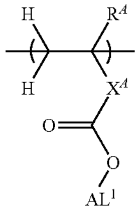

-continued (b)

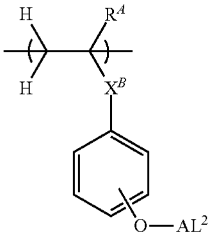

Herein $R^A$ is hydrogen or methyl, $X^A$ is a single bond, phenylene group, naphthylene group or (backbone)-C(═O)—O—$X^{A1}$—, $X^{A1}$ is a $C_1$-$C_{15}$ hydrocarbylene group which may contain a hydroxyl moiety, ether bond, ester bond or lactone ring, $X^B$ is a single bond or ester bond, $AL^1$ and $AL^2$ are each independently an acid labile group.

Preferably, the acid labile group has the formula (L1):

(L1)

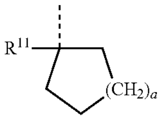

wherein $R^{11}$ is a $C_1$-$C_7$ hydrocarbyl group in which —$CH_2$— may be replaced by —O—, a is 1 or 2, and the broken line designates a valence bond.

In a preferred embodiment, the base polymer comprises recurring units having the formula (c):

(c)

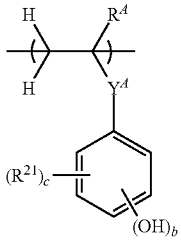

wherein $R^A$ is hydrogen or methyl, $Y^A$ is a single bond or ester bond, $R^{21}$ is fluorine, iodine or a $C_1$-$C_{10}$ hydrocarbyl group in which —$CH_2$— may be replaced by —O— or —C(═O)—, b is an integer of 1 to 5, c is an integer of 0 to 4, and b+c is from 1 to 5.

Preferably, the recurring units having a function of generating an acid upon exposure to light are units of at least one type selected from the formulae (d1) to (d4).

(d1)

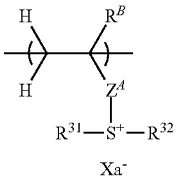

-continued (d2)

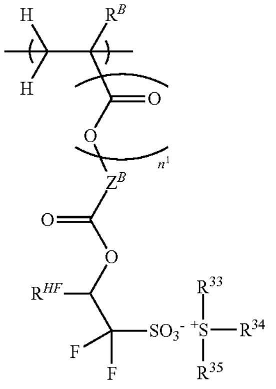

(d3)

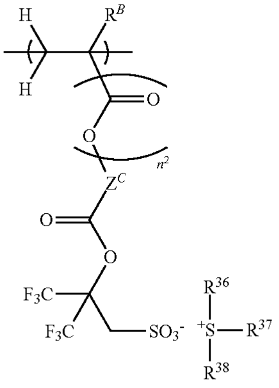

(d4)

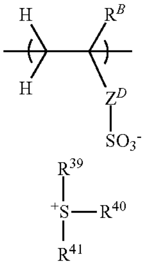

Herein $R^B$ is hydrogen, fluorine, methyl or trifluoromethyl. $Z^A$ is a single bond, phenylene group, —O—$Z^{A1}$—, —C(═O)—O—$Z^{A1}$— or —C(═O)—NH—$Z^{A1}$—, $Z^{A1}$ is a $C_1$-$C_{20}$ hydrocarbylene group which may contain a heteroatom. $Z^B$ and $Z^C$ are each independently a single bond or a $C_1$-$C_{20}$ hydrocarbylene group which may contain a heteroatom. $Z^D$ is a single bond, methylene, ethylene, phenylene, fluorinated phenylene, —O—$Z^{D1}$—, —C(═O)—O—$Z^{D1}$— or —C(═O)—NH—$Z^{D1}$—, wherein $Z^{D1}$ is an optionally substituted phenylene group. $R^{31}$ to $R^{41}$ are each independently a $C_1$-$C_{20}$ hydrocarbyl group which may contain a heteroatom, any two of $Z^A$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, and any two of $R^{39}$, $R^{40}$ and $R^{41}$ may bond together to form a ring with the sulfur atom to which they are attached. $R^{HF}$ is hydrogen or trifluoromethyl, $n^1$ is 0 or 1, $n^1$ is 0 when $Z^B$ is a single bond, $n^2$ is 0 or 1, $n^2$ is 0 when $Z^C$ is a single bond. $Xa^-$ is a non-nucleophilic counter ion.

In a still further aspect, the invention provides a pattern forming process comprising the steps of applying the chemically amplified resist composition defined above to form a resist film on a substrate, exposing a selected region of the resist film to KrF excimer laser, ArF excimer laser, EB or EUV, and developing the exposed resist film in a developer.

In one preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

Typically, the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

Advantageous Effects of Invention

The inventive chemically amplified resist composition comprising the onium salt compound as an acid diffusion inhibitor has a high sensitivity. When the resist composition is processed by lithography, a resist pattern exhibiting improved lithography performance factors such as CDU, and LWR can be formed.

DESCRIPTION OF THE PREFERRED EMBODIMENTS

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. The terms "group" and "moiety" are interchangeable. As used herein, the term "iodized" compound means an iodine-containing compound. In chemical formulae, the broken line denotes a valence bond; Me stands for methyl, tBu for tert-butyl, Ac for acetyl, and Ph for phenyl. It is understood that for some structures represented by chemical formulae, there can exist enantiomers and diastereomers because of the presence of asymmetric carbon atoms. In such a case, a single formula collectively represents all such isomers. The isomers may be used alone or in admixture.

The abbreviations have the following meaning.

EB: electron beam

EUV: extreme ultraviolet

GPC: gel permeation chromatography

Mw: weight average molecular weight

Mw/Mn: molecular weight dispersity

PAG: photoacid generator

PEB: post-exposure bake
LWR: line width roughness
CDU: critical dimension uniformity Onium Salt The invention provides an onium salt compound having the formula (1).

(1)

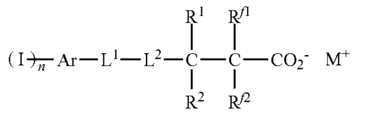

In formula (1), $R^1$ and $R^2$ are each independently hydrogen, hydroxyl or a $C_1$-$C_{12}$ hydrocarbyl group. The $C_1$-$C_{12}$ hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, n-hexyl, n-octyl, n-nonyl, and n-decyl; cyclic saturated hydrocarbyl groups such as cyclopentyl, cyclohexyl, and adamantyl; aryl groups such as phenyl; and combinations thereof.

Some or all of the hydrogen atoms in the hydrocarbyl group may be substituted by a moiety containing a heteroatom such as oxygen, sulfur, nitrogen or halogen, or —$CH_2$— in the hydrocarbyl group may be replaced by —O— or —C(═O)—, so that the group may contain a hydroxyl, cyano, carbonyl, ether bond, ester bond, carbonate bond, lactone ring, carboxylic anhydride or haloalkyl moiety. The constituent —$CH_2$— in the hydrocarbyl group may be one bonding to a carbon atom in formula (1). Examples of the substituted hydrocarbyl group include, but are not limited to, methoxy, ethoxy, propoxy, butoxy, phenoxy, 2-methoxyethoxy, acetyl, ethylcarbonyl, hexylcarbonyl, acetoxy, ethylcarbonyloxy, propylcarbonyloxy, pentylcarbonyloxy, hexylcarbonyloxy, heptylcarbonyloxy, methoxymethylcarbonyloxy, (2-methoxyethoxy)methylcarbonyloxy, methyloxycarbonyl, ethyloxycarbonyl, hexyloxycarbonyl, phenyloxycarbonyl, acetoxymethyl, phenoxymethyl, and methoxycarbonyloxy.

$R^1$ and $R^2$ may bond together to form a ring with the carbon atom to which they are attached. Exemplary rings include cyclopentane, cyclohexane and adamantane rings. It is preferred from the aspects of lithography performance and ease of synthesis that one of $R^1$ and $R^2$ be hydrogen. It is believed that when one of $R^1$ and $R^2$ is hydrogen, the space around the carboxylate site becomes sterically empty so that the onium salt compound acts efficiently as an acid diffusion inhibitor.

In formula (1), $R^{f1}$ and $R^{f2}$ are each independently hydrogen, fluorine or trifluoromethyl, at least one thereof being fluorine or trifluoromethyl. Most preferably, both $R^{f1}$ and $R^{f2}$ are fluorine.

In formula (1), $L^1$ is a single bond or $C_1$-$C_{15}$ hydrocarbylene group. The hydrocarbylene group may be saturated or unsaturated and straight, branched or cyclic. Examples thereof include alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, and tetradecane-1,14-diyl; cyclic saturated hydrocarbylene groups such as cyclopentanediyl, cyclohexanediyl, norbornanediyl, and adamantanediyl; aromatic hydrocarbylene groups such as phenylene and naphthylene, and combinations thereof. Some or all of the hydrogen atoms in the hydrocarbylene group may be substituted by a moiety containing a heteroatom such as oxygen, sulfur, nitrogen or halogen, and —$CH_2$— in the hydrocarbylene group may be replaced by —O— or —C(═O)—, so that the group may contain a hydroxyl, cyano, carbonyl, ether bond, ester bond, carbonate bond, lactone ring, carboxylic anhydride or haloalkyl moiety. The constituent —$CH_2$— in the hydrocarbylene group may be one bonding to Ar in formula (1).

In formula (1), $L^2$ is a single bond, ether bond or ester bond, preferably an ether bond or ester bond.

When both $L^1$ and $L^2$ are single bonds, $R^2$ is preferably a hydroxyl, hydrocarbyloxy or hydrocarbylcarbonyloxy group. That is, structures having the formula (1A) are preferred.

(1A)

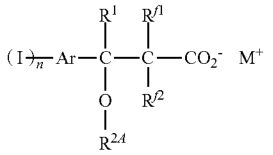

Herein $R^1$, $R^{f1}$, $R^{f2}$. n and $M^+$ are as defined above. Ar is defined below. $R^{2A}$ is hydrogen or a $C_1$-$C_{11}$ hydrocarbyl group which may contain a heteroatom, and —$CH_2$— in the hydrocarbyl group may be replaced by —O— or —C(═O)—.

In formula (1), Ar is a (n+1)-valent $C_3$-$C_{15}$ aromatic group. The aromatic group is obtained by removing (n+1) number of hydrogen atoms on aromatic ring from a $C_3$-$C_{15}$ aromatic compound. Examples of the $C_3$-$C_{15}$ aromatic compound include benzene, naphthalene, furan, thiophene, benzothiophene, indole, and oxazole. Of these, groups derived from benzene are preferred from the aspects of solubility, storage stability, and sensitivity. The groups derived from benzene are effective for properly suppressing acid diffusion and maintaining a high sensitivity. Some or all of the hydrogen atoms in the aromatic group may be substituted by substituents. Suitable substituents include fluorine, hydroxyl, and $C_1$-Cho hydrocarbyl groups in which —$CH_2$— may be replaced by —O— or —C(═O)—. The constituent —$CH_2$— in the hydrocarbyl group may be one bonding to the aromatic ring.

In formula (1), n is an integer of 1 to 5, preferably 1 to 3, more preferably 2 or 3. When n is 1 to 3, the EUV absorption efficiency is improved without detracting from the solubility in resist solvent, from which an improvement in sensitivity is expectable.

Of the onium salt compounds having formula (1), compounds having the following formula (2) are preferred.

(2)

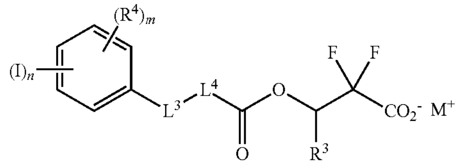

Herein $M^+$ is as defined above.

In formula (2), n is an integer of 1 to 5, m is an integer of 0 to 4, and n+m is from 1 to 5; m is preferably 0, 1 or 2.

In formula (2), $R^3$ is hydrogen or a $C_1$-Cho hydrocarbyl group which may contain a heteroatom. The hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, n-hexyl, n-octyl, n-nonyl, and n-decyl; cyclic saturated hydrocarbyl groups such as cyclopentyl, cyclohexyl, and adamantyl; aryl groups such as phenyl; and combinations thereof. In the hydrocarbyl groups, some or all of the hydrogen atoms may be substituted by a moiety containing a heteroatom such as oxygen, sulfur, nitrogen or halogen, and a moiety containing a heteroatom such as oxygen, sulfur or nitrogen may intervene in a carbon-carbon bond, so that the group may contain a hydroxyl, cyano, carbonyl, ether bond, ester bond, sulfonic acid ester bond, carbonate bond, lactone ring, sultone ring, carboxylic anhydride or haloalkyl moiety. Preferably $R^3$ is hydrogen, propyl, isopropyl, cyclohexyl, adamantyl, phenyl, 4-fluorophenyl, 4-trifluoromethylphenyl, 4-iodophenyl or 4-methoxyphenyl. More preferably $R^3$ is hydrogen, isopropyl, adamantyl, phenyl or 4-iodophenyl.

In formula (2), $R^4$ is fluorine, hydroxyl, or a $C_1$-$C_{15}$ hydrocarbyl group. The hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, n-hexyl, n-octyl, n-nonyl, and n-decyl; cyclic saturated hydrocarbyl groups such as cyclopentyl, cyclohexyl, and adamantyl; aryl groups such as phenyl; and combinations thereof. Some or all of the hydrogen atoms in the hydrocarbyl group may be substituted by a moiety containing a heteroatom such as oxygen, sulfur, nitrogen or halogen, and $—CH_2—$ in the hydrocarbyl group may be replaced by —O—, —C(=O)— or $—N(R^N)—$. $R^N$ is hydrogen or a $C_1$-$C_{10}$ hydrocarbyl group. Some hydrogen in the hydrocarbyl group $R^N$ may be substituted by a heteroatom-containing moiety, and $—CH_2—$ in the hydrocarbyl groups $R^N$ may be replaced by —O—, —C(=O)—, or $—S(=O)_2—$. That is, the hydrocarbyl groups $R^4$ and $R^N$ may contain a hydroxyl moiety, cyano moiety, carbonyl moiety, ether bond, ester bond, amide bond, carbonate bond, lactone ring, carboxylic anhydride, or haloalkyl moiety.

The constituent $—CH_2—$ in the hydrocarbyl group may be one bonding to a carbon atom on the benzene ring in formula (2). Examples of the substituted hydrocarbyl group include, but are not limited to, methoxy, ethoxy, n-propoxy, isopropoxy, n-butoxy, tert-butoxy, phenoxy, 2-methoxyethoxy, acetyl, ethylcarbonyl, hexylcarbonyl, acetoxy, ethylcarbonyloxy, propylcarbonyloxy, pentylcarbonyloxy, hexylcarbonyloxy, heptylcarbonyloxy, methoxymethylcarbonyloxy, (2-methoxyethoxy)methylcarbonyloxy, adamantylcarbonyloxy, methoxy carbonyl, ethoxy carbonyl, isopropoxy carbonyl, tert-butoxy carbonyl, tert-pentyloxycarbonyl, hexyloxycarbonyl, phenyloxycarbonyl, acetoxymethyl, phenoxymethyl, methoxycarbonyloxy, tert-butoxycarbonyloxy, methoxycarbonylamino, and tert-butoxycarbonylamino.

When m is 2 or more, a plurality of $R^4$ may be the same or different, or two $R^4$ may bond together to form a ring with the carbon atoms on the benzene ring to which they are attached. Examples of the ring are shown below, but not limited thereto. The broken line designates a point of attachment to $L^3$ in formula (2).

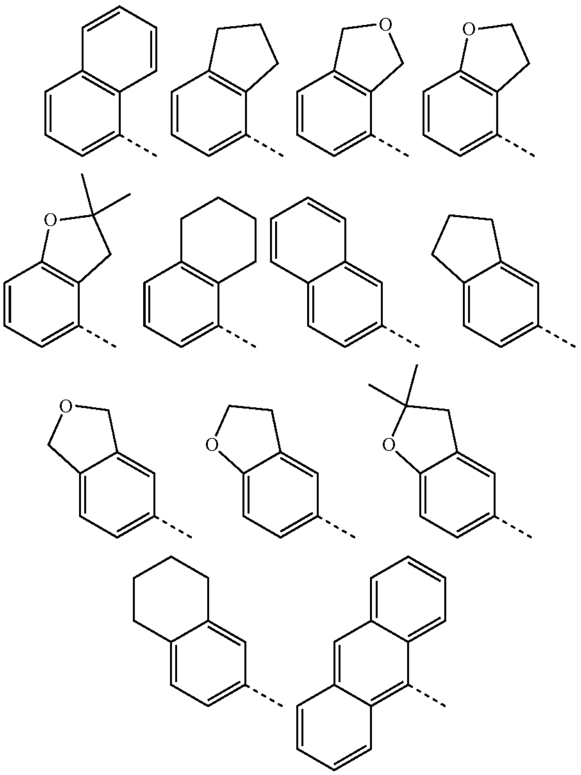

In formula (2), $L^3$ is a single bond, ether bond or ester bond.

In formula (2), $L^4$ is a single bond or $C_1$-Cho hydrocarbylene group which may contain a heteroatom. The hydrocarbylene group may be saturated or unsaturated and straight, branched or cyclic. Examples thereof include alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, 2,2-dimethylpropane-1,3-diyl; cyclic saturated hydrocarbylene groups such as cyclopentanediyl, cyclohexanediyl, norbornanediyl, and adamantanediyl; alkenediyl groups such as ethene-1,2-diyl, 1-propene-1,3-diyl, 2-butene-1,4-diyl, 1-methyl-1-butene-1,4-diyl; unsaturated alicyclic hydrocarbylene groups such as 2-cyclohexene-1,4-diyl; aromatic hydrocarbylene groups such as phenylene and naphthylene, and combinations thereof. Some or all of the hydrogen atoms in the hydrocarbylene group may be substituted by a moiety containing a heteroatom such as oxygen, sulfur, nitrogen or halogen, and a moiety containing a heteroatom such as oxygen, sulfur or nitrogen may intervene in a carbon-carbon bond in the hydrocarbylene group, so that the group may contain a hydroxyl, cyano, carbonyl, ether bond, ester bond, sulfonate bond, carbonate bond, lactone ring, sultone ring, carboxylic anhydride or haloalkyl moiety.

In formulae (1) and (2), $M^+$ is a sulfonium or iodonium cation, preferably a cation selected from the following formulae (M-1) to (M-4).

(M-1)

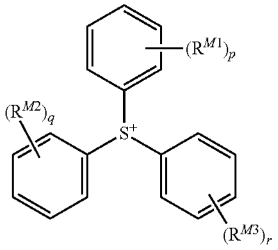

(M-2)

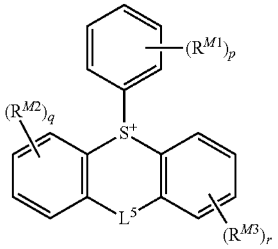

(M-3)

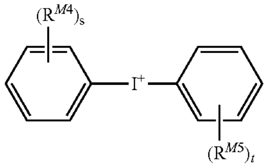

(M-4)

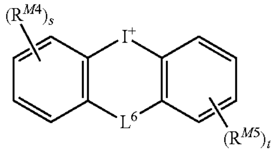

In formulae (M-1) to (M-4), $R^{M1}$, $R^{M2}$, $R^{M3}$, $R^{M4}$, and $R^{M5}$ are each independently halogen, hydroxyl, or a $C_1$-$C_{15}$ hydrocarbyl group. Suitable halogen atoms include fluorine, chlorine, bromine and iodine. The $C_1$-$C_{15}$ hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, n-hexyl, n-octyl, n-nonyl, and n-decyl; cyclic saturated hydrocarbyl groups such as cyclopentyl, cyclohexyl, and adamantyl; aromatic hydrocarbyl groups such as phenyl; and combinations thereof. Some or all of the hydrogen atoms in the hydrocarbyl group may be substituted by a moiety containing a heteroatom such as oxygen, sulfur, nitrogen or halogen, and —$CH_2$— in the hydrocarbyl group may be replaced by —O—, —C(═O)—, —S—, —S(═O)—, —S(═O)$_2$— or —N($R^N$)—. $R^N$ is as defined above. That is, the hydrocarbyl group may contain a hydroxyl, cyano, carbonyl, ether bond, ester bond, amide bond, thioether bond, sulfonic acid ester bond, carbonate bond, lactone ring, sultone ring, carboxylic anhydride or haloalkyl moiety. The constituent —$CH_2$— in the hydrocarbyl group may be one bonding to a carbon atom on the benzene ring in formulae (M-1) to (M-4). In this case, $R^{M1}$ to $R^{M5}$ may be hydrocarbyloxy, hydrocarbylcarbonyloxy, hydrocarbylthio, hydrocarbylcarbonyl, hydrocarbylsulfonyl, hydrocarbylamino, hydrocarbylsulfonylamino, or hydrocarbylcarbonylamino.

In formulae (M-2) and (M-4), $L^5$ and $L^6$ are each independently a single bond, —$CH_2$—, —O—, —C(═O)—, —S—, —S(═O)—, —S(═O)$_2$— or —N($R^N$)—, wherein $R^N$ is as defined above.

In formulae (M-1) to (M-4), p, q, r, s and t are each independently an integer of 0 to 5. When p is 2 or more, a plurality of $R^{M1}$ may be the same or different, and two $R^{M1}$ may bond together to form a ring with the carbon atoms on the benzene ring to which they are attached. When q is 2 or more, a plurality of $R^{M2}$ may be the same or different, and two $R^{M2}$ may bond together to form a ring with the carbon atoms on the benzene ring to which they are attached. When r is 2 or more, a plurality of $R^{M3}$ may be the same or different, and two $R^{M3}$ may bond together to form a ring with the carbon atoms on the benzene ring to which they are attached. When s is 2 or more, a plurality of $R^{M4}$ may be the same or different, and two $R^{M4}$ may bond together to form a ring with the carbon atoms on the benzene ring to which they are attached. When t is 2 or more, a plurality of $R^{M5}$ may be the same or different, and two $R^{M5}$ may bond together to form a ring with the carbon atoms on the benzene ring to which they are attached.

Examples of the sulfonium cation having formula (M-1) are given below, but not limited thereto.

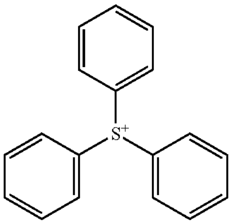
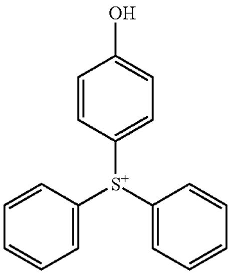

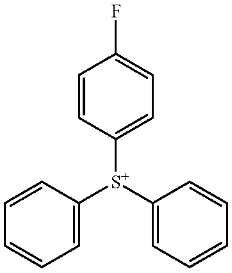
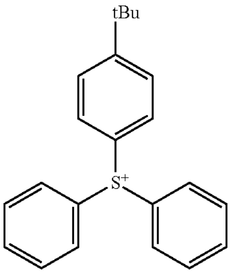

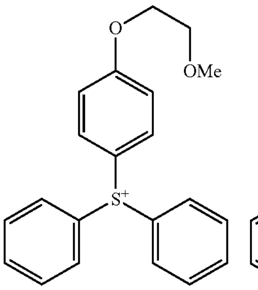
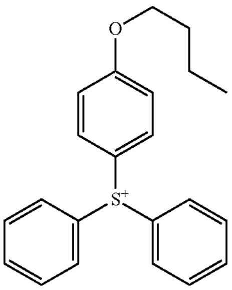

-continued
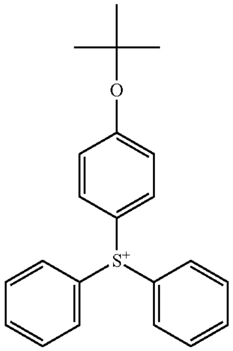
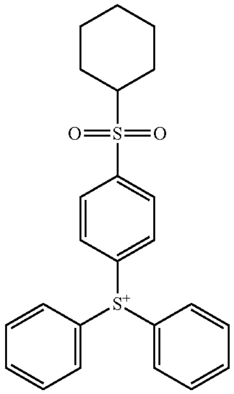
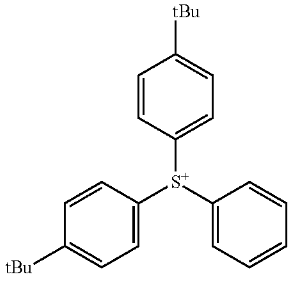
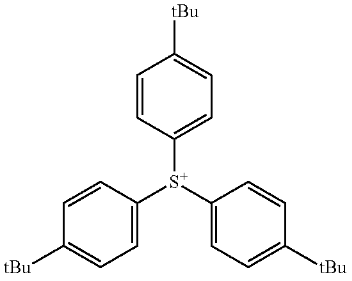
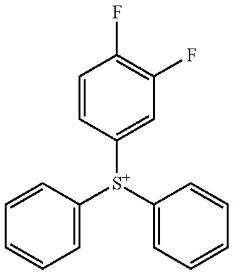
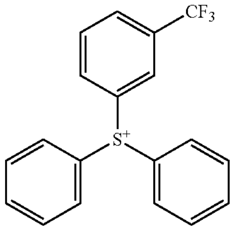
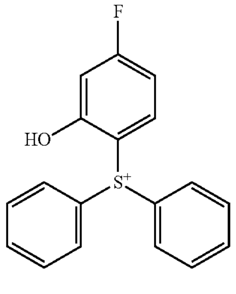
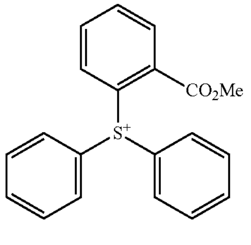
-continued
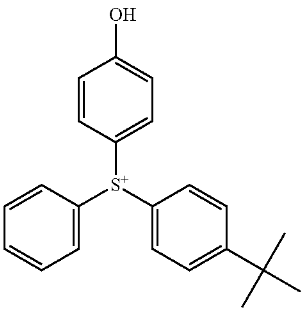
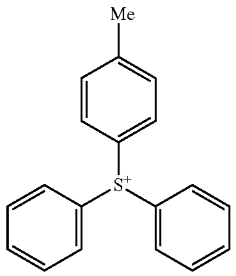
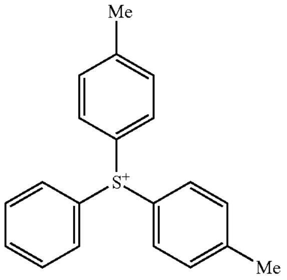
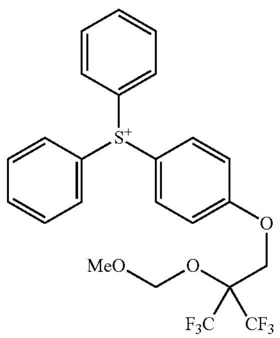
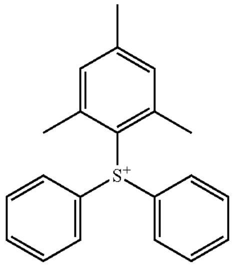
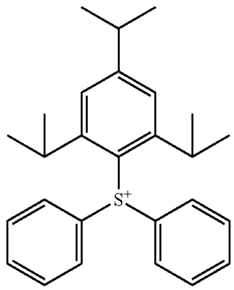
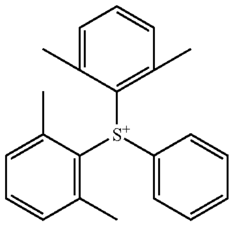
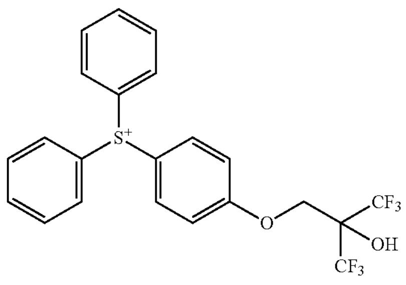

-continued
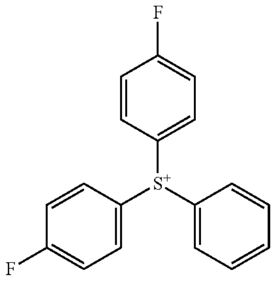
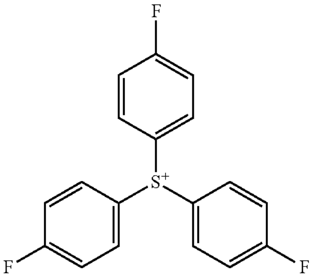
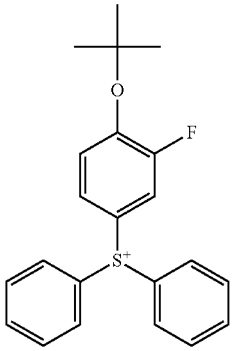
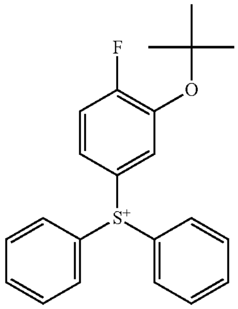
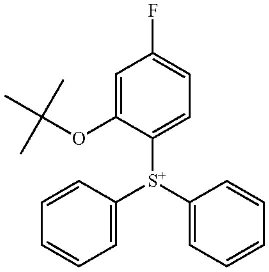
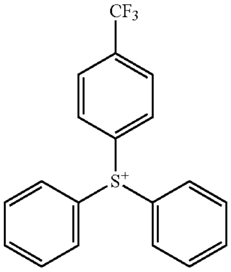
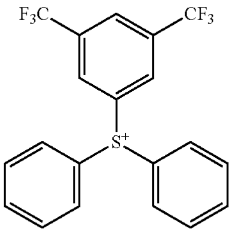
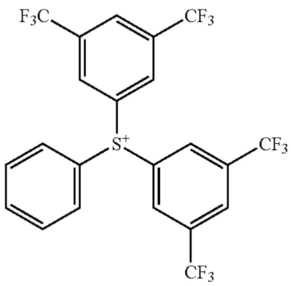
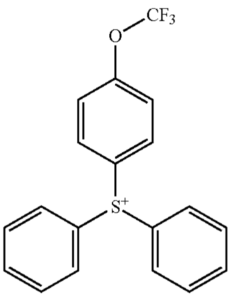
-continued
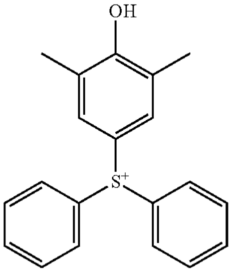
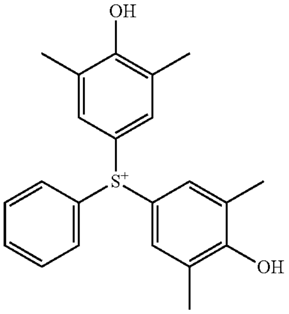
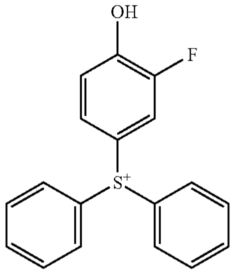
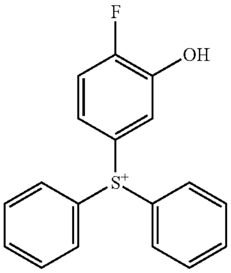
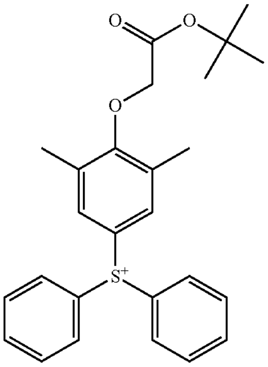
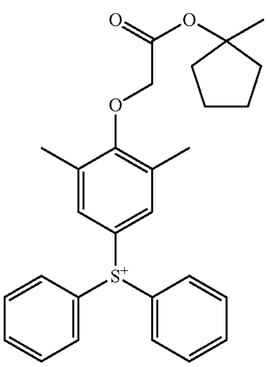
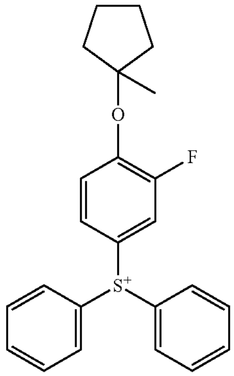
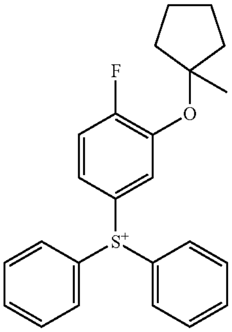
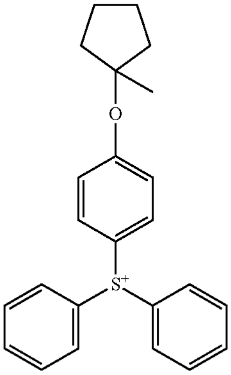

Examples of the sulfonium cation having formula (M-2) are given below, but not limited thereto.
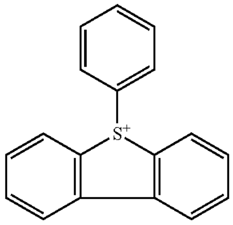
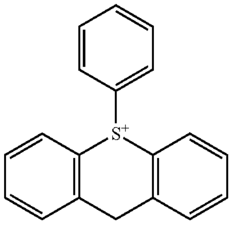
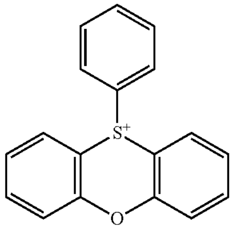
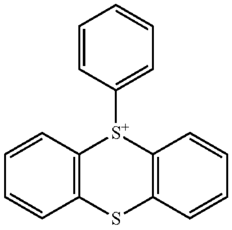
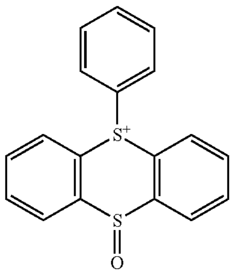
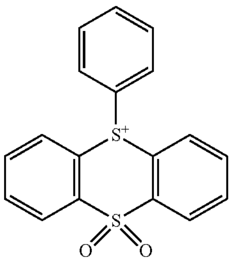
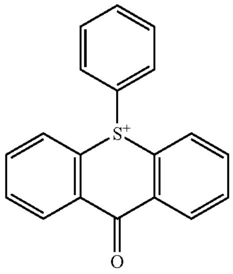
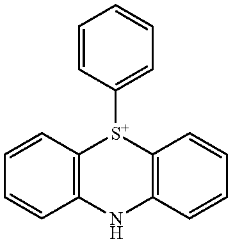
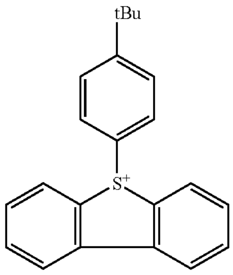
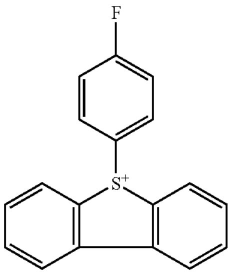
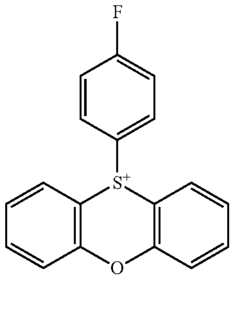
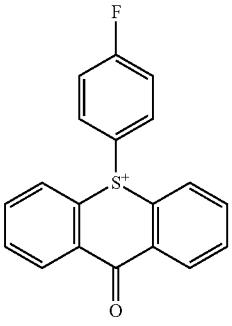
-continued
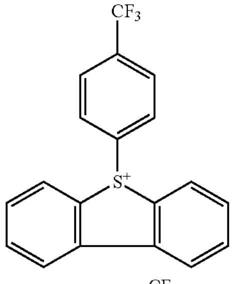
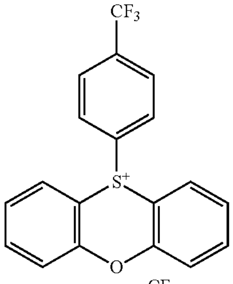
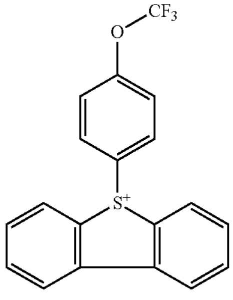
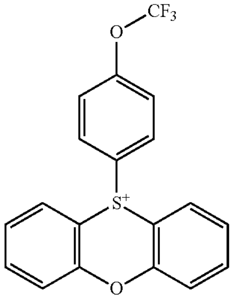
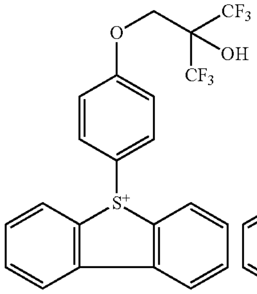
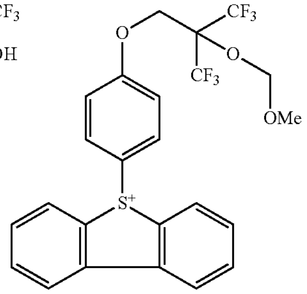
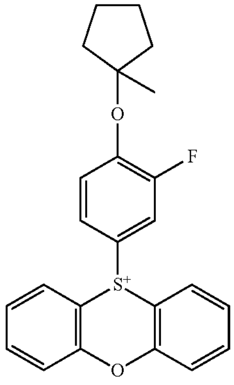
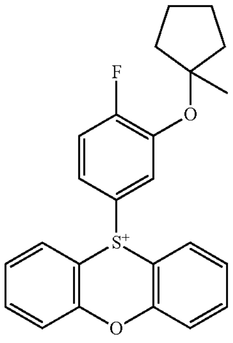
Examples of the iodonium cation having formula (M-3) are given below, but not limited thereto.
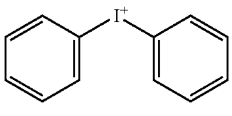
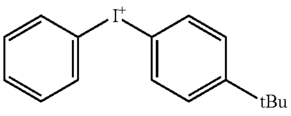
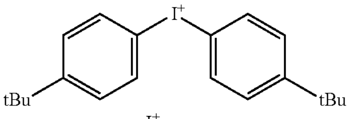
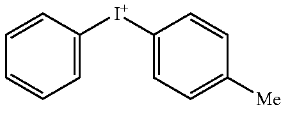

-continued
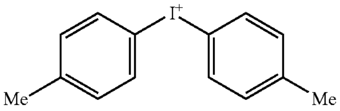
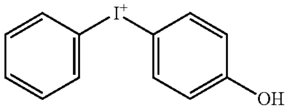
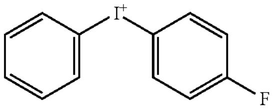
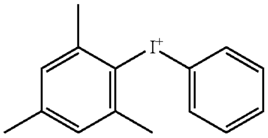
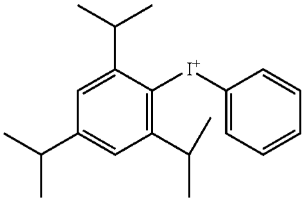
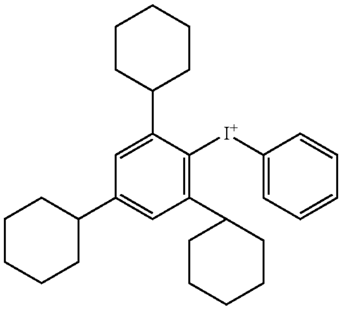
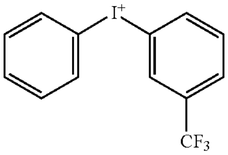
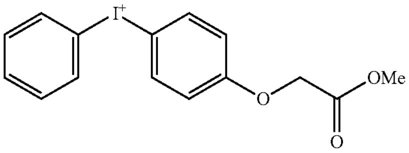
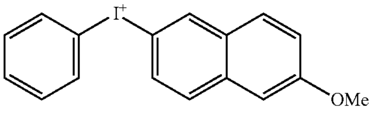
Examples of the iodonium cation having formula (M-4) are given below, but not limited thereto.
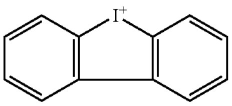
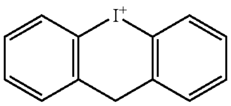
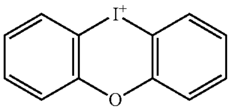
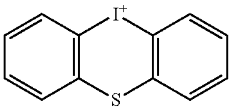
-continued
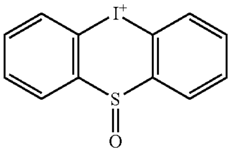
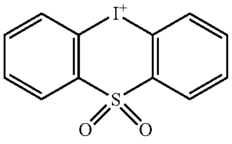
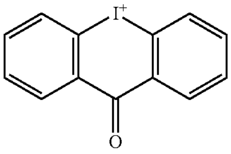
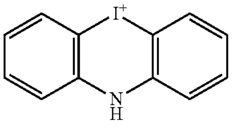
Suitable sulfonium cations other than the sulfonium cations having formulae (M-1) and (M-2) are given below, but not limited thereto.
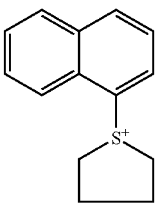
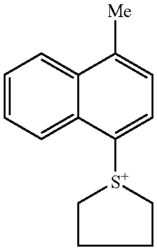
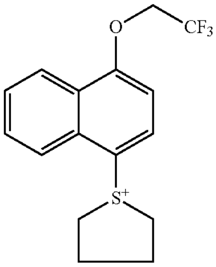
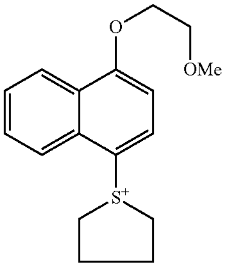
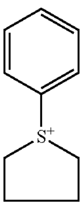
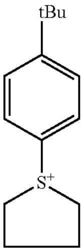
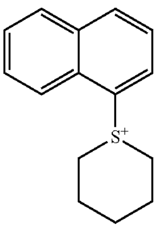
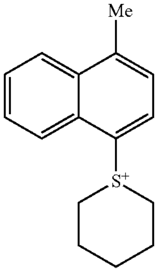
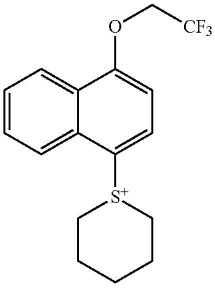
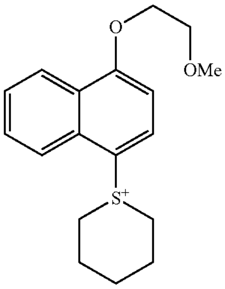
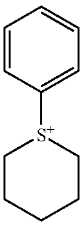
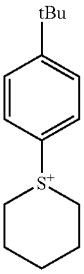
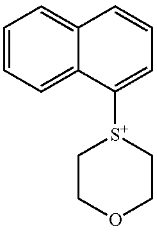

-continued
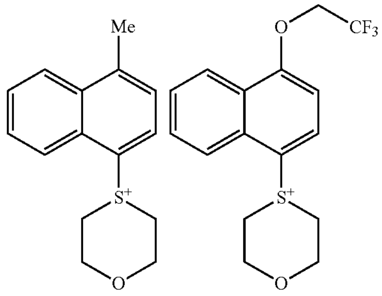
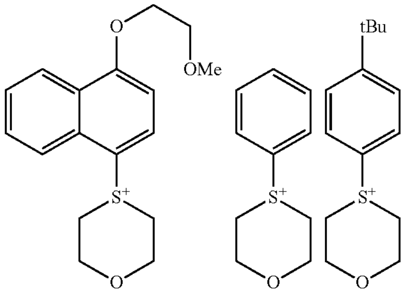
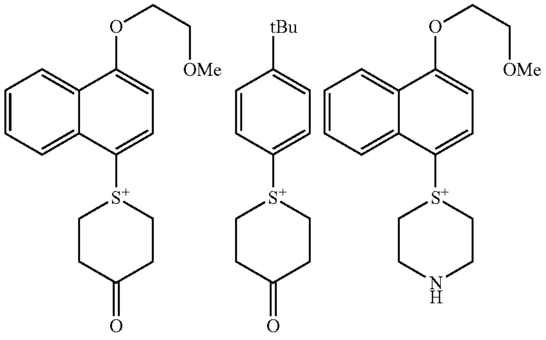
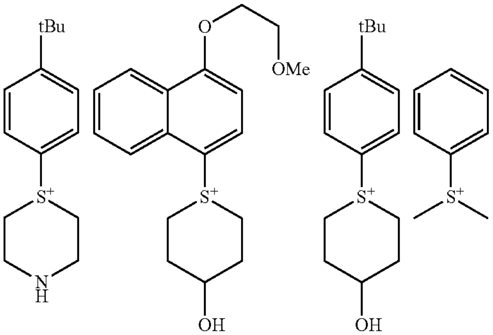
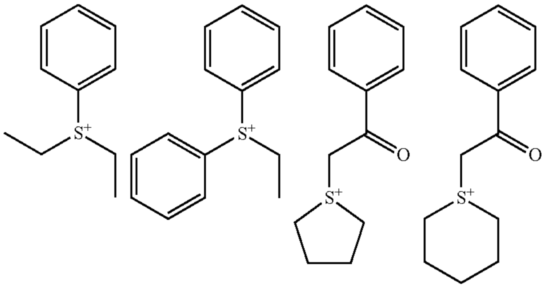
-continued
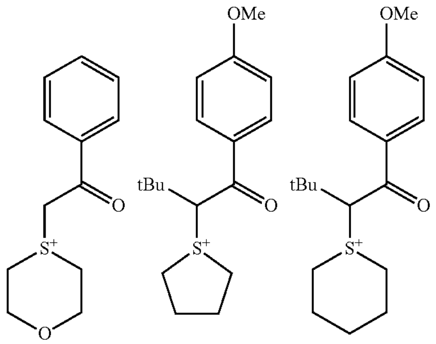
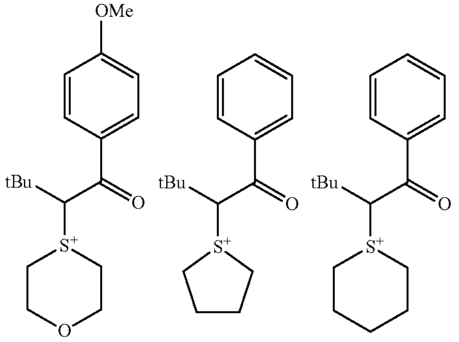
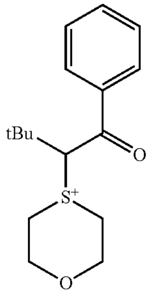
Of the compounds having formula (2), compounds having the following formulae (3) and (4) are more preferred.
(3)
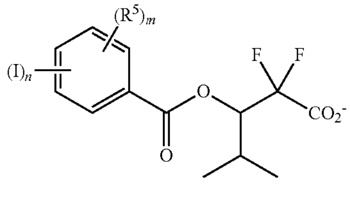
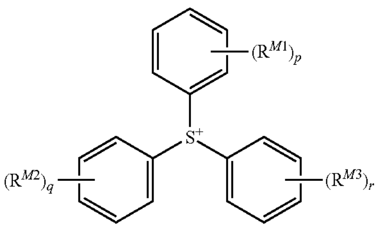

-continued (4)

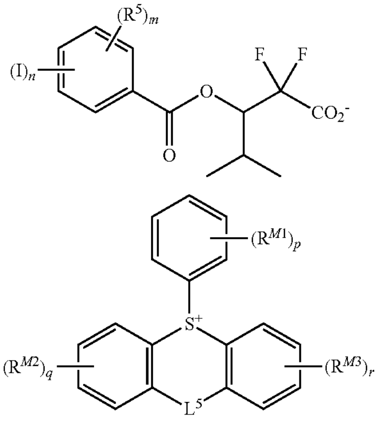

Herein $R^{M1}$, $R^{M2}$. $R^{M3}$, $L^5$, m, n, p, q, and r are as defined above.

In formulae (3) and (4), $R^5$ is fluorine, hydroxyl, or a $C_1$-$C_{10}$ hydrocarbyl group. Some hydrogen in the hydrocarbyl group may be substituted by a heteroatom-containing moiety, and —$CH_2$— in the hydrocarbyl group may be replaced by —O— or —C(═O)—. The constituent —$CH_2$— in the hydrocarbyl group may be one bonding to a carbon atom on the benzene ring in formula (3) or (4). When m is 2 or more, a plurality of $R^5$ may be the same or different, and two $R^5$ may bond together to form a ring with the carbon atoms to which they are attached.

Examples of the hydrocarbyl group and substituted hydrocarbyl group, represented by $R^5$, are as exemplified above for $R^4$, but of 1 to 10 carbon atoms. Illustrative examples include methyl, ethyl, propyl, isopropyl, butyl, sec-butyl, tert-butyl, pentyl, methoxy, ethoxy, propoxy, butoxy, methoxy ethoxy, acetoxy, acetyl, and trifluoromethyl, but are not limited thereto. Examples of the ring formed by $R^5$ are as exemplified above for the ring that two $R^4$, taken together, form with the carbon atoms to which they are attached.

Examples of the anion in the onium salt compound having formula (1) are shown below, but not limited thereto.

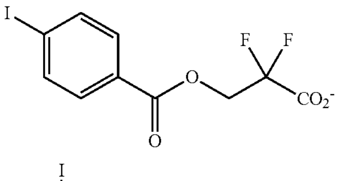

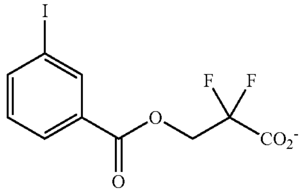

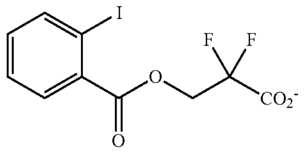

-continued

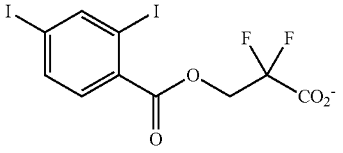

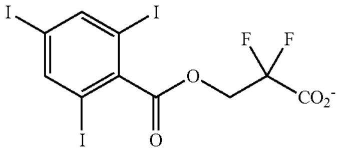

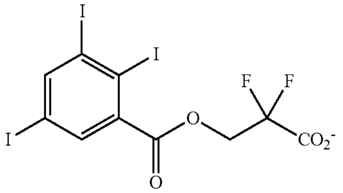

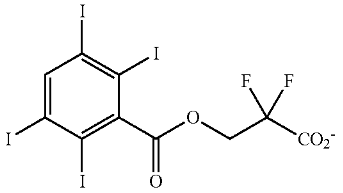

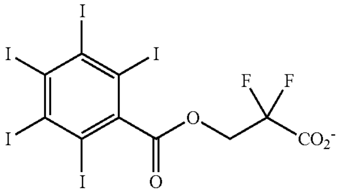

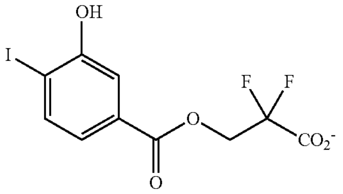

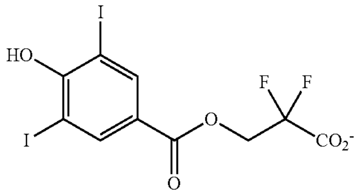

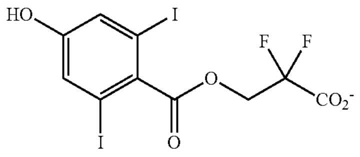

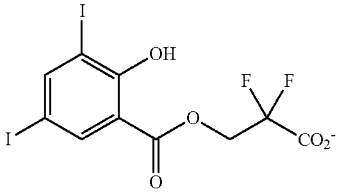

-continued
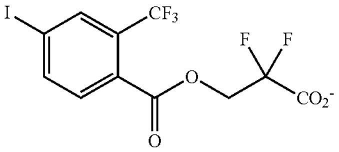
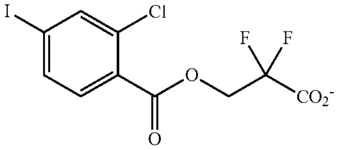
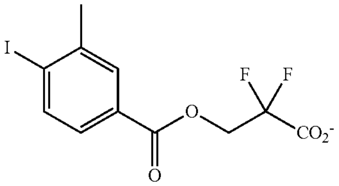
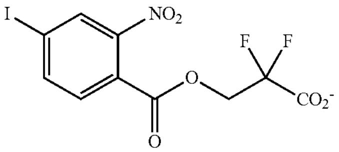
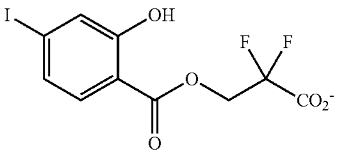
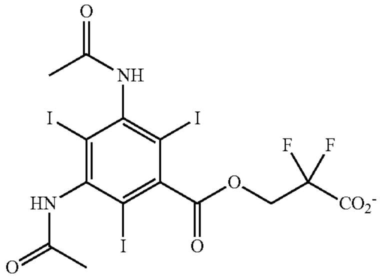
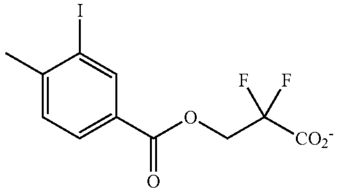
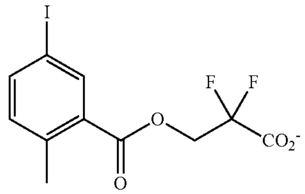
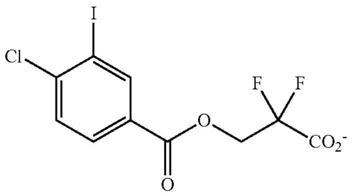
-continued
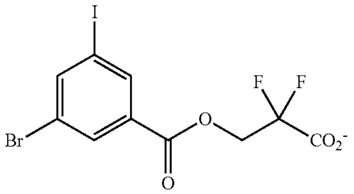
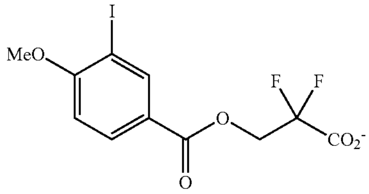
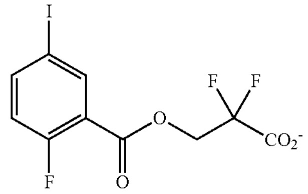
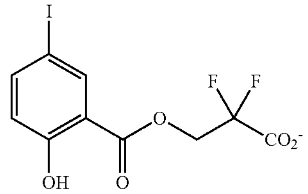
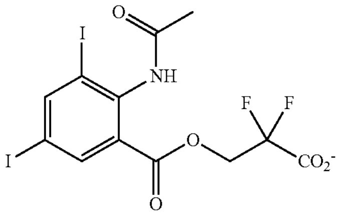
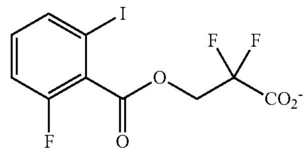
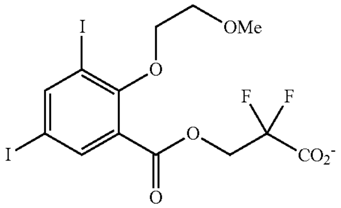
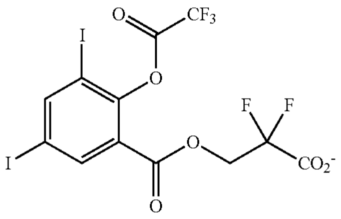

-continued
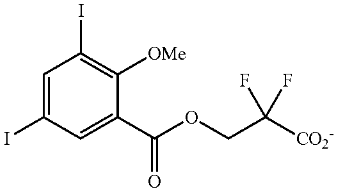
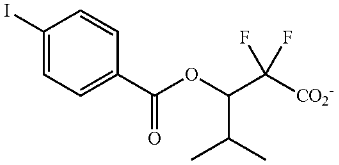
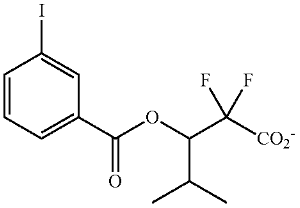
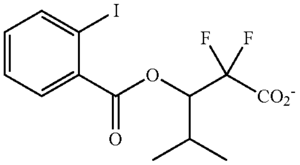
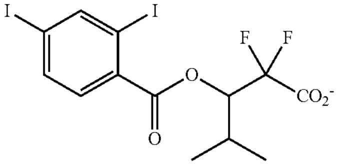
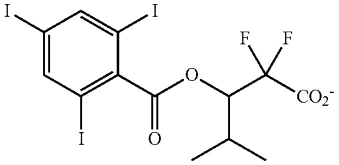
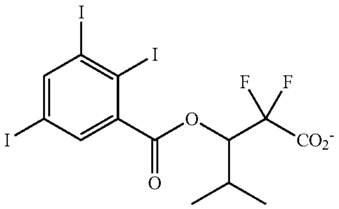
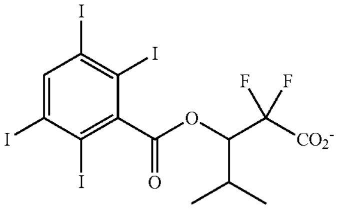
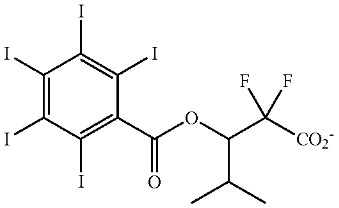
-continued
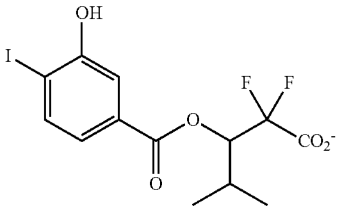
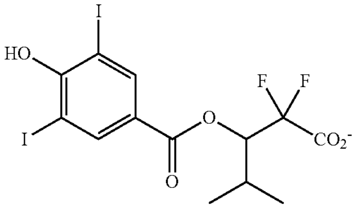
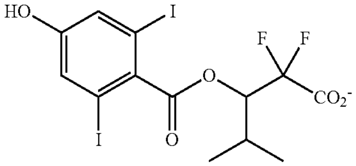
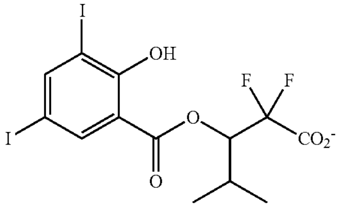
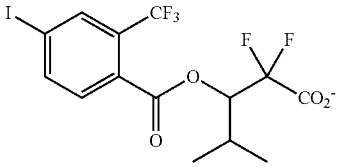
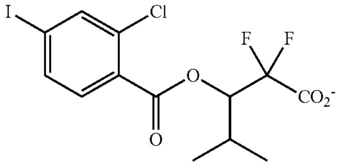
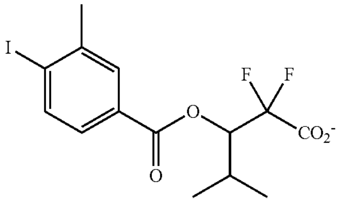
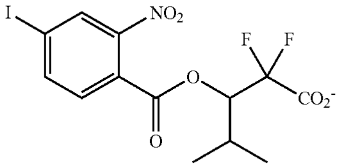
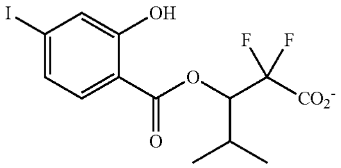

-continued
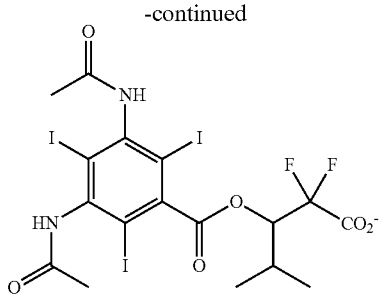
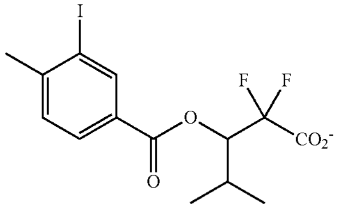
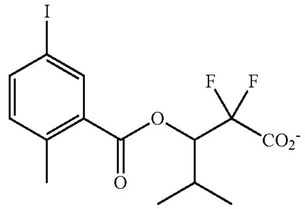
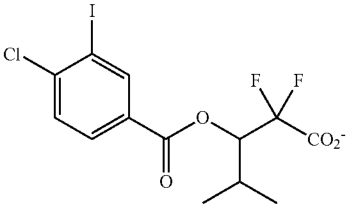
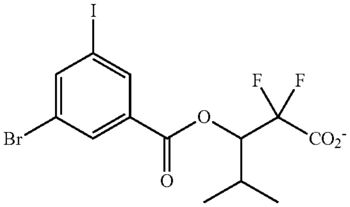
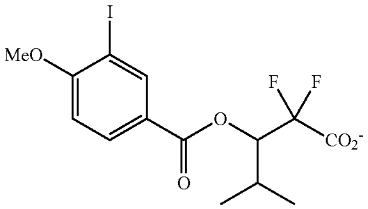
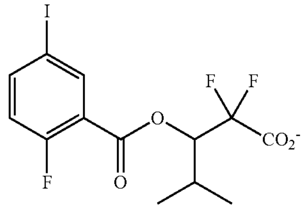
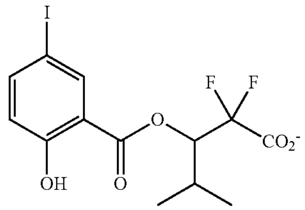
-continued
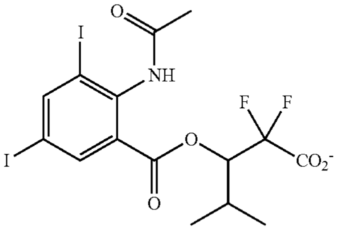
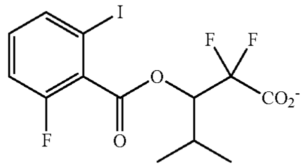
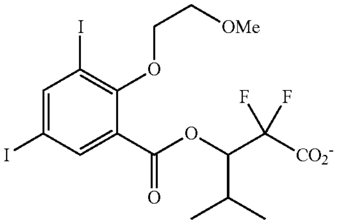
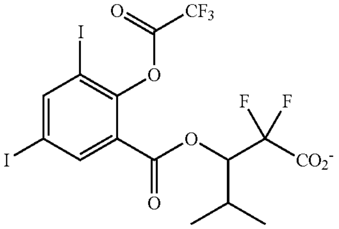
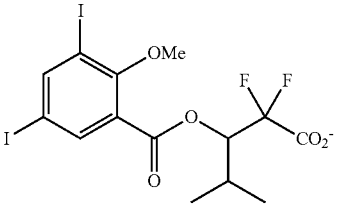
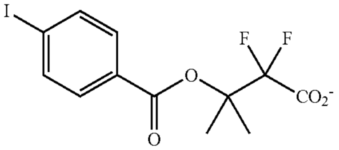
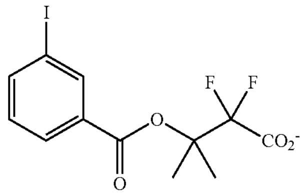
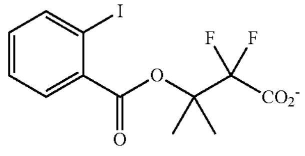
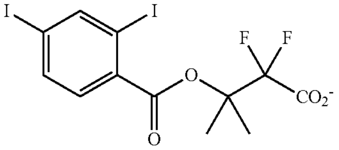

-continued
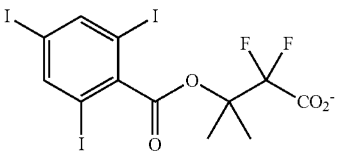
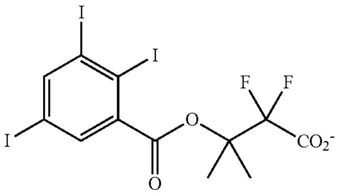
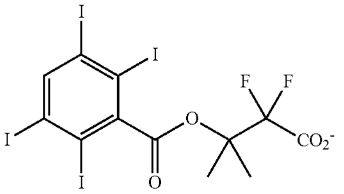
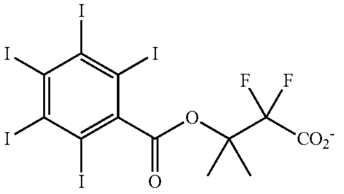
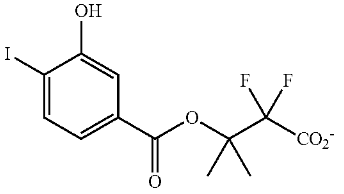
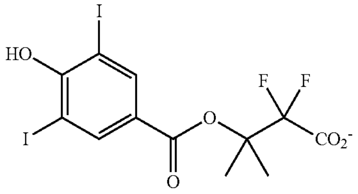
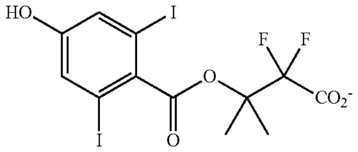
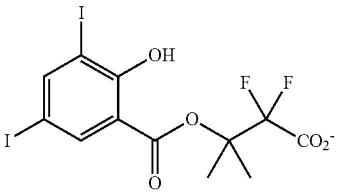
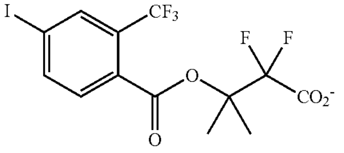
-continued
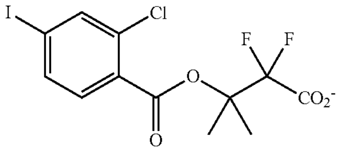
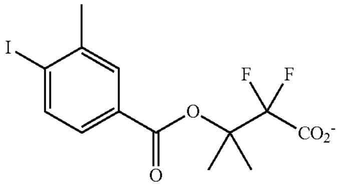
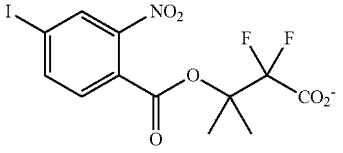
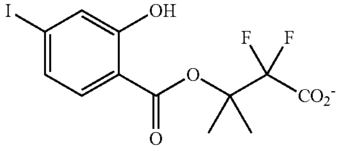
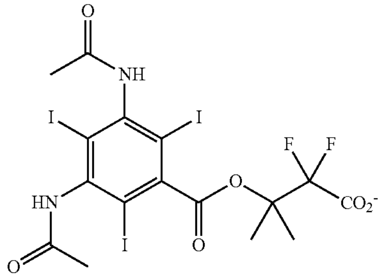
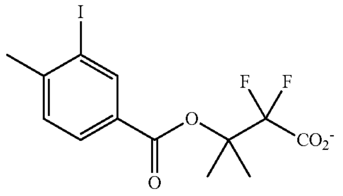
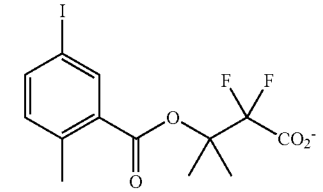
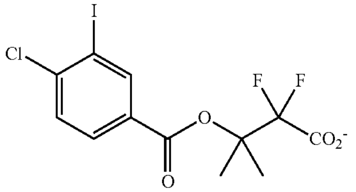
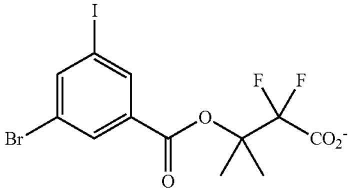

-continued
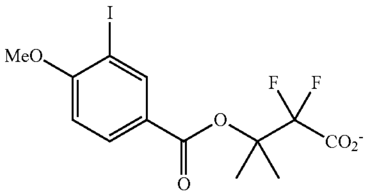
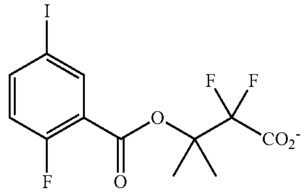
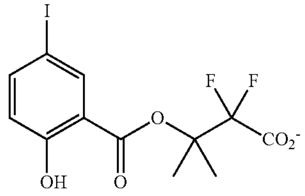
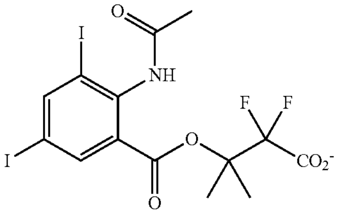
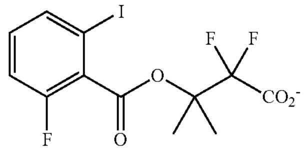
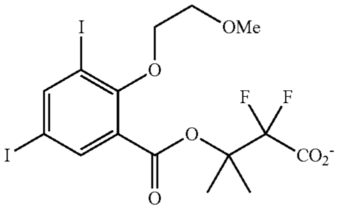
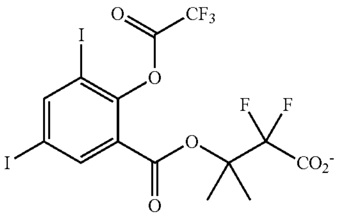
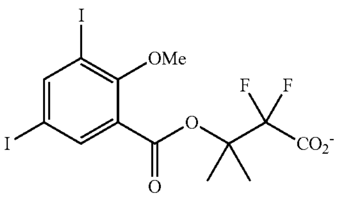
-continued
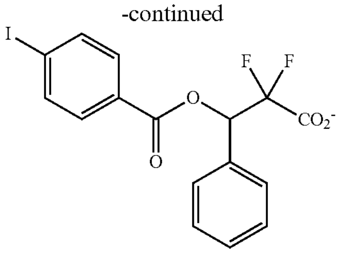
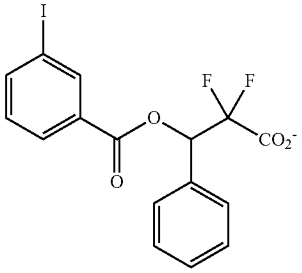
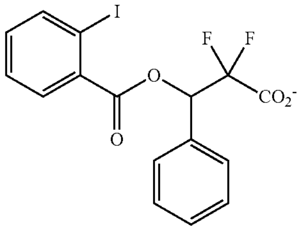
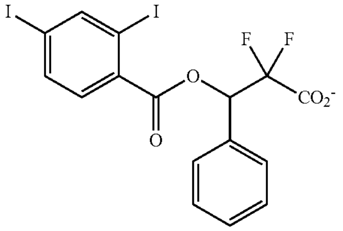
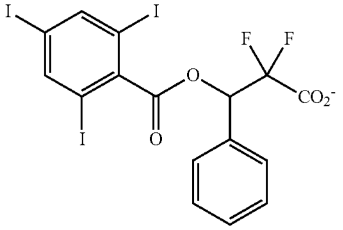
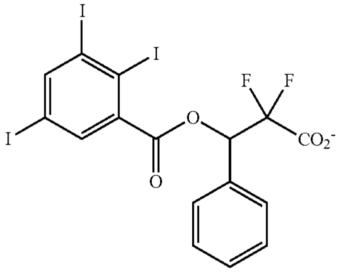
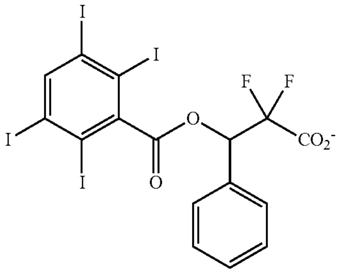

-continued
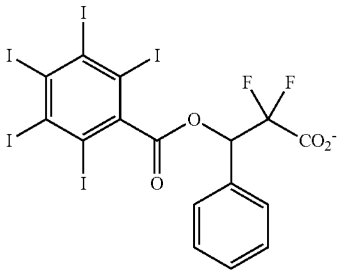
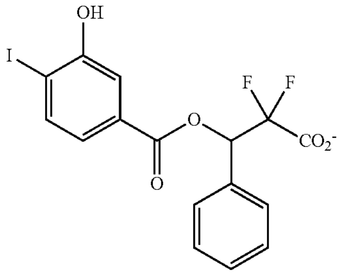
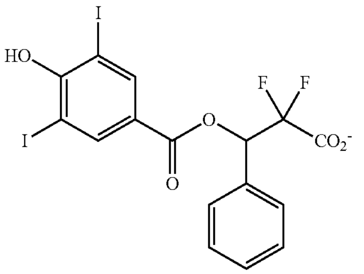
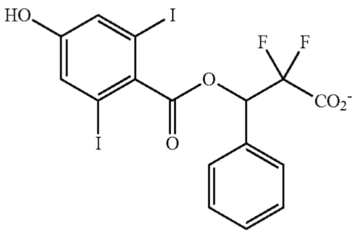
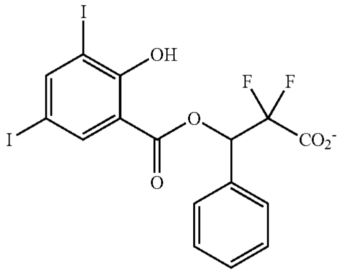
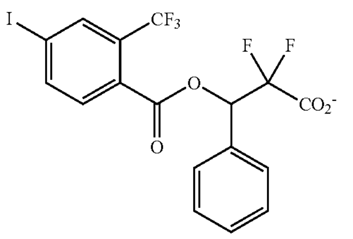
-continued
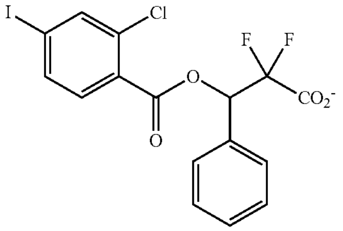
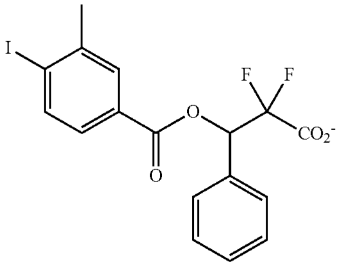
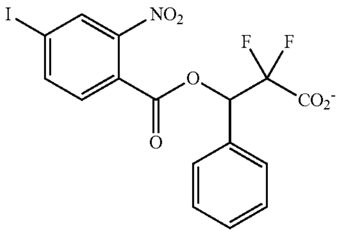
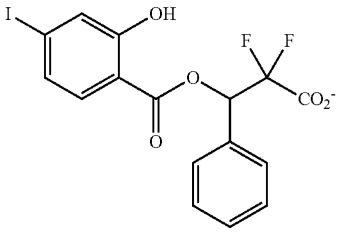
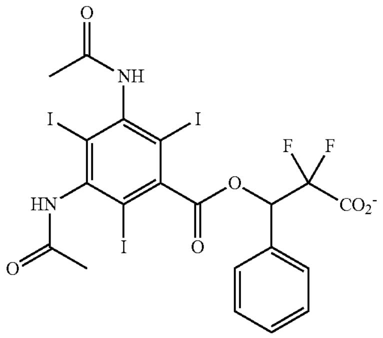
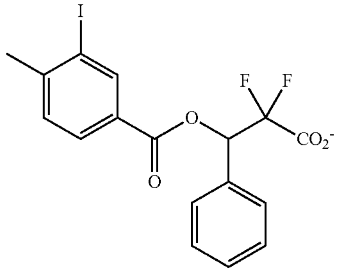

-continued
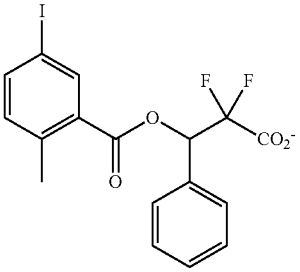
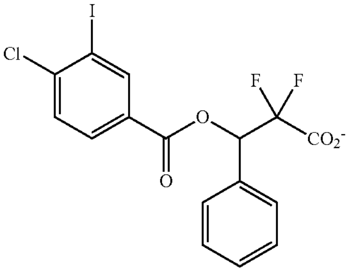
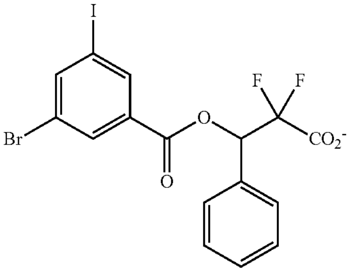
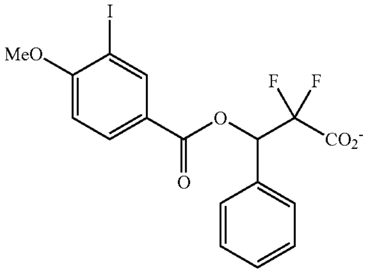
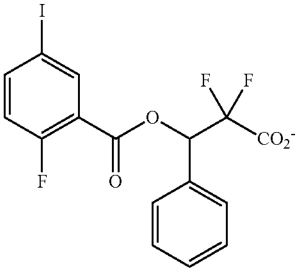
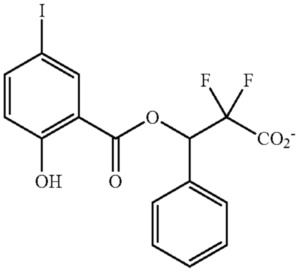
-continued
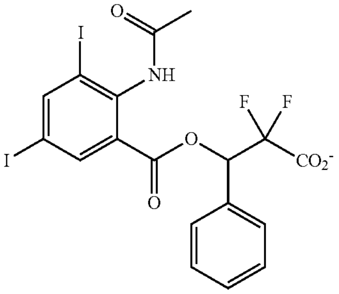
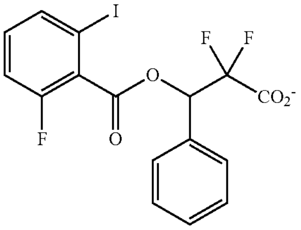
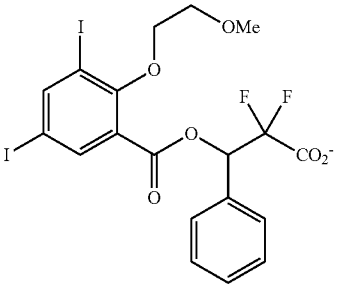
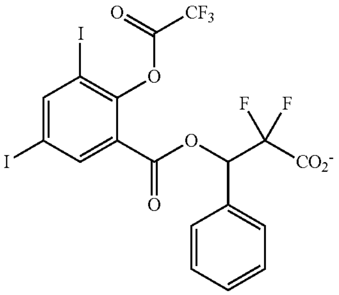
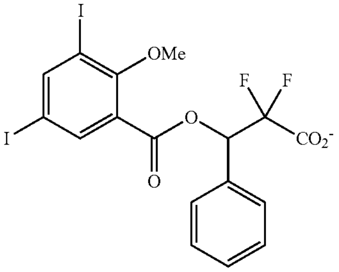
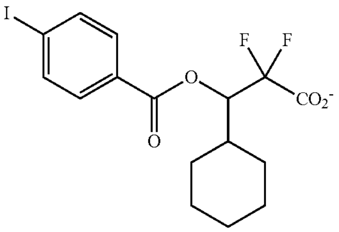

-continued
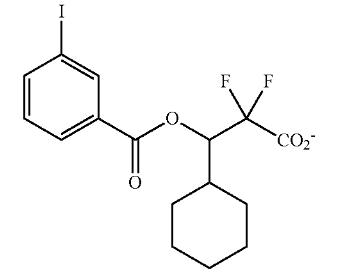
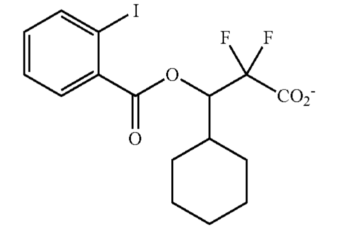
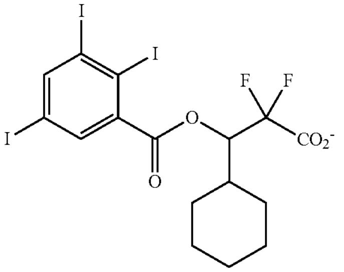
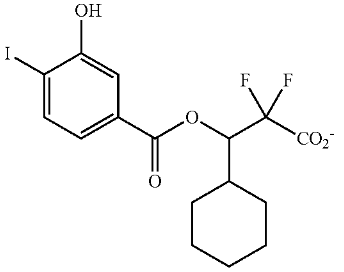
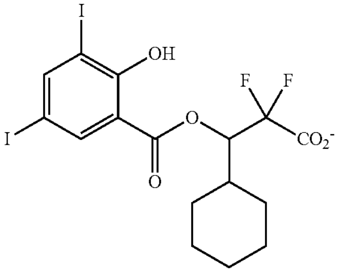
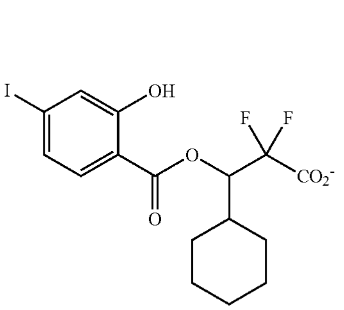
-continued
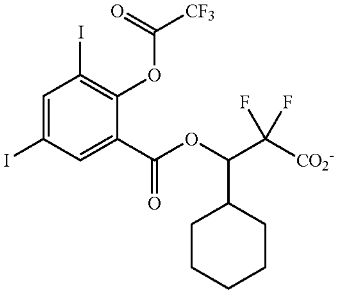
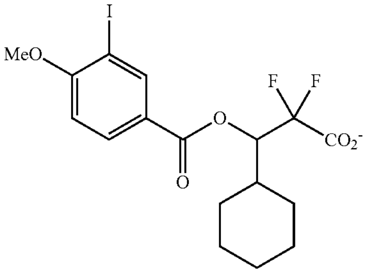
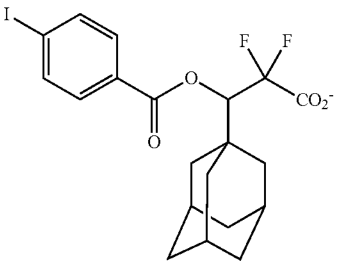
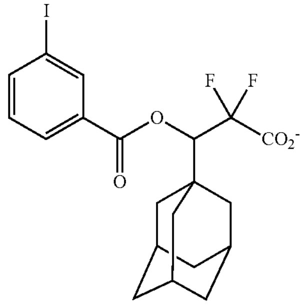
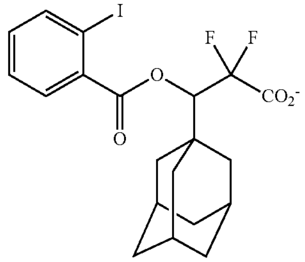
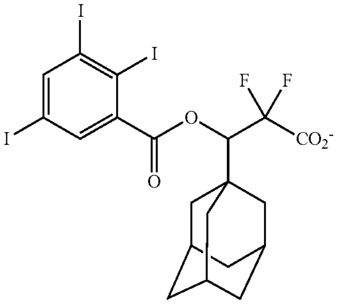

-continued
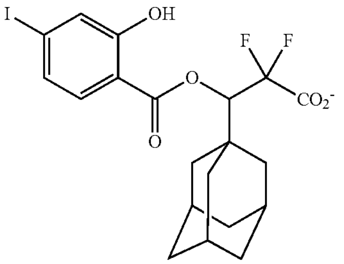
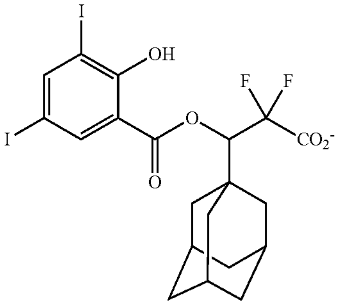
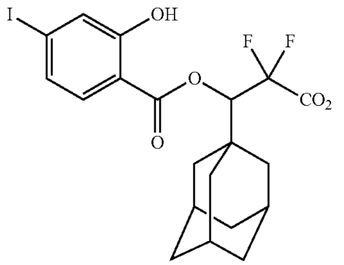
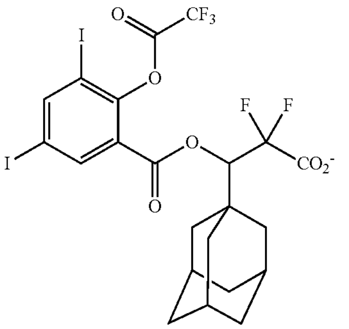
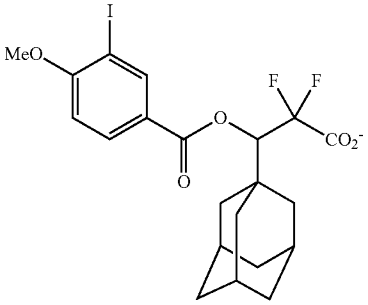
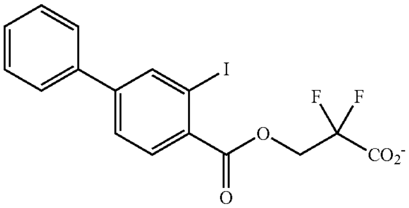
-continued
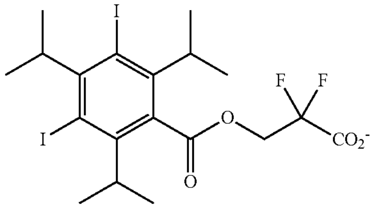
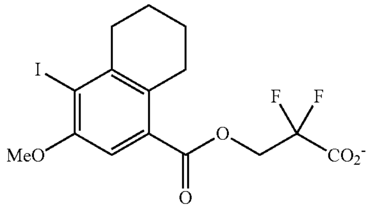
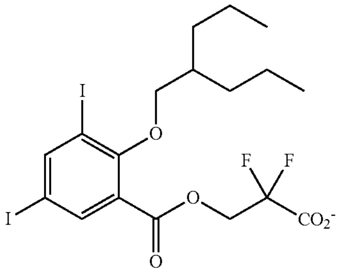
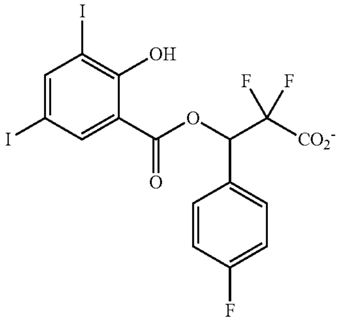
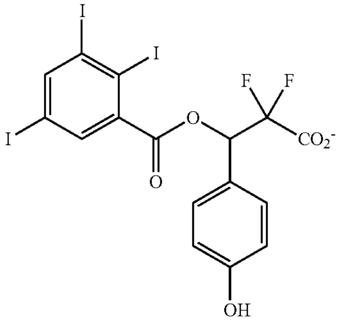
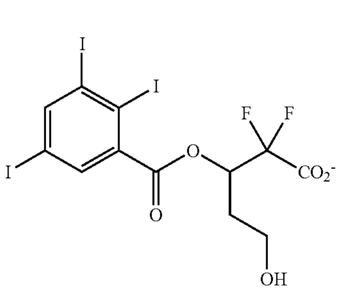

-continued
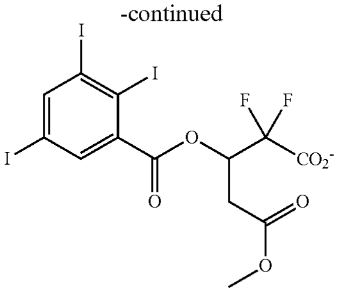
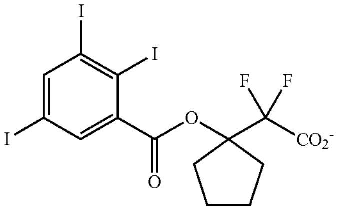
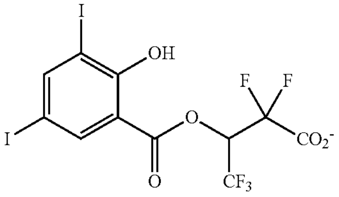
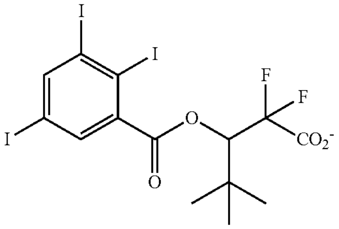
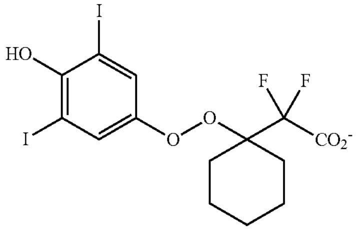
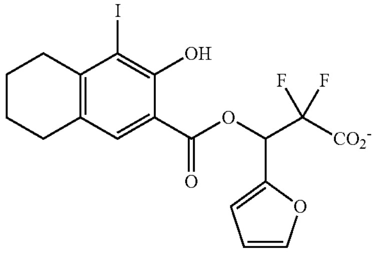
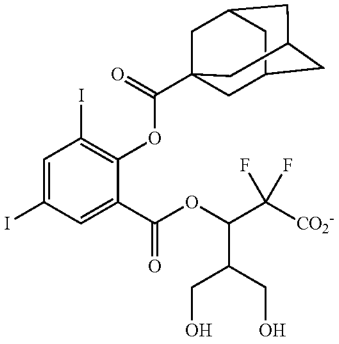
-continued
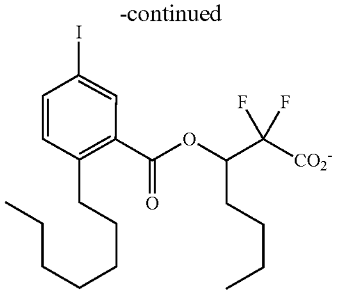
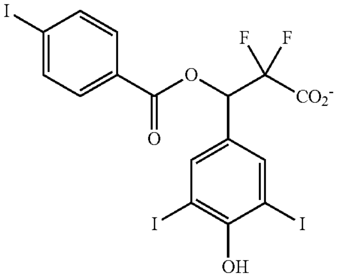
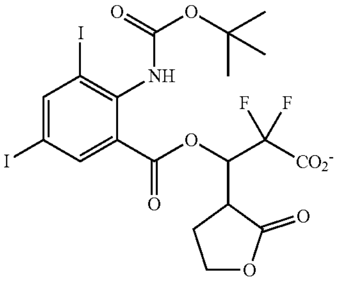
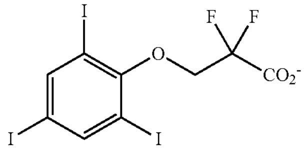
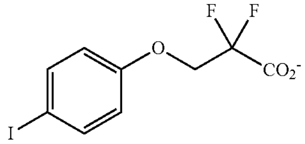
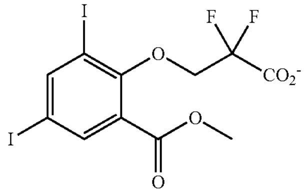
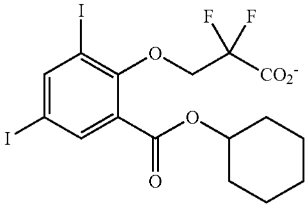
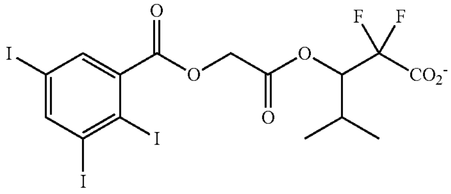

-continued
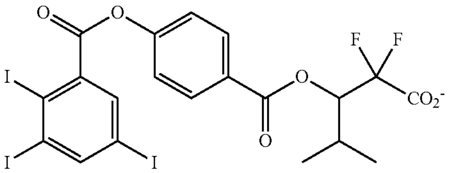
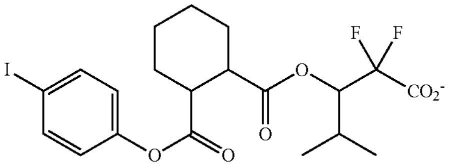
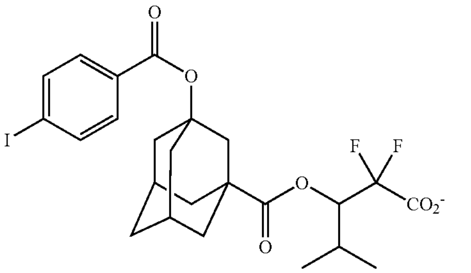
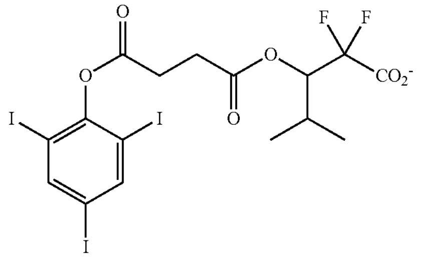
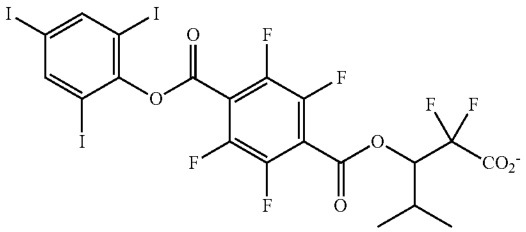
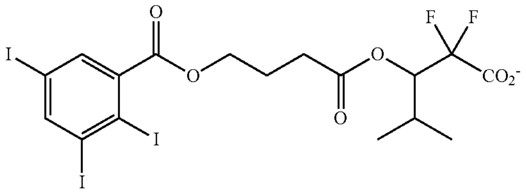
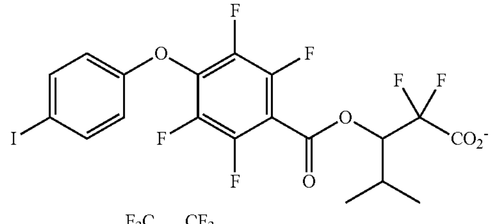
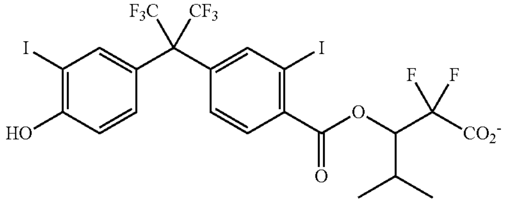
-continued
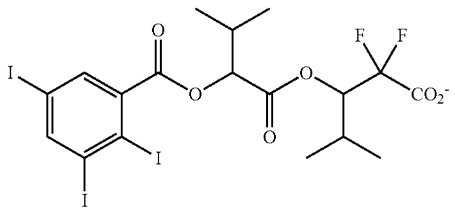
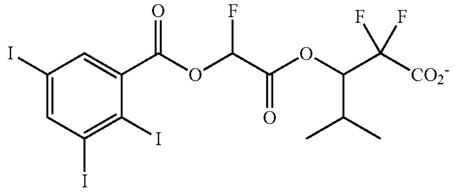
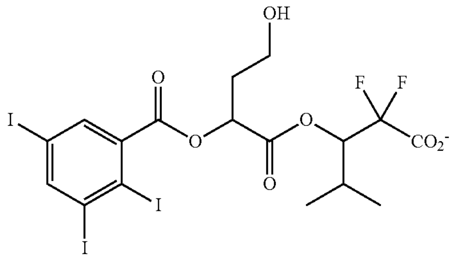
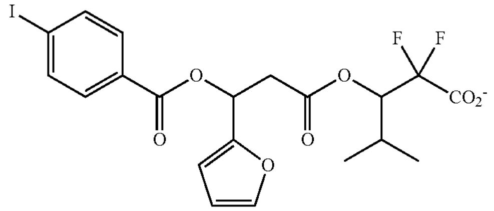
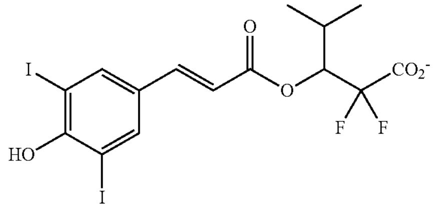
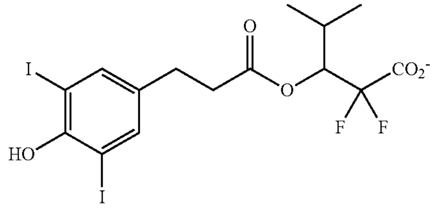
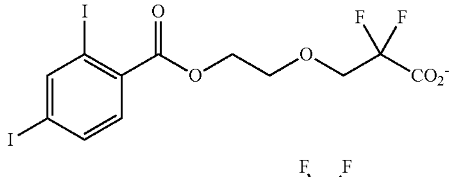
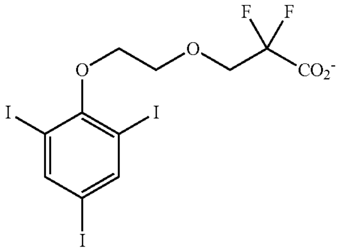

-continued
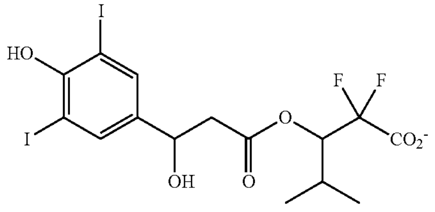
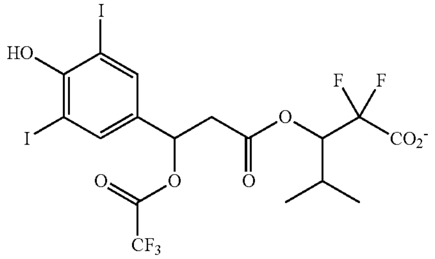
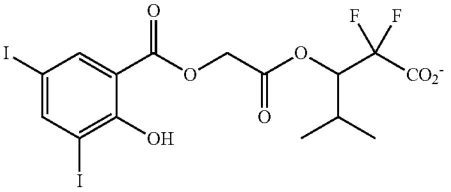
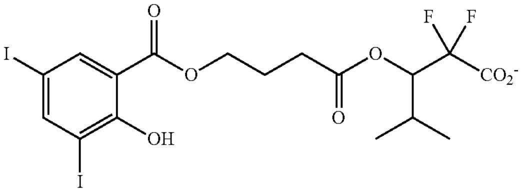
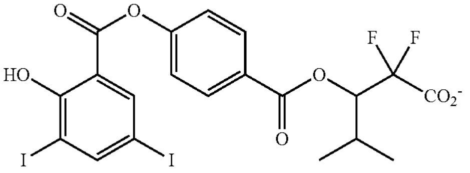
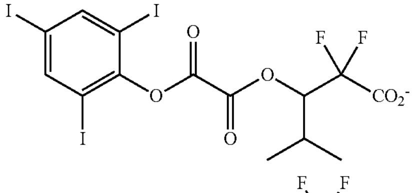
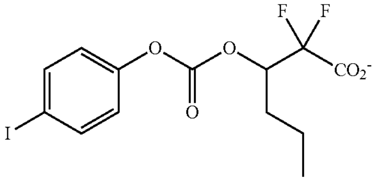
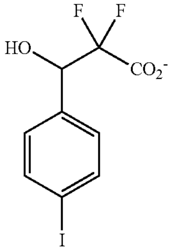
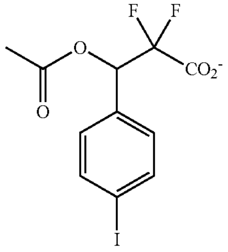
-continued
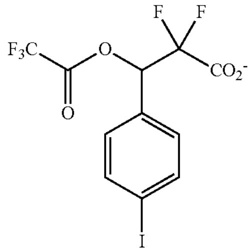
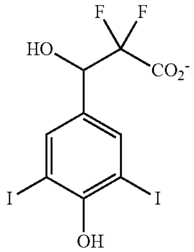
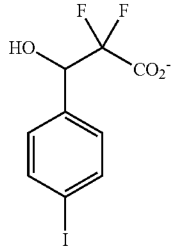
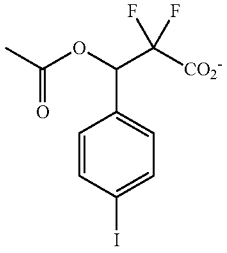
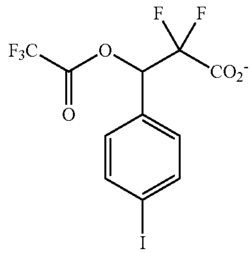
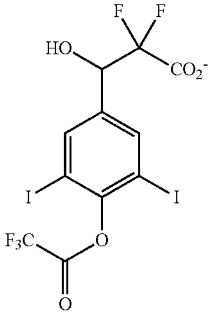
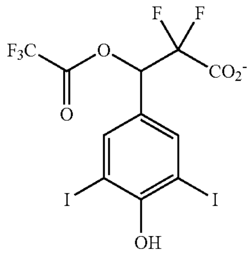
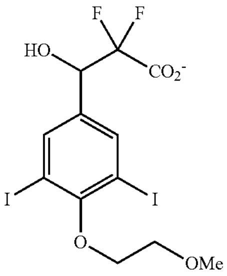
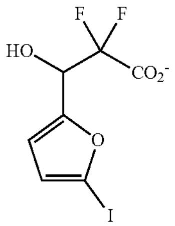
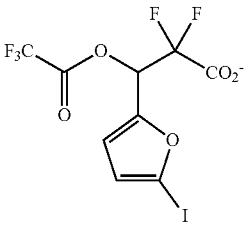
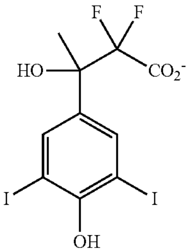
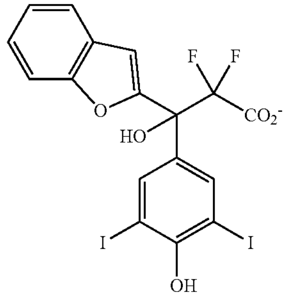

-continued
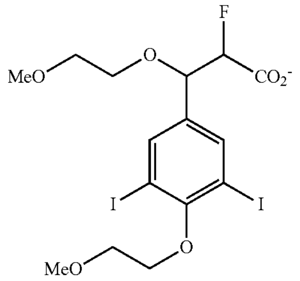
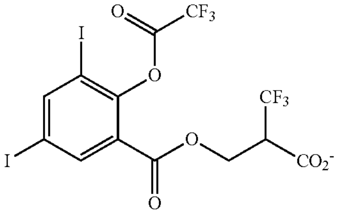
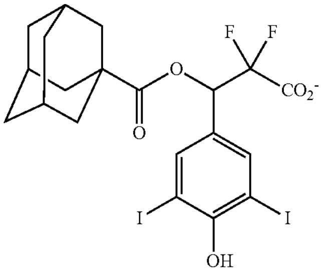
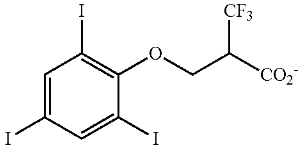
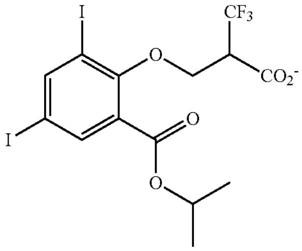
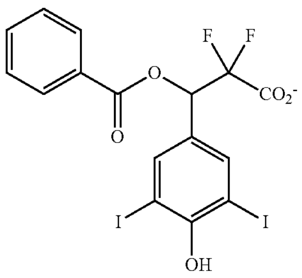
-continued
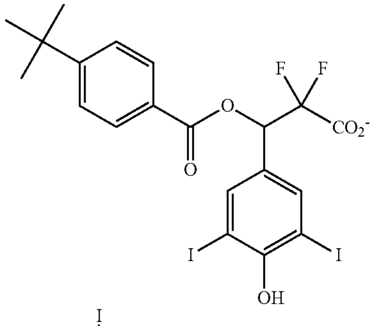
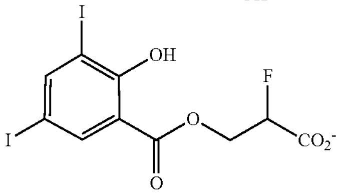
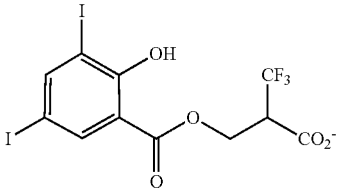
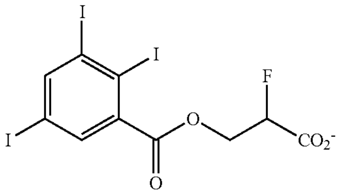
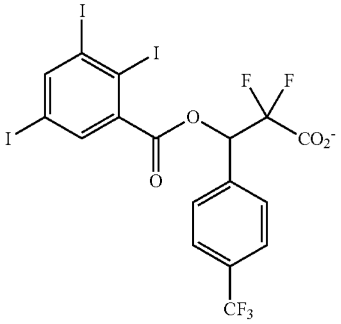
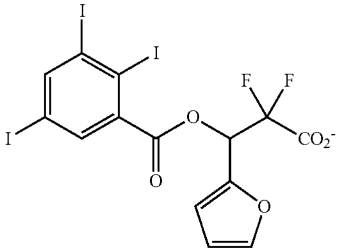
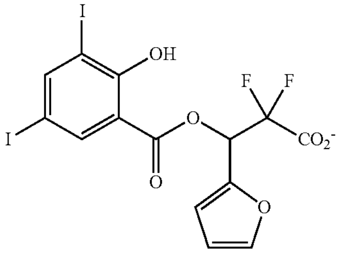

Of these, the following anions are preferred.

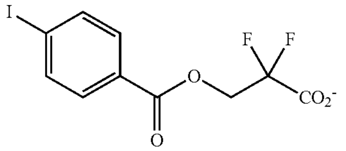
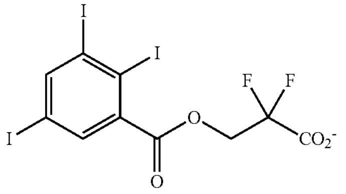
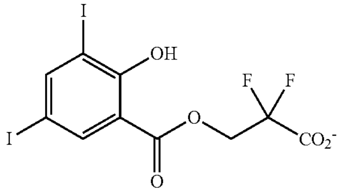
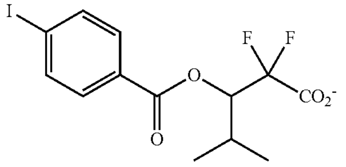
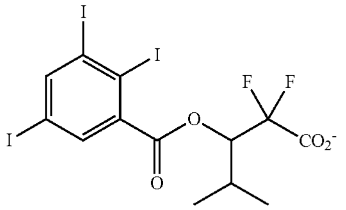
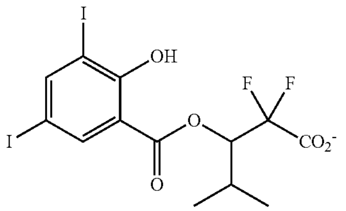
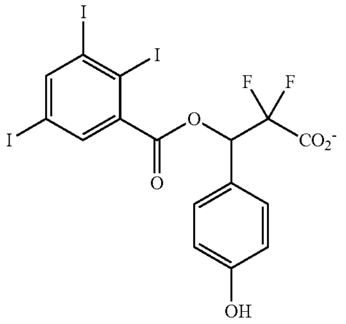
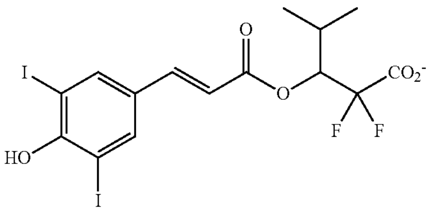

-continued

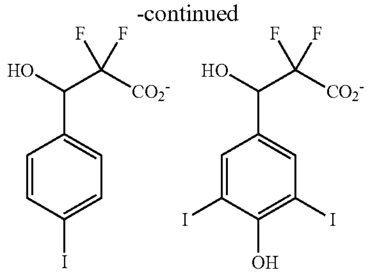

Exemplary structures for the onium salt compound of the invention include arbitrary combinations of cations with anions, both as exemplified above.

The onium salt compound of formula (1) wherein $L^2$ is an ester bond may be synthesized, for example, according to the following Scheme A.

Scheme A

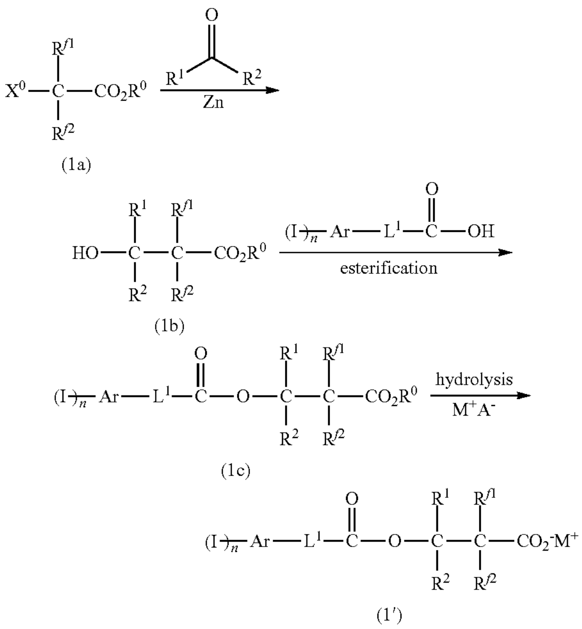

(1a) (1b) (1c) (1')

Herein $R^1$, $R^2$, $R^{f1}$, $R^{f2}$, $L^1$, Ar, n, and $M^+$ are as defined above. $X^0$ is chlorine, bromine or iodine. $R^0$ is a $C_1$-$C_5$ hydrocarbyl group. $A^-$ is an anion.

In the first step, an α-haloacetate (1a) is reacted with a carbonyl compound in the presence of zinc to synthesize an intermediate compound (1b). Those compounds (1a) wherein $X^0$ is chlorine or bromine and $R^0$ is methyl or ethyl are commercially available.

In the second step, intermediate compound (1b) is esterified with an iodized carboxylic acid to synthesize an intermediate compound (1c). For the esterification reaction, a condensing agent such as N,N'-diisopropylcarbodiimide, N,N'-dicyclohexylcarbodiimide, or 1-ethyl-3-(3-dimethylaminopropyl)carbodiimide hydrochloride may be used.

The intermediate compound (1c) may also be synthesized through other routes, for example, by converting an iodized carboxylic acid to an acid chloride with the aid of oxalyl chloride or thionyl chloride, and reacting the acid chloride with intermediate compound (1b) under basic conditions; by converting an iodized carboxylic acid to a mixed acid anhydride with the aid of methanesulfonic acid chloride or pivaloyl chloride, and reacting the anhydride with intermediate compound (1b) under basic conditions; or by heating intermediate compound (1b) and an iodized carboxylic acid in an organic solvent such as toluene under acidic conditions to effect dehydrating condensation.

In the third step, intermediate compound (1c) is hydrolyzed in a standard way to cleave the ester moiety $R^0$. The resulting carboxylate or carboxylic acid is subjected to salt exchange with an onium salt of the desired cation having the formula: $M^+A^-$, whereby the desired onium salt compound (1') is synthesized. It is noted that $A^-$ is preferably a chloride, bromide, iodide, methylsulfate or methanesulfonate anion because exchange reaction takes place in a quantitative manner. The salt exchange in the third step is readily accomplished by any well-known method, for example, with reference to JP-A 2007-145797.

The onium salt compound of formula (1) wherein $L^2$ is an ether bond may be synthesized, for example, according to the following Scheme B.

Scheme B

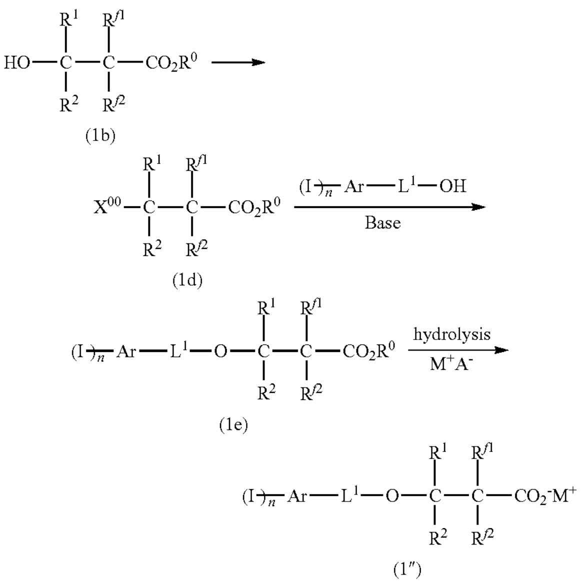

(1b)
(1d)
(1e)
(1")

Herein $R^1$, $R^2$, $R^{f1}$, $R^{f2}$, $L^1$, $R^0$, Ar, n, $M^+$ and $A^-$ are as defined above. $X^{00}$ is a leaving group.

Once intermediate compound (1b) is synthesized according to Scheme A, it is converted to an intermediate compound (1d) by replacing the hydroxyl group by a leaving group $X^{00}$. The leaving group may be a methansulfonate or p-toluenesulfonate. The conversion may be achieved by any well-known organic chemistry reaction. The intermediate compound (1d) is then reacted with an alcohol or phenol under basic conditions, to synthesize an intermediate compound (1e) via nucleophilic substitution reaction. Examples of the base used herein include amines such as triethylamine and diisopropylethylamine, and strong bases such as sodium carbonate, potassium carbonate, sodium hydroxide, potassium hydroxide, and sodium hydride. The final conversion from intermediate compound (1e) to the onium salt compound (1") may be conducted by the same method as in Scheme A. Notably, the onium salt compound of formula (1) wherein $L^2$ is an ester bond may also be synthesized by a similar method.

The onium salt compound of formula (1) wherein $L^2$ is a single bond and $R^2$ is —$OR^{2A}$ may be synthesized, for example, according to the following Scheme C.

Scheme C

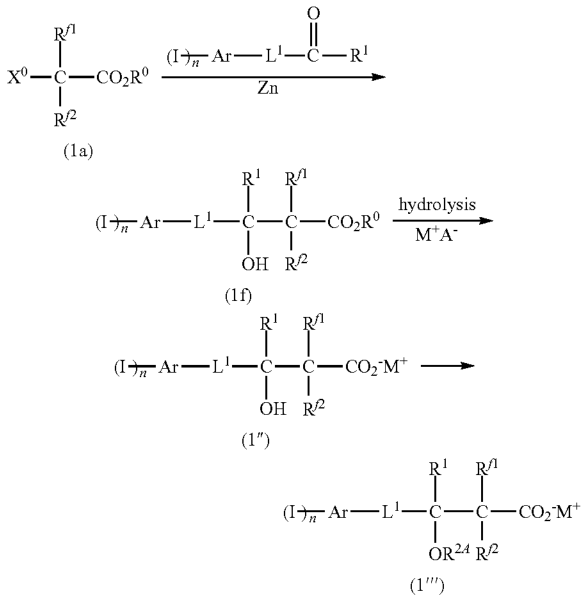

(1a)
(1f)
(1")
(1"')

Herein $R^1$, $R^{2A}$, $R^{f1}$, $R^{f2}$, $L^1$, $R^0$, $X^0$, $A^-$, Ar, n, and $M^+$ are as defined above.

In the first step, an α-haloacetate (1a) is reacted with an iodized carbonyl compound in the presence of zinc to synthesize an intermediate compound (1f). Those compounds (1a) wherein $X^0$ is chlorine or bromine and $R^0$ is methyl or ethyl are commercially available.

In the second step, intermediate compound (1f) is hydrolyzed in a standard way to cleave the ester moiety $R^0$. The resulting carboxylate or carboxylic acid is subjected to salt exchange with an onium salt of the desired cation having the formula: $M^+A^-$, whereby the desired carboxylic salt (1") is synthesized. It is noted that $A^-$ is preferably a chloride, bromide, iodide, methylsulfate or methanesulfonate anion because exchange reaction takes place in a quantitative manner.

The carboxylic salt (1") may be converted to the desired carboxylic salt (1"') by modifying the hydroxyl group on carboxylic salt (1") via well-known organic chemistry reaction. The modification may be achieved, for example, by reacting the salt with chloromethyl methyl ether under basic conditions into an acetal form. Also, the salt may be converted to an ether form by reacting with an alkyl halide, or methanesulfonate or p-toluenesulfonate form of a desired alcohol, under basic conditions. The desired carboxylic acid may be esterified by using a condensing agent or by reacting with a carboxylic chloride under basic conditions.

The synthesis methods mentioned above are merely exemplary and the method is not limited thereto.

A chemically amplified resist composition comprising the inventive onium salt compound is improved in sensitivity, LWR and CDU. Although the detail is not well understood, the following reason is presumed. The onium salt compound has a carboxylate anion which is substituted with fluorine or trifluoromethyl at α-position. As compared with conventional acid diffusion inhibitors of carboxylic salt type, the conjugated acid has a high acidity, providing a high sensitivity. As compared with acid diffusion inhibitors of alkanesulfonic acid type having a similarly high acidity, the quenching ability is high, which leads to improvements in lithography performance like LWR and CDU. Since the anion contains iodine, efficient absorption of EUV is possible. Therefore, the chemically amplified resist composition comprising the inventive onium salt compound exhibits a high sensitivity in the EUV lithography. Since the inventive onium salt compound containing iodine, which is an atom of large size, is sterically bulky, the acid diffusion is restrained by steric hindrance, leading to improvements in lithography performance like LWR and CDU.

Chemically Amplified Resist Composition

Another embodiment of the invention is a chemically amplified resist composition comprising (A) a base polymer adapted to change its solubility in a developer under the action of an acid, (B) a photoacid generator, (C-1) an acid diffusion inhibitor comprising the inventive onium salt compound, and (D) an organic solvent as essential components, and if necessary, (C-2) an acid diffusion inhibitor other than the inventive onium salt compound, (E) a surfactant, and (F) other components.

A further embodiment of the invention is a chemically amplified resist composition comprising (A') a base polymer adapted to change its solubility in a developer under the action of an acid, the base polymer comprising recurring units having a function of generating an acid upon exposure to light, (C-1) an acid diffusion inhibitor comprising the inventive onium salt compound, and (D) an organic solvent as essential components, and if necessary, (B) a photoacid generator, (C-2) an acid diffusion inhibitor other than the inventive onium salt compound, (E) a surfactant, and (F) other components.

(A) Base Polymer

Component (A) is a base polymer adapted to change its solubility in a developer under the action of an acid. It is preferably a polymer comprising recurring units having the formula (a) or recurring units having the formula (b), which are also referred to as recurring units (a) and (b), respectively.

(a)

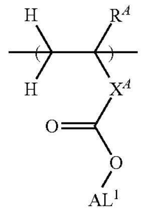

(b)

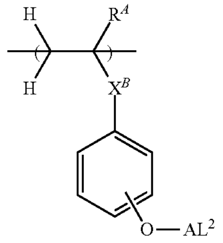

In formulae (a) and (b), $R^A$ is hydrogen or methyl. $X^A$ is a single bond, phenylene group, naphthylene group or (backbone)-C(=O)—O—$X^{A1}$—, wherein $X^{A1}$ is a $C_1$-$C_{15}$ hydrocarbylene group which may contain a hydroxyl moiety, ether bond, ester bond or lactone ring. $X^B$ is a single bond or ester bond. $AL^1$ and $AL^2$ are each independently an acid labile group. The hydrocarbylene group may be saturated or unsaturated and straight, branched or cyclic.

While the acid labile groups represented by $AL^1$ and $AL^2$ are not particularly limited, suitable acid labile groups include $C_4$-$C_{20}$ tertiary hydrocarbyl groups, trialkylsilyl groups in which each alkyl moiety has 1 to 6 carbon atoms, and $C_4$-$C_{20}$ oxoalkyl groups. With respect to the structure of these acid labile groups, reference should be made to U.S. Pat. No. 9,164,384 (JP-A 2014-225005, paragraphs [0016]-[0035]).

Acid labile groups having the following formula (L1) are preferred as $AL^1$ and $AL^2$.

(L1)

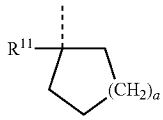

In formula (L1), $R^{11}$ is a $C_1$-$C_7$ hydrocarbyl group in which —$CH_2$— may be replaced by —O—, and "a" is 1 or 2.

Of the acid labile groups $AL^1$ and $AL^2$, the following groups are most preferred.

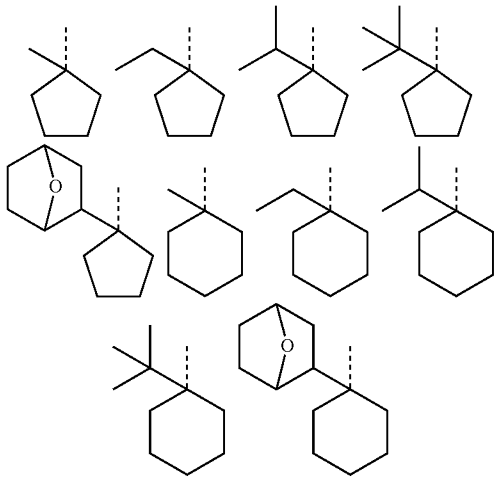

A resist composition comprising a base polymer containing recurring units (a) or (b) having an acid labile group and the inventive onium salt compound is improved in lithography performance. Although the detail is not well understood, the following reason is presumed. When a tertiary alicyclic hydrocarbyl group having formula (L1) is bonded to the ester site, the group becomes more acid labile or decomposable due to steric repulsion than other chainlike tertiary alkyl groups such as tert-butyl and tert-pentyl. Also, as compared with acid labile groups having adamantane ring, the acid labile group having formula (L1) allows for easy progress of acid-aided elimination reaction, tending to provide a high sensitivity. Therefore, when a tertiary alicyclic hydrocarbyl group is incorporated in the polarity switch unit of the base polymer in a resist composition, the dissolution contrast between exposed and unexposed regions is increased. While the inventive onium salt compound serves as an acid diffusion inhibitor, the carboxylic acid generated after quenching of a strong acid has a relatively high acidity. When the inventive onium salt compound is used in combination with acid labile group units having high reactivity, the acid generated after quenching promotes elimination reaction, though to a slight extent, leading to an improvement in contrast. As a result, lithography performance is improved. Although the acid labile group of tertiary ether type as represented by formula (b) is typically low in acid-aided elimination reactivity, the elimination reaction is promoted in the co-presence of a protonic hydroxyl group having high acidity like phenol. As a result, there are obtained similar effects to the aforementioned tertiary ester type.

Examples of the structure having formula (a) wherein $X^A$ is a variant include the structures described in U.S. Pat. No. 9,164,384 (JP-A 2014-225005, paragraph [0015]). Of these, preferred structures are shown below. Herein $R^A$ and $AL^1$ are as defined above.

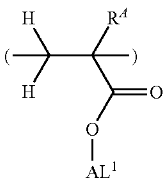
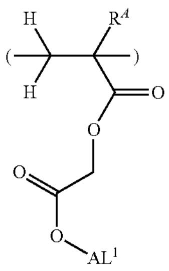
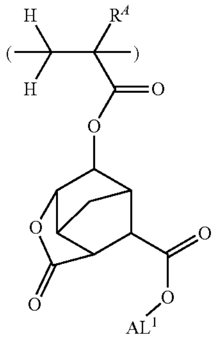
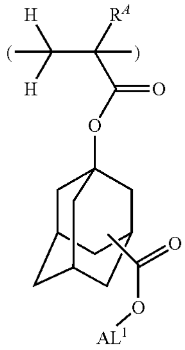
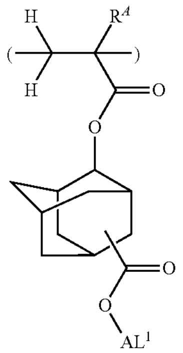
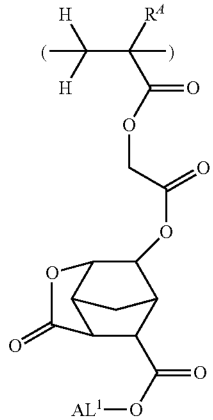

-continued

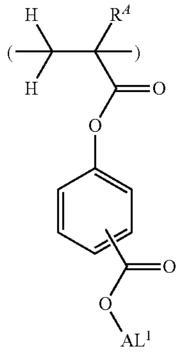
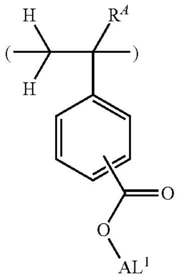

Examples of the recurring unit (a) are given below, but not limited thereto. Herein $R^A$ is as defined above.

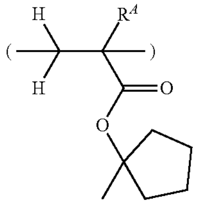
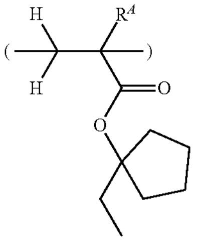
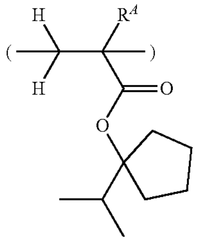
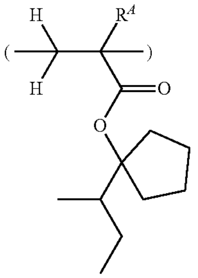
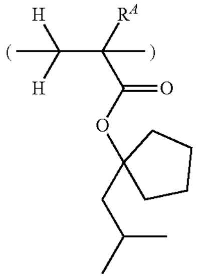
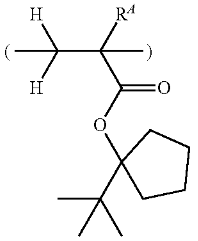
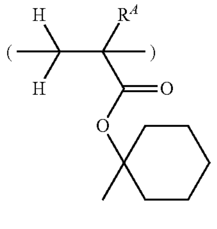
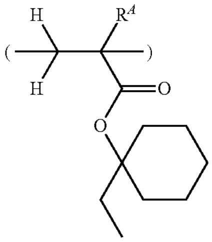

-continued
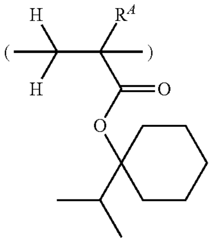
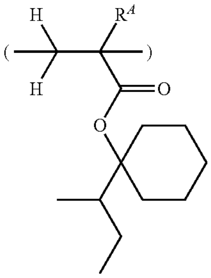
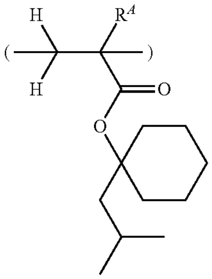
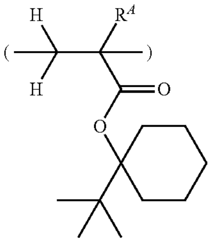
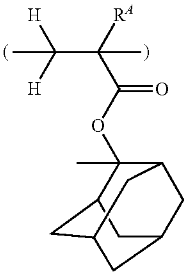
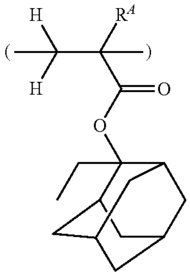
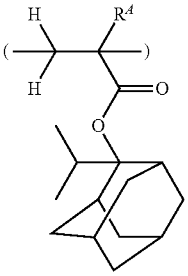
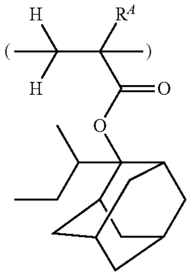
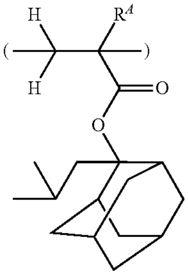
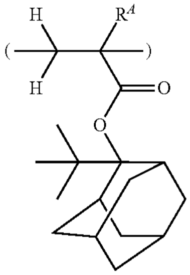
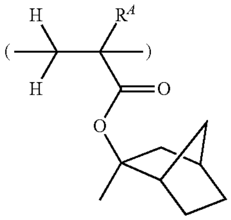
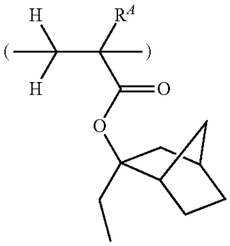
-continued
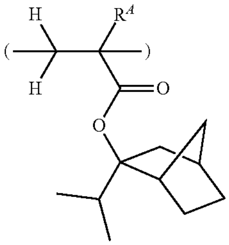
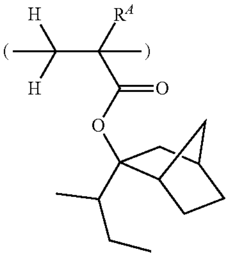
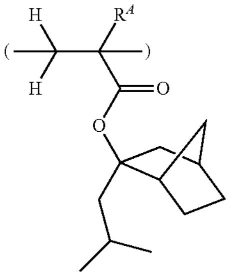
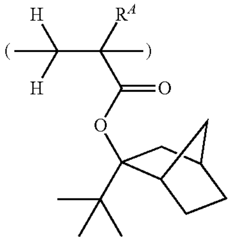
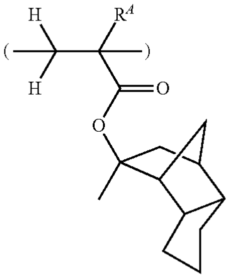
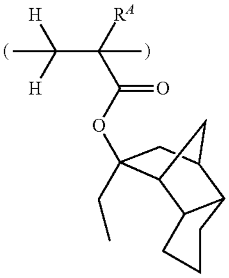
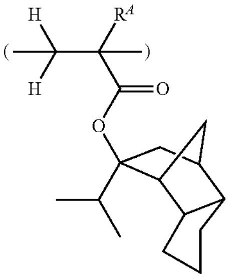
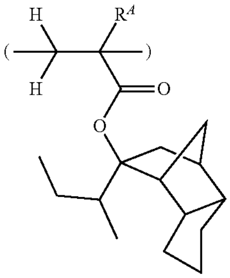
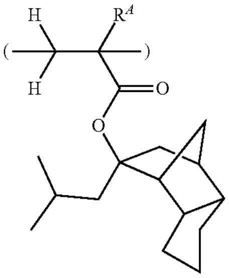
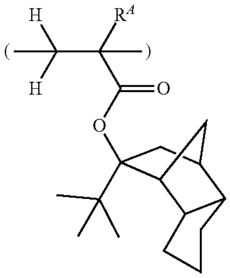
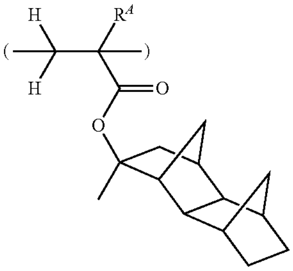

-continued
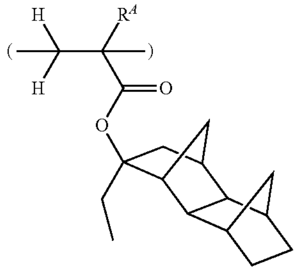
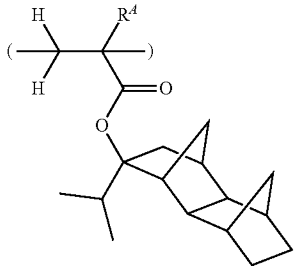
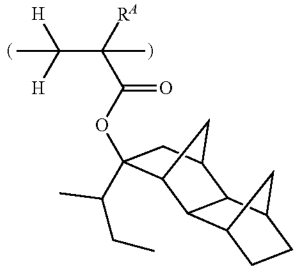
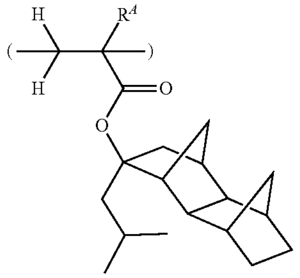
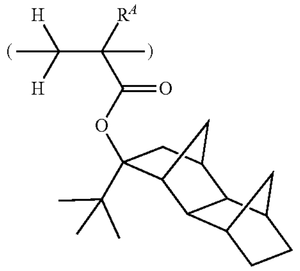
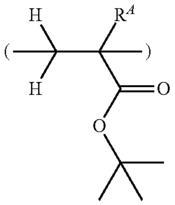
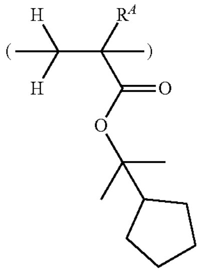
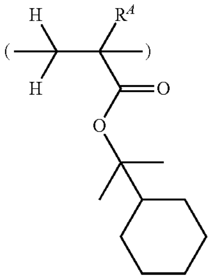
-continued
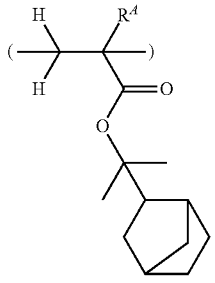
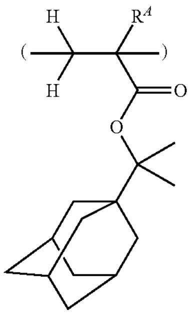
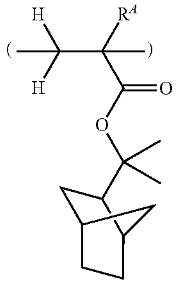
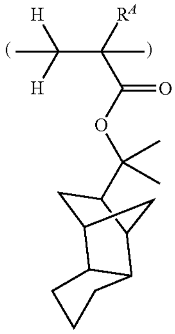
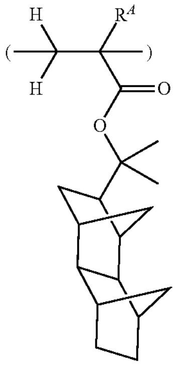
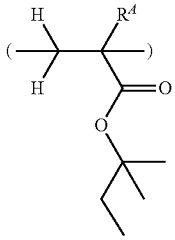
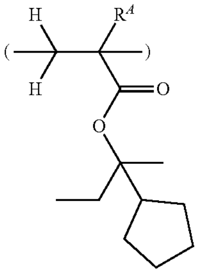
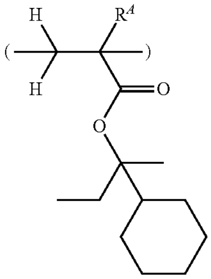
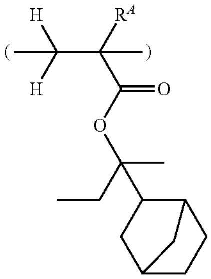
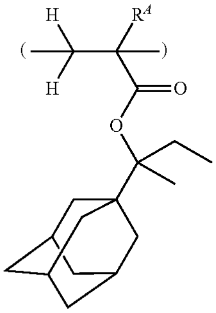

-continued
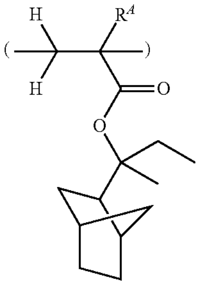
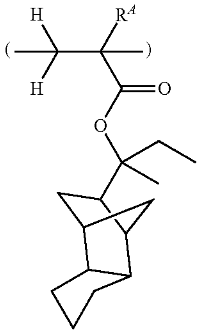
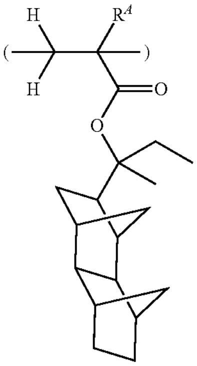
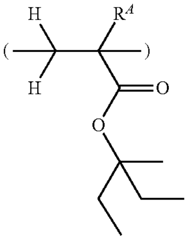
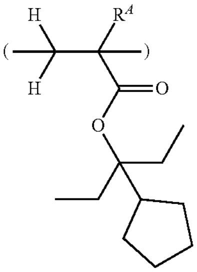
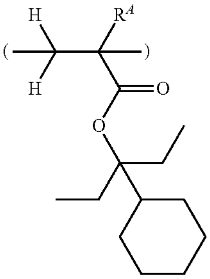
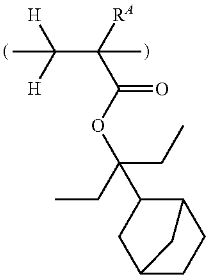
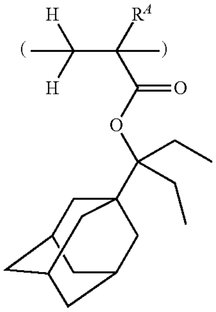
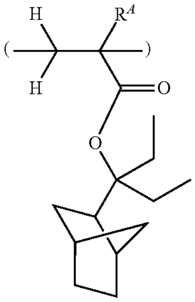
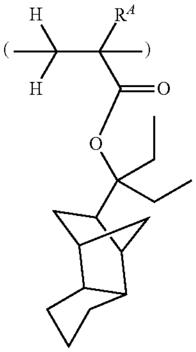
-continued
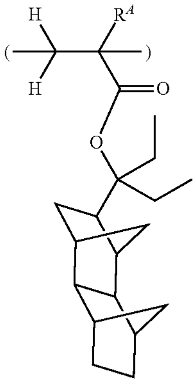
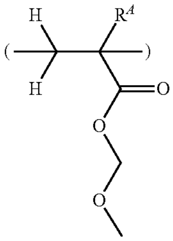
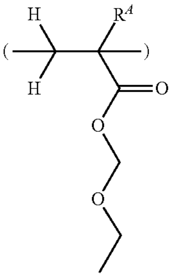
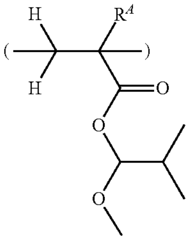
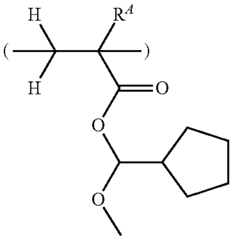
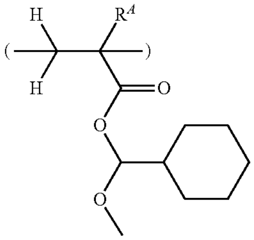
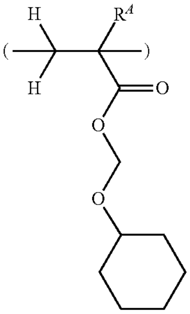
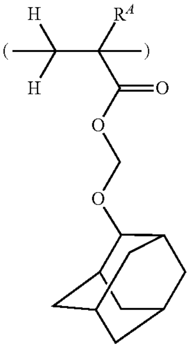
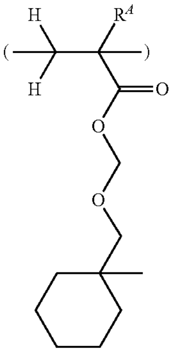
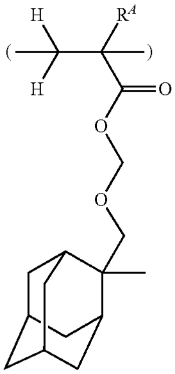

-continued
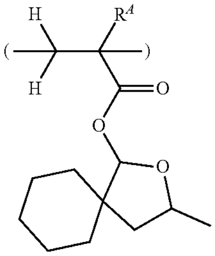
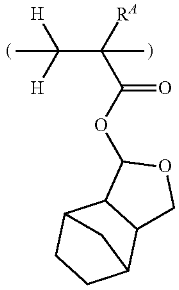
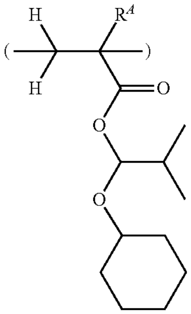
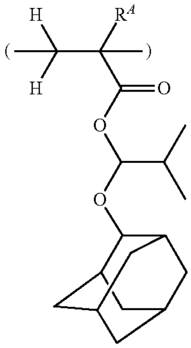
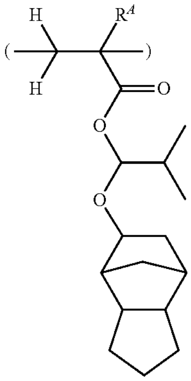
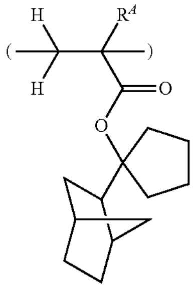
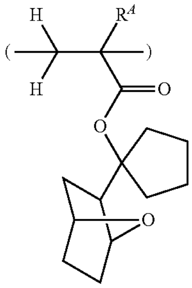
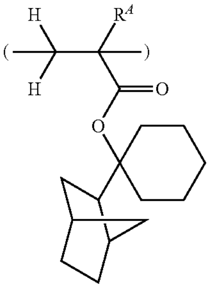
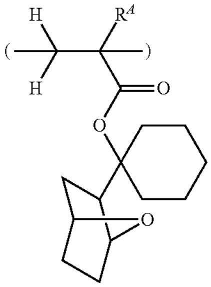
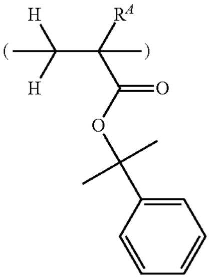
-continued
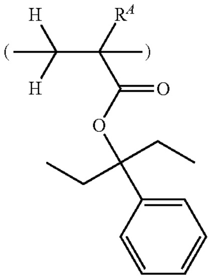
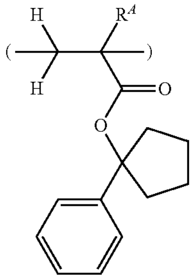
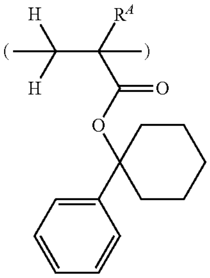
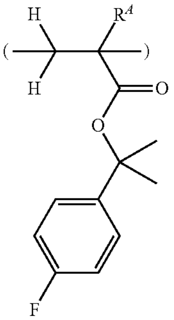
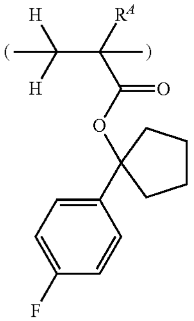
Examples of the recurring unit (b) are given below, but not limited thereto. Herein $R^A$ is as defined above.
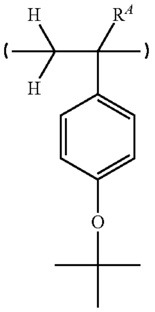
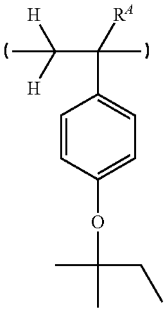
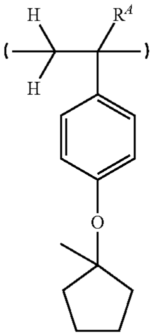

-continued
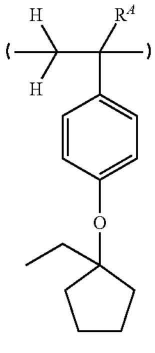
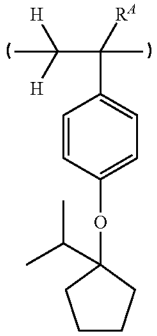
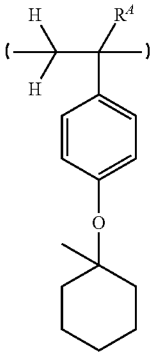
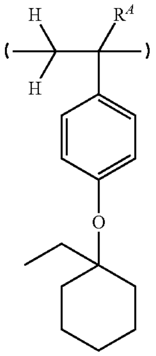
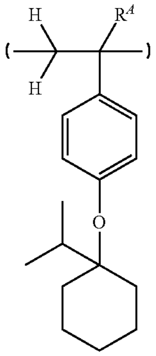
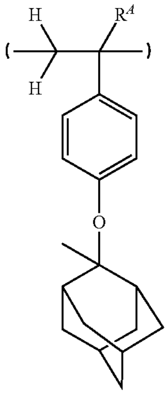
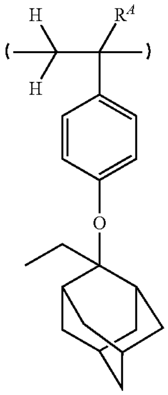
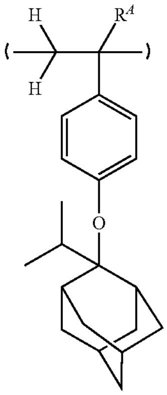
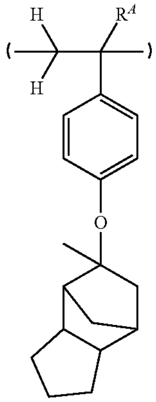
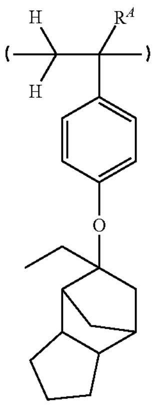
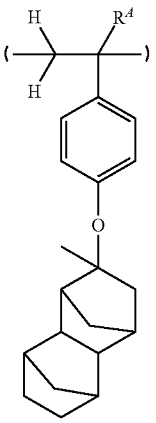
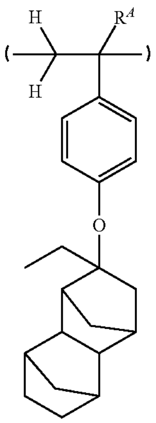
-continued
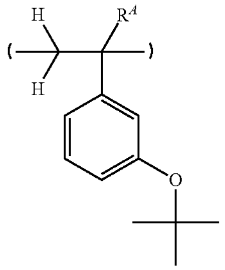
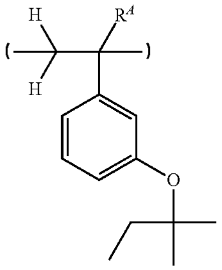
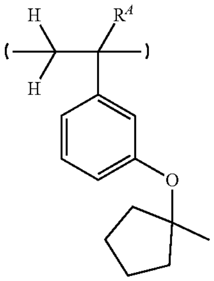
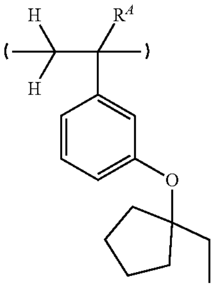
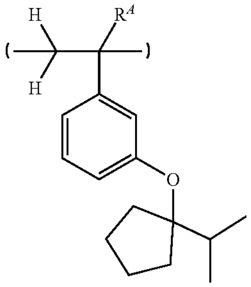
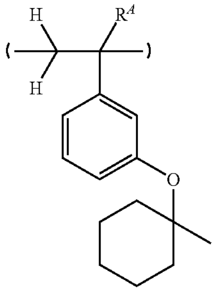
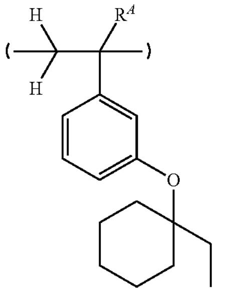
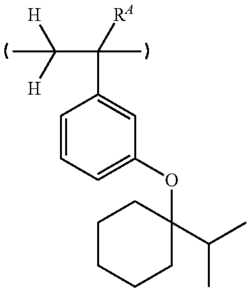
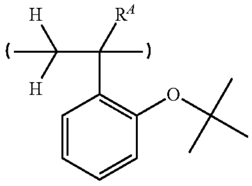
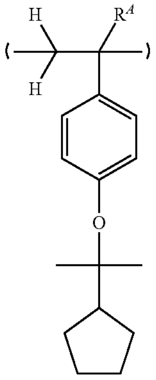

-continued

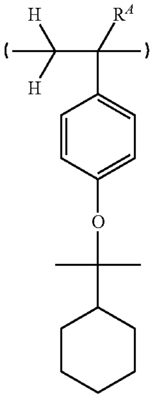
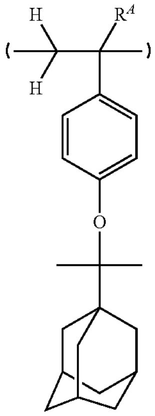
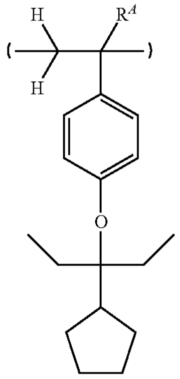
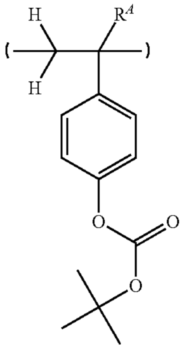
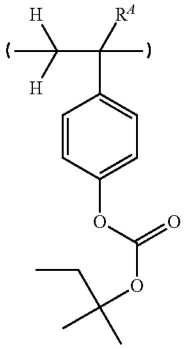
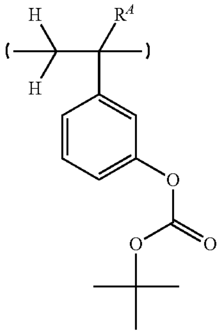
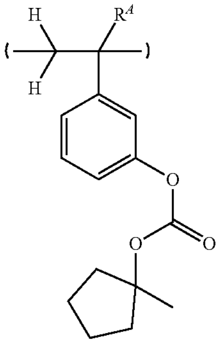
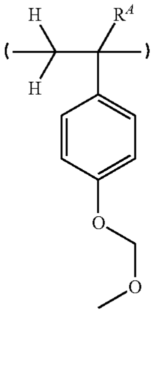
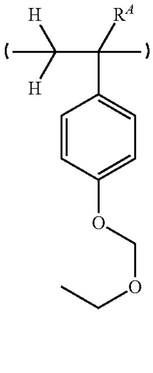
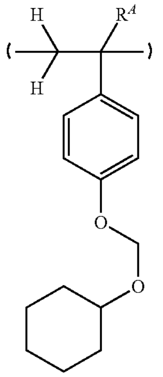

-continued

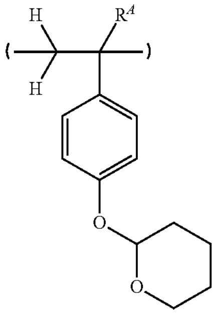
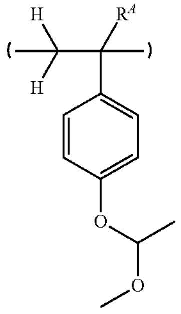
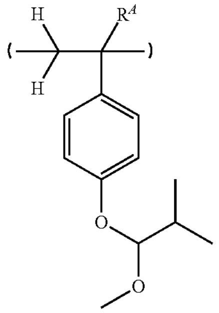
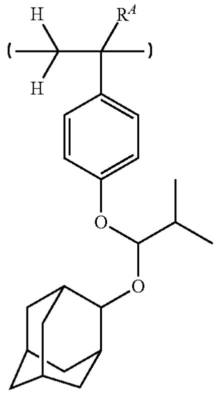
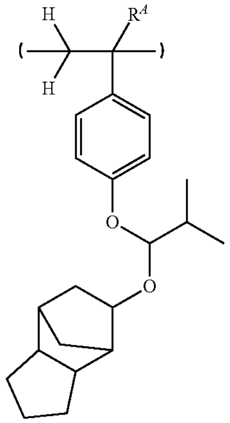
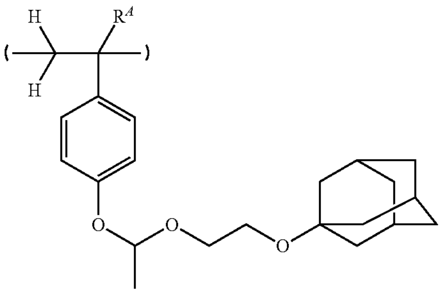

Although the above examples correspond to the unit wherein $X^A$ or $X^B$ is a single bond, combinations with similar acid labile groups are possible where $X^A$ or $X^B$ is other than a single bond. Examples of the units wherein $X^A$ is other than a single bond are as exemplified above. Examples of the units wherein $X^B$ is an ester bond correspond to the above-exemplified units wherein the single bond between the backbone and the benzene ring is replaced by an ester bond.

The base polymer may further comprise recurring units having the formula (c), which are also referred to as recurring units (c).

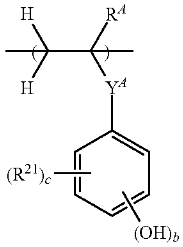

(c)

In formula (c), $R^A$ is hydrogen or methyl. $Y^A$ is a single bond or ester bond.

In formula (c), $R^{21}$ is fluorine, iodine or a $C_1$-$C_{10}$ hydrocarbyl group. The hydrocarbyl group may be saturated or unsaturated and straight, branched or cyclic. Examples include alkyl groups such as methyl, ethyl, propyl, isopropyl, n-butyl, sec-butyl, tert-butyl, n-pentyl, n-hexyl, n-octyl, n-nonyl, and n-decyl; cyclic saturated hydrocarbyl groups such as cyclopentyl, cyclohexyl, and adamantyl; aryl groups such as phenyl; and combinations thereof.

A constituent $—CH_2—$ in the hydrocarbyl group may be replaced by —O— or —C(═O)—. The constituent $—CH_2—$ in the hydrocarbyl group may be one bonding to a carbon atom on the benzene ring in formula (c). Examples of the substituted hydrocarbyl group include, but are not limited to, methoxy, ethoxy, propoxy, butoxy, phenoxy, 2-methoxyethoxy, acetyl, ethylcarbonyl, hexylcarbonyl, acetoxy, ethylcarbonyloxy, propylcarbonyloxy, pentylcarbonyloxy, hexylcarbonyloxy, heptylcarbonyloxy, methoxymethylcarbonyloxy, (2-methoxyethoxy)methylcarbonyloxy, methyloxycarbonyl, ethyloxycarbonyl, hexyloxycarbonyl, phenyloxycarbonyl, acetoxymethyl, phenoxymethyl, and methoxycarbonyloxy. Preferably $R^{21}$ is fluorine, iodine, methyl, acetyl or methoxy.

In formula (c), b is an integer of 1 to 5, c is an integer of 0 to 4, and b+c is 1 to 5. Preferably b is 1, 2 or 3, and c is 0, 1 or 2.

The recurring unit (c) serves to improve the adhesion to the substrate or the underlay film. Since the recurring unit (c) has a phenolic hydroxyl group with high acidity, it promotes the action of an acid generated upon exposure, contributing to a higher sensitivity, and becomes a proton source to the acid generated upon EUV exposure, from which an improvement in sensitivity is expectable.

Examples of the recurring unit (c) are given below, but not limited thereto. Herein $R^A$ is as defined above.

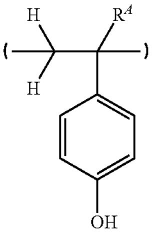
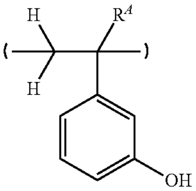
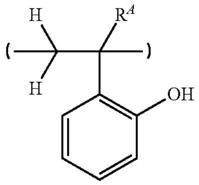

-continued

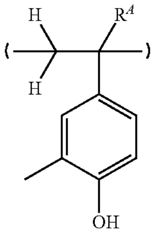
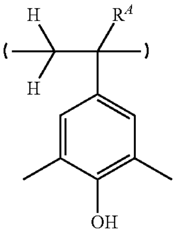
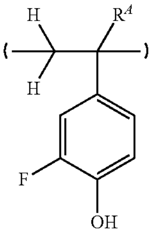
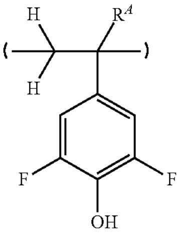
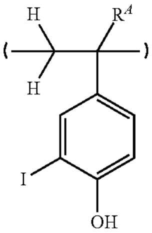
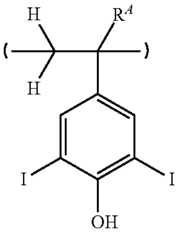
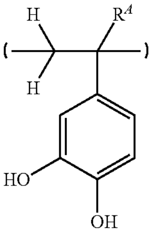
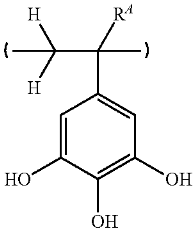
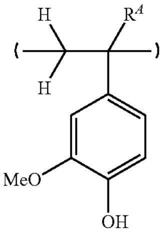
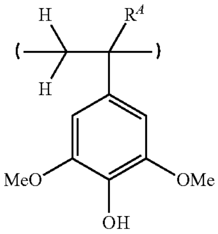
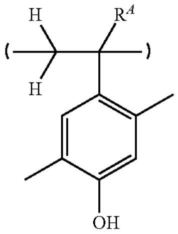
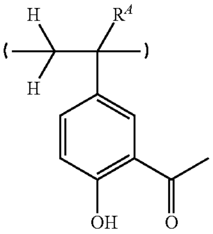
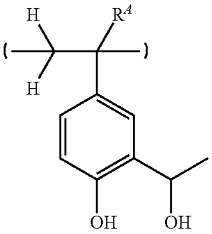
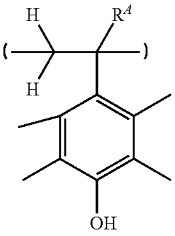
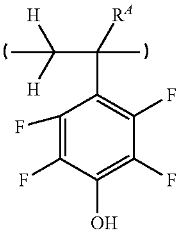
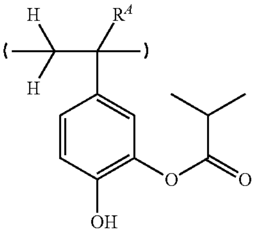
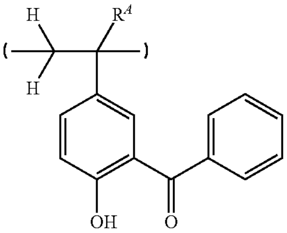

-continued
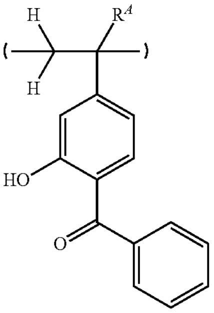
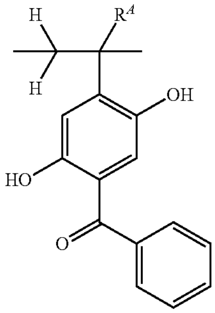
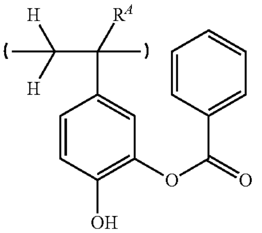
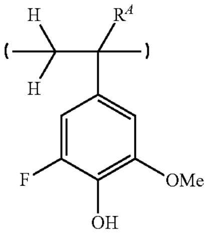
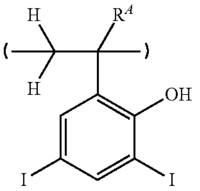
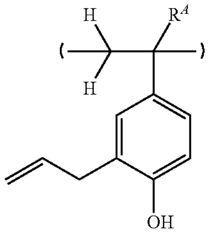
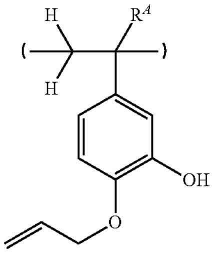
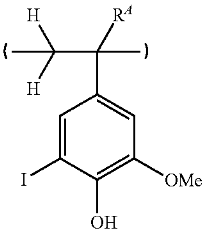
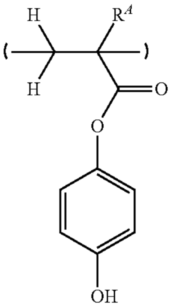
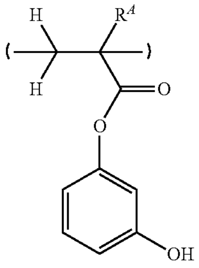
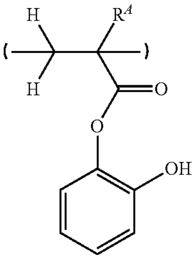
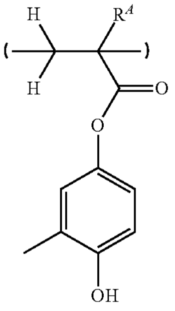
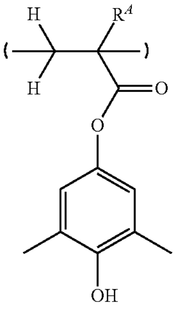
-continued
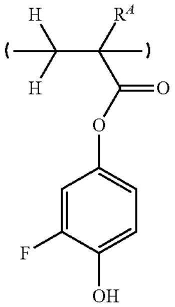
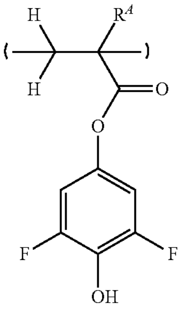
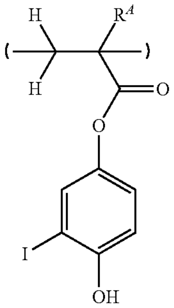
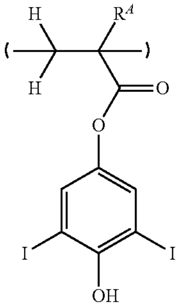
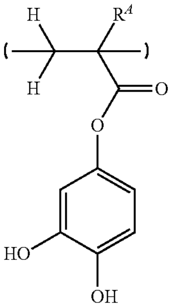
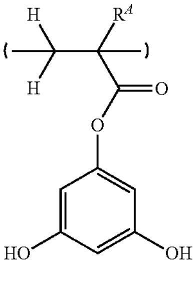
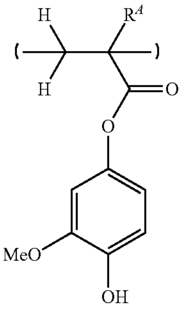
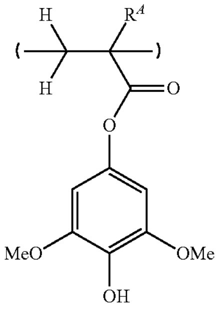
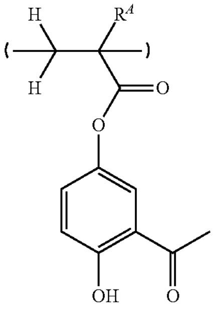
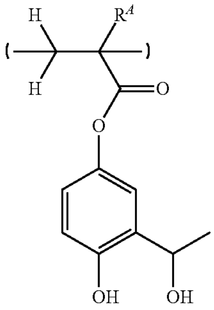
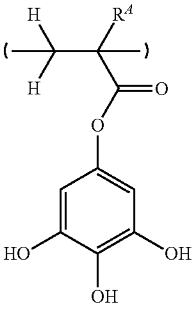
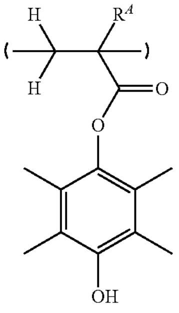
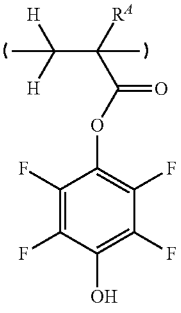

-continued
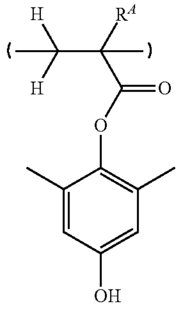
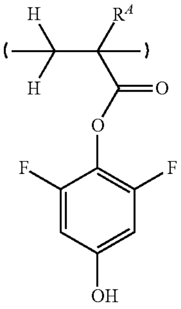
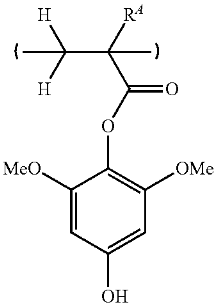
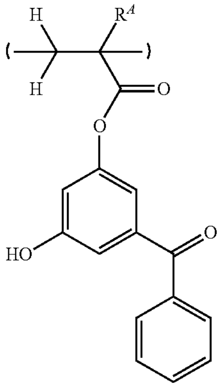
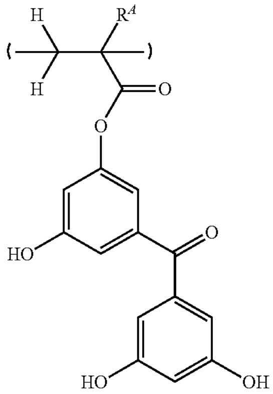
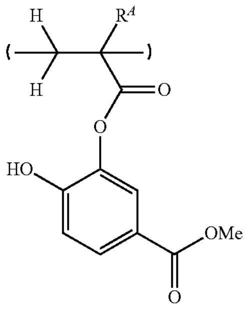
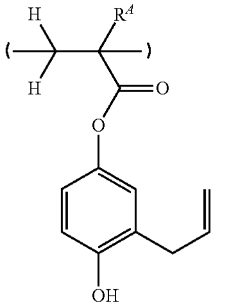
Of the above recurring units (c), the following units are preferred. Herein $R^A$ is as defined above.
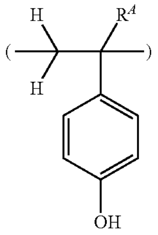
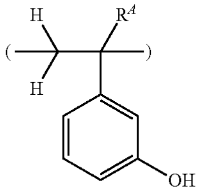
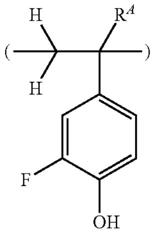
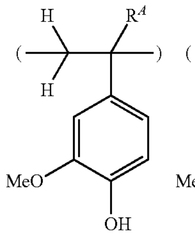
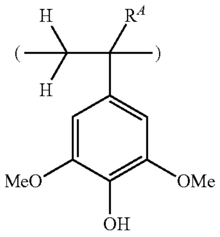
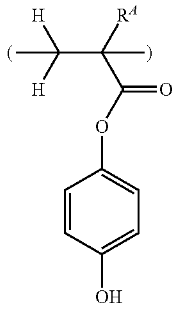
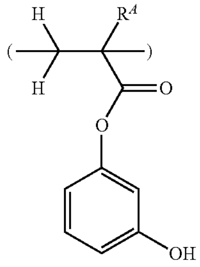
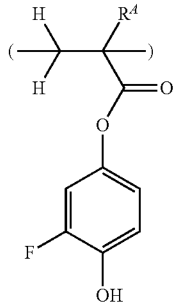
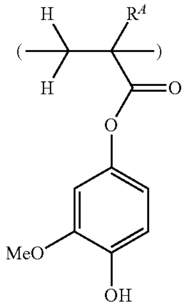
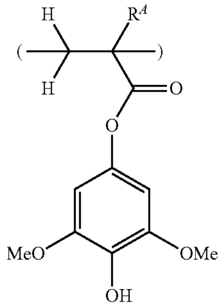
The base polymer may further comprise recurring units having the formula (d1), (d2), (d3) or (d4), which are also referred to as recurring units (d1) to (d4), respectively.
(d1)
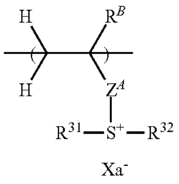

-continued (d2)

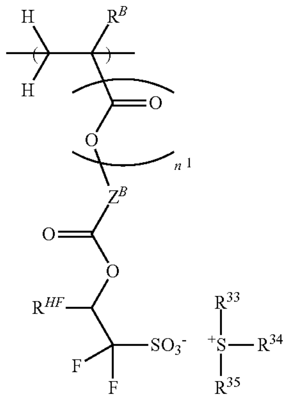

(d3)

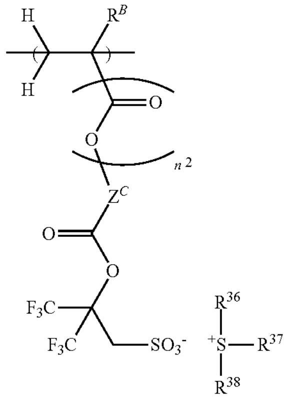

(d4)

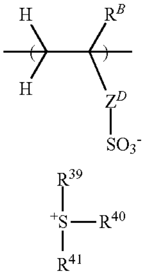

In formulae (d1) to (d4), $R^B$ is hydrogen, fluorine, methyl or trifluoromethyl. $Z^A$ is a single bond, phenylene, —O—$Z^{A1}$—, —C(═O)—O—$Z^{A1}$— or —C(═O)—NH—$Z^{A1}$—, wherein $Z^{A1}$ is a $C_1$-$C_{20}$ hydrocarbylene group which may contain a heteroatom. $Z^B$ and $Z^C$ are each independently a single bond or a $C_1$-$C_{20}$ hydrocarbylene group which may contain a heteroatom. $Z^D$ is a single bond, methylene, ethylene, phenylene, fluorinated phenylene, —O—$Z^{D1}$—, —C(═O)—O—$Z^{D1}$— or —C(═O)—NH—$Z^{D1}$—, wherein $Z^{D1}$ is an optionally substituted phenylene group.

The hydrocarbylene group represented by $Z^{A1}$ may be saturated or unsaturated and straight, branched or cyclic. Examples thereof include alkanediyl groups such as methylene, ethane-1,1-diyl, ethane-1,2-diyl, propane-1,2-diyl, propane-1,3-diyl, butane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, and 2,2-dimethylpropane-1,3-diyl; cyclic saturated hydrocarbylene groups such as cyclopentanediyl, cyclohexanediyl, norbornanediyl, and adamantanediyl; alkenediyl groups such as ethene-1,2-diyl, 1-propene-1,3-diyl, 2-butene-1,4-diyl, and 1-methyl-1-butene-1,4-diyl; unsaturated alicyclic hydrocarbylene groups such as 2-cyclohexene-1,4-diyl; aromatic hydrocarbylene groups such as phenylene and naphthylene, and combinations thereof. In these groups, some or all of the hydrogen atoms may be substituted by a moiety containing a heteroatom such as oxygen, sulfur, nitrogen or halogen, and a moiety containing a heteroatom such as oxygen, sulfur or nitrogen may intervene in a carbon-carbon bond, so that the group may contain a hydroxyl moiety, cyano moiety, carbonyl moiety, ether bond, ester bond, sulfonic acid ester bond, carbonate bond, lactone ring, sultone ring, carboxylic anhydride or haloalkyl moiety.

The hydrocarbylene groups represented by $Z^B$ and $Z^C$ may be saturated or unsaturated and straight, branched or cyclic. Examples thereof are as exemplified above for the hydrocarbylene group $Z^{A1}$.

In formulae (d1) to (d4), $R^{31}$ to $R^{41}$ are each independently a $C_1$-$C_{20}$ hydrocarbyl group which may contain a heteroatom. The hydrocarbyl group may be saturated or unsaturated and straight, branched or cyclic. Examples include alkyl groups such as methyl, ethyl, n-propyl, isopropyl, n-butyl, and tert-butyl, cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl, alkenyl groups such as vinyl, allyl, propenyl, butenyl, and hexenyl, unsaturated alicyclic hydrocarbyl groups such as cyclohexenyl, aryl groups such as phenyl and naphthyl, heteroaryl groups such as thienyl, aralkyl groups such as benzyl, 1-phenylethyl and 2-phenylethyl, and combinations thereof. Inter alia, aryl groups are preferred. In these groups, some or all of the hydrogen atoms may be substituted by a moiety containing a heteroatom such as oxygen, sulfur, nitrogen or halogen, and a moiety containing a heteroatom such as oxygen, sulfur or nitrogen may intervene in a carbon-carbon bond, so that the group may contain a hydroxyl moiety, cyano moiety, carbonyl moiety, ether bond, ester bond, sulfonic acid ester bond, carbonate bond, lactone ring, sultone ring, carboxylic anhydride or haloalkyl moiety.

$Z^A$ and $R^{31}$ to $R^{41}$ are preferably of a structure containing a phenyl group which is bonded to $S^+$ in the formula.

Any two of $Z^A$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, or any two of $R^{39}$, $R^{40}$ and $R^{41}$ may bond together to form a ring with the sulfur atom to which they are attached.

In formula (d2), $R^{HF}$ is hydrogen or trifluoromethyl.

In formula (d2), $n^1$ is 0 or 1, $n^1$ is 0 when $Z^B$ is a single bond. In formula (d3), $n^2$ is 0 or 1, $n^2$ is 0 when $Z^C$ is a single bond.

In formula (d1), $Xa^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; and methide ions such as tris(trifluoromethylsulfonyl)methide and tris(perfluoroethylsulfonyl)methide. Preferred are anions having the formulae (d1-1) and (d1-2).

(d1-1)
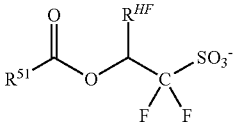
(d1-2)
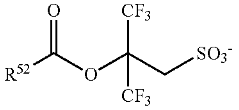
In formulae (d1-1) and (d1-2), $R^{51}$ and $R^{52}$ are each independently a $C_1$-$C_{40}$ hydrocarbyl group which may contain a heteroatom, and $R^{HF}$ is hydrogen or trifluoromethyl.
Examples of the anion having formula (d1-1) include the anions described in JP-A 2014-177407, paragraphs [0100]-[0101] and the anions shown below, but are not limited thereto. Herein $R^{HF}$ is as defined above.
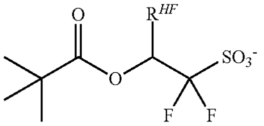
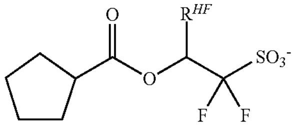
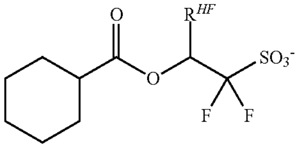
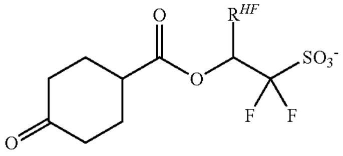
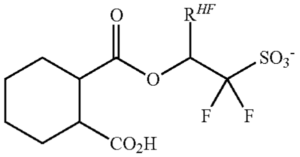
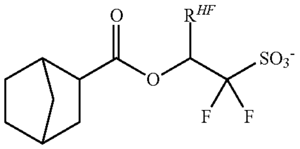
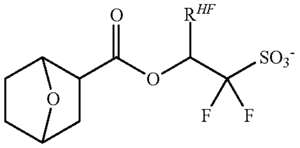
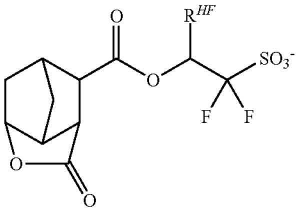
-continued
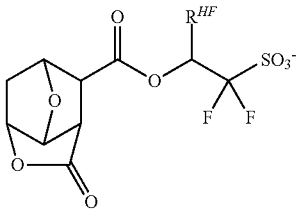
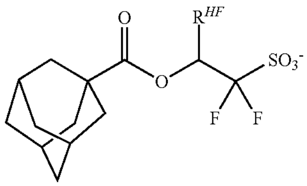
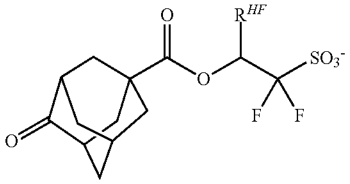
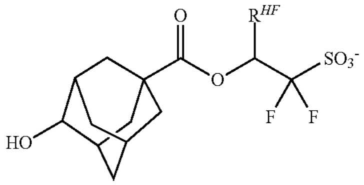
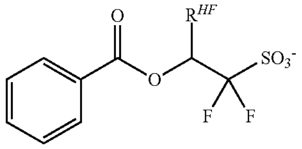
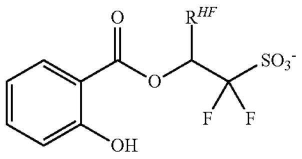
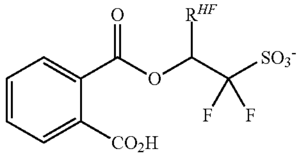
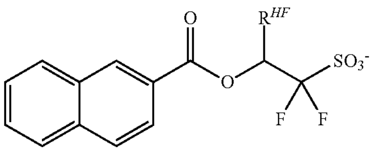
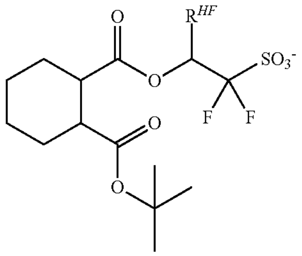

-continued
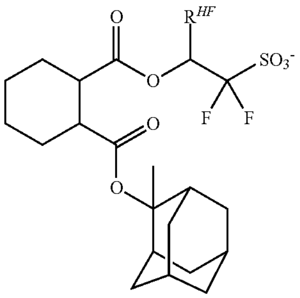
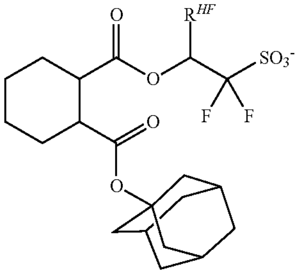
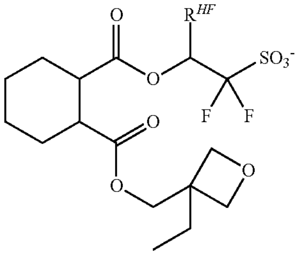
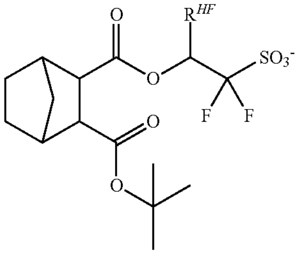
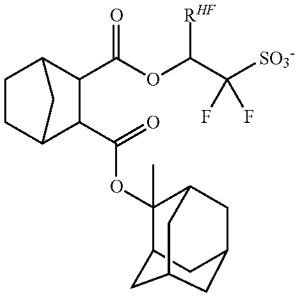
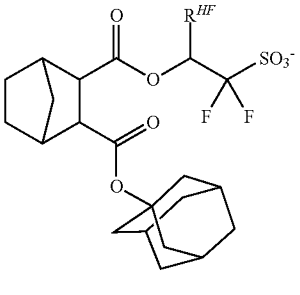
-continued
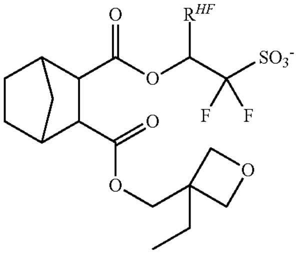
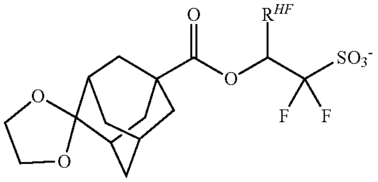
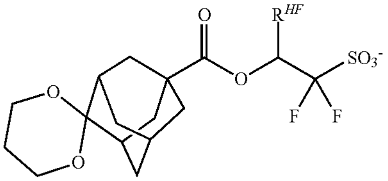
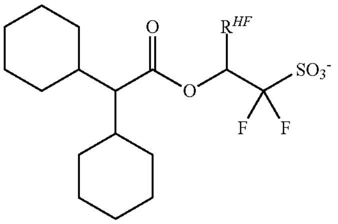
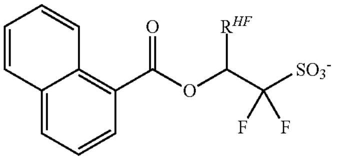
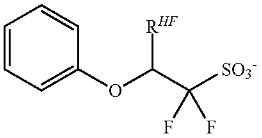
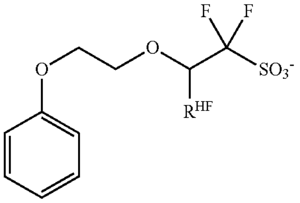
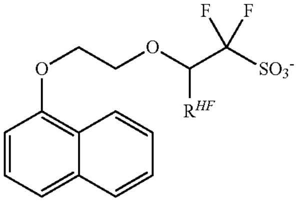
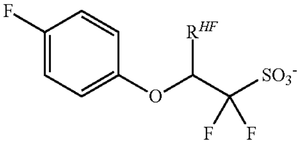

-continued
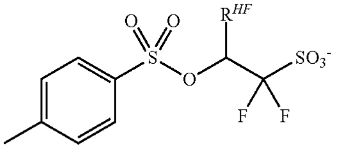
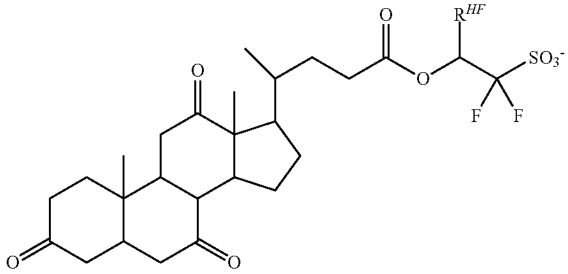
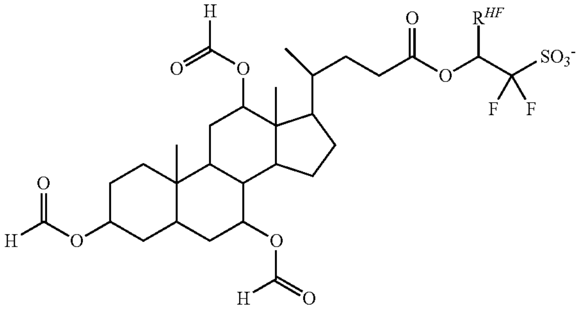
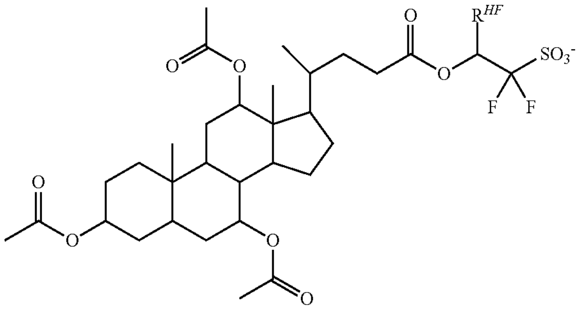
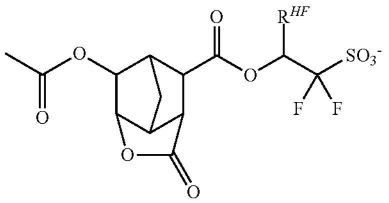
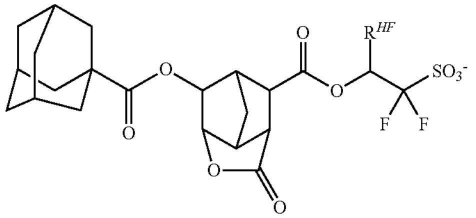
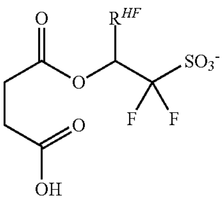
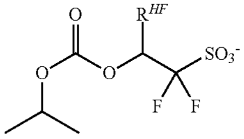
-continued
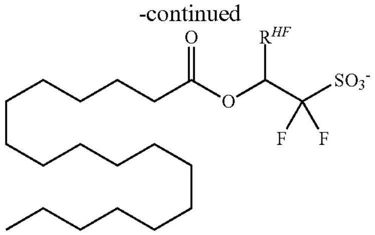
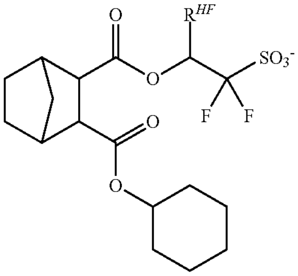
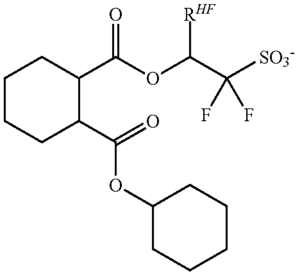
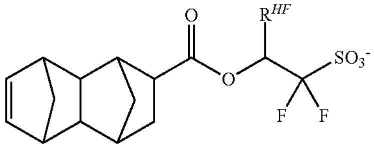
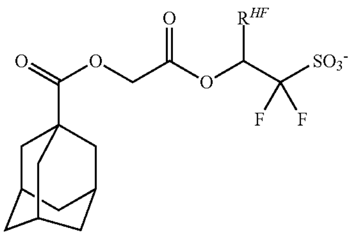
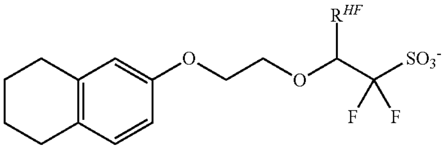
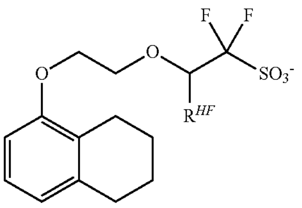
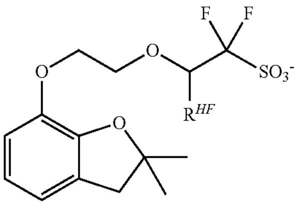

-continued
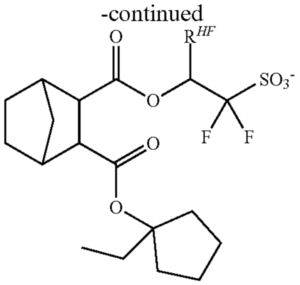
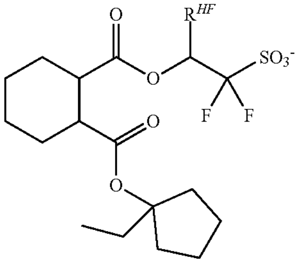
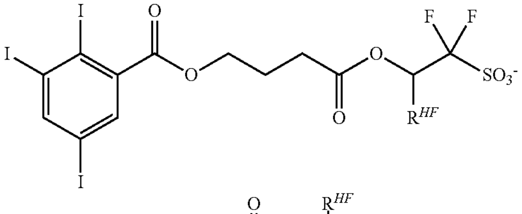
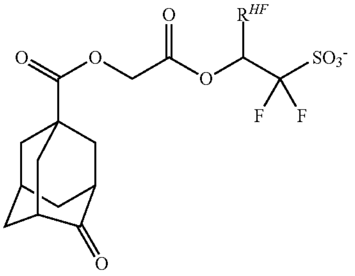
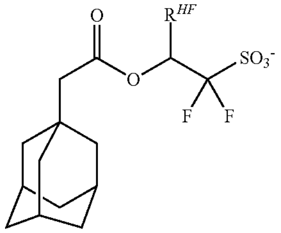
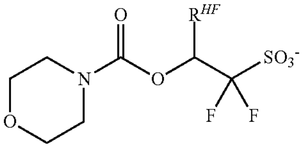
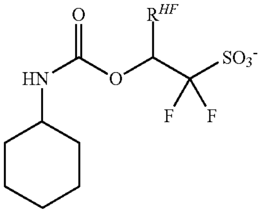
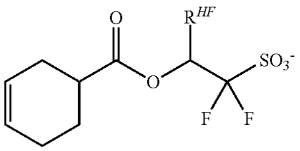
-continued
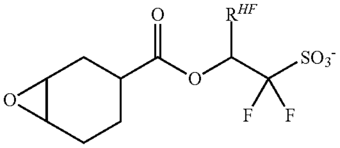
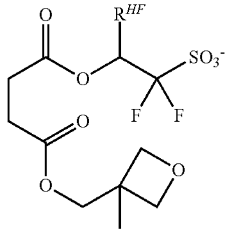
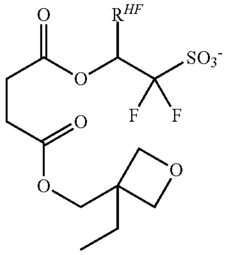
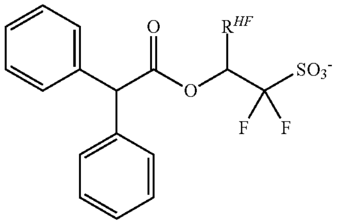
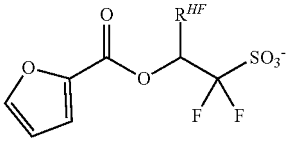
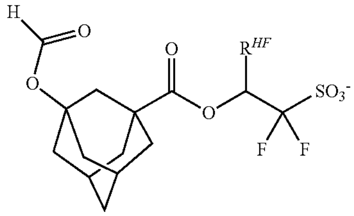
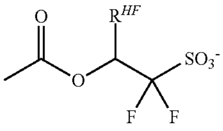
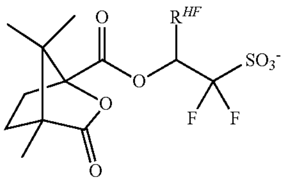
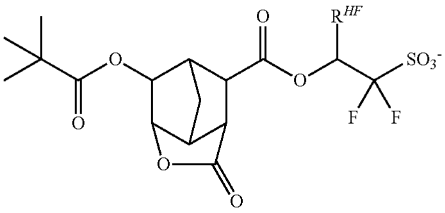
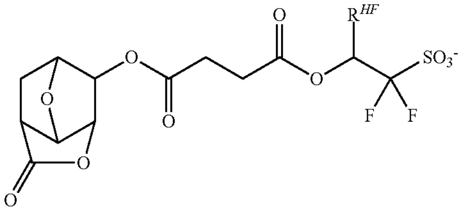

-continued
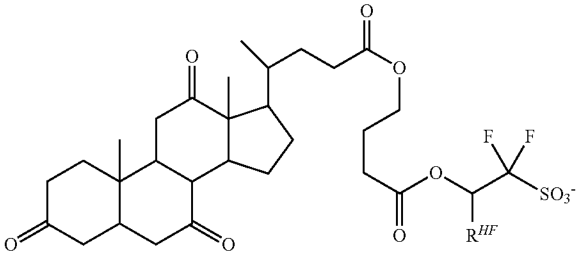
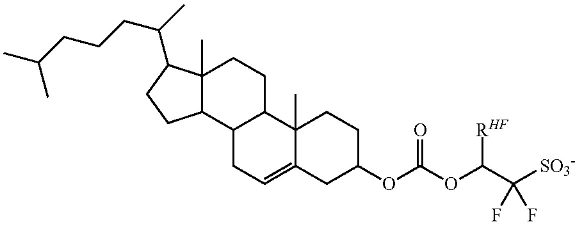
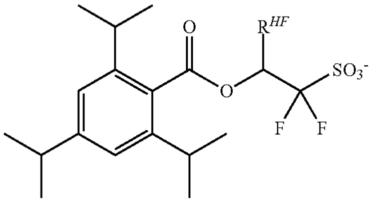
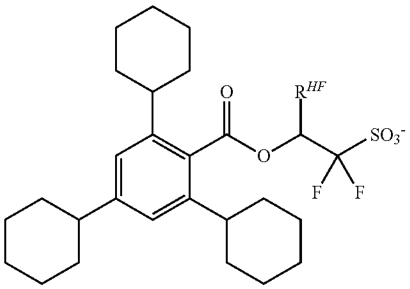
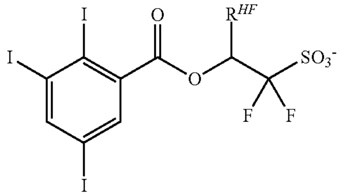
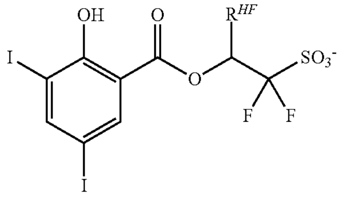
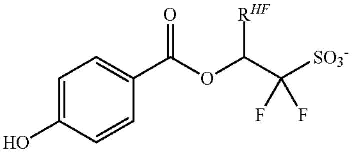
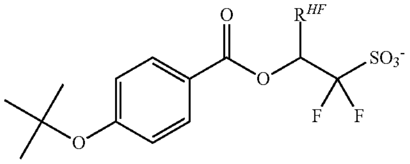
Examples of the anion having formula (d1-2) include the anions described in JP-A 2010-215608, paragraphs [0080]-[0081] and the anions shown below, but are not limited thereto.
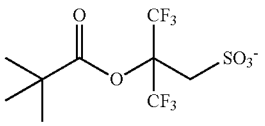
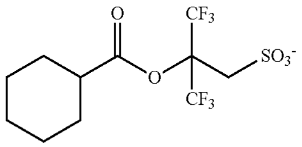
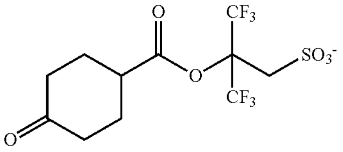
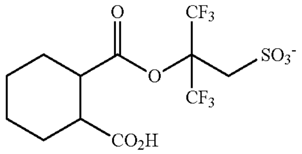
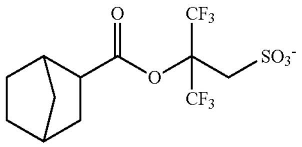
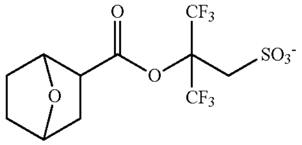
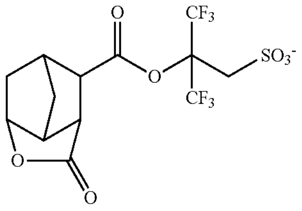
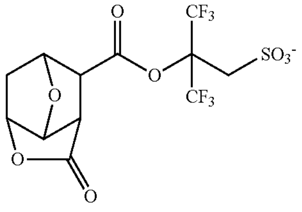
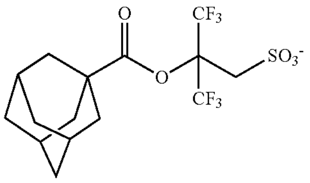

-continued
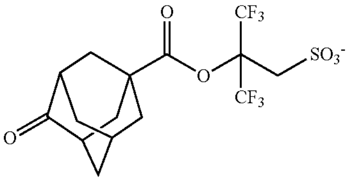
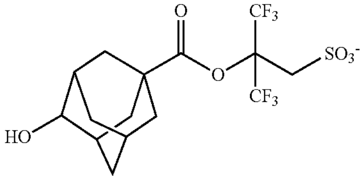
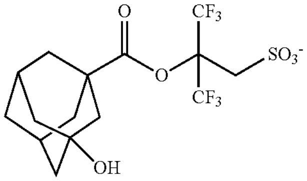
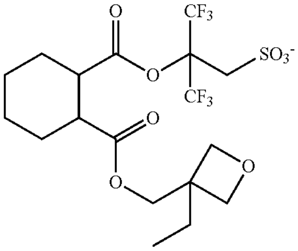
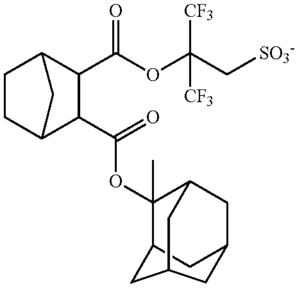
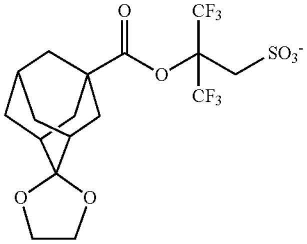
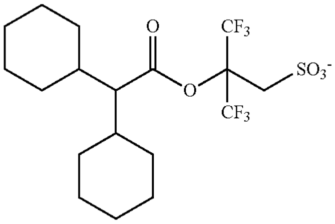
-continued
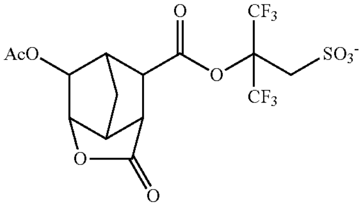
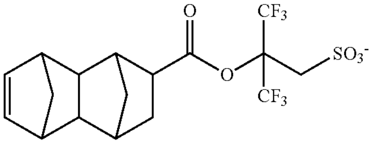
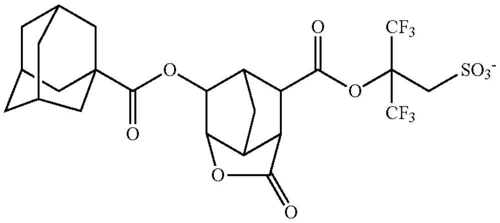
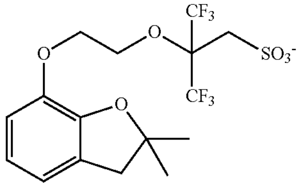
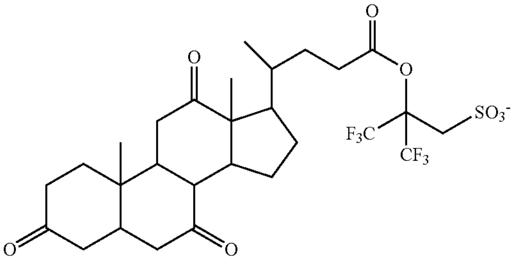
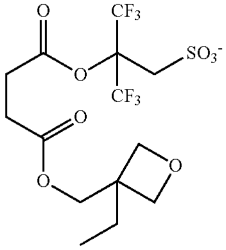
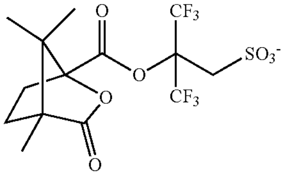
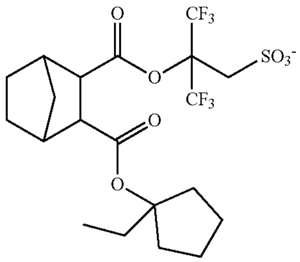
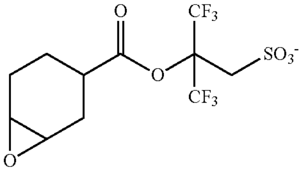

-continued

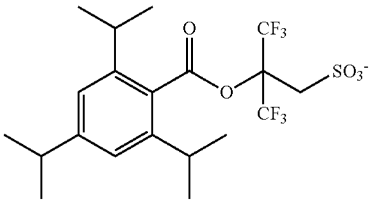

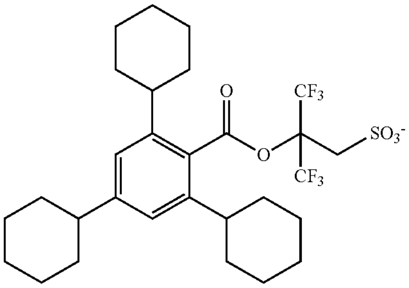

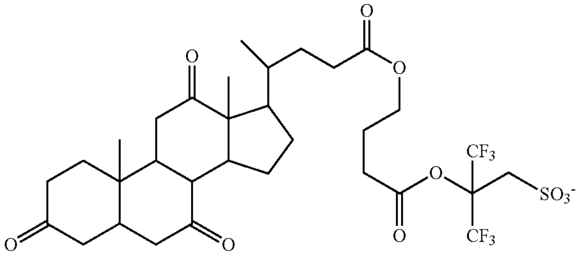

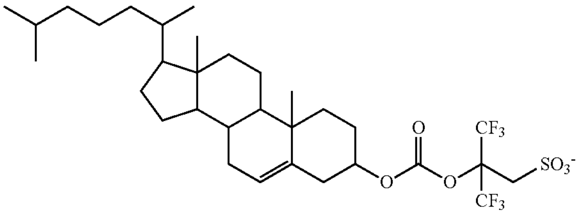

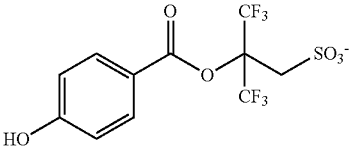

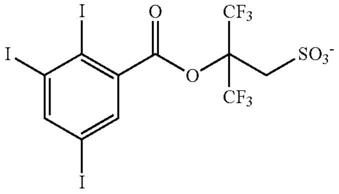

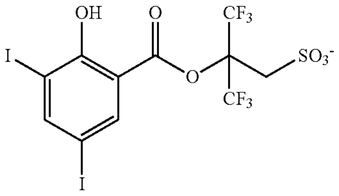

Examples of the anion in recurring unit (d2) include the anions described in JP-A 2014-177407, paragraphs [0021]-[0026], Exemplary structures of the anion wherein $R^{HF}$ is hydrogen include the anions described in JP-A 2010-116550, paragraphs [0021]-[0028], Exemplary structures of the anion wherein $R^{HF}$ is trifluoromethyl include the anions described in JP-A 2010-077404, paragraphs [0021]-[0027].

Examples of the anion in recurring unit (d3) correspond to the examples of the anion in recurring unit (d2) wherein $—CH(R^{HF})CF_2SO_3^-$ is replaced by $—C(CF_3)_2CH_2SO_3^-$.

Preferred examples of the anion in recurring units (d2) to (d4) are given below, but not limited thereto. Herein $R^B$ is as defined above.

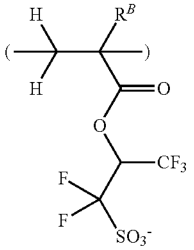

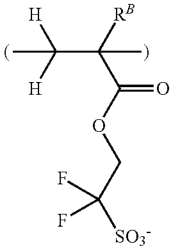

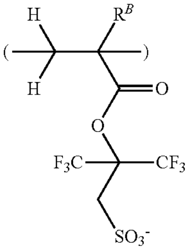

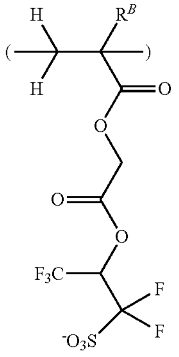

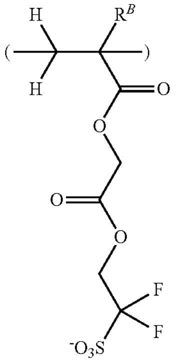

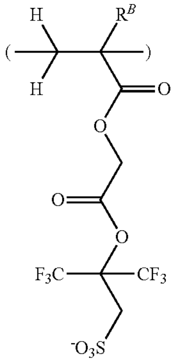

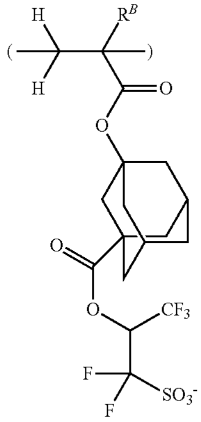

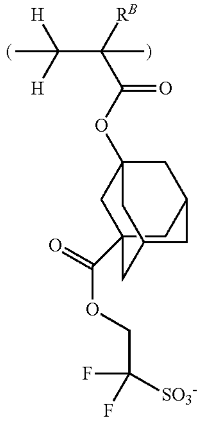

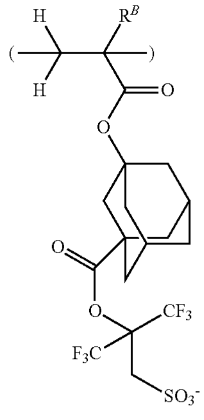

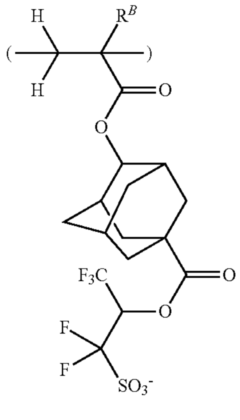

-continued
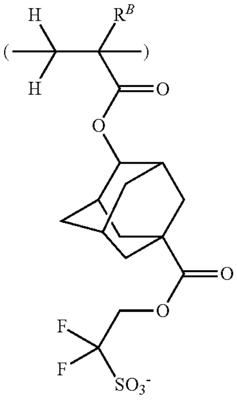
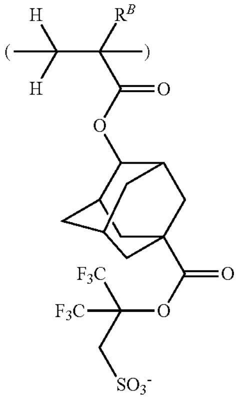
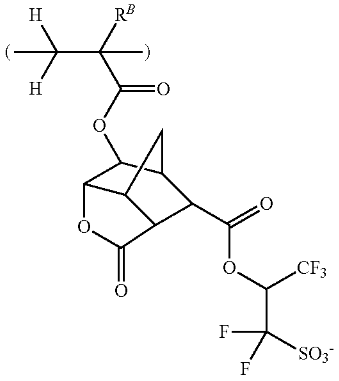
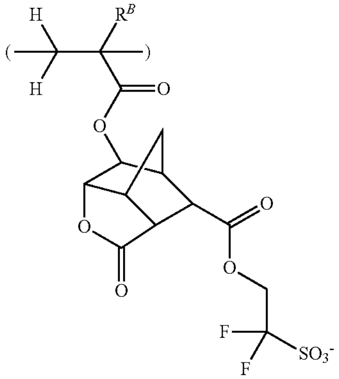
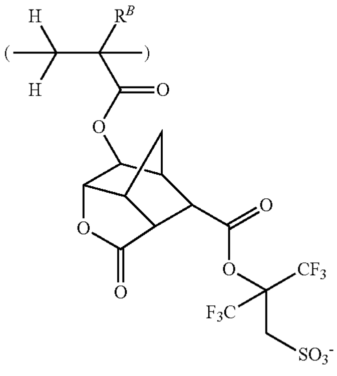
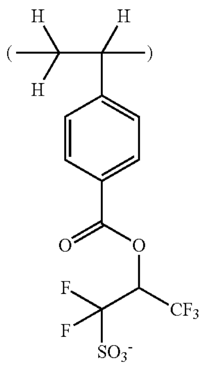
-continued
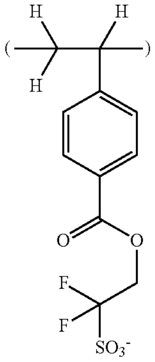
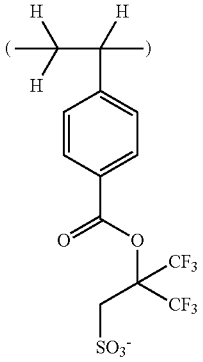
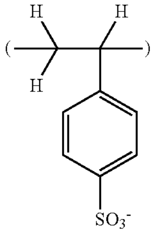
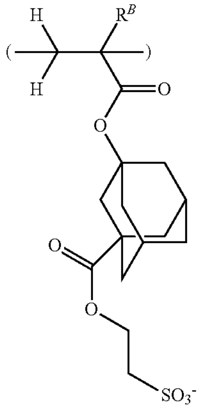
Examples of the sulfonium cation in recurring units (d2) to (d4) include those described in JP-A 2008-158339, paragraph [0223] as well as those exemplified above for the sulfonium cation $M^+$ in formula (1). Of these, the preferred cations are given below, but not limited thereto.
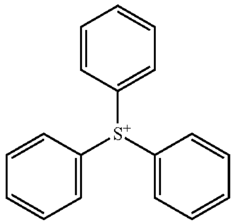
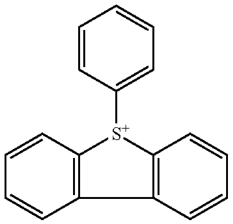
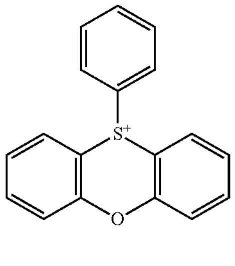
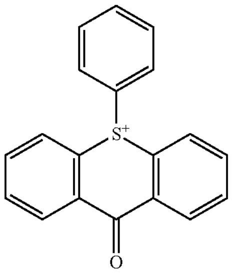

-continued
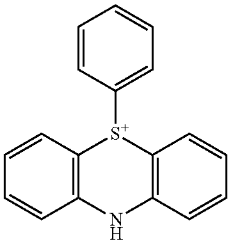
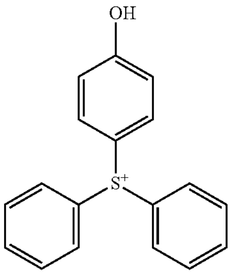
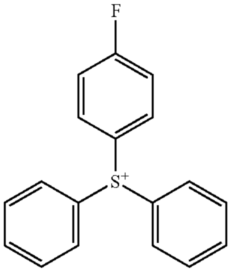
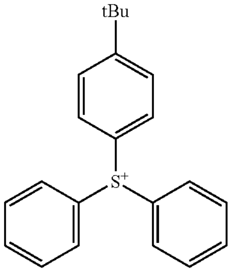
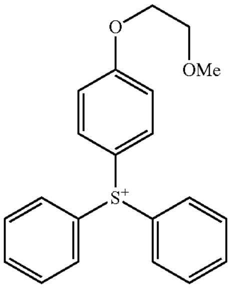
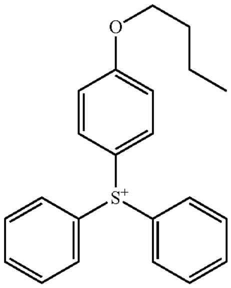
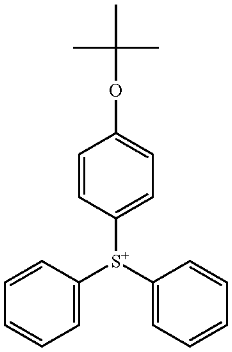
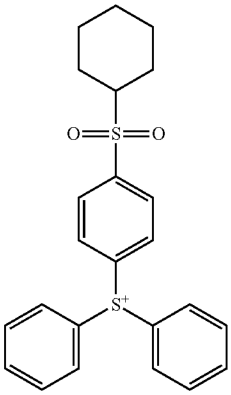
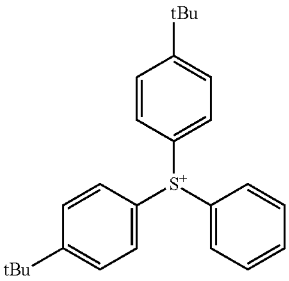
-continued
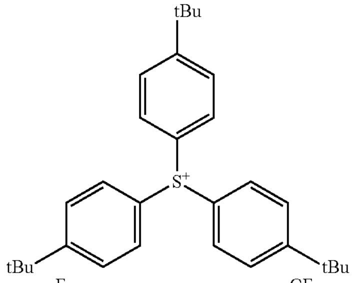
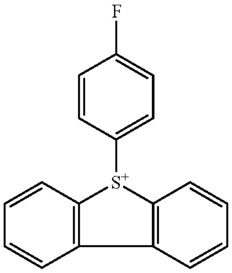
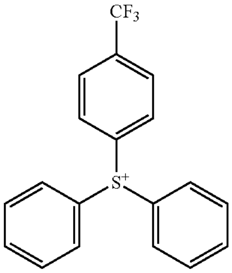
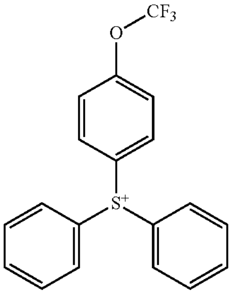
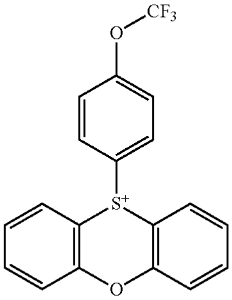
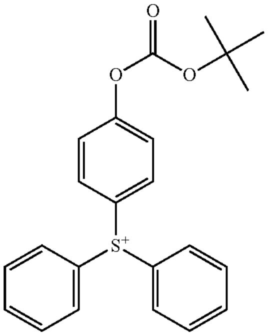
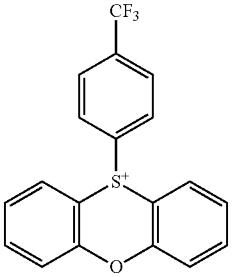
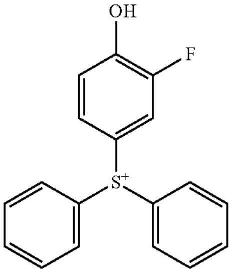
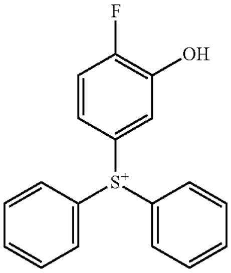
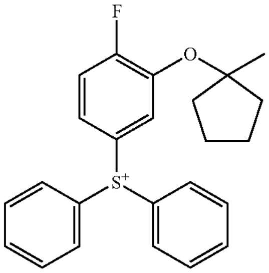

-continued

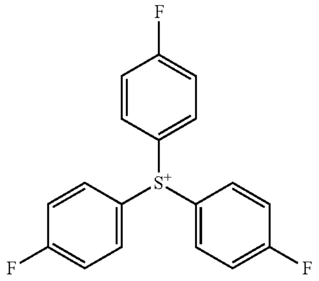

The recurring units (d1) to (d4) have the function of a photoacid generator. On use of a base polymer comprising recurring units (d1) to (d4), a photoacid generator of addition type to be described later may be omitted.

The base polymer may further comprise recurring units (e) containing a hydroxyl group (other than phenolic hydroxyl group), lactone ring, ether bond, ester bond, carbonyl group, cyano group or carboxyl group as another adhesive group.

Examples of the recurring units (e) are given below, but not limited thereto. Herein $R^A$ is as defined above.

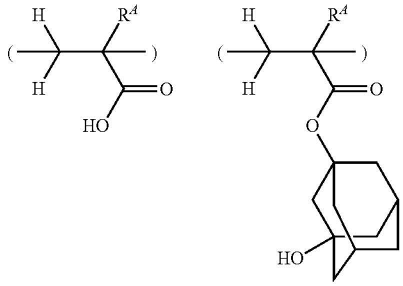

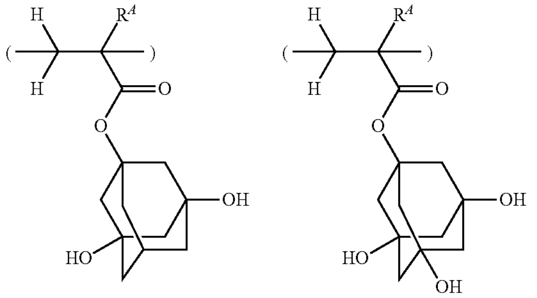

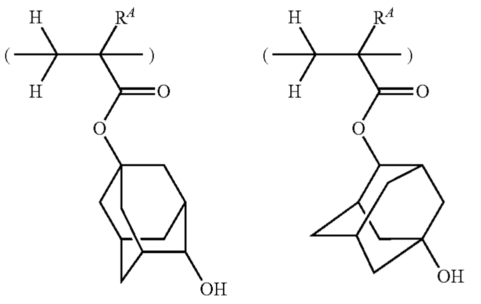

-continued

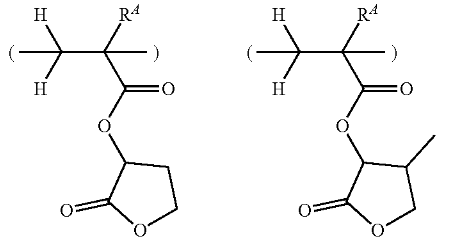

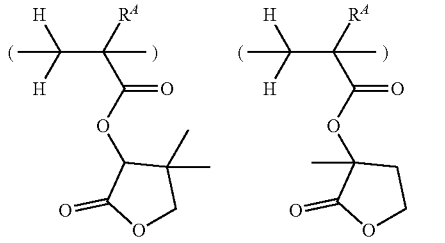

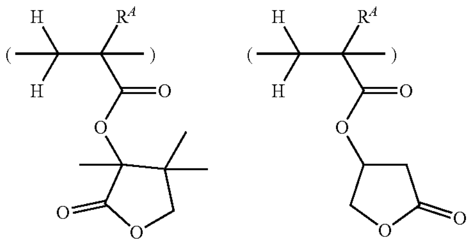

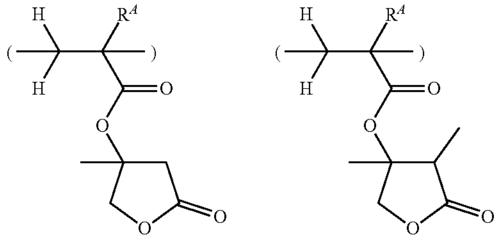

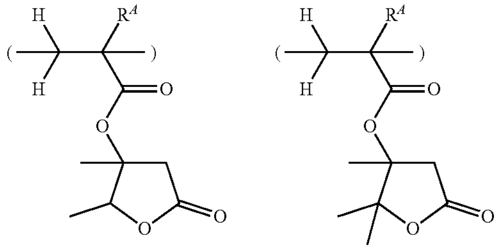

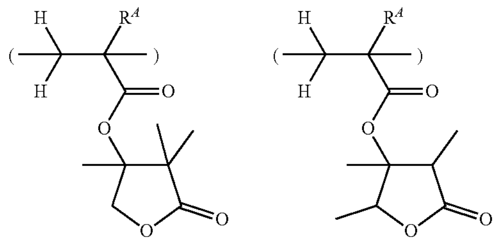

-continued
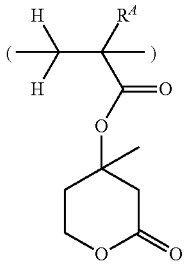
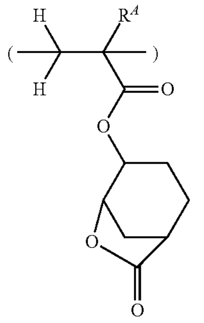
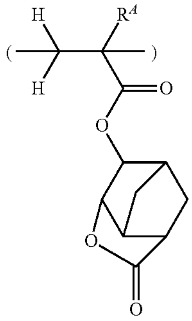
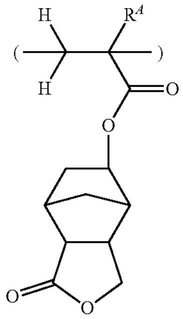
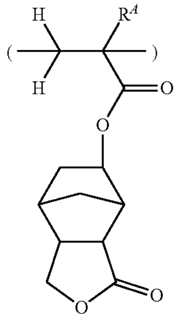
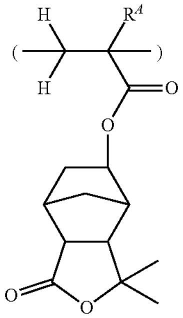
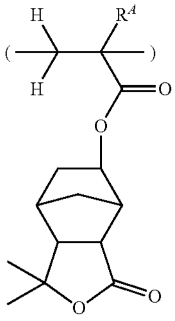
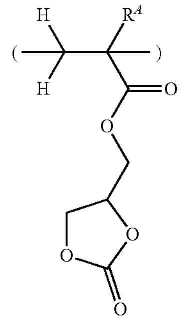
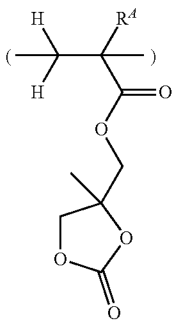
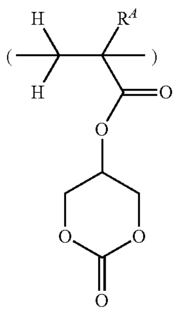
-continued
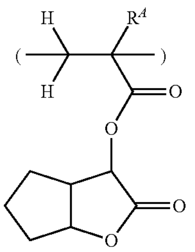
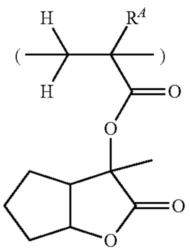
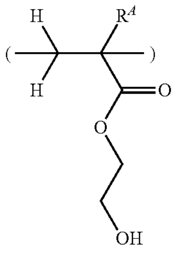
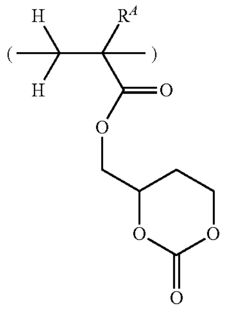
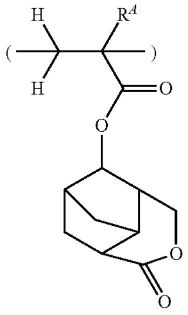
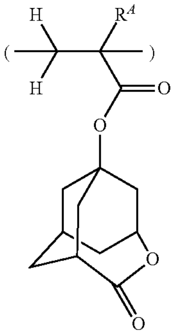
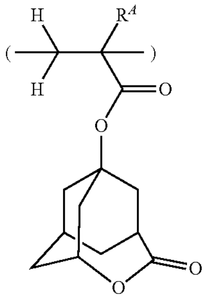
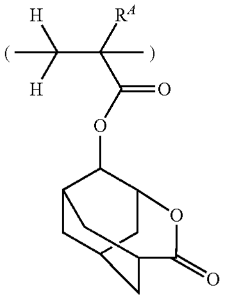
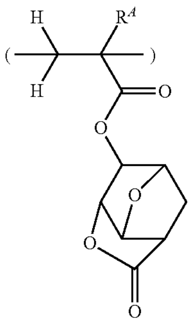
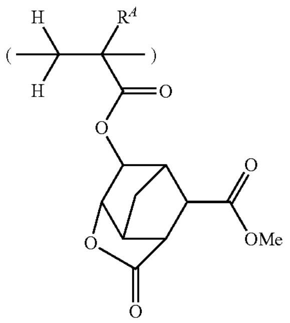

-continued
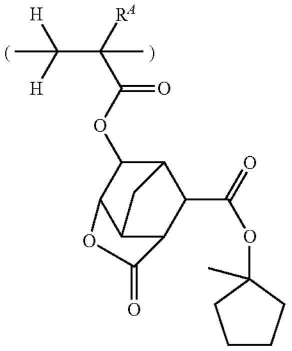
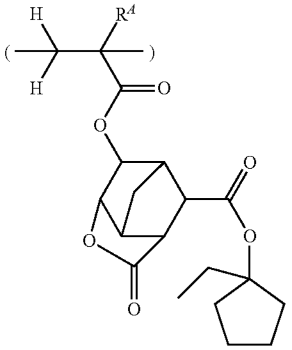
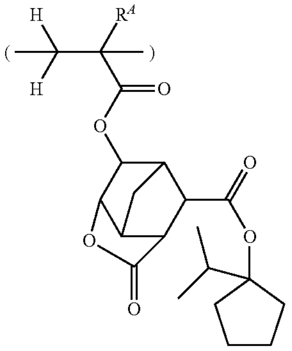
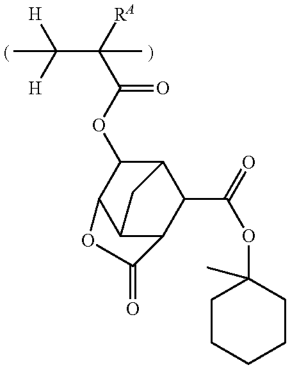
-continued
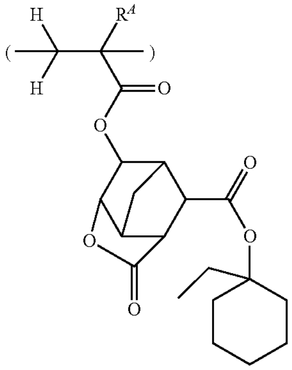
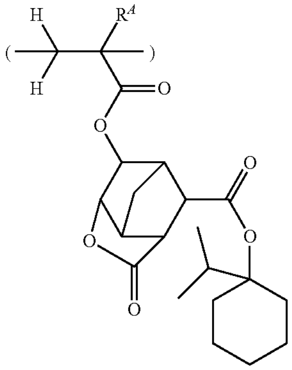
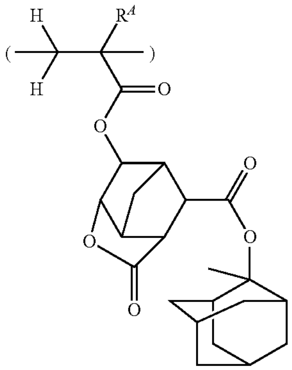
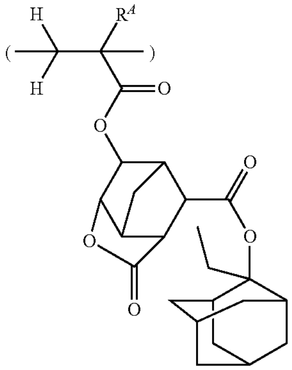

-continued
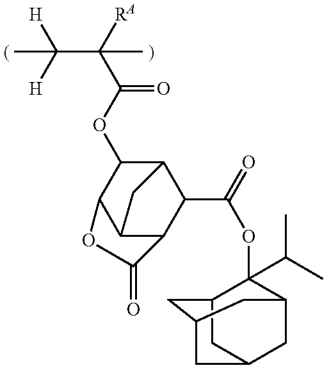
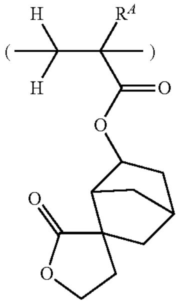
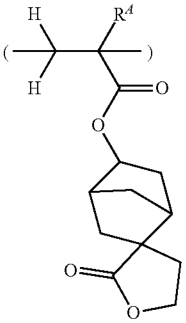
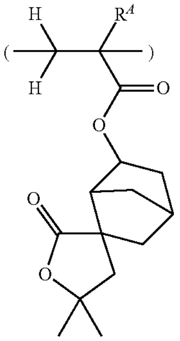
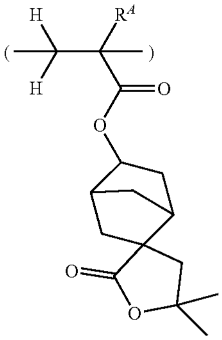
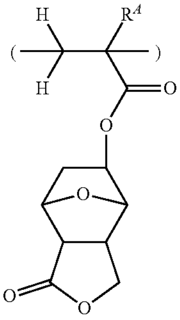
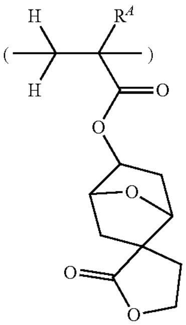
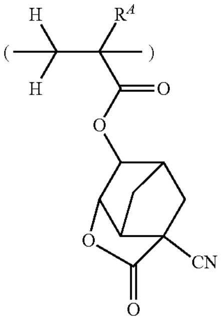
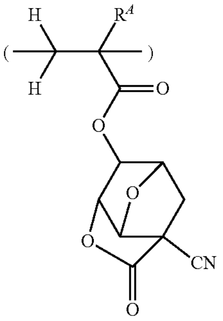
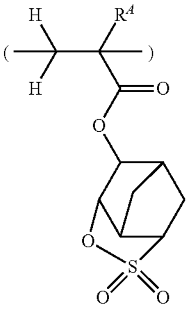
-continued
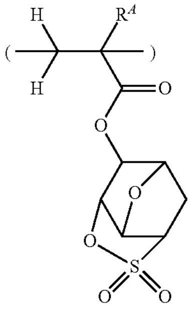
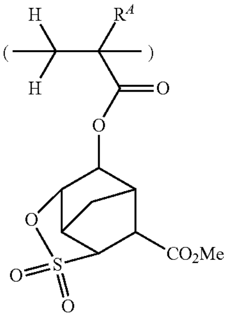
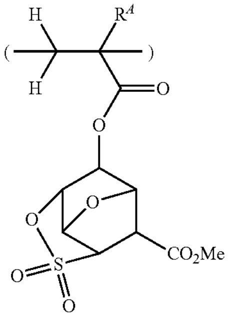
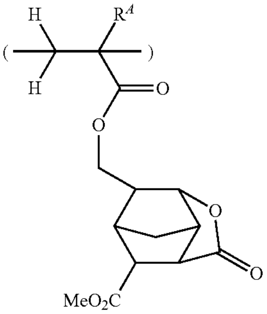
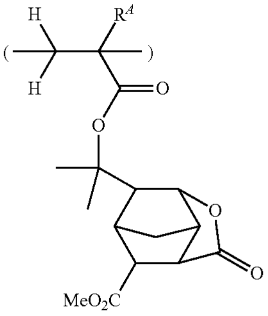
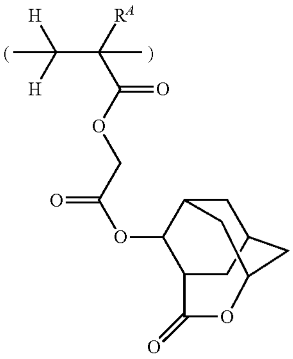
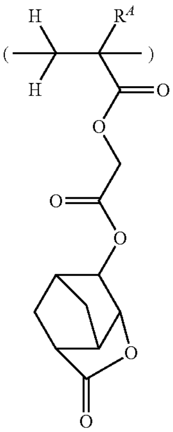
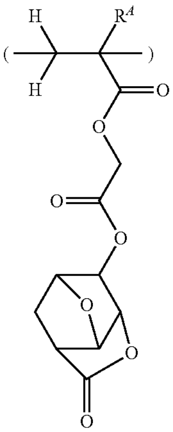

-continued
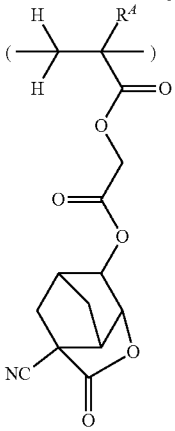
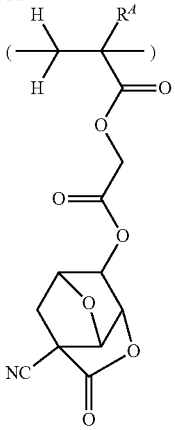
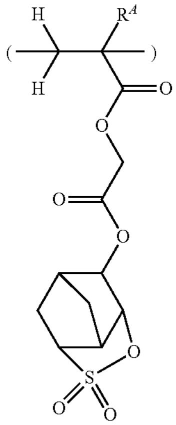
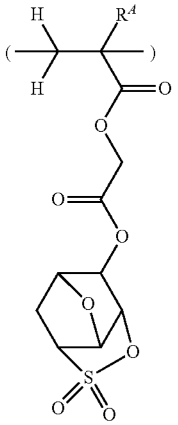
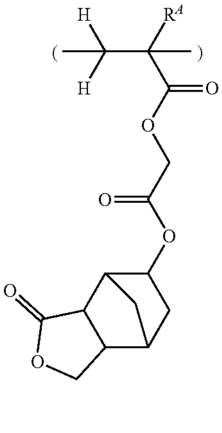
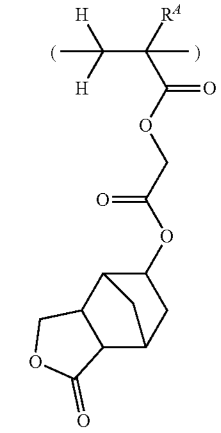
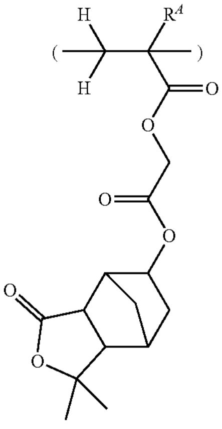
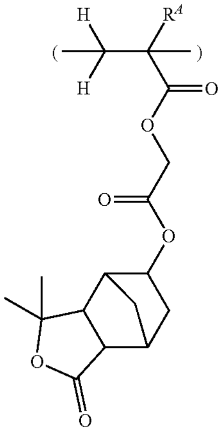
-continued
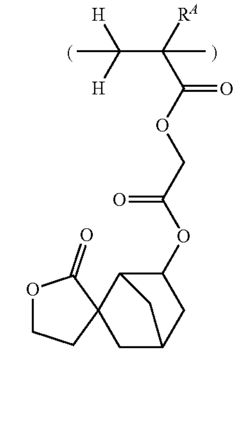
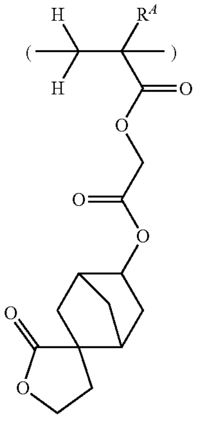
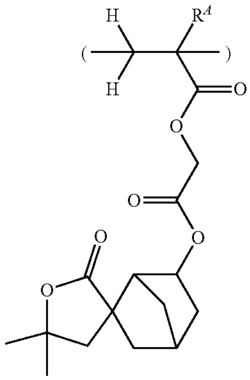
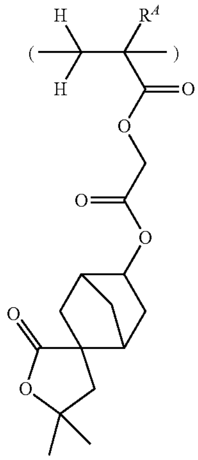
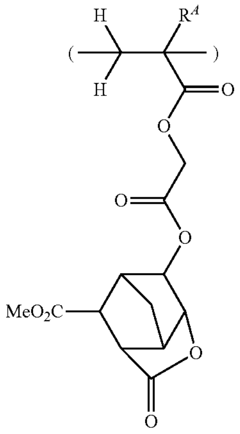
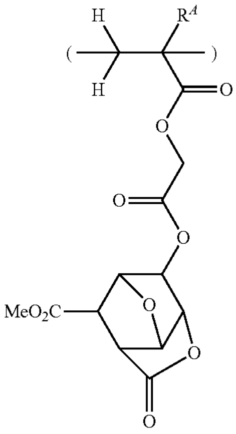
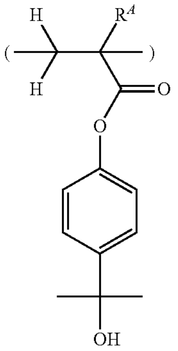
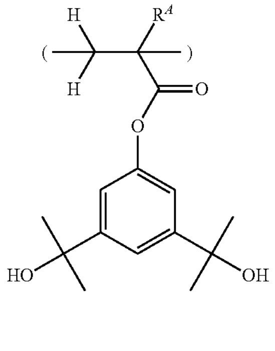

-continued
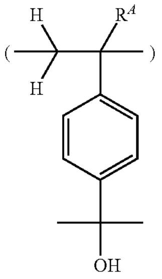
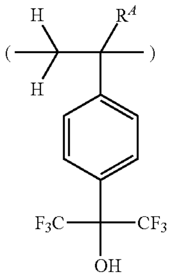
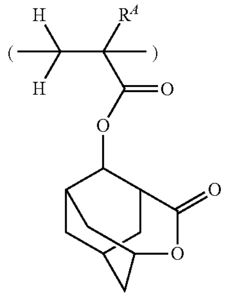
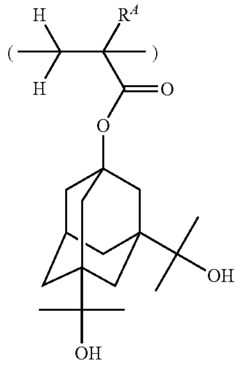
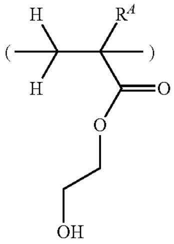
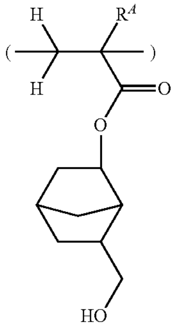
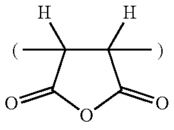
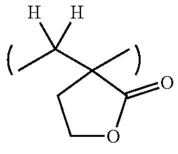
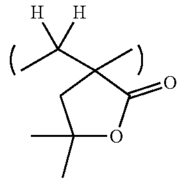
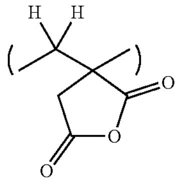
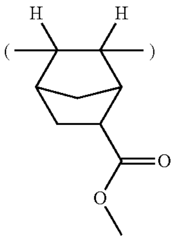
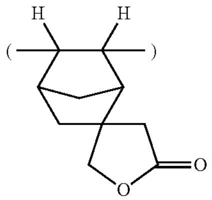
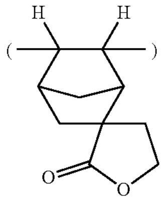
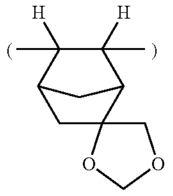
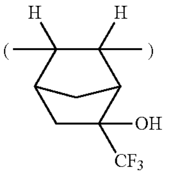
-continued
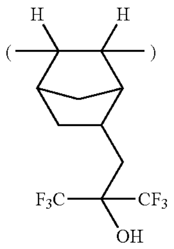
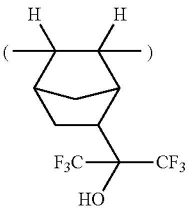
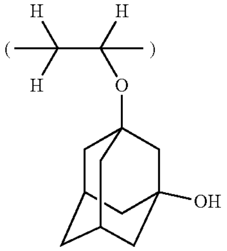
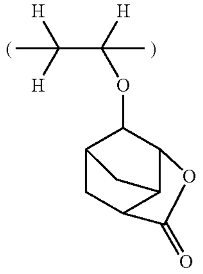
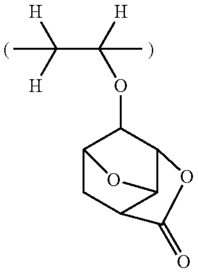
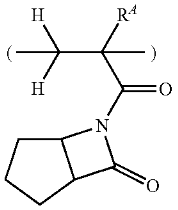
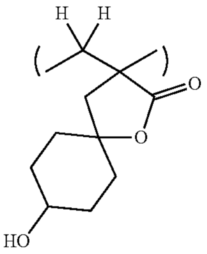
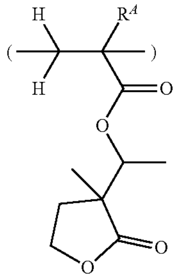
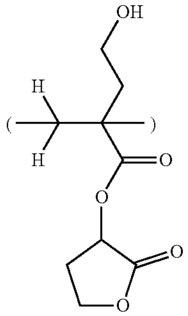
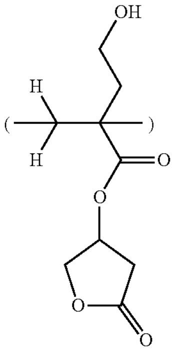

-continued

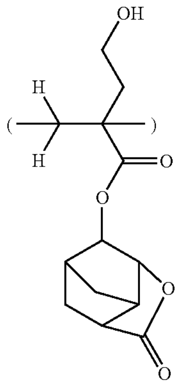

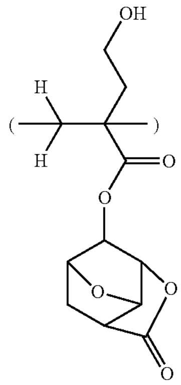

In addition to the foregoing examples, examples of the recurring units (e) include those described in JP-A 2014-225005, paragraphs [0045]-[0053], Of the foregoing, units having a hydroxyl group or lactone ring are preferred as the recurring unit (e), with preferred examples being shown below.

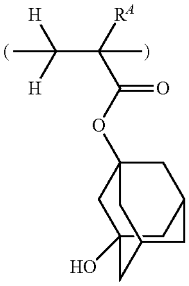

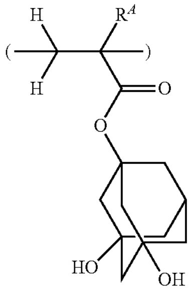

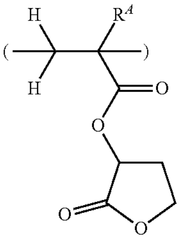

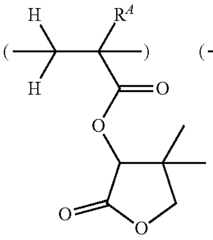

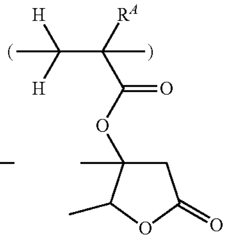

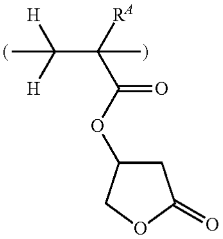

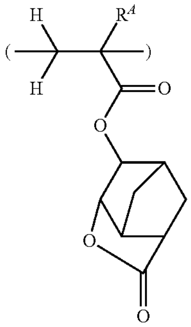

-continued

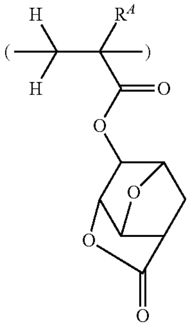

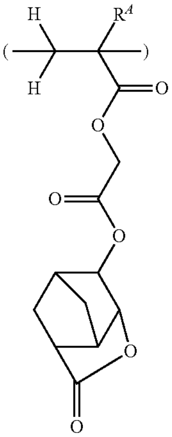

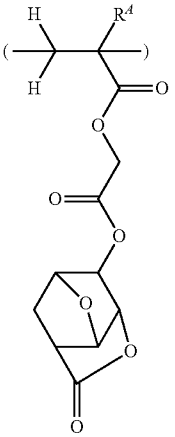

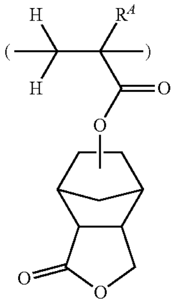

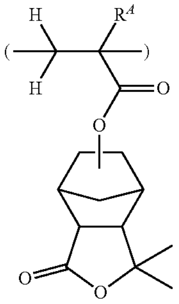

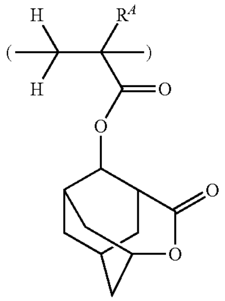

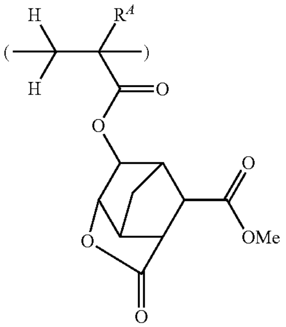

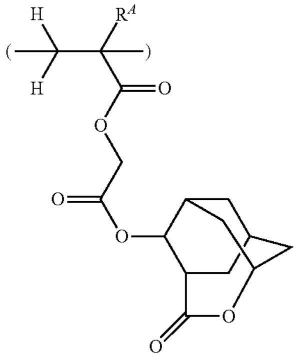

The base polymer may further comprise recurring units of the structure having a hydroxyl group protected with an acid labile group. The recurring unit of the structure having a hydroxyl group protected with an acid labile group is not particularly limited as long as the unit has at least one protected hydroxyl structure wherein a hydroxyl group is resumed as a result of decomposition of the protective group under the action of acid. Such recurring units are described in JP-A 2014-225005, paragraphs [0055]-[0065] and JP-A 2015-214634, paragraphs [0110]-[0115], The base polymer may further comprise other recurring units. Typical of the other recurring units are recurring units having an oxirane or oxetane ring. A polymer comprising recurring units having an oxirane or oxetane ring is crosslinked in exposed regions, leading to improvements in retention and etching resistance of a resist film in exposed regions.

The base polymer may further comprise still other recurring units, for example, units derived from substituted acrylates such as methyl crotonate, dimethyl maleate, and dimethyl itaconate, unsaturated carboxylic acids such as maleic acid, fumaric acid, and itaconic acid, cyclic olefins such as norbornene, norbornene derivatives, tetracyclo$[6.2.1.1^{3,6}.0^{2,7}]$dodecene derivatives, unsaturated acid anhydrides such as itaconic anhydride, vinyl aromatics such as styrene, tert-butoxystyrene, vinylnaphthalene, acetoxystyrene, and acenaphthylene, and other monomers.

The base polymer should preferably have a Mw of 1,000 to 500,000, more preferably 3,000 to 100,000, and even more preferably 4,000 to 20,000. A Mw within the range eliminates an extreme drop of etching resistance and provides satisfactory resolution due to a difference in dissolution rate before and after exposure. As used herein, Mw is measured versus polystyrene standards by GPC. Also preferably the polymer has a dispersity (Mw/Mn) of 1.20 to 2.50, more preferably 1.30 to 2.00.

The polymer may be synthesized by any method, for example, by using one or more monomers corresponding to the desired recurring units in an organic solvent, adding a radical polymerization initiator, and heating for polymerization. For the polymerization method, reference should be made to U.S. Pat. No. 9,256,127 (JP-A 2015-214634, paragraphs [0134]-[0137]). The acid labile group that has been incorporated in the monomer may be kept as such, or polymerization may be followed by protection or partial protection.

While the base polymer comprises recurring units derived from monomers, the molar fractions of respective units preferably fall in the following range (mol %), but are not limited thereto:

(I) 10 to 70 mol %, more preferably 20 to 65 mol %, even more preferably 30 to 60 mol % of recurring units of at least one type selected from recurring units (a) and (b), (II) 0 to 90 mol %, more preferably 15 to 80 mol %, even more preferably 30 to 60 mol % of recurring units (c) of at least one type, and optionally, (III) 0 to 30 mol %, more preferably 0 to 20 mol %, and even more preferably 0 to 15 mol % of recurring units of at least one type selected from recurring units (d1) to (d4), and optionally, (IV) 0 to 80 mol %, more preferably 0 to 70 mol %, and even more preferably 0 to 50 mol % of recurring units of at least one type selected from recurring units (e) and other recurring units.

The base polymer (A) may be used alone or in a combination of two or more polymers which are different in compositional ratio, Mw and/or Mw/Mn. In addition to the polymer, a hydrogenated product of ring-opening metathesis polymerization (ROMP) polymer may be used. The hydrogenated ROMP polymer is as described in JP-A 2003-066612.

(B) Photoacid Generator

The resist composition should comprise (B) a photoacid generator, which is sometimes referred to as PAG of addition type, when the base polymer does not contain any of recurring units (d1) to (d4). It is noted that a PAG of addition type may be added to even when the base polymer contains recurring units of at least one type selected from recurring units (d1) to (d4).

The PAG of addition type may be any compound capable of generating an acid upon exposure to high-energy radiation. Suitable PAGs include sulfonium salts, iodonium salts, sulfonyldiazomethanes, N-sulfonyloxydicarboxyimides, O-arylsulfonyloximes, and O-alkylsulfonyloximes, which may be used alone or in admixture. Suitable examples are described in JP-A 2007-145797, paragraphs [0102]-[0113], JP-A 2008-111103, paragraphs [0122]-[0142], JP-A 2014-001259, paragraphs [0081]-[0092], JP-A 2012-041320, JP-A 2012-153644, JP-A 2012-106986, and JP-A 2016-018007. The PAGs capable of generating partially fluorinated sulfonic acids described in the foregoing patent documents are preferably used in a resist composition because the strength and diffusion length of the generated acid are appropriate in the ArF lithography.

Preferred as the PAG (B) are sulfonium salts having the formula (5A) and iodonium salts having the formula (5B).

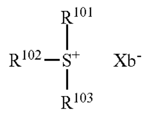

(5A)

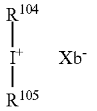

(5B)

In formulae (5A) and (5B), $R^{101}$, $R^{102}$, $R^{103}$, $R^{104}$ and $R^{105}$ are each independently a $C_1$-$C_{20}$ hydrocarbyl group which may contain a heteroatom. Examples of the hydrocarbyl group are as exemplified above for $R^{31}$ to $R^{41}$ in formulae (d1) to (d4). Any two of $R^{101}$, $R^{102}$ and $R^{103}$ may bond together to form a ring with the sulfur atom to which they are attached, and $R^{104}$ and $R^{105}$ may bond together to form a ring with the iodine atom to which they are attached. Examples of the ring include those exemplified above for the ring that any two of $R^{M1}$, $R^{M2}$ and $R^{M3}$, taken together, form with the sulfur atom to which they are attached, in formula (M-1), and those exemplified above for the ring that $R^{M4}$ and $R^{M5}$, taken together, form with the iodine atom to which they are attached, in formula (M-2). $R^{101}$ to $R^{105}$ are preferably of a structure containing a phenyl group which is bonded to $S^+$ or $I^+$ in the formula.

The sulfonium cation of the sulfonium salt having formula (5A) is described in JP-A 2014-001259, paragraphs [0082]-[0085], Exemplary sulfonium cations include those described in JP-A 2007-145797, paragraphs [0027]-[0033], JP-A 2010-113209, paragraph [0059], JP-A 2012-041320, JP-A 2012-153644, and JP-A 2012-106986, as well as those exemplified above for the sulfonium cation $M^+$ in formula (1).

Preferred examples of the cation of the sulfonium salt having formula (5A) are given below, but not limited thereto.

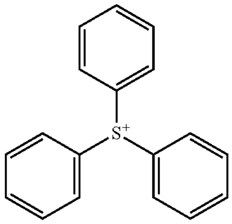
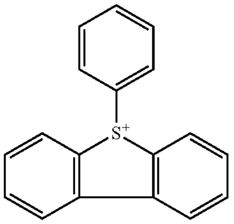
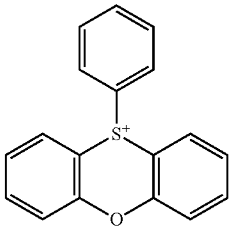
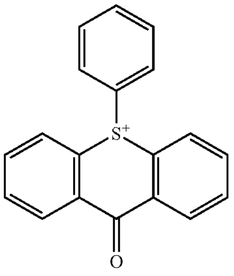
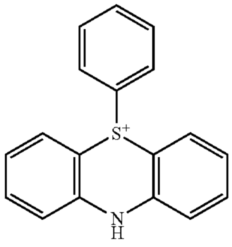
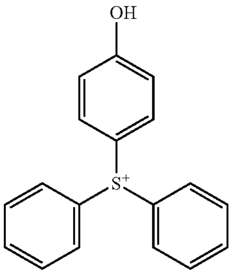
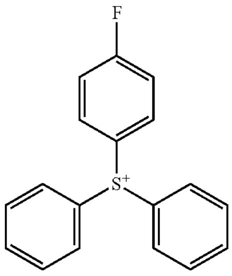
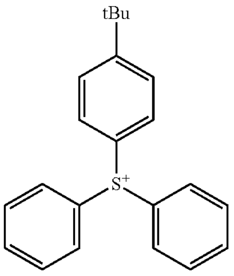
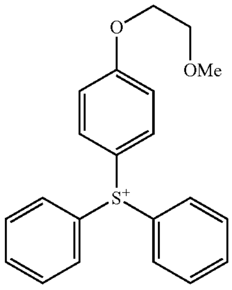
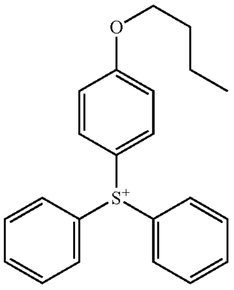
-continued
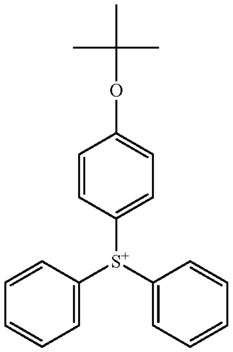
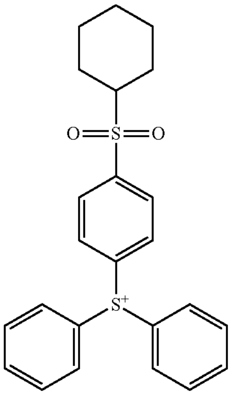
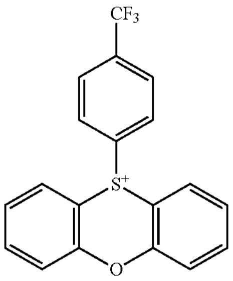
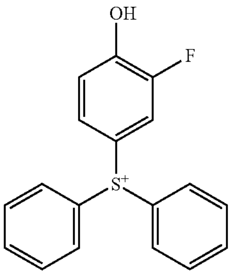
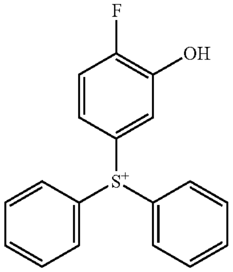
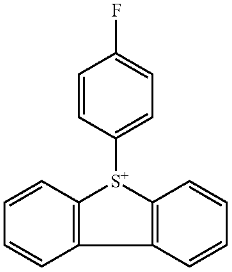
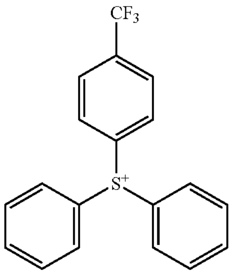
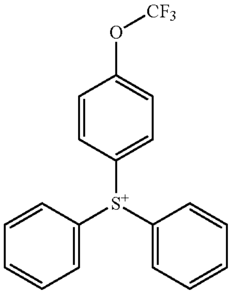
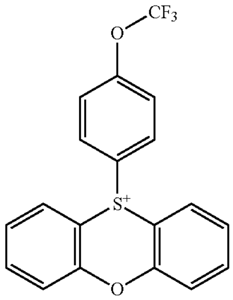
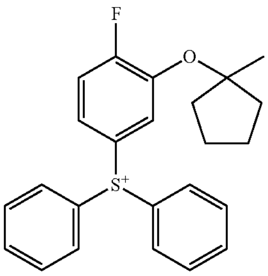

-continued

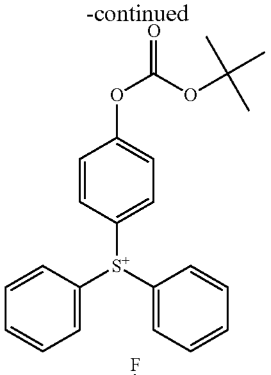

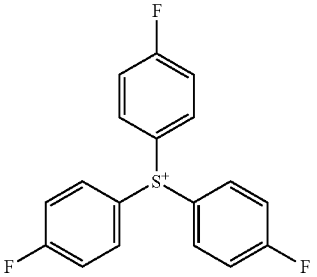

Specific examples of the cation of the sulfonium salt having formula (5A) include triphenylsulfonium, S-phenyldibenzothiophenium, (4-tert-butylphenyl)diphenylsulfonium, (4-fluorophenyl)diphenylsulfonium, and (4-hydroxyphenyl)diphenylsulfonium cations.

Examples of the cation of the iodonium salt having formula (5B) include those exemplified above for the iodonium cation $M^+$ in formula (1), with diphenyliodonium and di-tert-butylphenyliodonium cations being preferred.

In formulae (5A) and (5B), $Xb^-$ is an anion having the formula (6A) or (6B).

$$R^{fa}—CF_2—SO_3^- \tag{6A}$$

(6B)

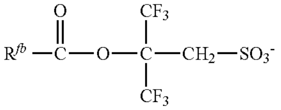

In formulae (6A) and (6B), $R^{fa}$ is fluorine, a $C_1$-$C_4$ perfluoroalkyl group, or a $C_1$-$C_{40}$ hydrocarbyl group which may contain a heteroatom, in which —$CH_2$— may be replaced by —O— or —C(═O)—. $R^{fb}$ is a $C_1$-$C_{40}$ hydrocarbyl group which may contain a heteroatom such as oxygen, sulfur, nitrogen or halogen, and in which —$CH_2$— may be replaced by —O— or —C(═O)—.

Preferred examples of the anion having formula (6A) include trifluoromethanesulfonate and nonafluorobutanesulfonate anions, and anions having the formula (6A').

(6A')

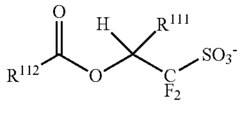

In formula (6A'), $R^{111}$ is hydrogen or trifluoromethyl, preferably trifluoromethyl. $R^{112}$ is a $C_1$-$C_{35}$ hydrocarbyl group in which some or all of the hydrogen atoms may be substituted by a moiety containing a heteroatom such as oxygen, sulfur, nitrogen or halogen, and in which —$CH_2$— may be replaced by —O— or —C(═O)—. The anion having formula (6A') is described in JP-A 2007-145797, JP-A 2008-106045, JP-A 2009-007327, JP-A 2009-258695, and JP-A 2012-181306. Examples of the anion having formula (6A) include those described in these patent documents and those exemplified above as the anion having formula (d1-1).

The anion having formula (6B) is described in JP-A 2010-215608 and JP-A 2014-133723. Examples of the anion having formula (6B) include those described in these patent documents and those exemplified above as the anion having formula (d1-2). Notably, the compound having the anion of formula (6B) does not have fluorine at the α-position relative to the sulfo group, but two trifluoromethyl groups at the (3-position. For this reason, it has a sufficient acidity to sever the acid labile groups in the base polymer. Thus the compound is an effective PAG.

Preferred examples of the anion $Xb^-$ are shown below, but not limited thereto. Herein $R^{HF}$ is hydrogen or trifluoromethyl.

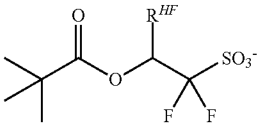

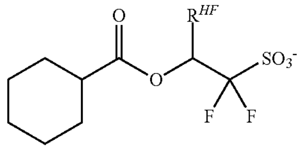

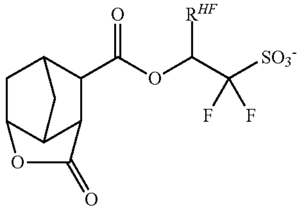

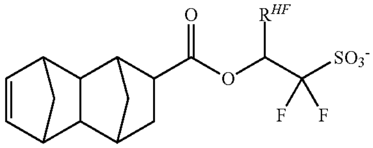

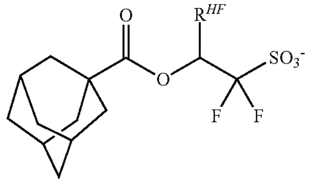

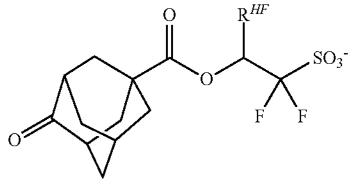

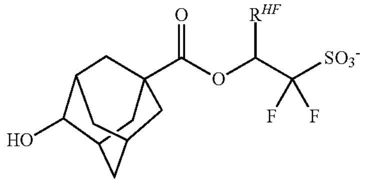

-continued
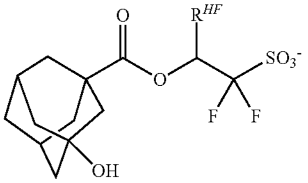
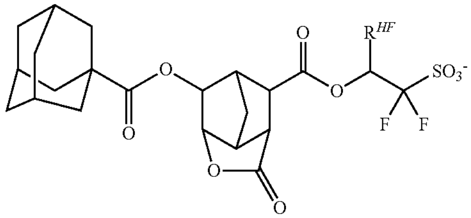
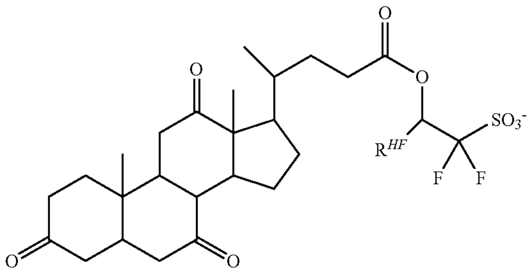
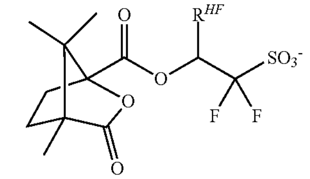
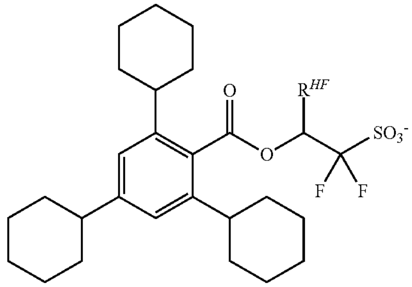
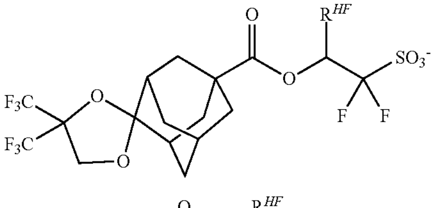
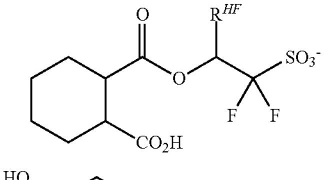
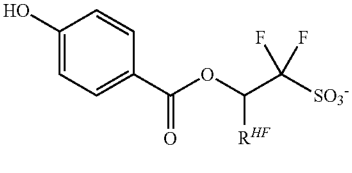
-continued
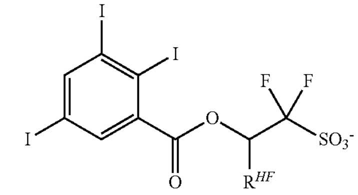
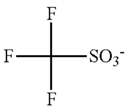
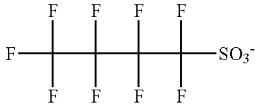
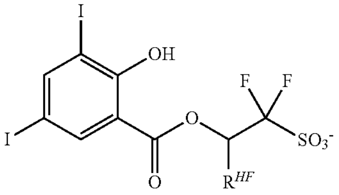
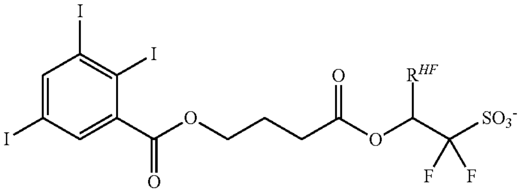
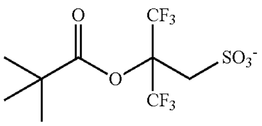
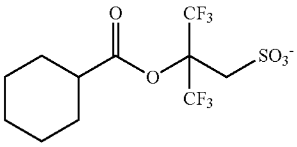
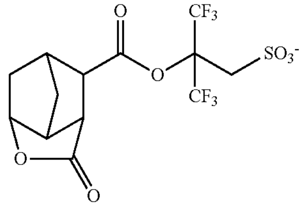
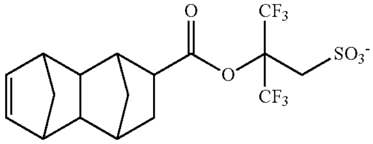
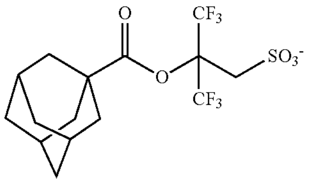
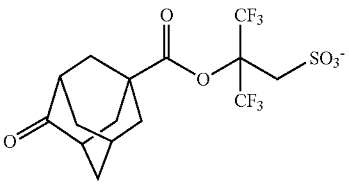
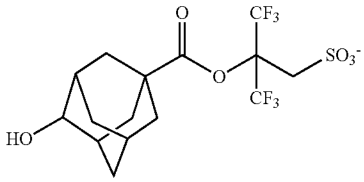

-continued

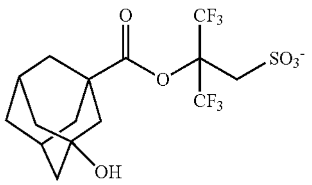

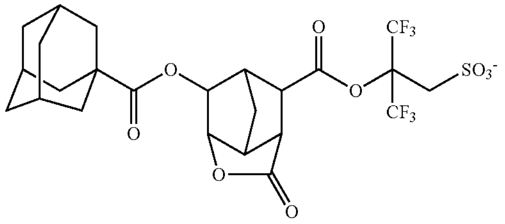

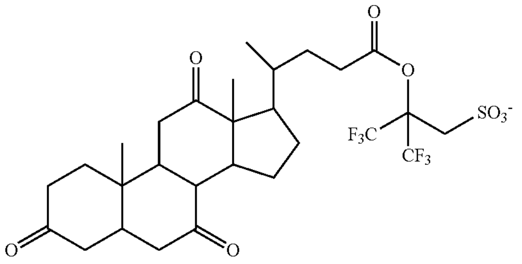

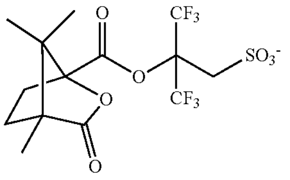

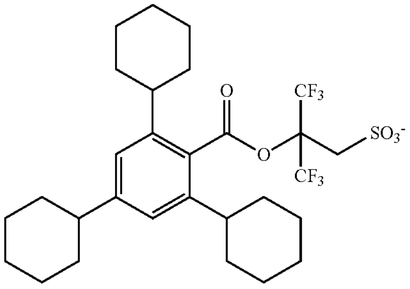

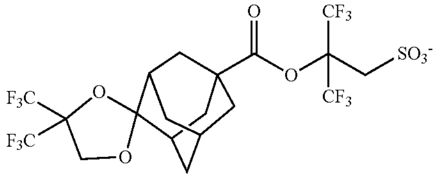

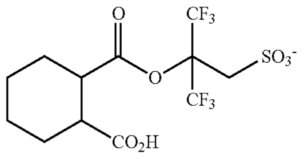

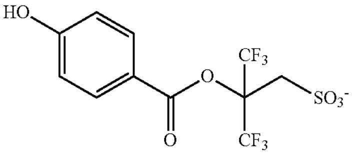

-continued

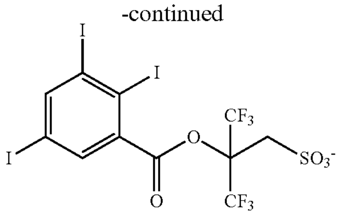

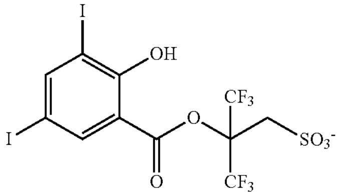

Exemplary structures for the PAG having formula (5A) or (5B) include arbitrary combinations of cations with anions, both as exemplified above, but are not limited thereto.

Another preferred example of the PAG (B) is a compound having the formula (7).

(7)

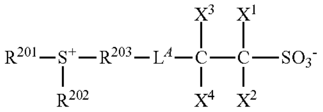

In formula (7), $R^{201}$ and $R^{202}$ are each independently a $C_1$-Cho hydrocarbyl group which may contain a heteroatom. $R^{203}$ is a $C_1$-$C_{30}$ hydrocarbylene group which may contain a heteroatom. Any two of $R^{201}$, $R^{202}$ and $R^{203}$ may bond together to form a ring with the sulfur atom to which they are attached. $L^A$ is a single bond, ether bond, ester bond, or a $C_1$-$C_{20}$ hydrocarbylene group which may contain a heteroatom, in which —$CH_2$— may be replaced by —O— or —C(=O)—. The constituent —$CH_2$— in the hydrocarbyl group may be one bonding to the carbon atom and/or $R^{203}$ in formula (7). $X^1$, $X^2$, $X^3$ and $X^4$ are each independently hydrogen, fluorine or trifluoromethyl, with at least one thereof being fluorine or trifluoromethyl.

Of the compounds having formula (7), those having formula (7') are more preferred.

(7')

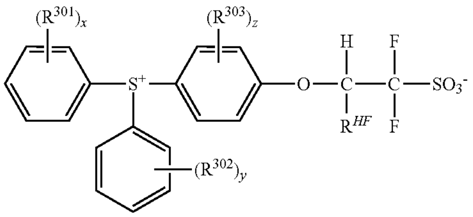

In formula (7'), $R^{HF}$ is hydrogen or trifluoromethyl, preferably trifluoromethyl. $R^{301}$, $R^{302}$ and $R^{303}$ are each independently a $C_1$-$C_{20}$ hydrocarbyl group in which some or all of the hydrogen atoms may be substituted by a moiety containing a heteroatom such as oxygen, sulfur, nitrogen or halogen, and in which —$CH_2$— may be replaced by —O— or —C(=O)—. The constituent —$CH_2$— in the hydrocarbyl group may be one bonding to a carbon atom on the benzene ring in formula (7'). The subscripts x and y are each independently an integer of 0 to 5, and z is an integer of 0 to 4.

The PAG having formula (7) or (7') is described in JP-A 2011-016746. Examples thereof include those exemplified for the sulfonium salt in the same patent document and those exemplified for the sulfonium salt in JP-A 2015-214634, paragraphs [0149]-[0150], Specific examples of the PAG having formula (7) are given below, but not limited thereto. Herein $R^{HF}$ is as defined above.

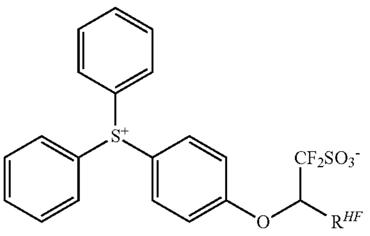

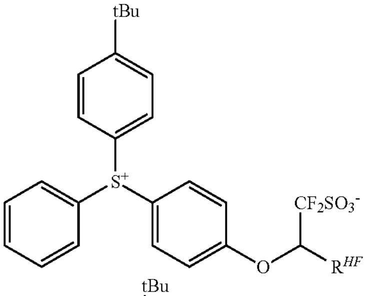

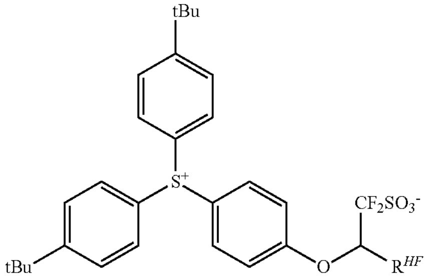

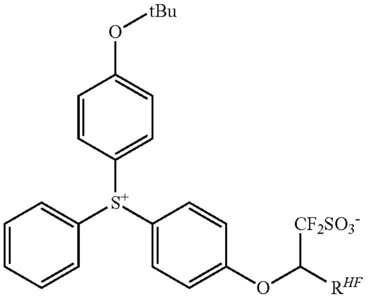

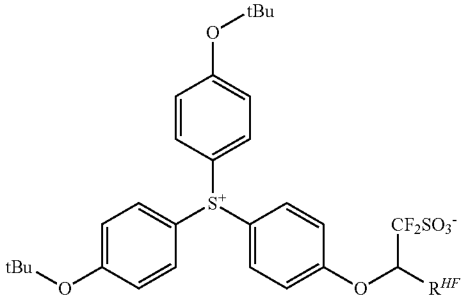

-continued

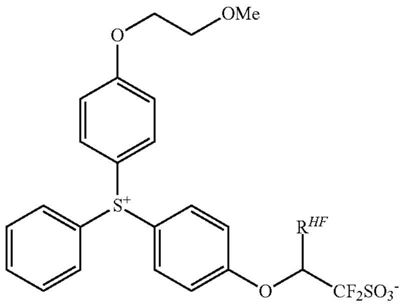

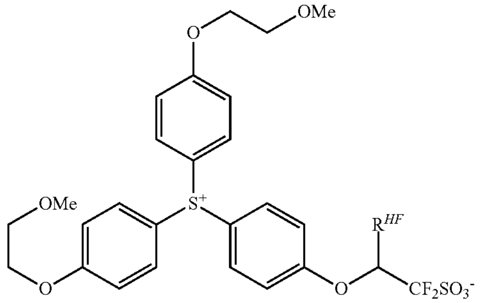

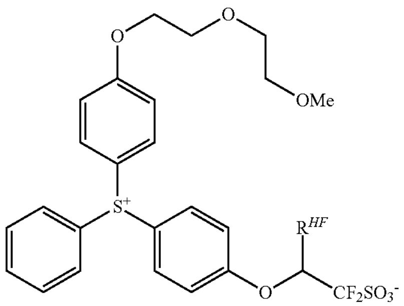

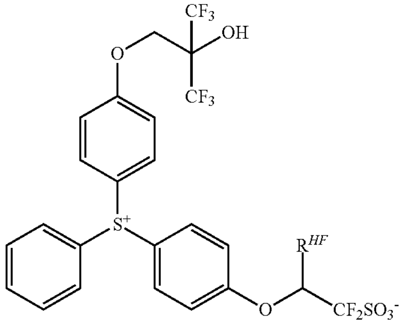

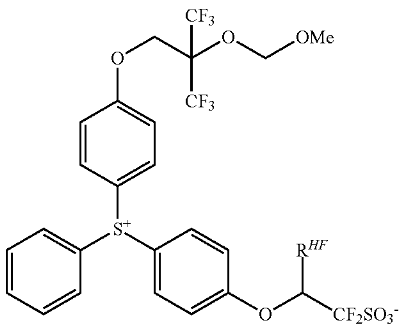

-continued

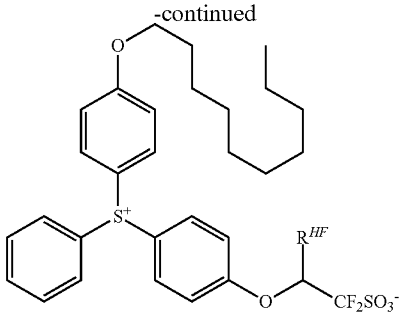

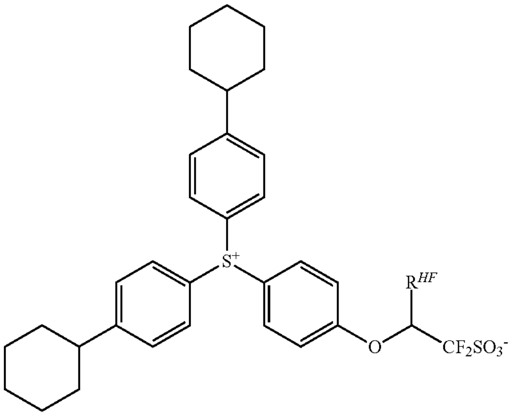

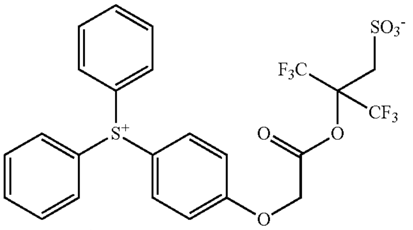

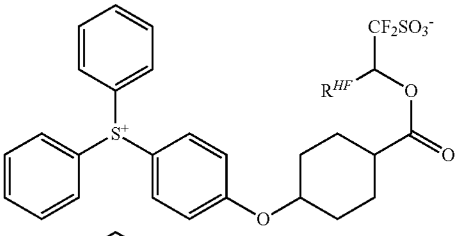

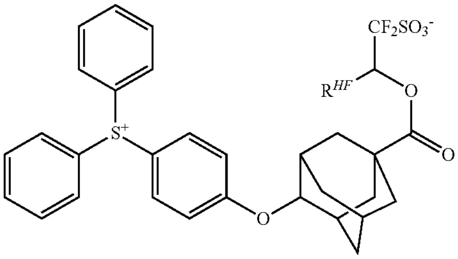

The PAG (B) is preferably added in an amount of 1 to 30 parts by weight, more preferably 2 to 25 parts by weight, even more preferably 4 to 20 parts by weight per 100 parts by weight of the base polymer (A). The PAG in the range eliminates the problems of degradation of resolution and formation of foreign matter after development or during stripping. The PAG may be used alone or in admixture.

(C) Acid Diffusion Inhibitor

The resist composition further comprises (C) an acid diffusion inhibitor. Component (C) should contain (C-1) the onium salt compound having formula (1) as an essential component and may contain (C-2) an acid diffusion inhibitor other than the onium salt compound having formula (1). As used herein, the “acid diffusion inhibitor” refers to a compound capable of holding down the diffusion rate when the acid generated by the PAG diffuses in the resist film.

The acid diffusion inhibitor (C-2) is typically selected from amine compounds and onium salts of weak acids such as α-non-fluorinated sulfonic acids and carboxylic acids.

Examples of the amine compound include primary, secondary, and tertiary amine compounds, specifically amine compounds having a hydroxyl group, ether bond, ester bond, lactone ring, cyano group or sulfonate bond. Primary and secondary amine compounds protected with a carbamate group are also included. Such protected amine compounds are effective when the resist composition contains a base labile component. Suitable acid diffusion inhibitors include the compounds described in JP-A 2008-111103, paragraphs [0146]-[0164], and JP 3790649 as well as the following compounds, but are not limited thereto.

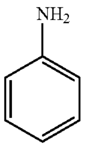
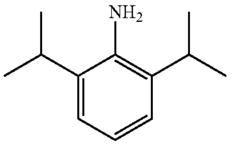
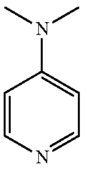

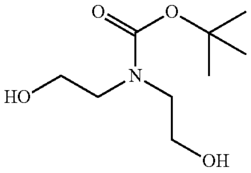
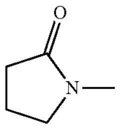
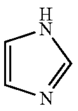

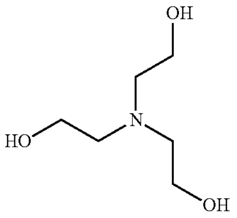
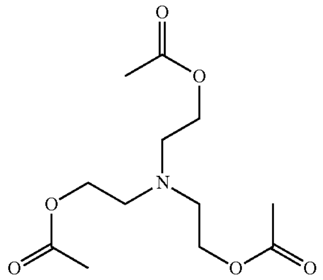

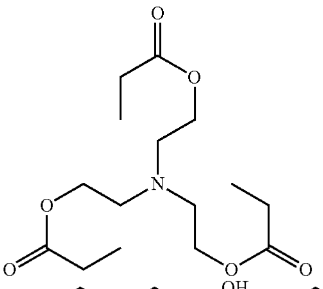
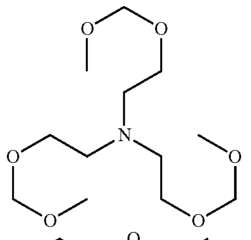

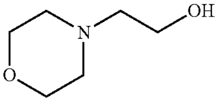
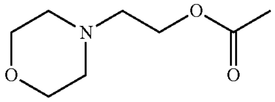

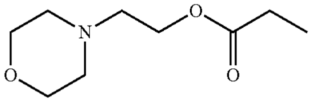

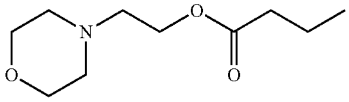

-continued
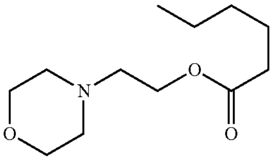
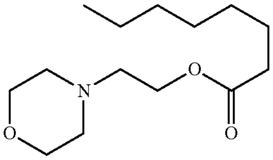
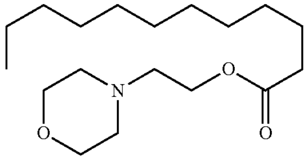
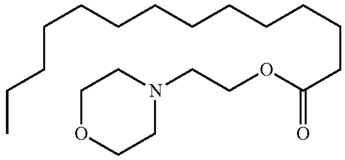
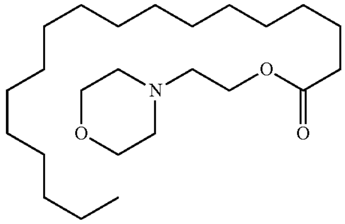
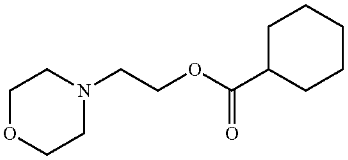
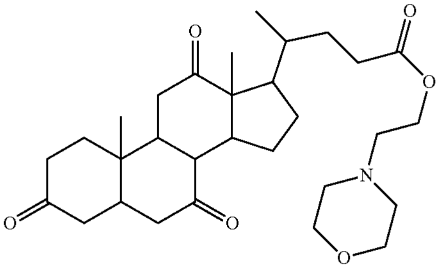
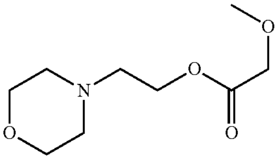
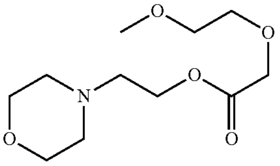
-continued
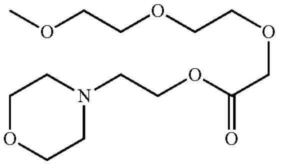
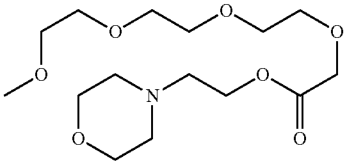
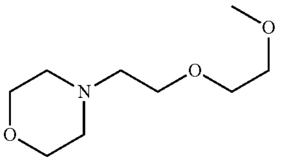
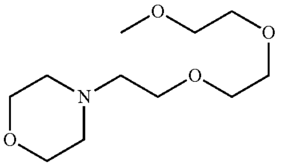
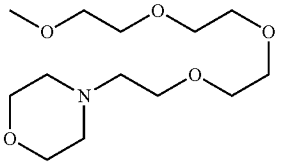
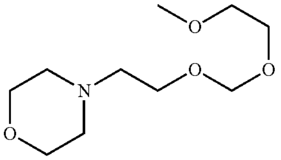
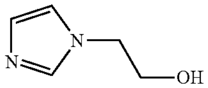
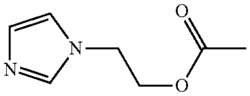
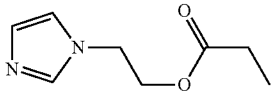
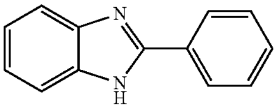
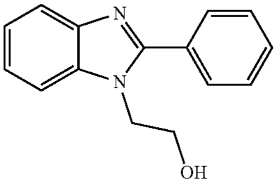
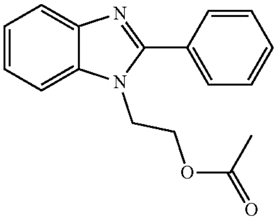
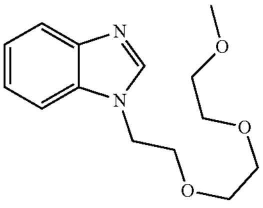

-continued

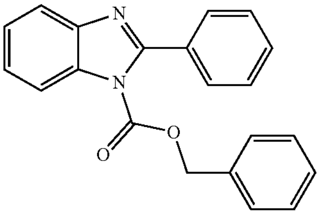

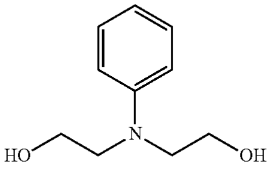

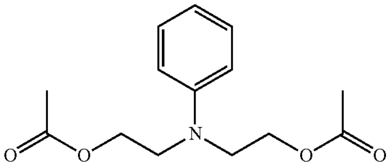

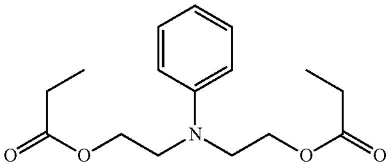

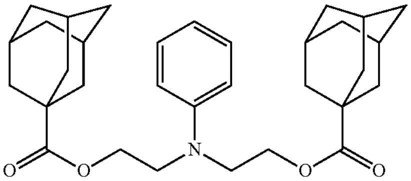

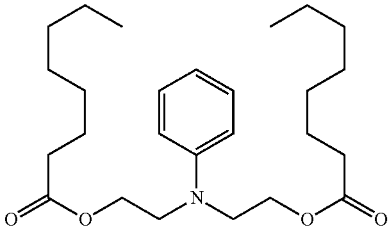

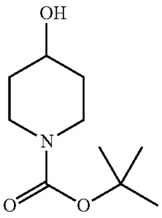

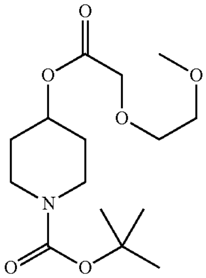

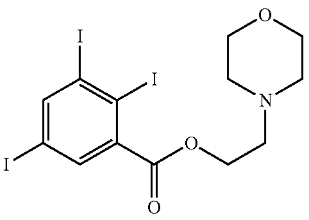

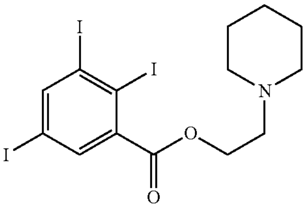

-continued

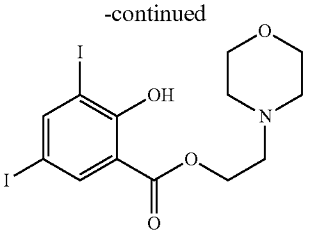

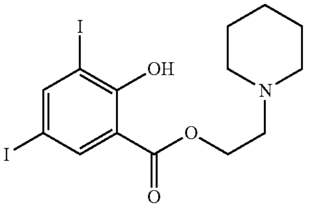

Suitable onium salts of α-non-fluorinated sulfonic acids and carboxylic acids include onium salt compounds having the formulae (8A) and (8B).

$$R^{q1}—SO_3^- \quad Mq^+ \qquad (8A)$$

$$R^{q2}—CO_2^- \quad Mq^+ \qquad (8B)$$

In formula (8A), $R^{q1}$ is hydrogen, methoxy, or a $C_1$-$C_{40}$ hydrocarbyl group which may contain a heteroatom, exclusive of the group wherein hydrogen bonded to the carbon atom at α-position relative to the sulfo group is substituted by fluorine or fluoroalkyl.

In formula (8B), $R^{q2}$ is hydrogen, hydroxyl or a $C_1$-$C_{40}$ hydrocarbyl group which may contain a heteroatom.

In formulae (8A) and (8B), $Mq^+$ is an onium cation, which is preferably selected from cations having the formulae (9A), (9B) and (9C).

(9A)

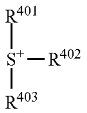

$$R^{404}—I^+—R^{405} \qquad (9B)$$

(9C)

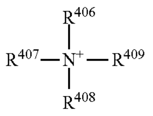

In formulae (9A) to (9C), $R^{401}$ to $R^{409}$ are each independently a $C_1$-$C_{40}$ hydrocarbyl group which may contain a heteroatom. A pair of $R^{401}$ and $R^{402}$, $R^{404}$ and $R^{405}$, or $R^{406}$ and $R^{407}$ may bond together to form a ring with the sulfur, iodine or nitrogen atom to which they are attached.

The optionally heteroatom-containing $C_1$-$C_{40}$ hydrocarbyl group, represented by $R^{q1}$, may be saturated or unsaturated and straight, branched or cyclic. Examples thereof include alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, and n-decyl; cyclic saturated hydrocarbyl groups such as cyclopentyl, cyclohexyl, cyclopentylmethyl, cyclopentylethyl, cyclopentyl-butyl, cyclohexylmethyl, cyclohexylethyl, cyclohexylbutyl, norbornyl, tricyclo[5.2.1.$0^{2,6}$]decanyl, adamantyl, and adamantylmethyl; alkenyl groups such as vinyl, allyl, propenyl, butenyl, and hexenyl; cyclic unsaturated hydrocarbyl groups such as cyclohexenyl; aryl groups such as phenyl and naphthyl; heteroaryl groups such as thienyl; hydroxyphenyl groups such as 4-hydroxyphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, 2,4-dimethylphenyl and 2,4,6-triisopropylphenyl; alkylnaphthyl groups such as methylnaphthyl and ethylnaphthyl; alkoxynaphthyl groups such as methoxynaphthyl, ethoxynaphthyl, n-propoxynaphthyl and n-butoxynaphthyl; dialkylnaphthyl groups such as dimethylnaphthyl and diethylnaphthyl; dialkoxynaphthyl groups such as dimethoxynaphthyl and diethoxynaphthyl; aralkyl groups such as benzyl, 1-phenylethyl and 2-phenylethyl; aryloxoalkyl groups, typically 2-aryl-2-oxoethyl groups such as 2-phenyl-2-oxoethyl, 2-(l-naphthyl)-2-oxoethyl, 2-(2-naphthyl)-2-oxoethyl; and combinations thereof. In the hydrocarbyl groups, some or all of the hydrogen atoms may be substituted by a moiety containing a heteroatom such as oxygen, sulfur, nitrogen or halogen, and a moiety containing a heteroatom such as oxygen, sulfur or nitrogen may intervene in a carbon-carbon bond, so that the group may contain a hydroxyl moiety, cyano moiety, carbonyl moiety, ether bond, ester bond, sulfonic acid ester bond, carbonate bond, lactone ring, sultone ring, carboxylic anhydride, or haloalkyl moiety.

The optionally heteroatom-containing $C_1$-$C_{40}$ hydrocarbyl group, represented by $R^{q2}$, may be saturated or unsaturated and straight, branched or cyclic. Examples thereof include those exemplified above for $R^{q1}$ and fluorinated alkyl groups such as trifluoromethyl, trifluoroethyl, 2,2,2-trifluoro-1-methyl-1-hydroxyethyl, and 2,2,2-trifluoro-1-(trifluoromethyl)-1-hydroxyethyl and fluorinated aryl groups such as pentafluorophenyl and 4-trifluoromethylphenyl.

The sulfonic acid onium salt having formula (8A) and the carboxylic acid onium salt having formula (8B) are described in JP-A 2008-158339 and JP-A 2010-155824. Examples thereof are as exemplified in these patent documents.

Examples of the anion in the sulfonic acid onium salt having formula (8A) are shown below, but not limited thereto.

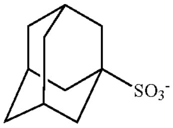
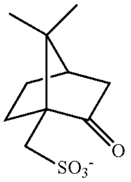
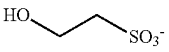
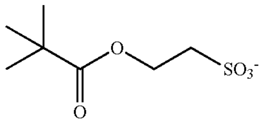
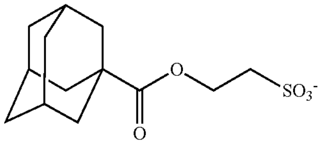

-continued

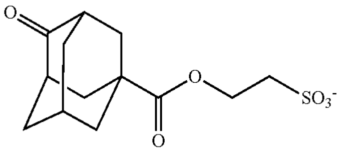
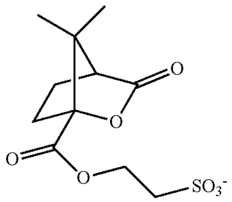
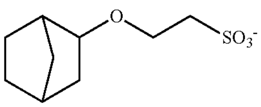
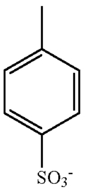
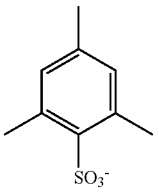
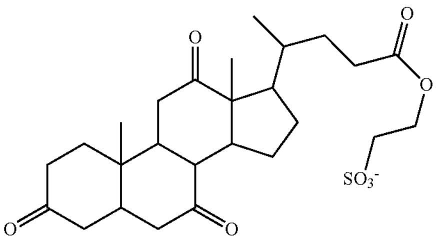
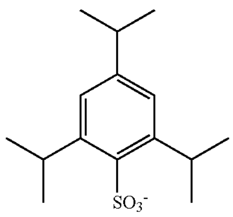
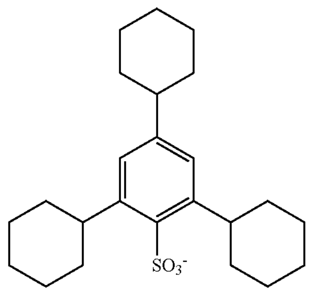
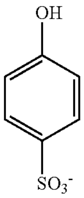
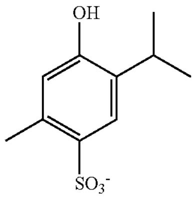
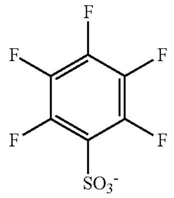
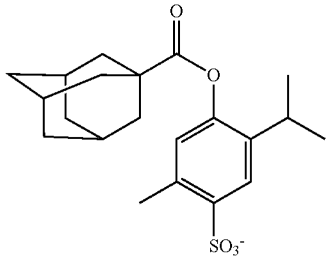

-continued
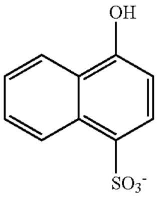
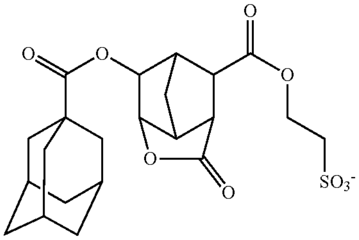
Examples of the anion in the carboxylic acid onium salt having formula (8B) are shown below, but not limited thereto.
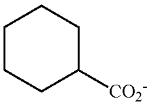
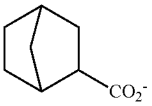
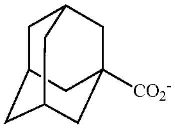
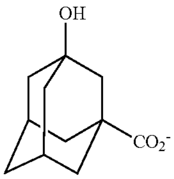
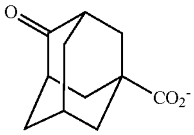
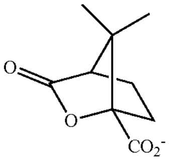
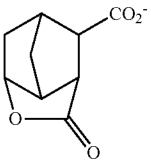
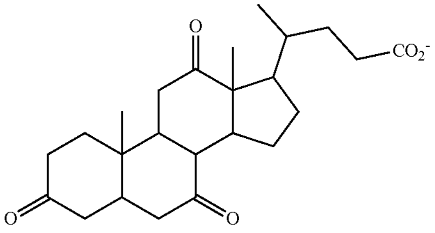
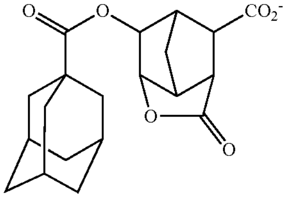
-continued
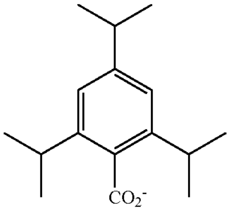
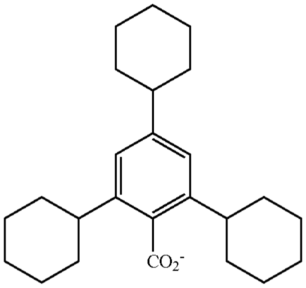
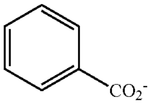
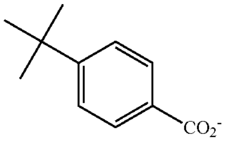
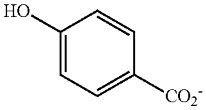
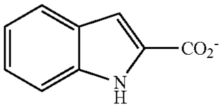
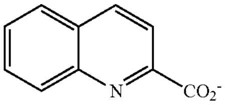
$CF_3CO_2^-$
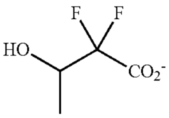
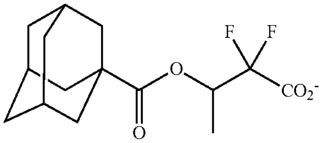
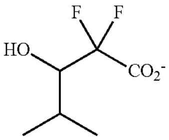
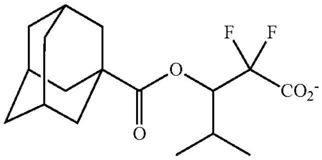
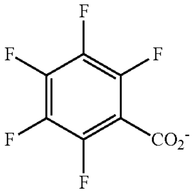
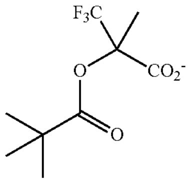
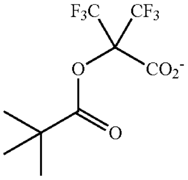
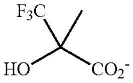
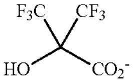
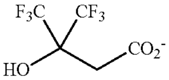
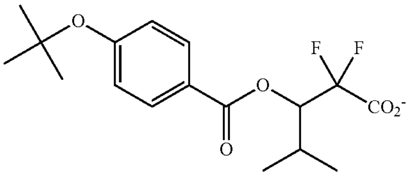

-continued

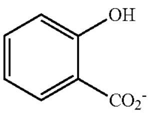

Examples of the cation in formula (9A) and the cation in formula (9B) are as exemplified above for the cation in formula (M-1) and the cation in formula (M-2), respectively, but not limited thereto. Examples of the cation in formula (9C) include tetramethylammonium, tetraethylammonium, tetrabutylammonium, trimethylbenzyl, and trimethylphenyl cations, but are not limited thereto. Inter alia, more preferred cations are shown below.

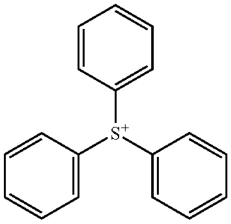

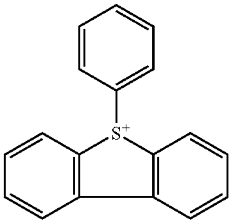

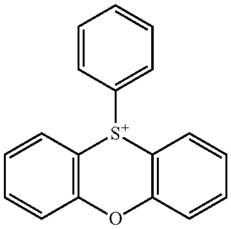

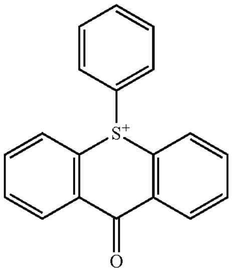

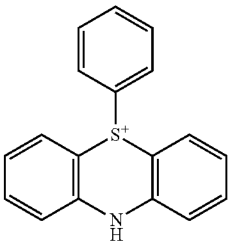

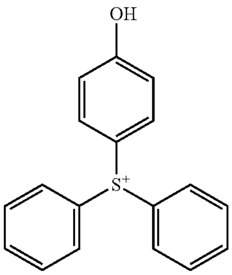

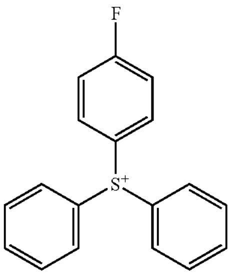

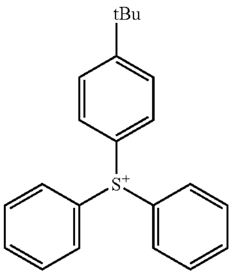

-continued

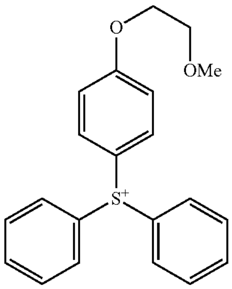

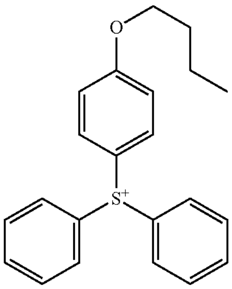

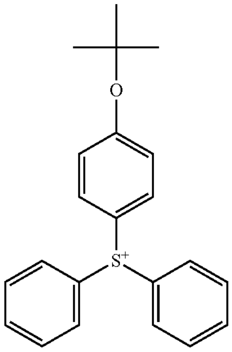

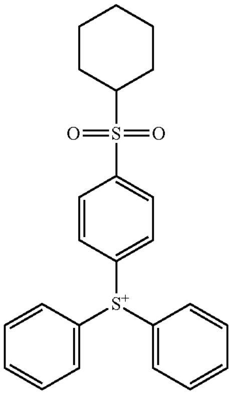

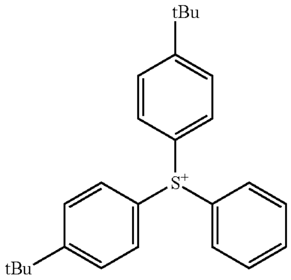

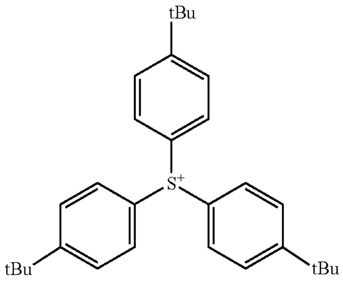

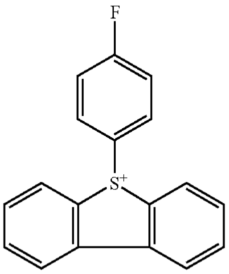

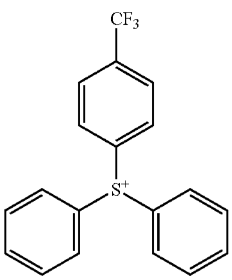

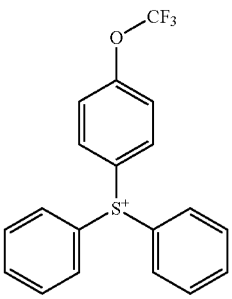

-continued

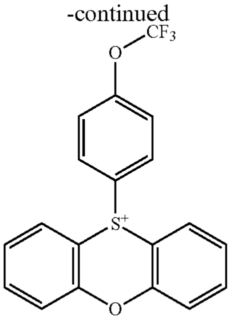

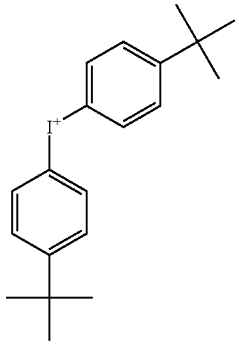

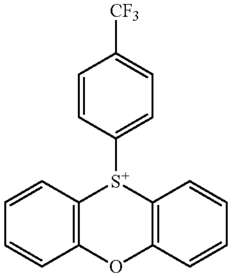

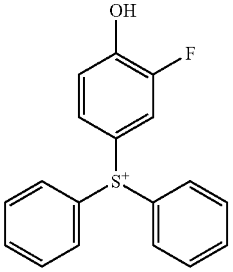

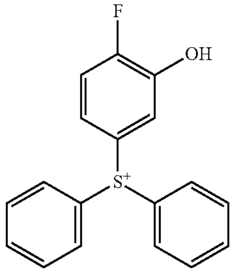

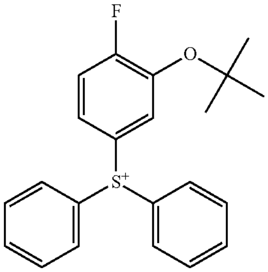

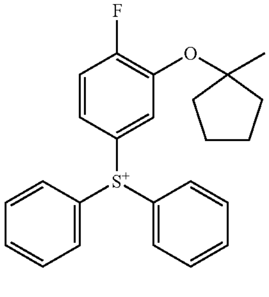

Examples of the sulfonic acid onium salt having formula (8A) and the carboxylic acid onium salt having formula (8B) include arbitrary combinations of anions with cations, both as exemplified above. These onium salts may be readily synthesized by ion exchange reaction according to any well-known organic chemistry technique. For the ion exchange reaction, reference may be made to JP-A 2007-145797, for example.

The onium salt having formula (8A) or (8B) functions as an acid diffusion inhibitor in the resist composition because the counter anion of the onium salt is a conjugated base of a weak acid. As used herein, the weak acid indicates an acidity insufficient to deprotect an acid labile group from an acid labile group-containing unit in the base polymer. The onium salt having formula (8A) or (8B) functions as an acid diffusion inhibitor when used in combination with an onium salt type PAG having a conjugated base of a strong acid (typically α-fluorinated sulfonic acid) as the counter anion. In a system using a mixture of an onium salt capable of generating a strong acid (e.g., α-fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

Since the onium salt compound having formula (8A) or (8B) wherein $Mq^+$ is a sulfonium cation (9A) or iodonium cation (9B) is photo-decomposable, the quenching ability is reduced and the concentration of strong acid derived from the PAG is increased in the region with high light intensity. Thus the contrast is improved in the exposed region. As a result, a pattern with improved LWR or CDU can be formed.

In case the acid labile group is an acetal group which is quite sensitive to acid, the acid for eliminating the protective group need not necessarily be an α-fluorinated sulfonic acid, imide acid or methide acid. Sometimes, deprotection reaction can take place even with an α-non-fluorinated sulfonic acid. In this case, an amine compound or carboxylic acid onium salt having formula (8B) is preferably used as the acid diffusion inhibitor.

Besides the onium salt, a betaine type compound of weak acid may also be used as the acid diffusion inhibitor. Suitable betaine type compounds are shown below, but not limited thereto.

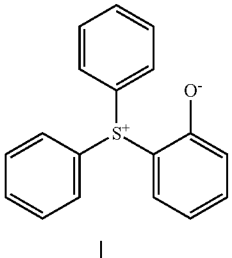

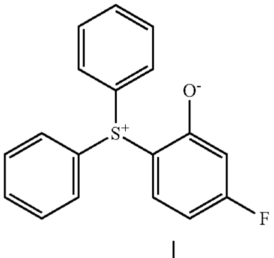

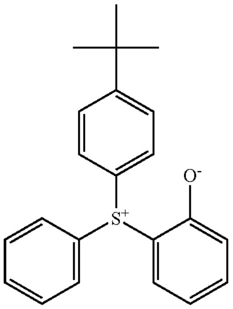

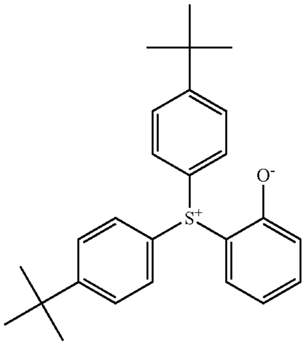

-continued

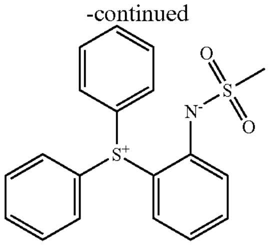

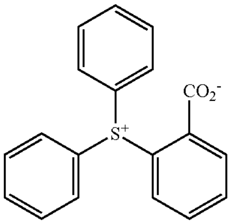

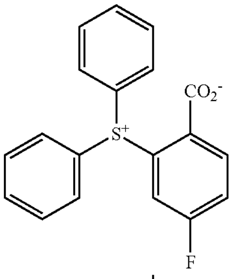

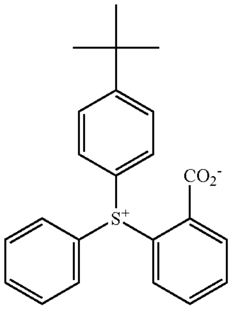

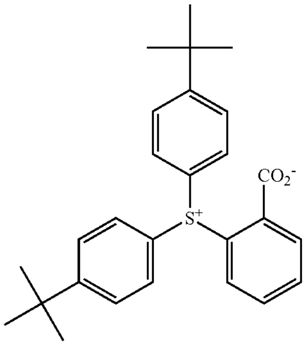

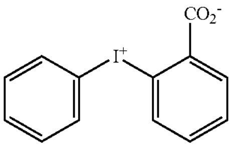

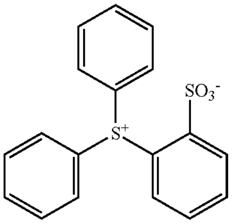

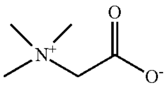

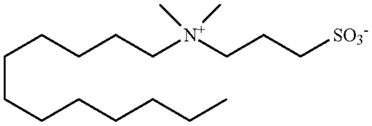

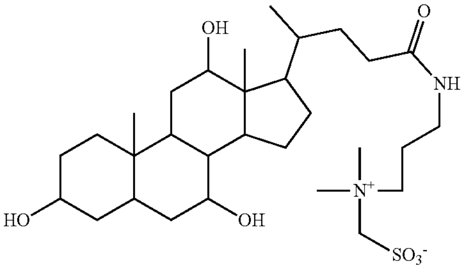

Besides the foregoing compounds, sulfonium or iodonium salts having $Cl^-$, $Br^-$ or $NO_3^-$ as the anion may be used as the acid diffusion inhibitor. Examples include triphenylsulfonium chloride, diphenyliodonium chloride, triphenylsulfonium bromide, and triphenylsulfonium nitrate. Since the conjugate acid corresponding to the anion has a low boiling point, the acid created after quenching of strong acid is readily removed from the resist film during PEB or the like. Due to easy removal of acid from within the resist film, acid diffusion is fully suppressed, resulting in an improvement in contrast.

Also a photo-decomposable onium salt having a nitrogen-containing substituent may be used as the acid diffusion inhibitor. The photo-decomposable onium salt functions as an acid diffusion inhibitor in the unexposed region, but as a so-called photo-degradable base in the exposed region because it loses the acid diffusion inhibitory ability due to neutralization thereof with the acid generated by itself. Using a photo-degradable base, the contrast between exposed and unexposed regions can be further enhanced. With respect to the photo-degradable base, reference may be made to JP-A 2009-109595, 2012-046501, and 2013-209360, for example.

Examples of the anion in the photo-degradable onium salt are shown below, but not limited thereto. Herein $R^{HF}$ is hydrogen or trifluoromethyl.

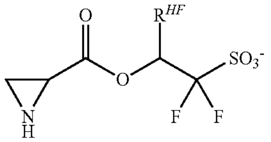

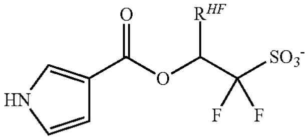

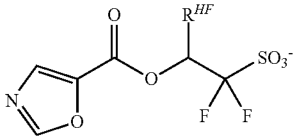

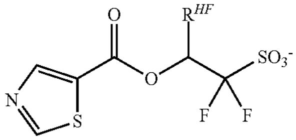

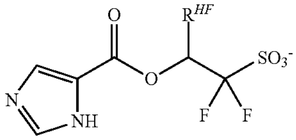

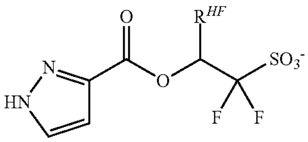

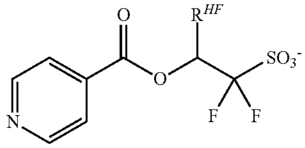

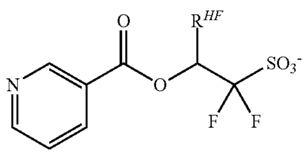

-continued
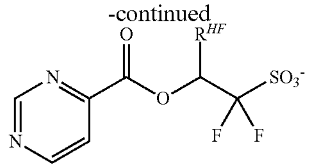
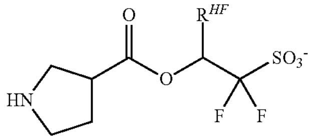
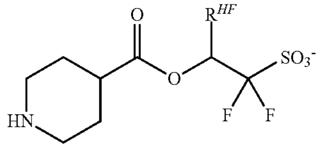
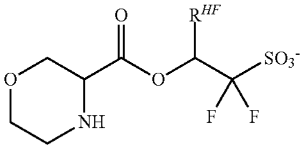
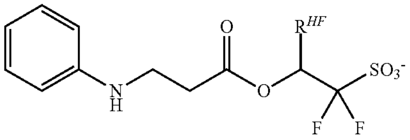
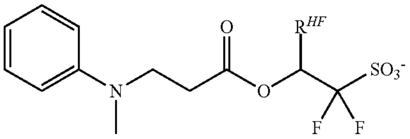
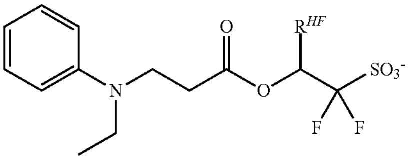
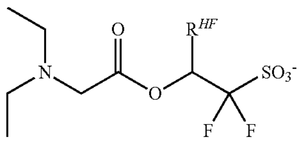
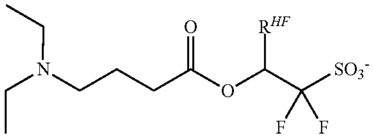
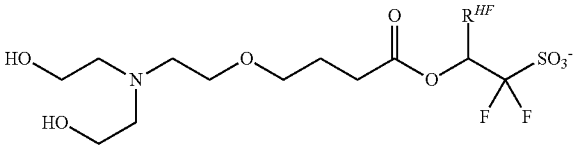
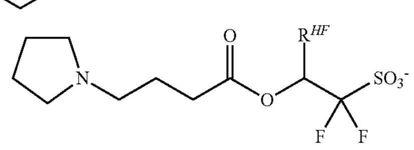
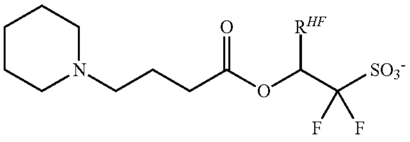
-continued
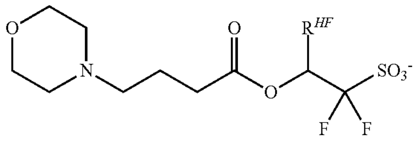
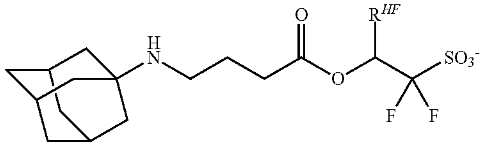
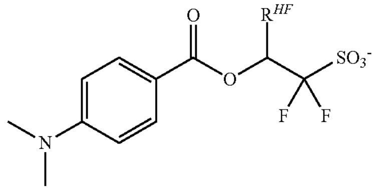
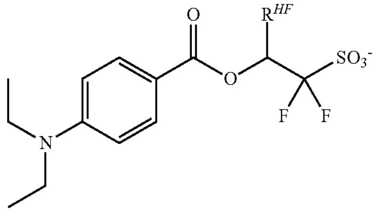
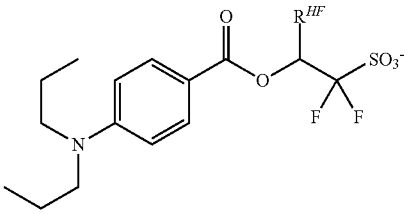
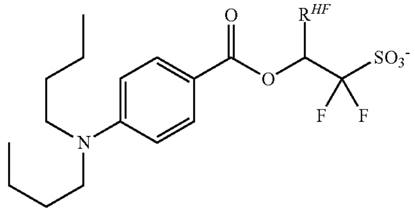
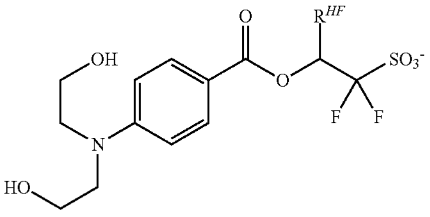
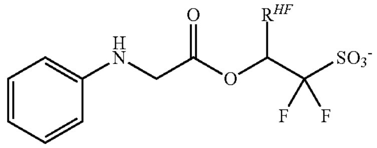
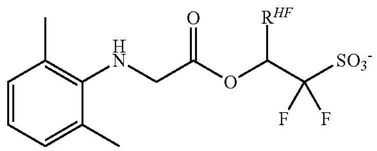

-continued
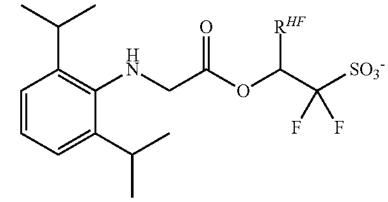
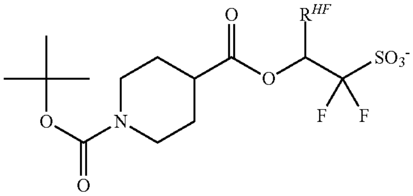
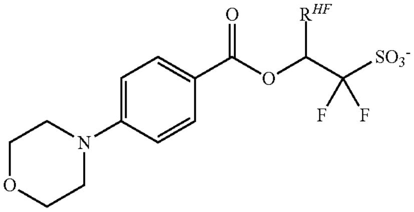
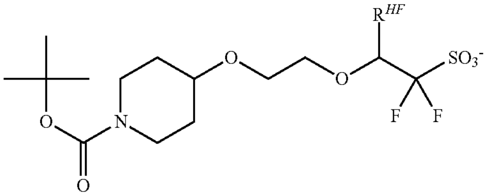
Examples of the cation in the photo-degradable onium salt are as exemplified above for the cation $M^+$ in formula (1). Inter aha, the following cations are preferred, but not limitative.
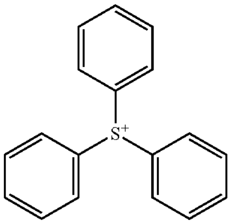
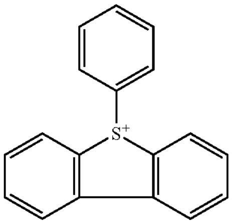
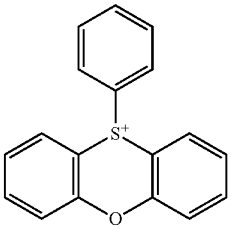
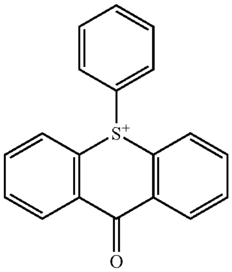
-continued
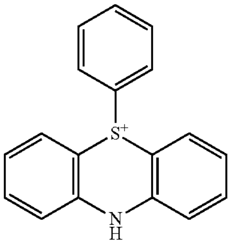
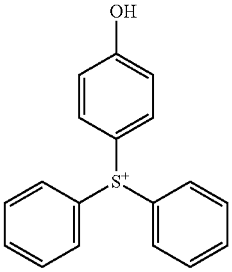 [SMILES: Oc1ccc([S+](c2ccccc2)c2ccccc2)cc1]
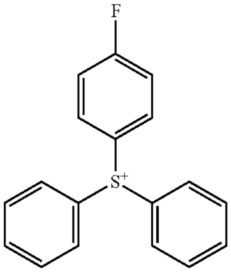
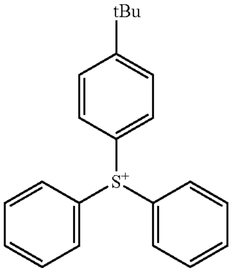
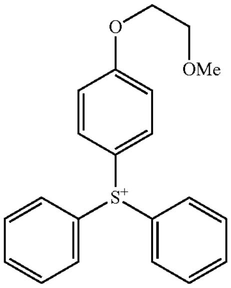
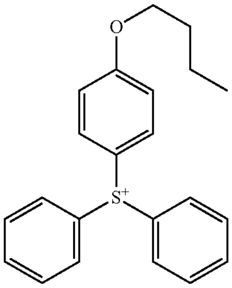
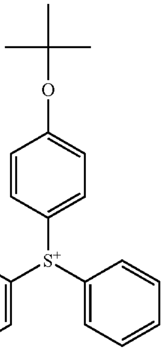
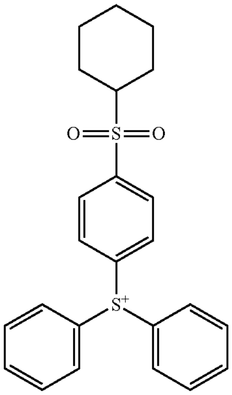
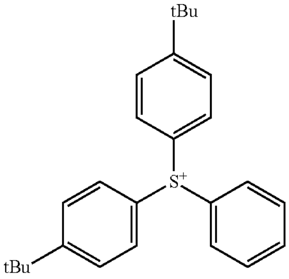

-continued

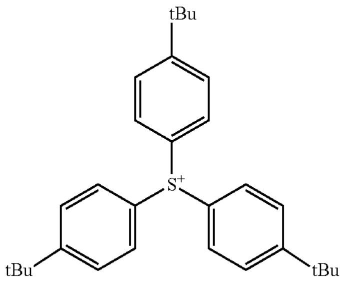

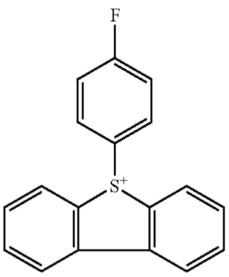

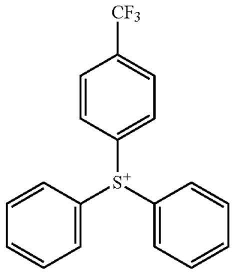

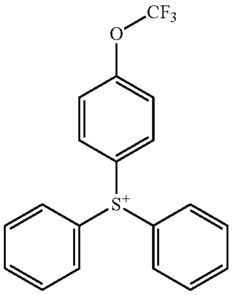

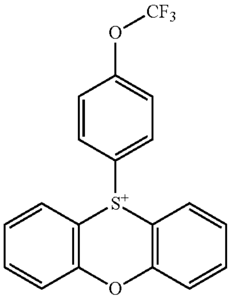

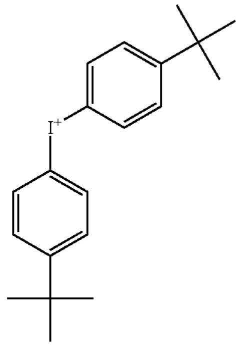

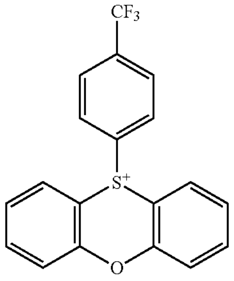

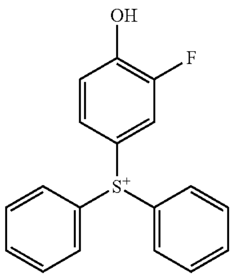

-continued

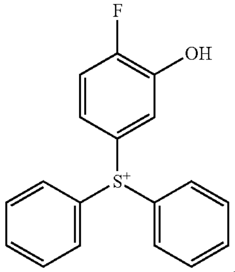

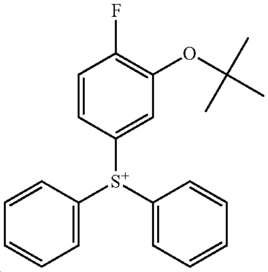

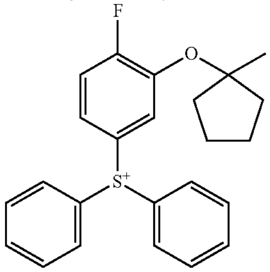

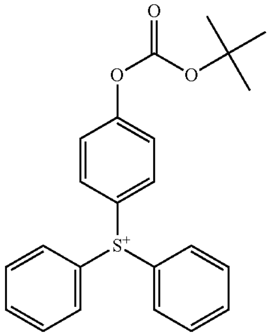

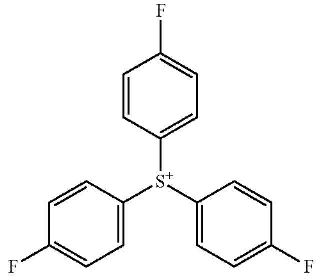

Examples of the photo-decomposable onium salt include arbitrary combinations of cations with anions, both as exemplified above, but are not limited thereto.

Component (C) is preferably used in an amount of 2 to 30 parts by weight, more preferably 2.5 to 20 parts by weight, even more preferably 4 to 15 parts by weight per 100 parts by weight of the base polymer (A). The acid diffusion inhibitor within the range allows for easy adjustment of resist sensitivity, holds down the diffusion rate of acid within the resist film (with improved resolution), suppresses a sensitivity change after exposure, reduces substrate or environment dependency, and improves exposure latitude and pattern profile. Also the addition of the acid diffusion inhibitor is effective for improving substrate adhesion. It is noted that the amount of component (C) is the total amount of the acid diffusion inhibitor in the form of the onium salt compound having formula (1) and the acid diffusion inhibitor other than the onium salt compound having formula (1). In the acid diffusion inhibitor (C), preferably the onium salt compound having formula (1) accounts for 50 to 100% by weight. The acid diffusion inhibitor as component (C) may be used alone or in admixture.

(D) Organic Solvent

The resist composition further comprises (D) an organic solvent. The organic solvent used herein is not particularly limited as long as the foregoing and other components are dissolvable therein. Examples of the organic solvent used herein are described in JP-A 2008-111103, paragraphs [0144]-[0145] (U.S. Pat. No. 7,537,880). Exemplary solvents include ketones such as cyclohexanone (CyHO) and methyl-2-n-pentyl ketone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone (GBL), which may be used alone or in admixture. Where an acid labile group of acetal form is used, a high boiling alcohol solvent such as diethylene glycol, propylene glycol, glycerol, 1,4-butanediol or 1,3-butanediol may be added to accelerate deprotection reaction of acetal.

Of these organic solvents, preference is given to 1-ethoxy-2-propanol, PGMEA, DAA, CyHO, and GBL and mixtures thereof because the PAG is highly soluble therein. The preferred solvent system is a mixture of PGMEA as solvent X and at least one of 1-ethoxy-2-propanol, DAA, CyHO, and GBL as solvent Y in a ratio X:Y of from 90:10 to 60:40.

The organic solvent (D) is preferably added in an amount of 100 to 8,000 parts, and more preferably 400 to 6,000 parts by weight per 100 parts by weight of the base polymer (A).

(E) Surfactant

In addition to the foregoing components, the resist composition may comprise (E) a surfactant which is commonly used for facilitating coating operation.

Component (E) is typically a surfactant which is insoluble or substantially insoluble in water and alkaline developer or a surfactant which is insoluble or substantially insoluble in water and soluble in alkaline developer.

For the surfactant which is insoluble or substantially insoluble in water and alkaline developer, reference should be made to JP-A 2010-215608 and JP-A 2011-016746. Suitable surfactants include FC-4430 (3M), Surflon® S-381, KH-20 and KH-30 (AGC Seimi Chemical Co., Ltd.), and Olfine® E1004 (Nisshin Chemical Co., Ltd.). Partially fluorinated oxetane ring-opened polymers having the structural formula (surf-1) are also useful.

(surf-1)

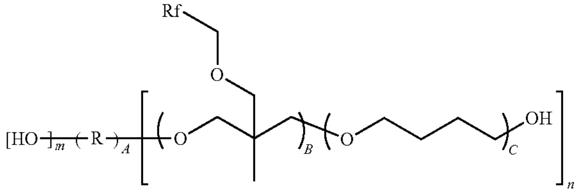

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

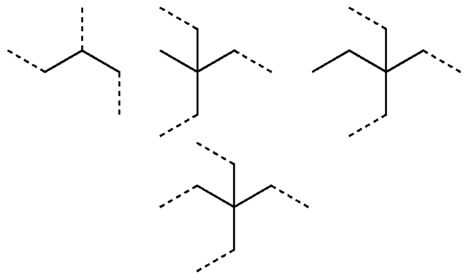

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist film surface for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water sliding.

Suitable polymeric surfactants include those containing recurring units of at least one type selected from the formulae (10A) to (10E).

(10A)

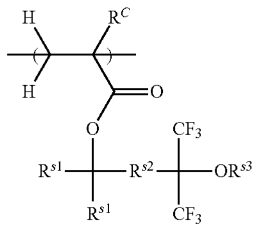

-continued (10B)

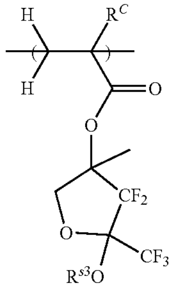

(10C)

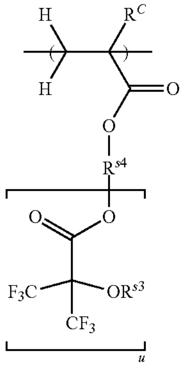

(10D)

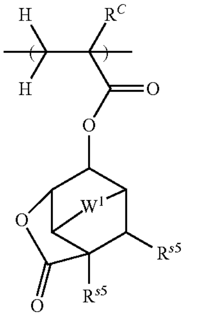

(10E)

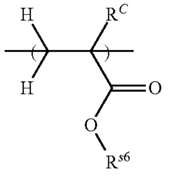

Herein, $R^C$ is hydrogen or methyl. $W^1$ is —$CH_2$—, —$CH_2CH_2$— or —O—, or two separate-H. $R^{s1}$ is each independently hydrogen or a $C_1$-$C_{10}$ hydrocarbyl group. $R^{s2}$ is a single bond or a $C_1$-$C_5$ alkanediyl group. $R^{s3}$ is each independently hydrogen, a $C_1$-$C_{15}$ hydrocarbyl or fluorinated hydrocarbyl group, or an acid labile group. When $R^{s3}$ is a hydrocarbyl or fluorinated hydrocarbyl group, an ether bond (—O—) or carbonyl moiety (—C(═O)—) may intervene in a carbon-carbon bond. $R^{s4}$ is a $C_1$-$C_{20}$ (u+1)-valent hydrocarbon or fluorinated hydrocarbon group, and u is an integer of 1 to 3. $R^{s5}$ is each independently hydrogen or a group having the formula: —C(═O)—O—$R^{s5A}$ wherein $R^{s5A}$ is a $C_1$-$C_{20}$ fluorinated hydrocarbyl group. $R^{s6}$ is a $C_1$-$C_{15}$ hydrocarbyl or fluorinated hydrocarbyl group in which —O— or —C(═O)— may intervene in a carbon-carbon bond.

The polymeric surfactant may further contain recurring units other than the recurring units having formulae (10A) to (10E). Typical other recurring units are those derived from methacrylic acid and α-trifluoromethylacrylic acid derivatives. In the polymeric surfactant, the content of the recurring units having formulae (10A) to (10E) is preferably at least 20 mol %, more preferably at least 60 mol %, most preferably 100 mol % of the overall recurring units.

For the surfactant which is insoluble or substantially insoluble in water and soluble in alkaline developer, reference may be made to JP-A 2008-122932, JP-A 2009-098638, JP-A 2009-191151, JP-A 2009-192784, JP-A 2009-276363, JP-A 2010-107695, JP-A 2010-134012, JP-A 2010-250105, and JP-A 2011-042789.

The amount of component (E) is preferably 0 to 20 parts by weight per 100 parts by weight of the base polymer (A). When added, the amount of component (E) is more preferably 0.001 to 15 parts by weight, even more preferably 0.01 to 10 parts by weight. The surfactant may be used alone or in admixture. The surfactant is also described in JP-A 2007-297590.

(F) Other Components

The resist composition may further comprise (F) another component, for example, a compound which is decomposed with an acid to generate another acid (i.e., acid amplifier compound), an organic acid derivative, a fluorinated alcohol, a crosslinker, a compound having a Mw of up to 3,000 which changes its solubility in developer under the action of an acid (i.e., dissolution inhibitor), and an acetylene alcohol. Specifically, the acid amplifier compound is described in JP-A 2009-269953 and JP-A 2010-215608 and preferably used in an amount of 0 to 5 parts, more preferably 0 to 3 parts by weight per 100 parts by weight of the base polymer (A). An extra amount of the acid amplifier compound can make the acid diffusion control difficult and cause degradations to resolution and pattern profile. With respect to the remaining additives, reference should be made to JP-A 2008-122932, paragraphs [0155]-[0182], JP-A 2009-269953 and JP-A 2010-215608.

The chemically amplified resist composition comprising the onium salt compound having formula (1) as an acid diffusion inhibitor, when processed by photolithography using high-energy radiation such as KrF excimer laser, ArF excimer laser, EB or EUV as the energy source, exhibits a high acid diffusion suppressing effect, and forms a pattern at a high contrast and with improved lithography performance factors such as CDU, LWR and sensitivity.

Process

A further embodiment of the invention is a pattern forming process using the chemically amplified resist composition defined above. The process includes the steps of applying the resist composition to form a resist film on a substrate, exposing a selected region of the resist film to high-energy radiation, and developing the exposed resist film in a developer. Any desired steps may be added to the process if necessary.

The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc.

The resist composition is applied onto a substrate by a suitable coating technique such as spin coating. The coating is prebaked on a hot plate preferably at a temperature of 60 to 180° C. for 10 to 600 seconds, more preferably at 70 to 150° C. for 15 to 300 seconds. The resulting resist film preferably has a thickness of 10 to 2,000 nm.

The resist film is then exposed to high-energy radiation. On use of KrF excimer laser, ArF excimer laser or EUV of wavelength 13.5 nm, the resist film is exposed through a mask having the desired pattern in a dose of preferably 1 to 200 $mJ/cm^2$, more preferably to 100 $mJ/cm^2$. On use of EB, a pattern may be written directly or through a mask having the desired pattern, preferably in a dose of 1 to 300 $\mu C/cm^2$, more preferably 10 to 200 $\mu C/cm^2$.

The exposure may be performed by conventional lithography whereas the immersion lithography of holding a liquid between the mask and the resist film may be employed if desired. In the immersion lithography, preferably a liquid having a refractive index of at least 1.0 is held between the resist film and the projection lens. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

With respect to the formation of a positive pattern using an alkaline aqueous solution as the developer, reference may be made to U.S. Pat. No. 8,647,808 (JP-A 2011-231312, paragraphs [0138]-[0146]). With respect to the formation of a negative pattern using an organic solvent as the developer, reference may be made to U.S. Pat. No. 9,256,127 (JP-A 2015-214634, paragraphs [0173]-[0183]).

Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning process may be used for pattern formation. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

With respect to the developer in the pattern forming process, examples of the aqueous alkaline solution include TMAH aqueous solutions as mentioned above and aqueous alkaline solutions described in JP-A 2015-180748, paragraphs [0148]-[0149], preferably 2 to 3% by weight TMAH aqueous solutions.

The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

A hole or trench pattern after development may be shrunk by the thermal flow, RELACS® (resolution enhancement lithography assisted by chemical shrink) or DSA (directed self-assembly) process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

When processed by photolithography, the chemically amplified resist composition comprising the onium salt compound having formula (1) as an acid diffusion inhibitor forms a fine size pattern with improved lithography performance factors such as CDU, LWR and sensitivity.

EXAMPLES

Examples of the invention are given below by way of illustration and not by way of limitation. The abbreviation "pbw" is parts by weight. For all polymers, Mw and Mn are determined by GPC versus polystyrene standards using tetrahydrofuran (THF) solvent.

Example 1-1

Synthesis of Acid Diffusion Inhibitor Q-1

(1) Synthesis of Compound SM-2

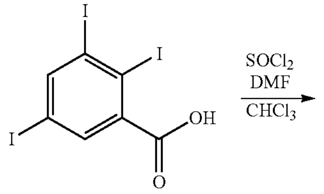

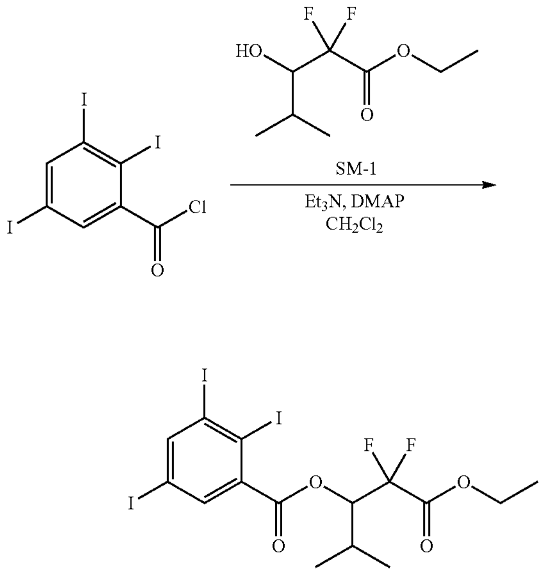

SM-2

In a reactor, 450 g of 2,3,5-triiodobenzoic acid, 3.3 g of N,N-dimethylformamide, and 3,150 g of chloroform were mixed and heated at 60° C., after which 214 g of thionyl chloride was added dropwise thereto. After overnight stirring, the reaction solution was concentrated at 50° C. under reduced pressure. The concentrate was combined with 900 g of hexane, followed by 2 hours of stirring for crystallization. The resulting solid was filtered and washed 4 times with hexane, obtaining 386 g of 2,3,5-triiodobenzoic acid chloride as wet crystals.

In a reactor, 343 g of 2,3,5-triiodobenzoic acid trichloride, 100 g of Compound SM-1 and 1,500 g of methylene chloride were mixed. Under ice cooling, a mixture of 77 g of triethylamine, 9.3 g of N,N-dimethylaminopyridine, and 100 g of methylene chloride was added dropwise to the solution, which was stirred overnight at room temperature. To the solution, 10 g of triethylamine was added, and a mixture of 43 g of 2,3,5-triiodobenzoic acid chloride and 250 g of methylene chloride was added dropwise. The solution was stirred overnight at room temperature. 1,500 g of 2.5 wt % hydrochloric acid was added to the reaction solution, which was stirred for 30 minutes to quench the reaction. The solid precipitate was filtered off and the organic layer was recovered. The organic layer was washed 3 times with 1,200 g of deionized water. With 17 g of activated carbon added, the organic layer was stirred for 1 hour. Thereafter, the activated carbon was filtered off. The filtrate was washed once with 1,200 g of saturated sodium hydrogencarbonate aqueous solution and 3 times with 1,200 g of deionized water. The organic layer was concentrated under reduced pressure, obtaining the desired Compound SM-2 as red oily matter (amount 360 g).

(2) Synthesis of Compound SM-3

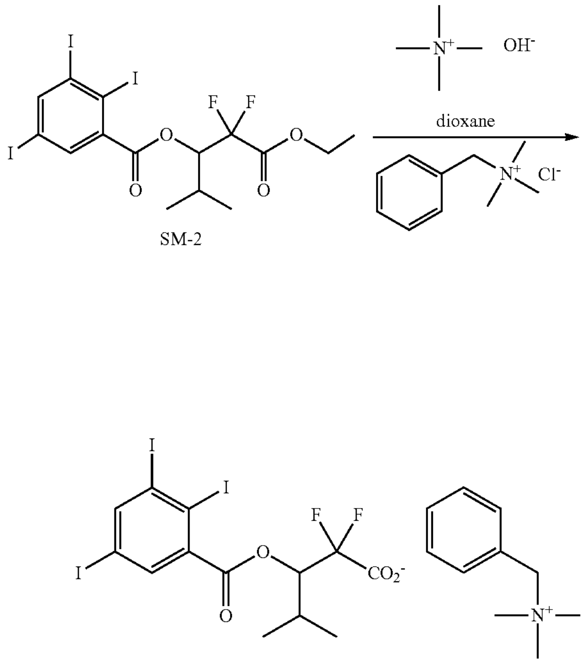

SM-3

To a solution of 360 g of Compound SM-2 in 1,080 g of dioxane, 189.7 g of 25 wt % TMAH aqueous solution was added dropwise at room temperature. After overnight stirring, the reaction solution was concentrated under reduced pressure. To the concentrate, 2,050 g of methylene chloride, 1,000 g of deionized water, and 113.6 g of benzyltrimethylammonium chloride were added and stirred at room temperature for 20 minutes. The organic layer was taken out and combined with 100 g of methanol. With 15 g of activated carbon added, the solution was stirred at room temperature overnight. After the activated carbon was filtered off, the filtrate was concentrated under reduced pressure. To the concentrate, 1,300 mL of diisopropyl ether was added. During 1.5 hours of stirring, solids precipitated. The solid precipitate was collected by filtration and washed once with diisopropyl ether, obtaining 415 g of crude crystals. The crude crystals were dissolved in 330 g of methanol. 2,000 g of deionized water and 300 mL of diisopropyl ether were added to the solution, followed by overnight stirring. The precipitated solid was collected by filtration and washed once with diisopropyl ether. The solid was dried at 60° C. in vacuum, obtaining the desired Compound SM-3 as solid (amount 286 g, two-step yield 68%).

(3) Synthesis of Acid Diffusion Inhibitor Q-1

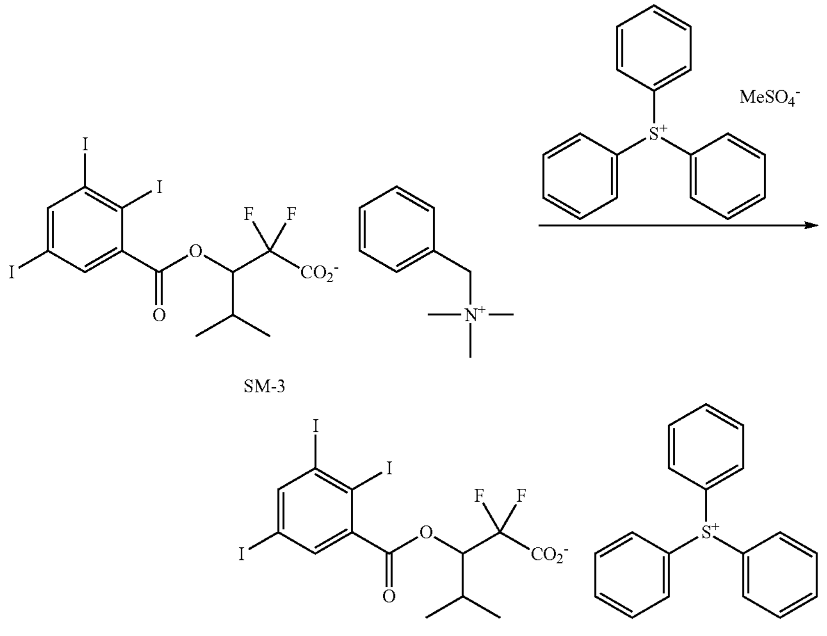

SM-3

Q-1

With stirring, 198 g of Compound SM-3, 1,200 g of methylene chloride, and 66 g of methanol were mixed. When Compound SM-3 was completely dissolved, 6.6 g of activated carbon was added to the solution, followed by overnight stirring. At the end of stirring, the activated carbon was filtered off. The solution was combined with 102.1 g of triphenylsulfonium methylsulfate and 300 g of deionized water and stirred at room temperature for 1.5 hours. Thereafter, the organic layer was taken out. The organic layer was washed 4 times with 300 g of deionized water, twice with 300 g of dilute oxalic acid aqueous solution, 3 times with 300 g of deionized water, twice with 300 g of dilute ammonia water, 5 times with 300 g of deionized water, and 4 times with 400 g of 25 wt % methanol aqueous solution. The organic layer was concentrated under reduced pressure. The concentrate was added to 600 g of diisopropyl ether and stirred, allowing crystals to precipitate. After precipitation, stirring was continued for a further 1 hour. The solid was filtered, washed once with diisopropyl ether, and dried at 50° C. in vacuum, obtaining the target acid diffusion inhibitor Q-1 as solid (amount 230.1 g, yield 91%). The spectral data of Q-1 are shown below. $^{1}$H-NMR (500 MHz, DMSO-$d_6$):

δ=0.93 (3H, d), 1.00 (3H, d), 2.14 (1H, m), 5.37 (1H, m), 7.70 (1H, d), 7.75-7.87 (15H, m), 8.37 (1H, d) ppm $^{19}$F-NMR (500 MHz, DMSO-$d_6$): δ=−113.1 (1F, dd), −109.9 (1F, dd) ppm IR (D-ATR):

ν=3059, 2968, 1737, 1652, 1520, 1476, 1447, 1381, 1269, 1232, 1184, 1102, 1034, 997, 939, 821, 796, 749, 700, 684, 502 $cm^{-1}$

Time-of-flight mass spectrometry (TOFMS; MALDI)

Positive $M^+$ 263.1 (corresponding to $C_{18}H_{15}S^+$)

Negative $M^-$ 648.8 (corresponding to $C_{13}H_{10}F_2I_3O_4^-$)

Example 1-2

Synthesis of Acid Diffusion Inhibitor Q-2

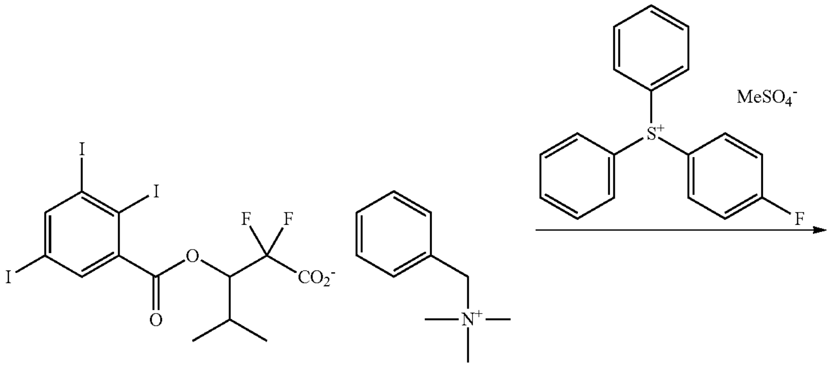

SM-3

-continued

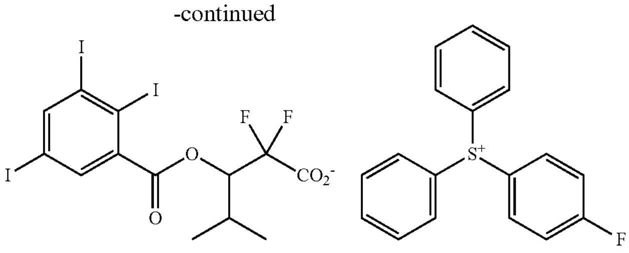

Q-2

In a reactor, 371 g of Compound SM-3, 2,400 g of methylene chloride and 150 g of methanol were stirred and mixed. When Compound SM-3 was completely dissolved, 11 g of activated carbon was added to the solution, followed by overnight stirring. At the end of stirring, the activated carbon was filtered off. The solution was combined with 190 g of (4-fluorophenyl)diphenylsulfonium methylsulfate and 840 g of deionized water and stirred at room temperature for 1 hour. Thereafter, the organic layer was taken out. The organic layer was washed twice with 600 g of deionized water, once with 600 g of dilute oxalic acid aqueous solution, 3 times with 600 g of deionized water, twice with 600 g of dilute ammonia water, 3 times with 600 g of deionized water, and 3 times with 20 wt % methanol aqueous solution. The organic layer was concentrated under reduced pressure. The concentrate was added to 1,000 g of diisopropyl ether and stirred, allowing crystals to precipitate. After precipitation, stirring was continued for a further 1 hour. The solid was filtered, washed once with diisopropyl ether, and dried at 50° C. in vacuum, obtaining the target acid diffusion inhibitor Q-2 as solid (amount 348 g, yield 82%). The spectral data of Q-2 are shown below.

$^{1}$H-NMR (500 MHz, DMSO-$d_6$): δ=0.93 (3H, d), 0.99 (3H, d), 2.14 (1H, m), 5.37 (1H, m), 7.64-7.68 (2H, m), 7.70 (1H, d), 7.75-7.87 (10H, m), 7.91-7.95 (2H, m), 8.37 (1H, d) ppm $^{19}$F-NMR (500 MHz, DMSO-$d_6$): δ=−113.1 (1F, dd), −109.9 (1F, dd), −104.6 (1F, m) ppm IR (D-ATR): ν=3058, 2969, 1737, 1652, 1587, 1521, 1492, 1476, 1446, 1392, 1269, 1235, 1184, 1102, 1034, 997, 939, 843, 821, 796, 748, 696, 683, 525, 504 $cm^{-1}$

TOFMS; MALDI

Positive $M^+$ 281.1 (corresponding to $C_{18}H_{14}FS^+$)

Negative $M^-$ 648.8 (corresponding to $C_{13}H_{10}F_2I_3O_4^-$)

Example 1-3

Synthesis of Acid Diffusion Inhibitor Q-3

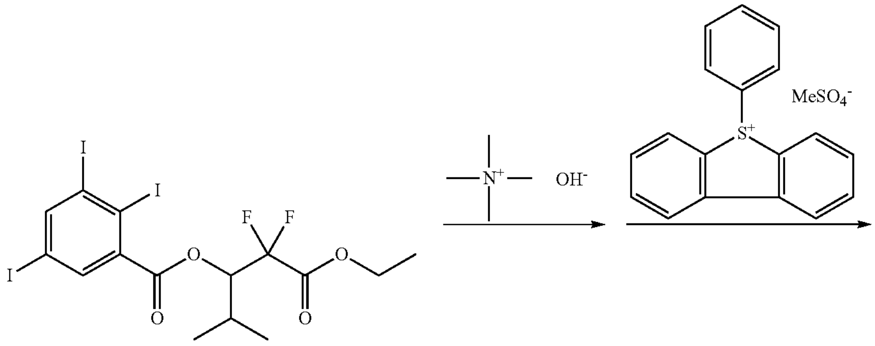

SM-2

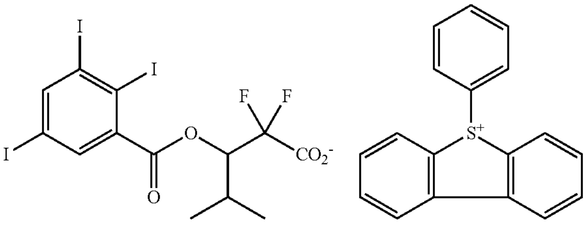

Q-3

In a reactor, 8.5 g of Compound SM-2 (purity 83 wt %), 18 g of tetrahydrofuran, and 18 g of deionized water were mixed. To the mixture, 5.9 g of 25 wt % TMAH aqueous solution was added dropwise, followed by overnight stirring. At the end of stirring, 60 g of methyl isobutyl ketone, 60 g of deionized water, 20 g of methanol and 8 g of S-phenyldibenzothiophenium methylsulfate were added. After stirring, the organic layer was taken out. The organic layer was washed 5 times with 40 g of deionized water and 3 times with 25 wt % methanol aqueous solution. The organic layer was concentrated at 50° C. under reduced pressure. The concentrate was added to 80 g of diisopropyl ether and stirred for 30 minutes, allowing solids to precipitate. The solid precipitate was filtered, washed twice with diisopropyl ether, and dried at 50° C. in vacuum, obtaining the target acid diffusion inhibitor Q-3 as solid (amount 7.5 g, yield 77%). The spectral data of Q-3 are shown below.

$^{1}$H-NMR (500 MHz, DMSO-$d_6$):

δ=0.93 (3H, d), 1.00 (3H, d), 2.14 (1H, m), 5.38 (1H, m), 7.55-7.62 (4H, m), 7.68 (1H, m), 7.70 (1H, d), 7.74 (2H, m), 7.95 (2H, m), 8.37 (1H, d), 8.38 (2H, d), 8.51 (2H, dd) ppm $^{19}$F-NMR (500 MHz, DMSO-$d_6$): δ=−113.1 (1F, dd), −109.9 (1F, dd) ppm IR (D-ATR): ν=3061, 2966, 1736, 1647, 1520, 1475, 1448, 1429, 1383, 1268, 1233, 1184, 1102, 1034, 997, 940, 895, 872, 821, 796, 758, 706, 680, 526, 489 $cm^{-1}$

TOFMS; MALDI

Positive $M^+$ 261.1 (corresponding to $C_{18}H_{13}S^+$)

Negative $M^-$ 648.8 (corresponding to $C_{13}H_{10}F_2I_3O_4^-$)

Example 1-4

Synthesis of Acid Diffusion Inhibitor Q-17

(1) Synthesis of Compound SM-5

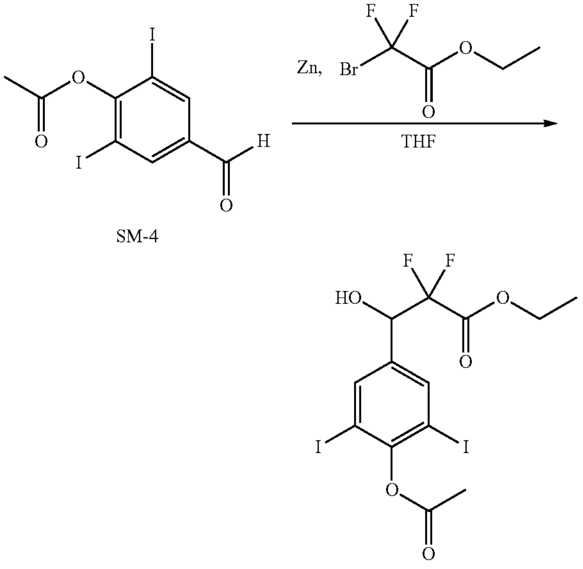

SM-4

SM-5

After 3.6 g of powdered zinc was dispersed in 30 mL of THF, the dispersion was heated at 50° C. 0.21 g of 1,2-dibromoethane was added to the dispersion, which was stirred while heating under reflux, thereby activating zinc. The internal temperature was lowered to 50° C., after which a mixture of 20.8 g of Compound SM-4, 12.2 g of ethyl bromodifluoroacetate, and 80 mL of THF was added dropwise. Stirring was continued at 50° C. for 5.5 hours. Thereafter, the reaction solution was ice cooled, and 12.0 g of 20 wt % hydrochloric acid was added thereto to quench the reaction. Further, 150 mL of toluene and 50 g of 2 wt % hydrochloric acid were added to the solution. After stirring, the organic layer was taken out. The organic layer was washed twice with 2 wt % hydrochloric acid and 5 times with 50 g of deionized water, and concentrated under reduced pressure. The resulting oil was purified by silica gel column chromatography. This was followed by crystallization from 300 mL of hexane, filtration, and vacuum drying, obtaining the desired compound SM-5 as white solid (amount 17.2 g, yield 63.8%).

(2) Synthesis of Compound SM-6

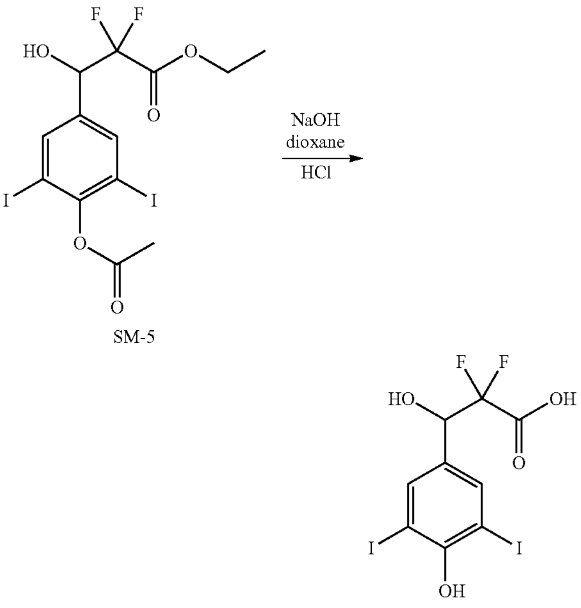

SM-5

SM-6

To a solution of 16.2 g of Compound SM-5 in 64 g of dioxane, 19.2 g of 25 wt % sodium hydroxide aqueous solution was added dropwise at room temperature. The solution was heated at 45° C. and stirred overnight. After the reaction solution was cooled, 24.1 g of 20 wt % hydrochloric acid was added to quench the reaction. To the solution, 100 mL of ethyl acetate and 50 mL of toluene were added. After stirring, the organic layer was taken out and washed 4 times with 30 mL of deionized water. The organic layer was concentrated under reduced pressure. The concentrate was dissolved in acetone, which was poured into 150 mL of hexane for crystallization. The solid precipitate was filtered, washed with 30 mL of hexane, and dried in vacuum, obtaining the desired compound SM-6 as solid (amount 15.3 g, two-step yield 92%).

(3) Synthesis of Acid Diffusion Inhibitor Q-17

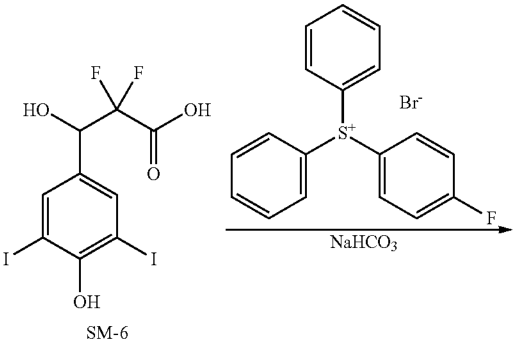

SM-6

-continued

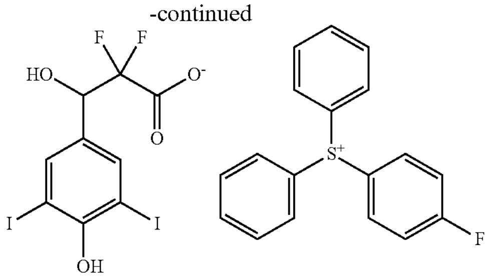

Q-17

With stirring, 5.6 g of Compound SM-6, 0.84 g of sodium hydrogencarbonate, 30 g of methyl isobutyl ketone, and 6 g of deionized water were mixed. The mixture was concentrated under reduced pressure. To the concentrate, 4.3 g of diphenyl(4-fluorophenyl)sulfonium bromide, 40 g of methyl isobutyl ketone, 10 g of 1-butanol, and 20 g of deionized water were added and stirred. The organic layer was taken out and washed 5 times with 20 g of deionized water. The organic layer was concentrated under reduced pressure. The concentrate was dissolved in 80 g of methylene chloride and 10 g of methanol. With 0.4 g of activated carbon added, the solution was stirred overnight. The activated carbon was filtered off and the filtrate was concentrated to under reduced pressure. The concentrate was dissolved in 16 g of acetone, and 50 mL of diisopropyl ether was added to the solution. After stirring, the supernatant was removed. To the oily residue, 50 mL of hexane was added. After stirring, the supernatant was removed. Further, 150 mL of methyl isobutyl ketone and 50 mL of methylene chloride were added to the residue and stirred, allowing solids to precipitate. The precipitate was filtered and dried in vacuum, obtaining the target acid diffusion inhibitor Q-17 as solid (amount 6.6 g, yield 88%). The spectral data of Q-17 are shown below.

$^1$H-NMR (500 MHz, DMSO-$d_6$):

δ=4.71 (1H, dd), 7.22 (1H, br), 7.64-7.69 (4H, m), 7.75-7.87 (10H, m), 7.91-7.95 (2H, m), 9.52 (1H, br) ppm $^{19}$F-NMR (500 MHz, DMSO-$d_6$):

δ=−115.7 (1F, dd), −110.7 (1F, dd), −104.6 (1F, m) ppm

IR (D-ATR):

ν=3271, 3054, 1641, 1589, 1493, 1477, 1447, 1392, 1321, 1268, 1246, 1178, 1161, 1112, 1094, 1063, 1000, 847, 818, 779, 741, 701, 681, 630, 526, 504, 493, 459 $cm^{-1}$

TOFMS; MALDI

Positive $M^+$ 281.1 (corresponding to $C_{18}H_{14}FS^+$)

Negative $M^-$ 468.8 (corresponding to $C_9H_5F_2I_2O_4^-$)

Example 1-5

Synthesis of Acid Diffusion Inhibitor Q-20

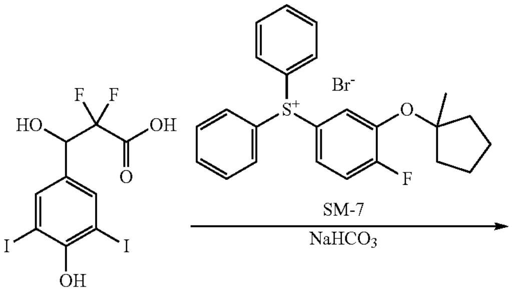

SM-6

-continued

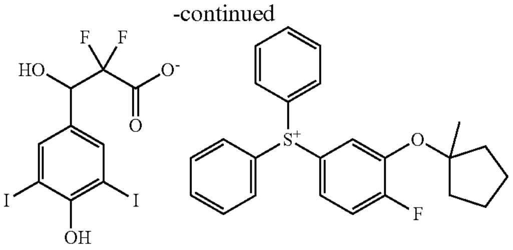

Q-20

With stirring, 5.6 g of Compound SM-6, 0.84 g of sodium hydrogencarbonate, 30 g of methyl isobutyl ketone, and 6 g of deionized water were mixed. The mixture was concentrated under reduced pressure. To the concentrate, 4.6 g of Compound SM-7, 40 g of methyl isobutyl ketone, 10 g of 1-butanol, and 20 g of deionized water were added. After 10 minutes of stirring, the organic layer was taken out. The organic layer was washed 5 times with 20 g of deionized water, and concentrated under reduced pressure. The concentrate was dissolved in 40 g of methylene chloride. With 0.4 g of activated carbon added, the solution was stirred for 5 hours. After the activated carbon was filtered off, the filtrate was concentrated under reduced pressure. The concentrate was dissolved in 10 g of acetone, to which 100 mL of methyl isobutyl ketone and 50 mL of diisopropyl ether were added. At the end of stirring, the supernatant was removed. To the oily residue was added 150 mL of diisopropyl ether. The mixture was stirred, allowing solids to precipitate. The solid precipitate was filtered and dried in vacuum, obtaining the target acid diffusion inhibitor Q-20 as solid (amount 6.5 g, yield 73.7%). The spectral data of Q-20 are shown below.

$^1$H-NMR (500 MHz, DMSO-$d_6$):

δ=1.32 (3H, s), 1.52-1.72 (6H, m), 1.93 (2H, m), 4.70 (1H, dd), 7.22 (1H, br), 7.39 (1H, ddd), 7.53 (1H, dd), 7.67 (1H, dd), 7.67 (2H, s), 7.74-7.88 (10H, m), 9.57 (1H, br) ppm $^{19}$F-NMR (500 MHz, DMSO-$d_6$): δ=−122.1 (1F, m), −115.7 (1F, dd), −110.7 (1F, dd) ppm

TOFMS; MALDI

Positive $M^+$ 379.2 (corresponding to $C_{24}H_{24}FOS^+$)

Negative $M^-$ 468.8 (corresponding to $C_9H_5F_2I_2O_4^-$)

Example 1-6

Synthesis of Acid Diffusion Inhibitor Q-21

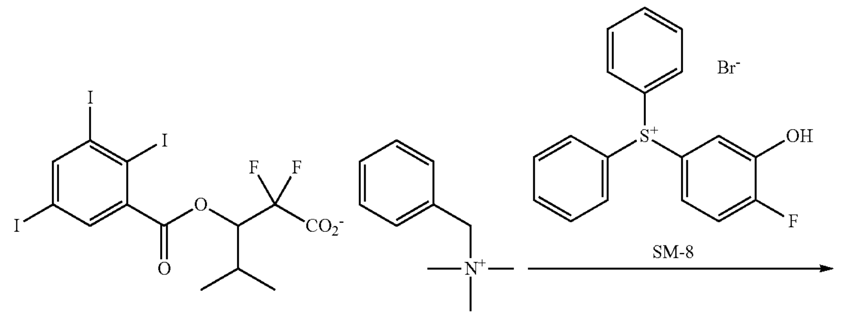

SM-8

SM-3

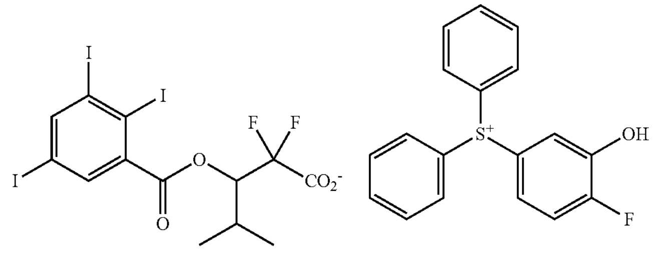

Q-21

In a reactor, 4.7 g of Compound SM-3, 2.5 g of Compound SM-8, 40 g of methyl isobutyl ketone, and 20 g of deionized water were mixed and stirred at room temperature for 1 hour, after which the organic layer was taken out. The organic layer was washed times with 20 g of deionized water and then concentrated under reduced pressure. The concentrate was dissolved in 30 g of methylene chloride. With 0.3 g of activated carbon added, the solution was stirred overnight. After the activated carbon was filtered off, the filtrate was concentrated under reduced pressure. To the concentrate, 50 mL of diisopropyl ether was added for crystallization. The solid precipitate was filtered and dried in vacuum, obtaining the target acid diffusion inhibitor Q-21 as solid (amount 5.3 g, yield 93.4%). The spectral data of Q-21 are shown below.

$^1$H-NMR (500 MHz, DMSO-$d_6$):

δ=0.93 (3H, d), 0.99 (3H, d), 2.13 (1H, m), 5.37 (1H, m), 7.22 (1H, m), 7.35 (1H, dd), 7.54 (1H, dd), 7.67 (1H, d), 7.72-7.79 (8H, m), 7.80-7.85 (2H, m), 8.37 (1H, d), 12.4 (1H, br) ppm $^{19}$F-NMR (500 MHz, DMSO-$d_6$):

δ=−127.7 (1F, m), −113.2 (1F, dd), −110.3 (1F, dd) ppm

IR (D-ATR):

ν=3062, 2969, 1734, 1644, 1603, 1576, 1519, 1475, 1446, 1393, 1367, 1268, 1233, 1210, 1183, 1120, 1103, 1042, 998, 940, 897, 871, 821, 796, 747, 698, 683, 600, 508, 495 cm$^{-1}$

TOFMS; MALDI

Positive $M^+$ 297.1 (corresponding to $C_{18}H_{14}FOS^+$)

Negative $M^-$ 648.8 (corresponding to $C_{13}H_{10}F_2I_3O_4^-$)

Example 1-7

Synthesis of Acid Diffusion Inhibitor Q-22

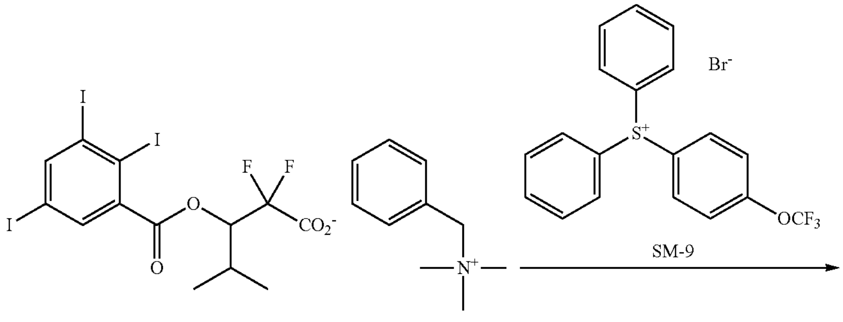

SM-9

SM-3

-continued

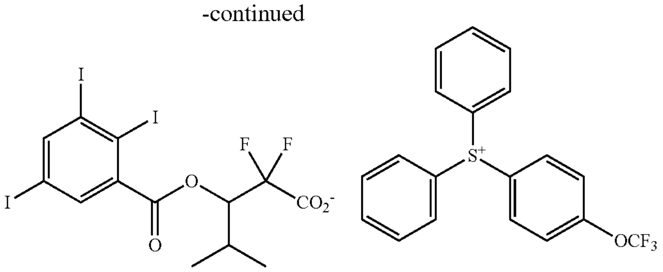

Q-22

In a reactor, 21.0 g of Compound SM-3, 12.8 g of Compound SM-9, 100 g of methyl isobutyl ketone, and 70 g of deionized water were mixed and stirred at room temperature overnight, after which the organic layer was taken out. To the organic layer, 1.1 g of Compound SM-9 and 55 g of deionized water were added to perform two cycles of additional salt exchange. Thereafter, the organic layer was washed 5 times with 50 g of deionized water and then concentrated under reduced pressure. The concentrate was dissolved in 100 g of methylene chloride. With 1.3 g of activated carbon added, the solution was stirred overnight. After the activated carbon was filtered off, the filtrate was concentrated under reduced pressure, obtaining the target acid diffusion inhibitor Q-22 as pale yellow oily matter (amount 28.9 g, yield 99%). The spectral data of Q-22 are shown below.

$^{1}$H-NMR (500 MHz, DMSO-$d_6$):

δ=0.93 (3H, d), 1.00 (3H, d), 2.14 (1H, m), 5.37 (1H, m), 7.70 (1H, d), 7.76-7.81 (6H, m), 7.83-7.88 (6H, m), 7.96 (2H, m), 8.38 (1H, d) ppm $^{19}$F-NMR (500 MHz, DMSO-$d_6$):

δ=−113.1 (1F, dd), −109.9 (1F, dd), −57.9 (3F, s) ppm

TOFMS; MALDI

Positive $M^+$ 347.1 (corresponding to $C_{19}H_{14}F_3OS^+$)

Negative $M^-$ 648.8 (corresponding to $C_{13}H_{10}F_2I_3O_4^-$)

Example 1-8

Synthesis of Acid Diffusion Inhibitor Q-23

(1) Synthesis of Compound SM-10

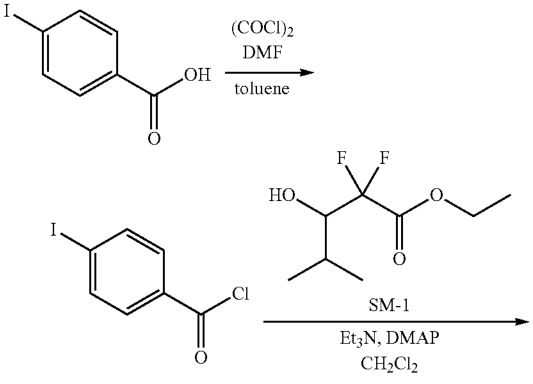

-continued

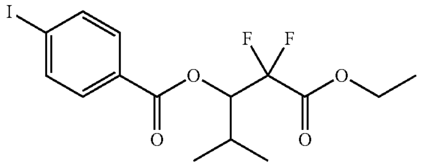

SM-10

In a reactor, 109.1 g of 4-iodobenzoic acid, 0.3 g of N,N-dimethylformamide, and 400 g of toluene were mixed and heated at 40° C., to which 67.0 g of oxalyl chloride was added dropwise. After 3.5 hours of stirring, the reaction solution was concentrated at 50° C. under reduced pressure, obtaining 118.0 g of 4-iodobenzoic chloride as solid.

Next, 118.0 g of 4-iodobenzoic chloride, 78.5 g of Compound SM-1, and 520 g of methylene chloride were mixed. Under ice cooling, a mixture of 56.7 g of triethylamine, 4.9 g of N,N-dimethylaminopyridine, and 80 g of methylene chloride was added dropwise. The reaction solution was stirred at room temperature overnight. Under ice cooling, 100 mL of saturated sodium hydrogencarbonate aqueous solution and 100 mL of deionized water were added to the reaction solution to quench the reaction. The organic layer was taken out. The organic layer was washed once with 200 g of 4 wt % hydrochloric acid, once with 200 g of deionized water, once with 200 mL of saturated sodium hydrogencarbonate aqueous solution, and twice with 200 g of deionized water. With 12.2 g of activated carbon added, the organic layer was stirred overnight. The activated carbon was filtered off. The filtrate was concentrated under reduced pressure, obtaining the desired Compound SM-10 as oily matter (amount 151.4 g, yield 84.6%).

(2) Synthesis of Compound SM-11

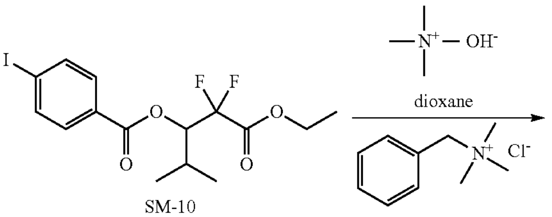

SM-10

-continued

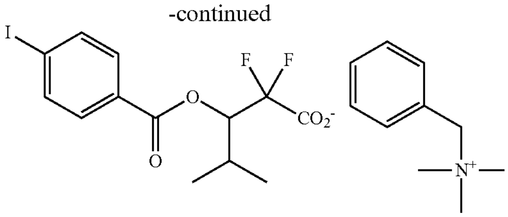

SM-11

At room temperature, 154.5 g of 25 wt % TMAH aqueous solution was added dropwise to a solution of 199.7 g of Compound SM-10 in 100 g of dioxane, followed by overnight stirring. The reaction solution was concentrated under reduced pressure. Then 500 g of methylene chloride, 250 g of deionized water, and 124.2 g of benzyltrimethylammonium chloride were added to the concentrate, which was stirred at room temperature for 10 minutes. The organic layer was taken out and washed 3 times with 250 g of deionized water. The organic layer was concentrated under reduced pressure. 1,000 mL of diisopropyl ether was added to the concentrate and stirred, after which the supernatant was removed. 500 mL of hexane was added to the oily residue and stirred, after which the supernatant was removed. The oily matter was dissolved in methanol. The solution was concentrated under reduced pressure, obtaining the desired Compound SM-11 as oily matter (amount 214.6 g, two-step yield 83.2%).

(3) Synthesis of Acid Diffusion Inhibitor Q-23

A reactor was charged with 111 g of Compound SM-11, 500 g of methylene chloride, 83.7 g of triphenylsulfonium methylsulfate, 2.5 g of 29 wt % ammonia water, and 350 g of deionized water, which were stirred at room temperature for 1 hour. The organic layer was taken out. The organic layer was washed 3 times with 300 g of deionized water, twice with 300 g of dilute oxalic acid aqueous solution, twice with 300 g of deionized water, twice with 300 g of dilute ammonia water, 3 times with 300 g of deionized water, and 3 times with 300 g of 25 wt % methanol aqueous solution. The organic layer was concentrated under reduced pressure. 380 g of tert-butyl methyl ether was added to the concentrate and stirred, after which the supernatant was removed. 130 g of PGMEA was added to the oily residue and stirred, allowing solids to precipitate, and 380 g of tert-butyl methyl ether was further added and stirred. The solid precipitate was filtered and dried in vacuum, obtaining the target acid diffusion inhibitor Q-23 as solid (amount 96.2 g, yield 73.8%). The spectral data of Q-23 are shown below.

$^{1}$H-NMR (500 MHz, DMSO-$d_6$):

δ=0.87 (3H, d), 0.92 (3H, dd), 2.13 (1H, m), 5.46 (1H, ddd), 7.72 (2H, m), 7.75-7.87 (15H, m), 7.94 (2H, m) ppm $^{19}$F-NMR (500 MHz, DMSO-$d_6$):

δ=−115.2 (1F, dd), −107.7 (1F, dd) ppm

TOFMS; MALDI

Positive $M^+$ 263.1 (corresponding to $C_{18}H_{15}S^+$)

Negative $M^-$ 397.0 (corresponding to $C_{13}H_{12}F_2IO_4^-$)

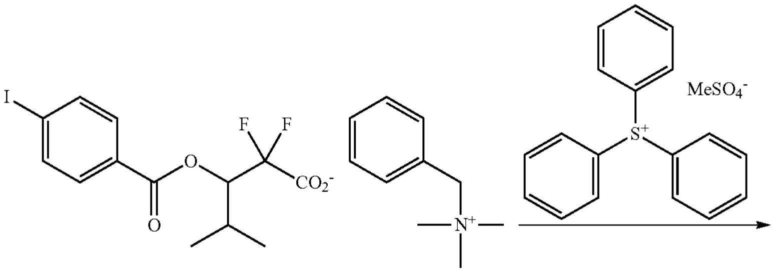

SM-11

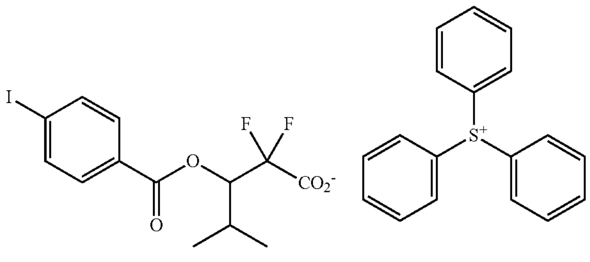

Q-23

Example 1-9

Synthesis of Acid Diffusion Inhibitor Q-24

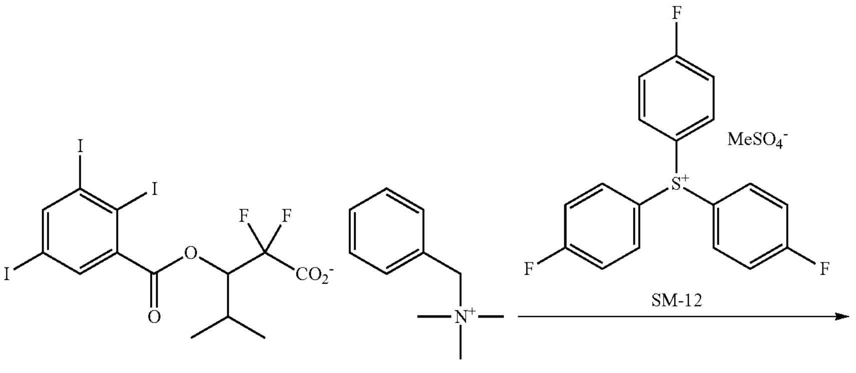

SM-3

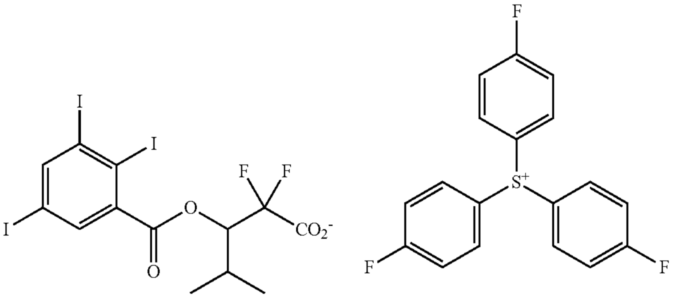

Q-24

A reactor was charged with 150.0 g of Compound SM-3, 104.5 g of Compound SM-12, 1160 g of methylene chloride, and 740 g of deionized water, which were stirred at room temperature for 1 hour. The organic layer was taken out, and washed 4 times with 280 g of deionized water. With 9.0 g of activated carbon added, the organic layer was stirred overnight. After the activated carbon was filtered off, the organic layer was washed twice with 280 g of dilute oxalic acid aqueous solution, 3 times with 280 g of deionized water, twice with 280 g of dilute ammonia water, and 4 times with 280 g of deionized water. The organic layer was concentrated under reduced pressure, obtaining the target acid diffusion inhibitor Q-24 as oily matter (amount 160.7 g, yield 88.6%). The spectral data of Q-24 are shown below.

$^{1}$H-NMR (500 MHz, DMSO-$d_6$):

δ=0.93 (3H, d), 1.00 (3H, d), 2.14 (1H, m), 5.37 (1H, m), 7.66 (6H, m), 7.70 (1H, d), 7.93 (6H, m), 8.38 (1H, d) ppm $^{19}$F-NMR (500 MHz, DMSO-$d_6$):

δ=−113.1 (1F, dd), −109.9 (1F, dd), −104.7 (3F, m) ppm

IR (D-ATR):

ν=3399, 3098, 3053, 2969, 2880, 1737, 1709, 1652, 1586, 1521, 1491, 1394, 1364, 1268, 1240, 1185, 1161, 1102, 1035, 1006, 939, 839, 797, 747, 701, 519 $cm^{-1}$

TOFMS; MALDI

Positive $M^+$ 317.1 (corresponding to $C_{18}H_{12}F_3S^+$)

Negative $M^-$ 648.8 (corresponding to $C_{13}H_{10}F_2I_3O_4^-$)

Example 1-10

Synthesis of Acid Diffusion Inhibitor Q-25

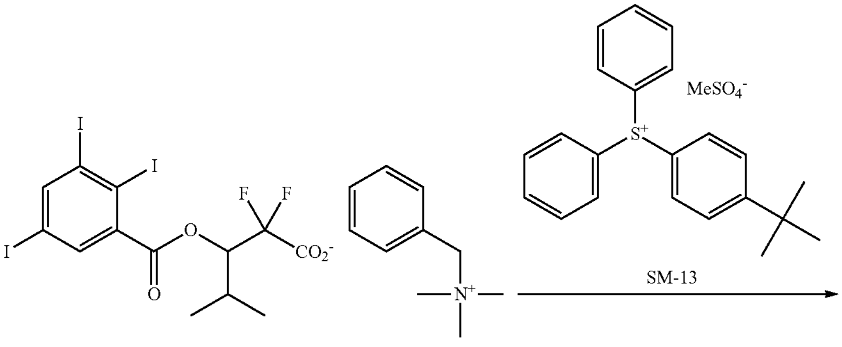

SM-13

SM-3

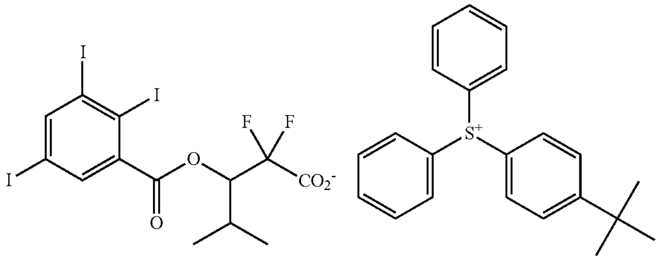

Q-25

A reactor was charged with 20.0 g of Compound SM-3, 12.4 g of Compound SM-13, 110 g of methyl isobutyl ketone, 11 g of methanol, and 63 g of deionized water, which were stirred at room temperature for 1 hour. The organic layer was taken out. The organic layer was washed 3 times with 50 g of deionized water, 3 times with 100 g of 20 wt % methanol aqueous solution, once with 50 g of dilute ammonia water, and 7 times with 20 wt % methanol aqueous solution. The organic layer was concentrated under reduced pressure. 70 g of diisopropyl ether was added to the concentrate and stirred, after which the supernatant was removed. 100 g of hexane was added to the oily residue and stirred overnight, allowing solids to precipitate. The solid precipitate was filtered and dried in vacuum, obtaining the target acid diffusion inhibitor Q-25 as solid (amount 15.9 g, yield 64.8%). The spectral data of Q-25 are shown below.

$^{1}$H-NMR (500 MHz, DMSO-$d_6$):

δ=0.93 (3H, d), 0.99 (3H, d), 1.30 (9H, s), 2.14 (1H, m), 5.37 (1H, m), 7.70 (1H, d), 7.73-7.82 (12H, m), 7.82-7.87 (2H, m), 8.37 (1H, d) ppm $^{19}$F-NMR (500 MHz, DMSO-$d_6$): δ=−113.1 (1F, dd), −109.9 (1F, dd) ppm

TOFMS; MALDI

Positive $M^+$ 319.2 (corresponding to $C_{22}H_{23}S^+$)

Negative $M^-$ 648.8 (corresponding to $C_{13}H_{10}F_2I_3O_4^-$)

Example 1-11

Synthesis of Acid Diffusion Inhibitor Q-26

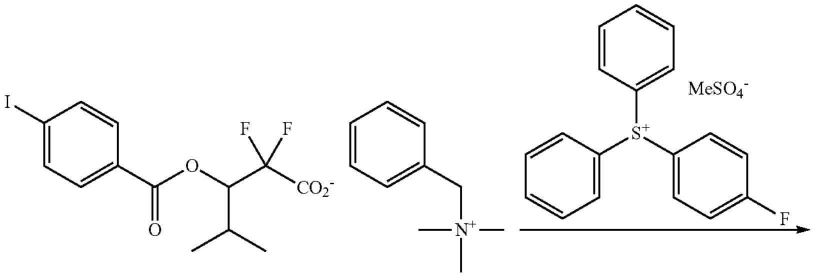

SM-11

-continued

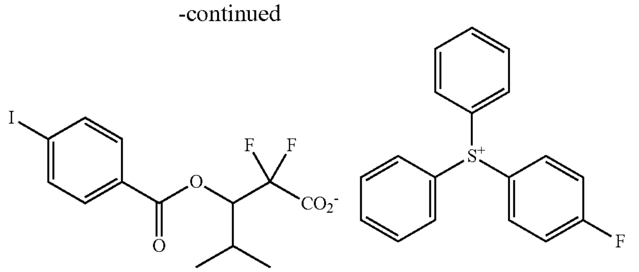

Q-26

A reactor was charged with 120 g of Compound SM-11, 875 g of methylene chloride, 112.2 g of diphenyl(4-fluorophenyl)sulfonium methylsulfate, and 400 g of deionized water, which were stirred at room temperature for 1 hour. The organic layer was taken out. It was washed 5 times with 200 g of deionized water, twice with 300 g of dilute oxalic acid aqueous solution, 3 times with 300 g of deionized water, twice with 300 g of dilute ammonia water, 4 times with 300 g of deionized water, and 4 times with 300 g of 20 wt % methanol aqueous solution. The organic layer was concentrated under reduced pressure. The concentrate was dissolved in 120 g of PGMEA. 600 g of hexane was added to the solution and stirred for 20 minutes, after which the supernatant was removed. 500 g of hexane was added to the oily residue and stirred, after which the supernatant was removed. The oily residue was concentrated under reduced pressure, obtaining the target acid diffusion inhibitor Q-26 as oily matter (amount 150 g, yield 92.6%). The spectral data of Q-26 are shown below.

$^1$H-NMR (500 MHz, DMSO-$d_6$):

δ=0.87 (3H, d), 0.92 (3H, dd), 2.13 (1H, m), 5.46 (1H, ddd), 7.67 (2H, m), 7.72 (2H, m), 7.75-7.87 (10H, m), 7.91-7.96 (4H, m) ppm $^{19}$F-NMR (500 MHz, DMSO-$d_6$): δ=−115.2 (1F, dd), −107.8 (1F, d), −104.6 (1F, m) ppm

TOFMS; MALDI

Positive $M^+$ 281.1 (corresponding to $C_{18}H_{14}FS^+$)

Negative $M^-$ 397.0 (corresponding to $C_{13}H_{12}F_2IO_4^-$)

Example 1-12

Synthesis of Acid Diffusion Inhibitor Q-27

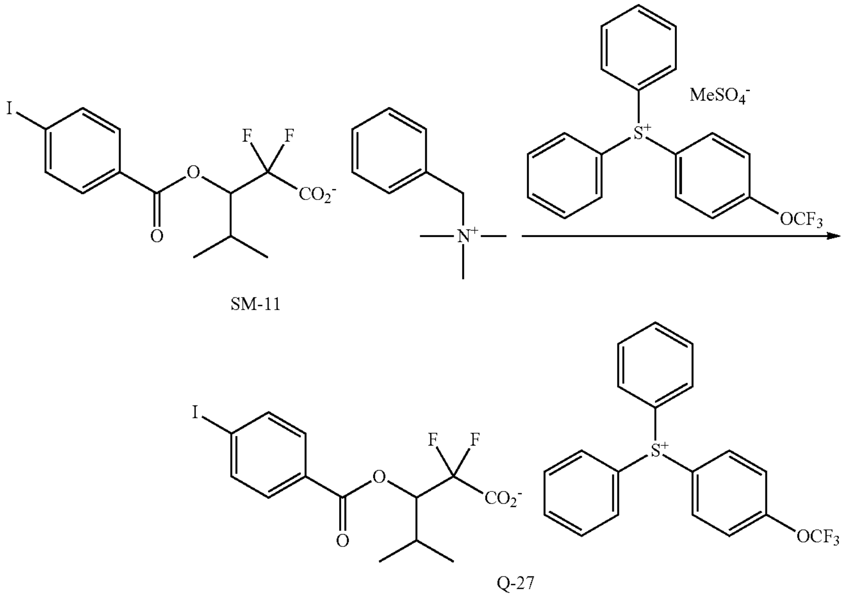

SM-11

Q-27

A reactor was charged with 11.1 g of Compound SM-11, 80 g of methylene chloride, 10.2 g of diphenyl(4-trifluoromethylphenyl)sulfonium methylsulfate, and 20 g of deionized water, which were stirred at room temperature for 30 minutes. The organic layer was taken out. It was washed 3 times with 20 g of deionized water, twice with 20 g of dilute oxalic acid aqueous solution, twice with 20 g of deionized water, once with 20 g of dilute ammonia water, and 4 times with 20 g of deionized water. The organic layer was concentrated under reduced pressure. 50 g of diisopropyl ether was added to the concentrate and stirred, after which the supernatant was removed. 50 g of hexane was added to the residue and stirred, after which the supernatant was removed. The oily residue was dissolved in 40 g of methyl isobutyl ketone. The solution was washed 3 times with 25 g of 20 wt % methanol aqueous solution. The organic layer was concentrated under reduced pressure, obtaining the target acid diffusion inhibitor Q-27 as oily matter (amount 8.9 g, yield 50.6%). The spectral data of Q-27 are shown below.

$^1$H-NMR (500 MHz, DMSO-$d_6$):

δ=0.87 (3H, d), 0.92 (3H, dd), 2.13 (1H, m), 5.46 (1H, ddd), 7.72 (2H, m), 7.76-7.81 (6H, m), 7.83-7.88 (6H, m), 7.94 (2H, m), 7.96 (2H, m) ppm $^{19}$F-NMR (500 MHz, DMSO-$d_6$): δ=−115.2 (1F, dd), −107.6 (1F, dd), −57.9 (3F, s) ppm

IR (D-ATR):

ν=3402, 3061, 2969, 1724, 1652, 1587, 1479, 1447, 1393, 1263, 1213, 1178, 1113, 1102, 1038, 1009, 926, 882, 846, 795, 753, 683, 529, 502 $cm^{-1}$

TOFMS; MALDI

Positive $M^+$ 347.1 (corresponding to $C_{19}H_{14}F_3S^+$)

Negative $M^-$ 397.0 (corresponding to $C_{13}H_{12}F_2IO_4^-$)

Example 1-13

Synthesis of Acid Diffusion Inhibitor Q-28 isobutyl ketone to the concentrate and concentrating the solution under reduced pressure. 90 g of diisopropyl ether was added to the solution and stirred, after which the supernatant was removed. 90 g of diisopropyl ether was added to the residue and stirred, allowing solids to precipitate. The solid precipitate was filtered and dried in vacuum, obtaining the target acid diffusion inhibitor Q-28 as solid (amount 12.6 g, yield 83.7%). The spectral data of Q-28 are shown below.

$^1$H-NMR (500 MHz, DMSO-$d_6$):

δ=0.89 (3H, d), 0.93 (3H, dd), 2.14 (1H, m), 5.46 (1H, ddd), 7.12 (2H, m), 7.60-7.66 (4H, m), 7.68 (2H, m), 7.72 (2H, m), 7.82-7.87 (4H, m), 7.93 (2H, m), 11.81 (1H, br) ppm $^{19}$F-NMR (500 MHz, DMSO-$d_6$): δ=−115.1 (1F, dd), −108.2 (1F, d), −105.5 (1F, m) ppm

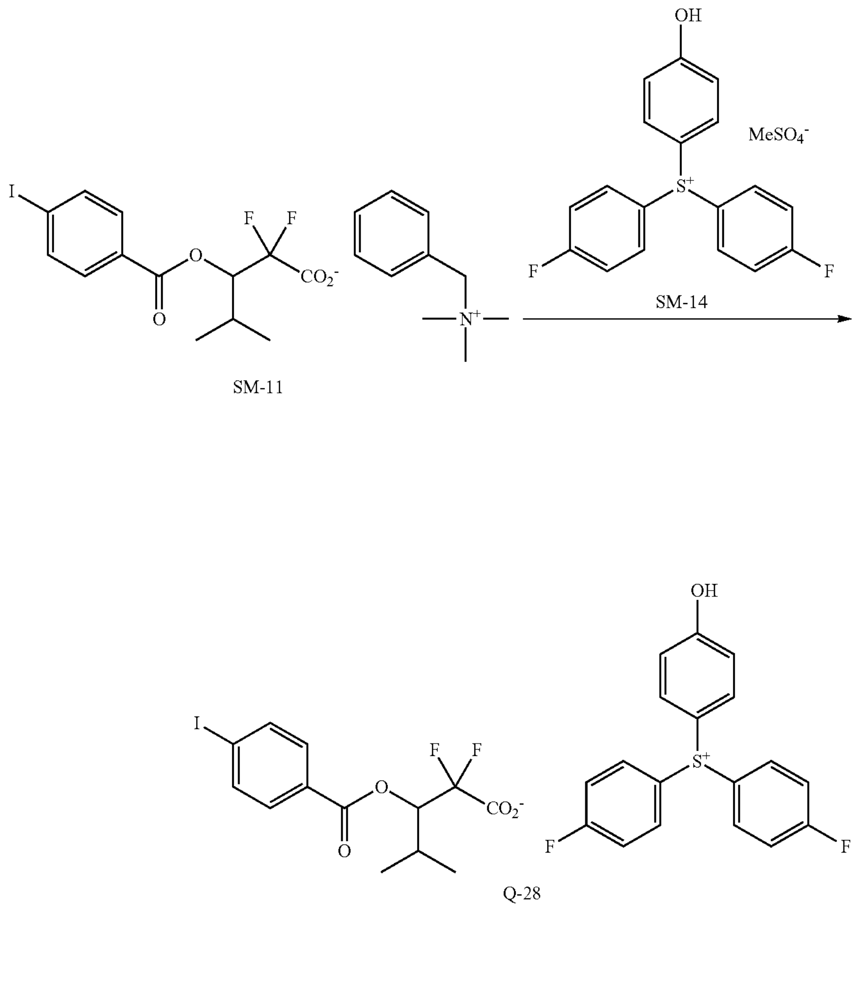

A reactor was charged with 11.5 g of Compound SM-11, 485 g of methylene chloride, 9.9 g of Compound SM-14, and 225 g of deionized water, which were stirred at room temperature for 2 hours. The organic layer was taken out. It was washed 6 times with 100 g of deionized water and twice with 100 g of 10 wt % methanol aqueous solution. The organic layer was concentrated under reduced pressure. Solvent replacement was carried out by adding methyl

IR (D-ATR):

ν=3413, 3100, 3061, 2971, 2880, 2797, 2681, 2595, 1723, 1645, 1587, 1492, 1393, 1301, 1266, 1241, 1177, 1162, 1102, 1073, 1042, 1009, 943, 882, 838, 794, 753, 682, 658, 626, 519, 433 $cm^{-1}$

TOFMS; MALDI

Positive $M^+$ 315.1 (corresponding to $C_{18}H_{13}F_2OS^+$)

Negative $M^-$ 397.0 (corresponding to $C_{13}H_{12}F_2IO_4^-$)

Example 1-14

Synthesis of Acid Diffusion Inhibitor Q-29

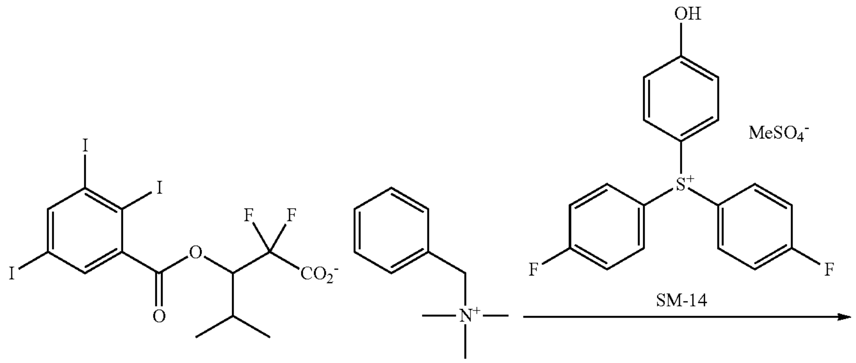

SM-14

SM-3

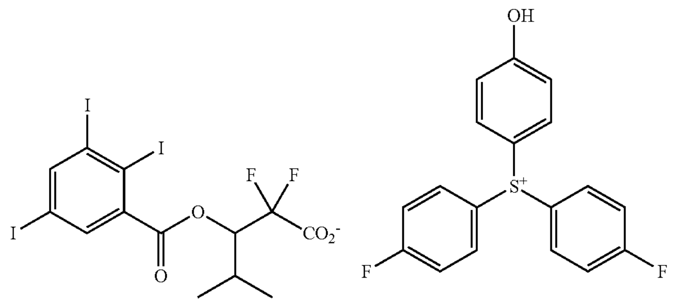

Q-29

A reactor was charged with 12.9 g of Compound SM-3, 350 g of methylene chloride, 7.3 g of Compound SM-14, and 165 g of deionized water, which were stirred at room temperature for 1 hour. The organic layer was taken out. It was washed 3 times with 100 g of deionized water and 3 times with 100 g of 10 wt % methanol aqueous solution. The organic layer was concentrated under reduced pressure. Solvent replacement was carried out by adding methyl isobutyl ketone to the concentrate and concentrating the solution under reduced pressure. 80 g of diisopropyl ether was added to the solution, allowing solids to precipitate. The solid precipitate was filtered and dried in vacuum, obtaining the target acid diffusion inhibitor Q-29 as solid (amount 13.4 g, yield 81.3%). The spectral data of Q-29 are shown below.

$^1$H-NMR (500 MHz, DMSO-$d_6$):

δ=0.94 (3H, d), 1.01 (3H, d), 2.15 (1H, m), 5.38 (1H, ddd), 7.13 (2H, m), 7.60-7.65 (4H, m), 7.68 (2H, m), 7.69 (1H, d), 7.82-7.87 (4H, m), 8.37 (1H, d), 11.92 (1H, br) ppm $^{19}$F-NMR (500 MHz, DMSO-$d_6$):

δ=−113.1 (1F, dd), −110.3 (1F, dd), −105.4 (1F, m) ppm

IR (D-ATR):

ν=3398, 3099, 3062, 2970, 2880, 2798, 2681, 2597, 1738, 1645, 1587, 1574, 1522, 1491, 1396, 1300, 1267, 1238, 1183, 1161, 1102, 1072, 1042, 1005, 941, 896, 872, 835, 797, 771, 745, 701, 519, 433 $cm^{-1}$

TOFMS; MALDI

Positive $M^+$ 315.1 (corresponding to $C_{18}H_{13}F_2OS^+$)

Negative $M^-$ 648.8 (corresponding to $C_{13}H_{10}F_2I_3O_4^-$)

Examples 1-15 to 1-29

Synthesis of Acid Diffusion Inhibitors Q-4 to Q-16, Q-18 and Q-19

Acid diffusion inhibitors Q-4 to Q-16, Q-18 and Q-19 as shown below were synthesized in accordance with Examples 1-1 to 1-12.

Q-4

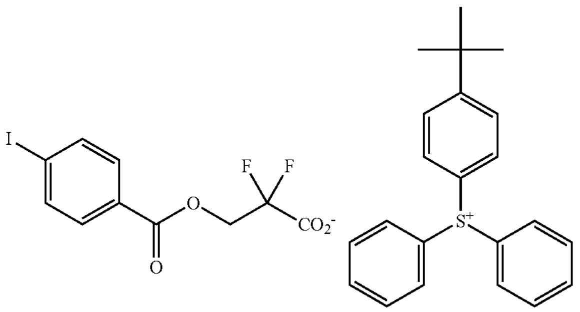

-continued
Q-5
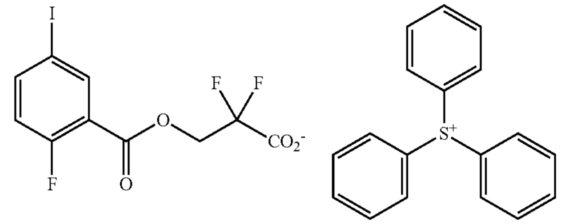
Q-6
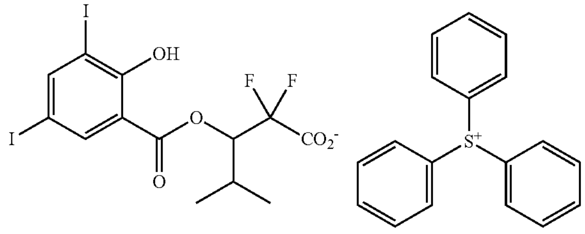
Q-7
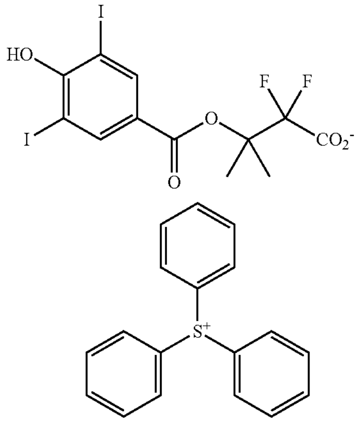
Q-8
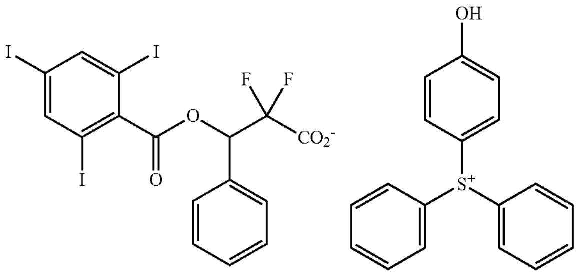
Q-9
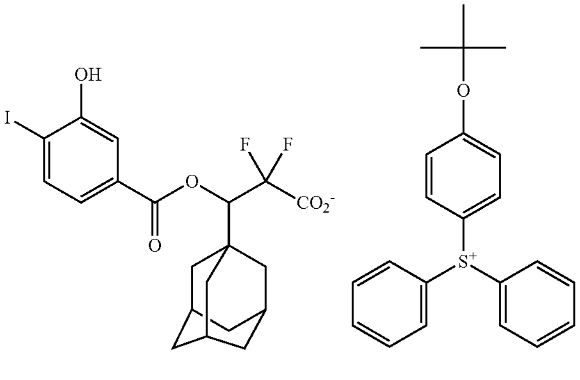
-continued
Q-10
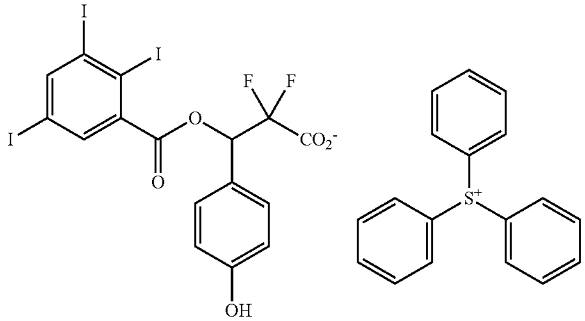
Q-11
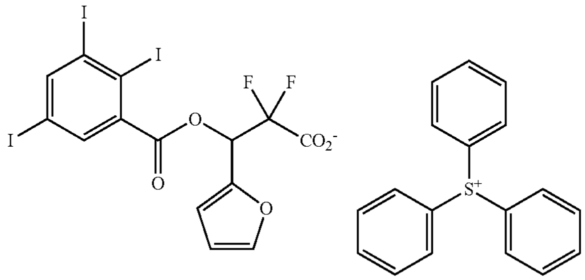
Q-12
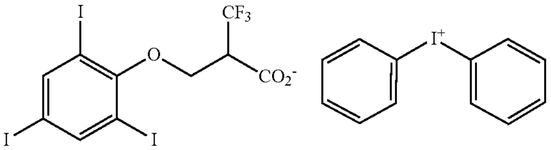
Q-13
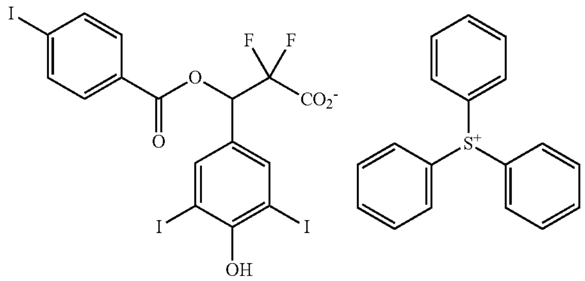
Q-14
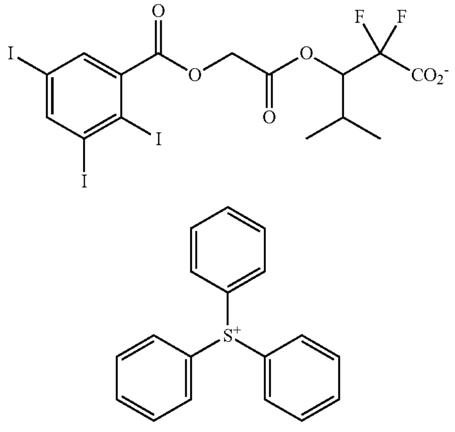

-continued

Q-15

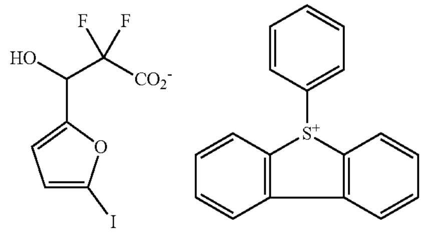

Q-16

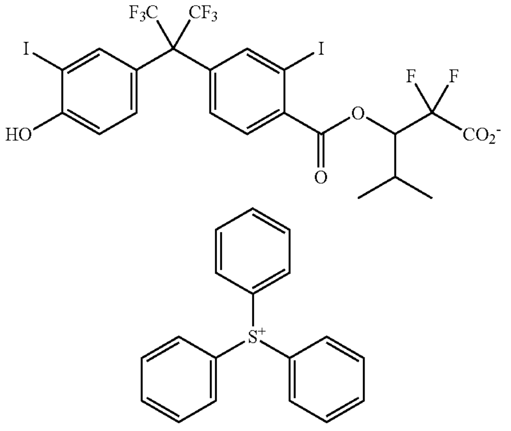

Q-18

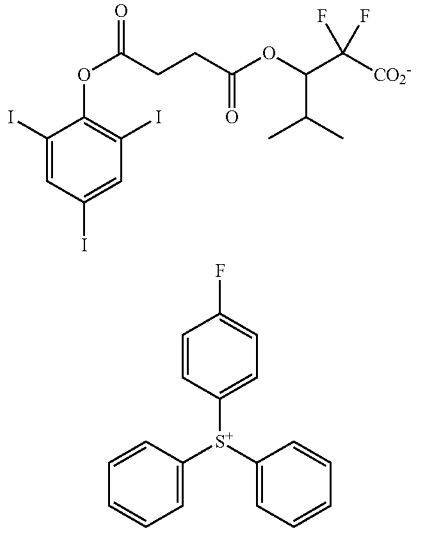

Q-19

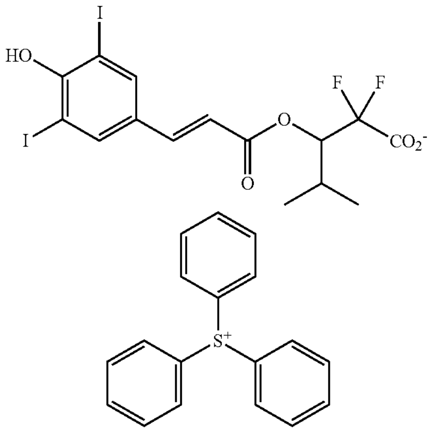

Synthesis Example 1

Synthesis of Polymer P-1

In nitrogen atmosphere, 22 g of 1-tert-butylcyclopentyl methacrylate, 17 g of 2-oxotetrahydrofuran-3-yl methacrylate, 0.48 g of dimethyl 2,2'-azobis(2-methylpropionate) (V-601 by Wako Pure Chemical Industries, Ltd.), 0.41 g of 2-mercaptoethanol, and 50 g of methyl ethyl ketone were combined to form a monomer/initiator solution. A flask in nitrogen atmosphere was charged with 23 g of methyl ethyl ketone, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The solid precipitate was collected by filtration, washed twice with 240 g of methanol, and vacuum dried at 50° C. for 20 hours, obtaining Polymer P-1 in white powder form (amount 36 g, yield 90%). Polymer P-1 had a Mw of 8,500 and a dispersity Mw/Mn of 1.63.

Polymer P-1

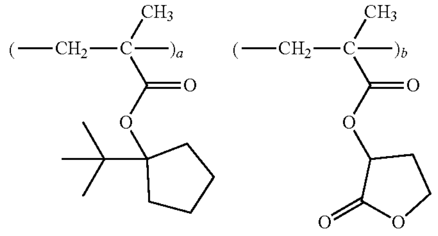

(a = 50, b = 50)
Mw = 8,500
Mw/Mn = 1.63

Synthesis Examples 2 to 5

Synthesis of Polymers P-2 to P-5

Polymers P-2 to P-5 were synthesized by the same procedure as in Synthesis Example 1 aside from changing the type and amount of monomers.

Polymer P-2

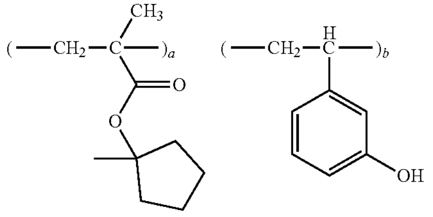

(a = 60, b = 40)
Mw = 9,000
Mw/Mn = 1.88

-continued

Polymer P-3

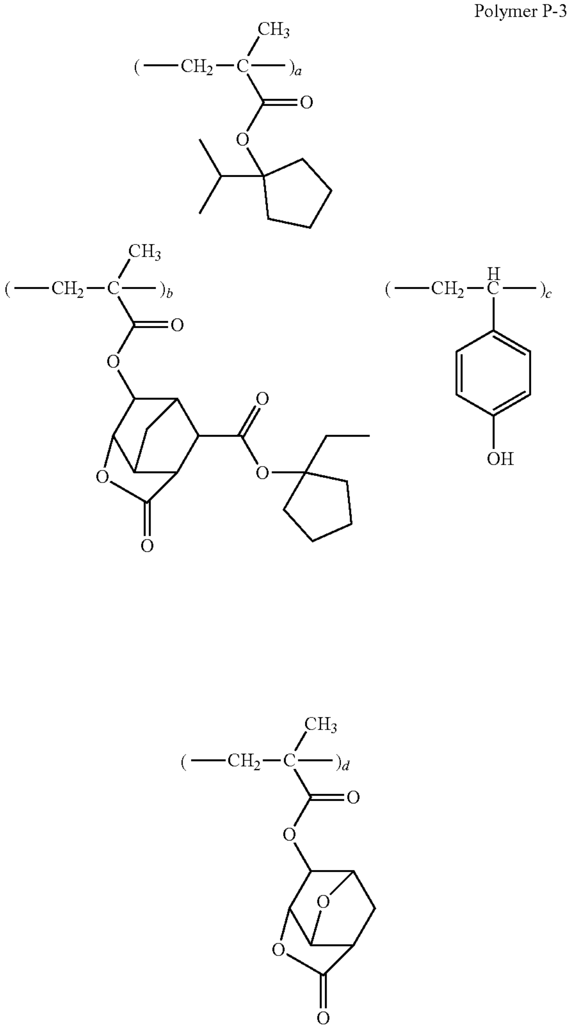

(a = 45, b = 10,
c = 35, d = 10)
Mw = 9,400
Mw/Mn = 1.86

Polymer P-4

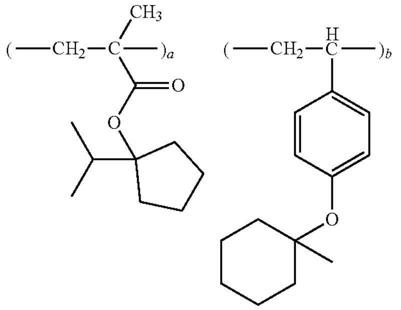

-continued

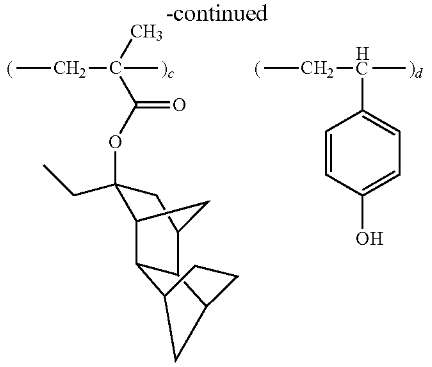

(a = 35, b = 15,
c = 10, d = 40)
Mw = 9,400
Mw/Mn = 1.78

Polymer P-5

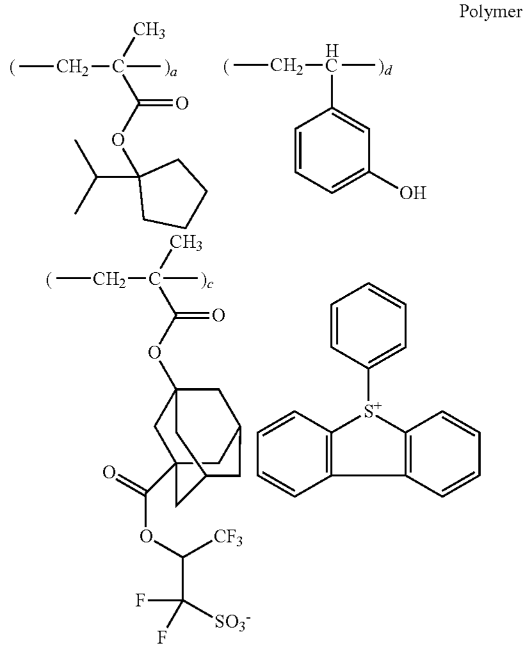

(a = 55, b = 30, c = 15)
Mw = 10,800
Mw/Mn = 1.79

Examples 2-1 to 2-68 and Comparative Examples 1-1 to 1-26

Preparation of Chemically Amplified Resist Compositions

Chemically amplified resist compositions were prepared by dissolving the components shown in Tables 1 to 4 in a solvent containing 0.01 wt % of surfactant Polyfox 636 (Omnova Solutions, Inc.), and filtering the solution through a Teflon® filter with a pore size of 0.2 μm.

The photoacid generators PAG-1 to PAG-4, solvents, comparative acid diffusion inhibitors Q-A to Q-J, and alkali-soluble surfactant SF-1 in Tables 1 to 4 are identified below.

Photoacid Generators PAG-1 to PAG-4:
PAG-1
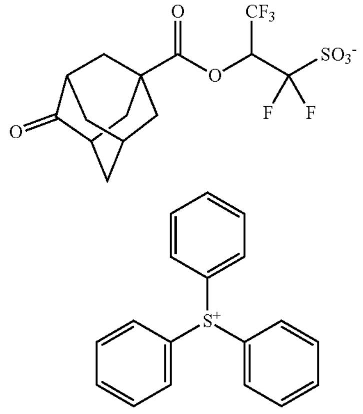
PAG-2
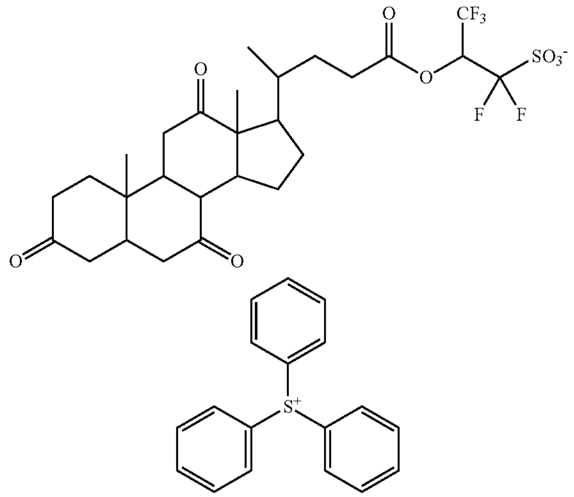
PAG-3
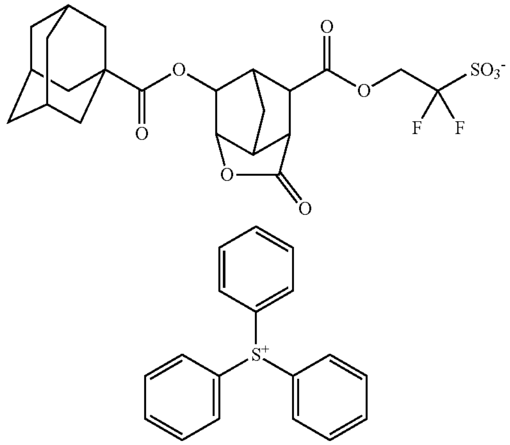
PAG-4
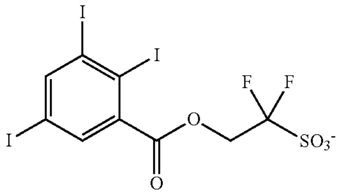
-continued
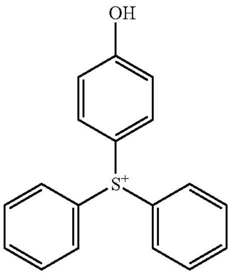
Solvent:
PGMEA=propylene glycol monomethyl ether acetate
GBL=γ-butyrolactone
CyHO=cyclohexanone
DAA=diacetone alcohol
Acid Diffusion Inhibitors Q-A to Q-J:
Q-A
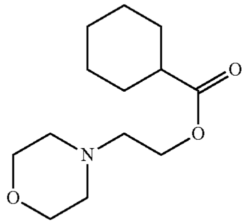
Q-B
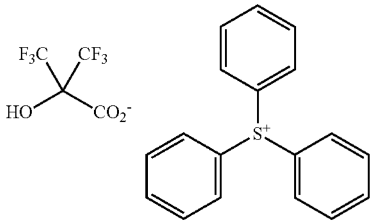
Q-C
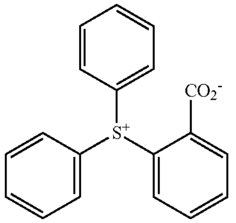
Q-D
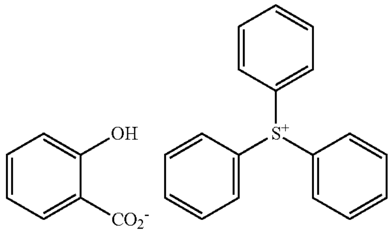

-continued

Q-E

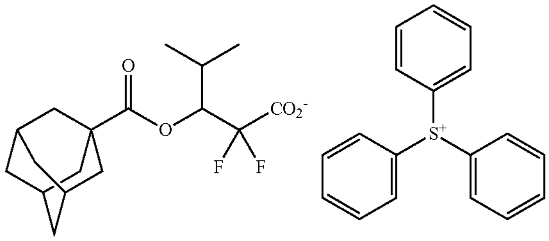

Q-F

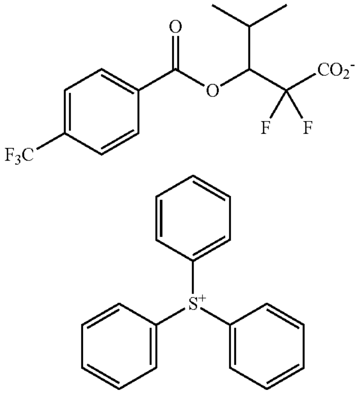

Q-G

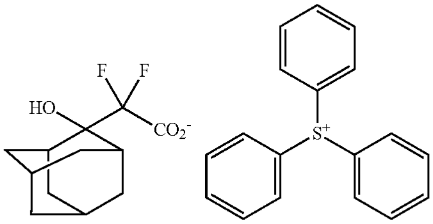

Q-H

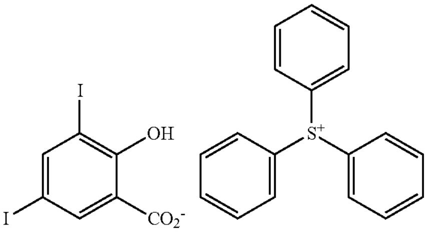

Q-I

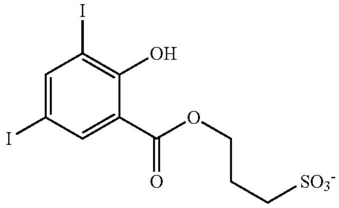

-continued

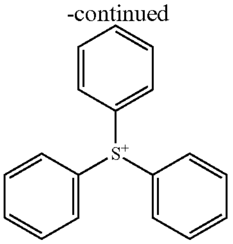

Q-J

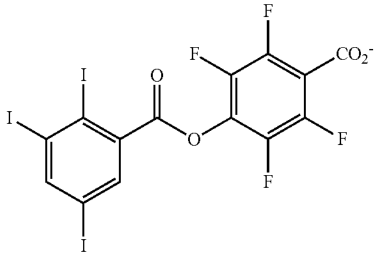

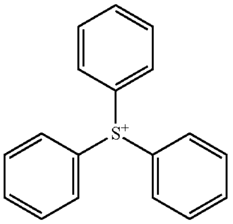

Alkali-soluble surfactant SF-1: poly(2,2,3,3,4,4,4-heptafluoro-1-isobutyl-1-butyl methacrylate/9-(2,2,2-trifluoro-1-trifluoromethylethyloxycarbonyl)-4-oxatricyclo[4.2.1.$0^{3,7}$]nonan-5-on-2-yl methacrylate)

SF-1

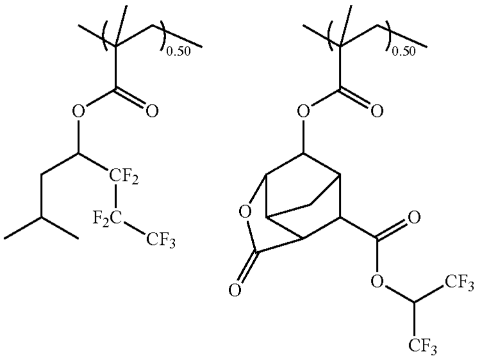

Mw = 7,700
Mw/Mn = 1.82

TABLE 1

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-1 | R-1 | P-1 (100) | PAG-1 (8.0) | Q-1 (5.0) | SF-1 (3.0) | PGMEA/GBL (1,920/480) |
| 2-2 | R-2 | P-1 (100) | PAG-1 (8.0) | Q-6 (5.0) | SF-1 (3.0) | PGMEA/GBL (1,920/480) |
| 2-3 | R-3 | P-1 (100) | PAG-1 (8.0) | Q-15 (4.7) | SF-1 (3.0) | PGMEA/GBL (1,920/480) |

TABLE 1-continued

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-4 | R-4 | P-1 (100) | PAG-1 (8.0) | Q-17 (5.0) | SF-1 (3.0) | PGMEA/GBL (1,920/480) |
| 2-5 | R-5 | P-1 (100) | PAG-1 (8.0) | Q-19 (5.0) | SF-1 (3.0) | PGMEA/GBL (1,920/480) |
| 2-6 | R-6 | P-1 (100) | PAG-2 (8.0) | Q-2 (4.9) | SF-1 (3.0) | PGMEA/GBL (1,920/480) |
| 2-7 | R-7 | P-1 (100) | PAG-3 (8.0) | Q-17 (4.9) | SF-1 (3.0) | PGMEA/GBL (1,920/480) |
| 2-8 | R-8 | P-2 (100) | PAG-3 (20.0) | Q-1 (10.0) | SF-1 (3.0) | PGMEA/DAA (2,100/900) |
| 2-9 | R-9 | P-2 (100) | PAG-3 (20.0) | Q-2 (10.0) | SF-1 (3.0) | PGMEA/DAA (2,100/900) |
| 2-10 | R-10 | P-2 (100) | PAG-3 (20.0) | Q-3 (10.0) | SF-1 (3.0) | PGMEA/DAA (2,100/900) |
| 2-11 | R-11 | P-2 (100) | PAG-3 (20.0) | Q-4 (9.9) | SF-1 (3.0) | PGMEA/DAA (2,100/900) |
| 2-12 | R-12 | P-2 (100) | PAG-3 (20.0) | Q-5 (10.0) | SF-1 (3.0) | PGMEA/DAA (2,100/900) |
| 2-13 | R-13 | P-2 (100) | PAG-3 (20.0) | Q-6 (10.0) | SF-1 (3.0) | PGMEA/DAA (2,100/900) |
| 2-14 | R-14 | P-2 (100) | PAG-3 (20.0) | Q-7 (10.0) | SF-1 (3.0) | PGMEA/DAA (2,100/900) |
| 2-15 | R-15 | P-2 (100) | PAG-3 (20.0) | Q-8 (9.9) | SF-1 (3.0) | PGMEA/DAA (2,100/900) |
| 2-16 | R-16 | P-2 (100) | PAG-3 (20.0) | Q-9 (9.8) | SF-1 (3.0) | PGMEA/DAA (2,100/900) |
| 2-17 | R-17 | P-2 (100) | PAG-3 (20.0) | Q-10 (10.0) | SF-1 (3.0) | PGMEA/DAA (2,100/900) |
| 2-18 | R-18 | P-2 (100) | PAG-3 (20.0) | Q-11 (10.0) | SF-1 (3.0) | PGMEA/DAA (2,100/900) |
| 2-19 | R-19 | P-2 (100) | PAG-3 (20.0) | Q-12 (10.0) | SF-1 (3.0) | PGMEA/DAA (2,100/900) |
| 2-20 | R-20 | P-2 (100) | PAG-3 (20.0) | Q-13 (10.0) | SF-1 (3.0) | PGMEA/DAA (2,100/900) |
| 2-21 | R-21 | P-2 (100) | PAG-3 (20.0) | Q-14 (9.7) | SF-1 (3.0) | PGMEA/DAA (2,100/900) |
| 2-22 | R-22 | P-2 (100) | PAG-3 (20.0) | Q-15 (10.0) | SF-1 (3.0) | PGMEA/DAA (2,100/900) |
| 2-23 | R-23 | P-2 (100) | PAG-3 (20.0) | Q-16 (10.0) | SF-1 (3.0) | PGMEA/DAA (2,100/900) |
| 2-24 | R-24 | P-2 (100) | PAG-3 (20.0) | Q-17 (10.0) | SF-1 (3.0) | PGMEA/DAA (2,100/900) |
| 2-25 | R-25 | P-2 (100) | PAG-3 (20.0) | Q-18 (9.8) | SF-1 (3.0) | PGMEA/DAA (2,100/900) |

TABLE 2

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-26 | R-26 | P-2 (100) | PAG-3 (20.0) | Q-19 (10.0) | SF-1 (3.0) | PGMEA/DAA (2,100/900) |
| 2-27 | R-27 | P-3 (100) | PAG-4 (20.0) | Q-1 (7.3) Q-B (2.8) | SF-1 (3.0) | PGMEA/DAA/CyHO (2,100/600/300) |
| 2-28 | R-28 | P-3 (100) | PAG-4 (20.0) | Q-2 (7.3) Q-B (2.8) | SF-1 (3.0) | PGMEA/DAA/CyHO (2,100/600/300) |
| 2-29 | R-29 | P-3 (100) | PAG-4 (20.0) | Q-3 (7.3) Q-B (2.8) | SF-1 (3.0) | PGMEA/DAA/CyHO (2,100/600/300) |
| 2-30 | R-30 | P-3 (100) | PAG-4 (20.0) | Q-17 (7.3) Q-A (1.0) | SF-1 (3.0) | PGMEA/DAA/CyHO (2,100/600/300) |
| 2-31 | R-31 | P-3 (100) | PAG-4 (20.0) | Q-19 (8.0) Q-C (2.1) | SF-1 (3.0) | PGMEA/DAA/CyHO (2,100/600/300) |
| 2-32 | R-32 | P-4 (100) | PAG-3 (20.0) | Q-2 (8.0) Q-B (2.1) | SF-1 (3.0) | PGMEA/DAA (2,100/900) |
| 2-33 | R-33 | P-4 (100) | PAG-3 (20.0) | Q-3 (8.0) Q-B (2.1) | SF-1 (3.0) | PGMEA/DAA (2,100/900) |
| 2-34 | R-34 | P-4 (100) | PAG-4 (20.0) | Q-17 (10.0) | SF-1 (3.0) | PGMEA/DAA (2,100/900) |
| 2-35 | R-35 | P-4 (100) | PAG-4 (20.0) | Q-19 (10.0) | SF-1 (3.0) | PGMEA/DAA (2,100/900) |
| 2-36 | R-36 | P-5 (100) | — | Q-1 (10.3) | SF-1 (3.0) | PGMEA/DAA (2,100/900) |

TABLE 2-continued

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-37 | R-37 | P-5 (100) | — | Q-2 (10.0) | SF-1 (3.0) | PGMEA/DAA (2,100/900) |
| 2-38 | R-38 | P-5 (100) | — | Q-3 (10.0) | SF-1 (3.0) | PGMEA/DAA (2,100/900) |
| 2-39 | R-39 | P-5 (100) | — | Q-6 (10.0) | SF-1 (3.0) | PGMEA/DAA (2,100/900) |
| 2-40 | R-40 | P-5 (100) | — | Q-11 (9.8) | SF-1 (3.0) | PGMEA/DAA (2,100/900) |
| 2-41 | R-41 | P-5 (100) | — | Q-12 (9.5) | SF-1 (3.0) | PGMEA/DAA (2,100/900) |
| 2-42 | R-42 | P-5 (100) | — | Q-15 (10.0) | SF-1 (3.0) | PGMEA/DAA (2,100/900) |
| 2-43 | R-43 | P-5 (100) | — | Q-17 (10.0) | SF-1 (3.0) | PGMEA/DAA (2,100/900) |
| 2-44 | R-44 | P-5 (100) | — | Q-19 (9.9) | SF-1 (3.0) | PGMEA/DAA (2,100/900) |
| 2-45 | R-45 | P-5 (100) | PAG-3 (5.0) | Q-1 (18.0) | SF-1 (3.0) | PGMEA/DAA (2,100/900) |
| 2-46 | R-46 | P-5 (100) | PAG-3 (5.0) | Q-2 (18.0) | SF-1 (3.0) | PGMEA/DAA (2,100/900) |
| 2-47 | R-47 | P-5 (100) | PAG-3 (5.0) | Q-3 (18.0) | SF-1 (3.0) | PGMEA/DAA (2,100/900) |
| 2-48 | R-48 | P-5 (100) | PAG-4 (5.0) | Q-17 (18.0) | SF-1 (3.0) | PGMEA/DAA (2,100/900) |
| 2-49 | R-49 | P-5 (100) | PAG-4 (5.0) | Q-19 (17.6) | SF-1 (3.0) | PGMEA/DAA (2,100/900) |

TABLE 3

| Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 2-50 | R-50 | P-2 (100) | PAG-3 (20.0) | Q-20 (9.8) | SF-1 (3.0) | PGMEA/DAA (2,100/900) |
| 2-51 | R-51 | P-2 (100) | PAG-3 (20.0) | Q-21 (10.0) | SF-1 (3.0) | PGMEA/DAA (2,100/900) |
| 2-52 | R-52 | P-2 (100) | PAG-3 (20.0) | Q-22 (10.0) | SF-1 (3.0) | PGMEA/DAA (2,100/900) |
| 2-53 | R-53 | P-2 (100) | PAG-3 (20.0) | Q-23 (10.0) | SF-1 (3.0) | PGMEA/DAA (2,100/900) |
| 2-54 | R-54 | P-2 (100) | PAG-3 (20.0) | Q-24 (10.0) | SF-1 (3.0) | PGMEA/DAA (2,100/900) |
| 2-55 | R-55 | P-2 (100) | PAG-3 (20.0) | Q-25 (9.7) | SF-1 (3.0) | PGMEA/DAA (2,100/900) |
| 2-56 | R-56 | P-2 (100) | PAG-3 (20.0) | Q-26 (10.0) | SF-1 (3.0) | PGMEA/DAA (2,100/900) |
| 2-57 | R-57 | P-2 (100) | PAG-3 (20.0) | Q-27 (10.0) | SF-1 (3.0) | PGMEA/DAA (2,100/900) |
| 2-58 | R-58 | P-2 (100) | PAG-3 (20.0) | Q-28 (9.9) | SF-1 (3.0) | PGMEA/DAA (2,100/900) |
| 2-59 | R-59 | P-2 (100) | PAG-3 (20.0) | Q-29 (9.9) | SF-1 (3.0) | PGMEA/DAA (2,100/900) |
| 2-60 | R-60 | P-5 (100) | — | Q-22 (10.0) | SF-1 (3.0) | PGMEA/DAA (2,100/900) |
| 2-61 | R-61 | P-5 (100) | — | Q-23 (10.0) | SF-1 (3.0) | PGMEA/DAA (2,100/900) |
| 2-62 | R-62 | P-5 (100) | — | Q-24 (10.0) | SF-1 (3.0) | PGMEA/DAA (2,100/900) |
| 2-63 | R-63 | P-5 (100) | — | Q-26 (10.0) | SF-1 (3.0) | PGMEA/DAA (2,100/900) |
| 2-64 | R-64 | P-5 (100) | — | Q-27 (10.0) | SF-1 (3.0) | PGMEA/DAA (2,100/900) |
| 2-65 | R-65 | P-5 (100) | PAG-3 (5.0) | Q-24 (18.0) | SF-1 (3.0) | PGMEA/DAA (2,100/900) |
| 2-66 | R-66 | P-1 (100) | PAG-2 (8.0) | Q-23 (5.0) | SF-1 (3.0) | PGMEA/GBL (1,920/480) |
| 2-67 | R-67 | P-1 (100) | PAG-3 (8.0) | Q-24 (4.9) | SF-1 (3.0) | PGMEA/GBL (1,920/480) |
| 2-68 | R-68 | P-1 (100) | PAG-3 (8.0) | Q-27 (4.8) | SF-1 (3.0) | PGMEA/GBL (1,920/480) |

TABLE 4

| Comparative Example | Resist composition | Polymer (pbw) | Photoacid generator (pbw) | Acid diffusion inhibitor (pbw) | Surfactant (pbw) | Solvent (pbw) |
|---|---|---|---|---|---|---|
| 1-1 | CR-1 | P-1 (100) | PAG-1 (8.0) | Q-A (2.9) | SF-1 (3.0) | PGMEA/GBL (1,920/480) |
| 1-2 | CR-2 | P-1 (100) | PAG-1 (8.0) | Q-B (5.0) | SF-1 (3.0) | PGMEA/GBL (1,920/480) |
| 1-3 | CR-3 | P-1 (100) | PAG-1 (8.0) | Q-C (4.6) | SF-1 (3.0) | PGMEA/GBL (1,920/480) |
| 1-4 | CR-4 | P-1 (100) | PAG-1 (8.0) | Q-D (4.8) | SF-1 (3.0) | PGMEA/GBL (1,920/480) |
| 1-5 | CR-5 | P-1 (100) | PAG-1 (8.0) | Q-E (5.0) | SF-1 (3.0) | PGMEA/GBL (1,920/480) |
| 1-6 | CR-6 | P-1 (100) | PAG-1 (8.0) | Q-F (5.0) | SF-1 (3.0) | PGMEA/GBL (1,920/480) |
| 1-7 | CR-7 | P-1 (100) | PAG-1 (8.0) | Q-H (4.9) | SF-1 (3.0) | PGMEA/GBL (1,920/480) |
| 1-8 | CR-8 | P-1 (100) | PAG-1 (8.0) | Q-I (5.0) | SF-1 (3.0) | PGMEA/GBL (1,920/480) |
| 1-9 | CR-9 | P-2 (100) | PAG-3 (20.0) | Q-A (6.0) | SF-1 (3.0) | PGMEA/DAA (2,100/900) |
| 1-10 | CR-10 | P-2 (100) | PAG-3 (20.0) | Q-B (10.0) | SF-1 (3.0) | PGMEA/DAA (2,100/900) |
| 1-11 | CR-11 | P-2 (100) | PAG-3 (20.0) | Q-C (9.5) | SF-1 (3.0) | PGMEA/DAA (2,100/900) |
| 1-12 | CR-12 | P-2 (100) | PAG-3 (20.0) | Q-D (9.8) | SF-1 (3.0) | PGMEA/DAA (2,100/900) |
| 1-13 | CR-13 | P-2 (100) | PAG-3 (20.0) | Q-E (10.0) | SF-1 (3.0) | PGMEA/DAA (2,100/900) |
| 1-14 | CR-14 | P-2 (100) | PAG-3 (20.0) | Q-F (10.0) | SF-1 (3.0) | PGMEA/DAA (2,100/900) |
| 1-15 | CR-15 | P-2 (100) | PAG-3 (20.0) | Q-G (10.0) | SF-1 (3.0) | PGMEA/DAA (2,100/900) |
| 1-16 | CR-16 | P-2 (100) | PAG-3 (20.0) | Q-H (9.9) | SF-1 (3.0) | PGMEA/DAA (2,100/900) |
| 1-17 | CR-17 | P-2 (100) | PAG-3 (20.0) | Q-I (10.0) | SF-1 (3.0) | PGMEA/DAA (2,100/900) |
| 1-18 | CR-18 | P-2 (100) | PAG-3 (20.0) | Q-J (10.0) | SF-1 (3.0) | PGMEA/DAA (2,100/900) |
| 1-19 | CR-19 | P-3 (100) | PAG-4 (20.0) | Q-F (7.3) Q-B (2.8) | SF-1 (3.0) | PGMEA/DAA/CyHO (2,100/600/300) |
| 1-20 | CR-20 | P-3 (100) | PAG-4 (20.0) | Q-H (7.3) Q-B (2.8) | SF-1 (3.0) | PGMEA/DAA/CyHO (2,100/600/300) |
| 1-21 | CR-21 | P-4 (100) | PAG-3 (20.0) | Q-F (8.0) Q-B (2.1) | SF-1 (3.0) | PGMEA/DAA (2,100/900) |
| 1-22 | CR-22 | P-4 (100) | PAG-3 (20.0) | Q-H (8.0) Q-B (2.1) | SF-1 (3.0) | PGMEA/DAA (2,100/900) |
| 1-23 | CR-23 | P-4 (100) | PAG-3 (20.0) | Q-I (8.0) Q-B (2.1) | SF-1 (3.0) | PGMEA/DAA (2,100/900) |
| 1-24 | CR-24 | P-5 (100) | — | Q-F (10.0) | SF-1 (3.0) | PGMEA/DAA (2,100/900) |
| 1-25 | CR-25 | P-5 (100) | — | Q-H (10.0) | SF-1 (3.0) | PGMEA/DAA (2,100/900) |
| 1-26 | CR-26 | P-5 (100) | — | Q-I (10.0) | SF-1 (3.0) | PGMEA/DAA (2,100/900) |

Examples 3-1 to 3-10 and Comparative Examples 2-1 to 2-8

ArF Lithography Patterning Test

On a silicon substrate, an antireflective coating solution (ARC-29A by Nissan Chemical Corp.) was coated and baked at 180° C. for 60 seconds to form an ARC of 100 nm thick. On the ARC, each of the resist compositions (R-1 to R-7, R-66 to R-68, CR-1 to CR-8) was spin coated and baked on a hotplate at 100° C. for 60 seconds to form a resist film of 90 nm thick.

Using an ArF excimer laser scanner (NSR-S610C by Nikon Corp., NA 1.30, σ 0.94/0.74, dipole 35 deg. illumination, 6% halftone phase shift mask), the resist film was exposed by the immersion lithography. Water was used as the immersion liquid. After exposure, the resist film was baked (PEB) at 85° C. for 60 seconds and developed in 2.38 wt % TMAH aqueous solution for 60 seconds to form a line-and-space (LS) pattern.

The LS pattern as developed was observed under CD-SEM (CG-5000 by Hitachi High-Technologies Corp.) and evaluated for sensitivity and LWR by the following methods. The results are shown in Table 5.

Evaluation of Sensitivity

The optimum dose (Eop) is a dose (mJ/cm$^2$) which provides a LS pattern having a line width of 40 nm at a pitch of 80 nm and reported as sensitivity. A smaller value indicates a higher sensitivity.

Evaluation of LWR

On the L/S pattern formed by exposure in the optimum dose Eop, the line width was measured at longitudinally spaced apart 10 points, from which a 3-fold value (3σ) of standard deviation (σ) was determined and reported as LWR. A smaller value of 3σ indicates a pattern having a lower roughness and more uniform line width. A pattern with a LWR value of 2.5 nm or less is rated good while a pattern with a LWR value in excess of 2.5 nm is rated NG.

TABLE 5

| | | Resist composition | Eop ($mJ/cm^2$) | LWR (nm) |
|---|---|---|---|---|
| Example | 3-1 | R-1 | 35 | Good (2.4) |
| | 3-2 | R-2 | 34 | Good (2.4) |
| | 3-3 | R-3 | 32 | Good (2.2) |
| | 3-4 | R-4 | 33 | Good (2.3) |
| | 3-5 | R-5 | 34 | Good (2.3) |
| | 3-6 | R-6 | 36 | Good (2.3) |
| | 3-7 | R-7 | 37 | Good (2.1) |
| | 3-8 | R-66 | 33 | Good (2.3) |
| | 3-9 | R-67 | 37 | Good (2.2) |
| | 3-10 | R-68 | 35 | Good (2.4) |
| Comparative Example | 2-1 | CR-1 | 46 | NG (3.3) |
| | 2-2 | CR-2 | 40 | NG (2.6) |
| | 2-3 | CR-3 | 46 | NG (2.8) |
| | 2-4 | CR-4 | 48 | NG (2.9) |
| | 2-5 | CR-5 | 34 | NG (2.6) |
| | 2-6 | CR-6 | 35 | NG (2.7) |
| | 2-7 | CR-7 | 47 | NG (2.8) |
| | 2-8 | CR-8 | 33 | NG (3.0) |

As is evident from Table 5, the chemically amplified resist compositions containing onium salt compounds within the scope of the invention exhibit a good balance of sensitivity and LWR. The resist compositions are useful as the ArF immersion lithography material.

Examples 4-1 to 4-58 and Comparative Examples 3-1 to 3-18

EUV Lithography Test

Each of the resist compositions (R-8 to R-65, CR-9 to CR-26) was spin coated on a silicon substrate having a 20-nm coating of silicon-containing spin-on hard mask SHB-A940 (silicon content 43 wt %, Shin-Etsu Chemical Co., Ltd.) and prebaked on a hotplate at 105° C. for 60 seconds to form a resist film of 50 nm thick. Using an EUV scanner NXE3300 (ASML, NA 0.33, σ 0.9/0.6, quadrupole illumination), the resist film was exposed to EUV through a mask bearing a hole pattern having a pitch 46 nm+20% bias (on-wafer size). The resist film was baked (PEB) on a hotplate at 90° C. for 60 seconds and developed in a 2.38 wt % TMAH aqueous solution for 30 seconds to form a hole pattern having a size of 23 nm.

The hole pattern as developed was observed under CD-SEM (CG-5000 by Hitachi High-Technologies Corp.) and evaluated for sensitivity and CDU by the following methods. The results are shown in Tables 6 to 8.

Evaluation of Sensitivity

The optimum dose (Eop) is a dose ($mJ/cm^2$) which provides a hole pattern having a hole size of 23 nm and reported as sensitivity. A smaller value indicates a higher sensitivity.

Evaluation of CDU

For the hole pattern at the optimum dose (Eop), the size of 50 holes within the same dose shot was measured, from which a 3-fold value (3σ) of standard deviation (σ) was computed and reported as CDU. A smaller value of CDU indicates better dimensional uniformity of hole pattern. The sample was rated good for a CDU value of up to 3.0 nm and NG for a CDU value in excess of 3.0 nm.

TABLE 6

| | | Resist composition | Eop ($mJ/cm^2$) | CDU (nm) |
|---|---|---|---|---|
| Example | 4-1 | R-8 | 28 | Good (2.8) |
| | 4-2 | R-9 | 28 | Good (2.8) |
| | 4-3 | R-10 | 28 | Good (2.7) |
| | 4-4 | R-11 | 30 | Good (2.9) |
| | 4-5 | R-12 | 27 | Good (2.9) |
| | 4-6 | R-13 | 28 | Good (2.8) |
| | 4-7 | R-14 | 27 | Good (2.7) |
| | 4-8 | R-15 | 30 | Good (2.9) |
| | 4-9 | R-16 | 30 | Good (3.0) |
| | 4-10 | R-17 | 29 | Good (2.9) |
| | 4-11 | R-18 | 28 | Good (2.9) |
| | 4-12 | R-19 | 29 | Good (3.0) |
| | 4-13 | R-20 | 29 | Good (2.8) |
| | 4-14 | R-21 | 30 | Good (3.0) |
| | 4-15 | R-22 | 30 | Good (2.8) |
| | 4-16 | R-23 | 29 | Good (2.9) |
| | 4-17 | R-24 | 27 | Good (2.7) |
| | 4-18 | R-25 | 30 | Good (2.9) |
| | 4-19 | R-26 | 27 | Good (2.7) |
| | 4-20 | R-27 | 28 | Good (2.7) |
| | 4-21 | R-28 | 28 | Good (2.7) |
| | 4-22 | R-29 | 28 | Good (2.7) |
| | 4-23 | R-30 | 30 | Good (2.8) |
| | 4-24 | R-31 | 29 | Good (2.6) |
| | 4-25 | R-32 | 29 | Good (2.9) |
| | 4-26 | R-33 | 28 | Good (2.9) |
| | 4-27 | R-34 | 27 | Good (2.7) |
| | 4-28 | R-35 | 27 | Good (2.7) |
| | 4-29 | R-36 | 24 | Good (2.5) |
| | 4-30 | R-37 | 25 | Good (2.4) |
| | 4-31 | R-38 | 25 | Good (2.5) |
| | 4-32 | R-39 | 26 | Good (2.4) |
| | 4-33 | R-40 | 26 | Good (2.5) |
| | 4-34 | R-41 | 25 | Good (2.6) |
| | 4-35 | R-42 | 25 | Good (2.4) |
| | 4-36 | R-43 | 24 | Good (2.3) |
| | 4-37 | R-44 | 23 | Good (2.3) |
| | 4-38 | R-45 | 23 | Good (2.2) |
| | 4-39 | R-46 | 23 | Good (2.2) |
| | 4-40 | R-47 | 22 | Good (2.2) |
| | 4-41 | R-48 | 22 | Good (2.3) |
| | 4-42 | R-49 | 22 | Good (2.1) |

TABLE 7

| | | Resist composition | Eop ($mJ/cm^2$) | CDU (nm) |
|---|---|---|---|---|
| Example | 4-43 | R-50 | 30 | Good (2.8) |
| | 4-44 | R-51 | 29 | Good (2.7) |
| | 4-45 | R-52 | 29 | Good (2.9) |
| | 4-46 | R-53 | 28 | Good (2.8) |
| | 4-47 | R-54 | 29 | Good (2.7) |
| | 4-48 | R-55 | 27 | Good (2.8) |
| | 4-49 | R-56 | 26 | Good (2.9) |
| | 4-50 | R-57 | 28 | Good (2.8) |
| | 4-51 | R-58 | 28 | Good (2.8) |
| | 4-52 | R-59 | 29 | Good (2.7) |
| | 4-53 | R-60 | 23 | Good (2.4) |
| | 4-54 | R-61 | 24 | Good (2.5) |
| | 4-55 | R-62 | 25 | Good (2.2) |
| | 4-56 | R-63 | 25 | Good (2.5) |
| | 4-57 | R-64 | 23 | Good (2.4) |
| | 4-58 | R-65 | 22 | Good (2.1) |

TABLE 8

| | | Resist composition | Eop ($mJ/cm^2$) | CDU (nm) |
|---|---|---|---|---|
| Comparative Example | 3-1 | CR-9 | 42 | NG (3.6) |
| | 3-2 | CR-10 | 33 | NG (3.1) |
| | 3-3 | CR-11 | 40 | NG (3.3) |
| | 3-4 | CR-12 | 39 | NG (3.4) |
| | 3-5 | CR-13 | 32 | NG (3.1) |

TABLE 8-continued

| | Resist composition | Eop (mJ/cm$^2$) | CDU (nm) |
|---|---|---|---|
| 3-6 | CR-14 | 32 | NG (3.3) |
| 3-7 | CR-15 | 42 | NG (3.4) |
| 3-8 | CR-16 | 34 | NG (3.2) |
| 3-9 | CR-17 | 27 | NG (3.7) |
| 3-10 | CR-18 | 30 | NG (3.6) |
| 3-11 | CR-19 | 32 | NG (3.2) |
| 3-12 | CR-20 | 37 | NG (3.2) |
| 3-13 | CR-21 | 32 | NG (3.3) |
| 3-14 | CR-22 | 38 | NG (3.3) |
| 3-15 | CR-23 | 28 | NG (3.6) |
| 3-16 | CR-24 | 27 | NG (3.1) |
| 3-17 | CR-25 | 32 | NG (3.1) |
| 3-18 | CR-26 | 24 | NG (3.4) |

As is evident from Tables 6 to 8, the chemically amplified resist compositions containing onium salt compounds within the scope of the invention exhibit high sensitivity and satisfactory values of CDU. The resist compositions are useful as the EUV lithography material.

Japanese Patent Application No. 2019-223621 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A chemically amplified resist composition comprising (A) a base polymer adapted to change its solubility in a developer under the action of an acid, (B) a photoacid generator, (C) an acid diffusion inhibitor selected from the group consisting of an onium salt selected from the formulae Q-1, Q-2 and Q-24:

Q-1

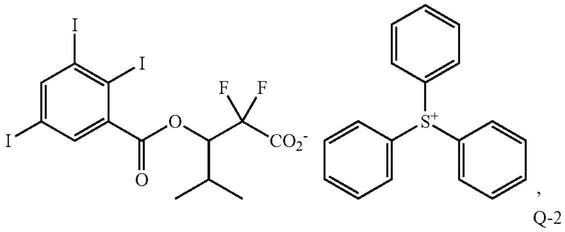

,

Q-2

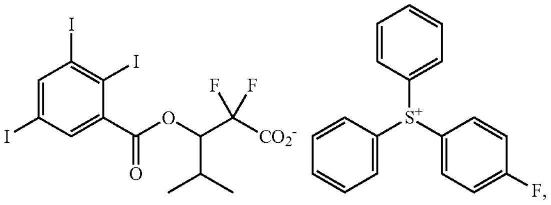

-continued

Q-24

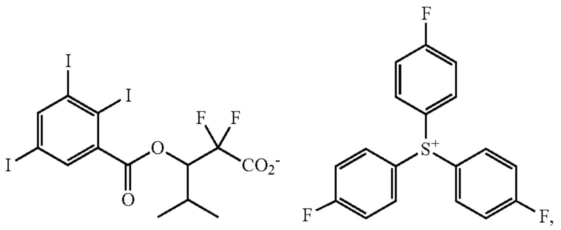

and (D) an organic solvent, wherein the photoacid generator is a sulfonium salt having the formula (5A), an iodonium salt having the formula (5B), and the base polymer comprises recurring units having the formula (a):

(5A)

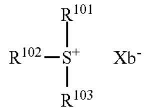

(5B)

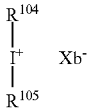

wherein $R^{101}$, $R^{102}$, $R^{103}$, $R^{104}$ and $R^{105}$ are each independently a $C_1$-$C_{20}$ hydrocarbyl group which may contain a heteroatom, any two of $R^{101}$, $R^{102}$ and $R^{103}$ may bond together to form a ring with the sulfur atom to which they are attached, and $R^{104}$ and $R^{105}$ may bond together to form a ring with the iodine atom to which they are attached, $Xb^-$ is an anion having the formula (6A'):

(6A')

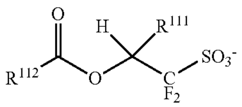

wherein $R^{111}$ is hydrogen or trifluoromethyl, $R^{112}$ is a $C_1$-$C_{35}$ hydrocarbyl group in which some or all of the hydrogen atoms may be substituted by a moiety containing a heteroatom selected from oxygen, sulfur nitrogen and fluorine, and in which —$CH_2$— may be replaced by —O— or —C(═O)—, (a)

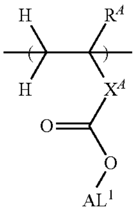

wherein $R^A$ is hydrogen or methyl, $X^A$ is a single bond, phenylene group, naphthylene group or (backbone)-C (=O)—O—$X^{A1}$—, $X^{A1}$ is a $C_1$-$C_{15}$ hydrocarbylene group which may contain a hydroxyl moiety, ether bond, ester bond or lactone ring, $AL^1$ is an acid labile group having the formula (L1):

(L1)

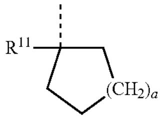

wherein $R^{11}$ is a $C_1$-$C_7$ hydrocarbyl group in which —$CH_2$— may be replaced by —O—, a is 1 or 2, and the broken line designates a valence bond.

2. A chemically amplified resist composition consisting of (A') a base polymer adapted to change its solubility in a developer under the action of an acid, the base polymer comprising recurring units having a function of generating an acid upon exposure to light, (C) an acid diffusion inhibitor selected from the group consisting of an onium salt selected from the following formulae:

Q-1

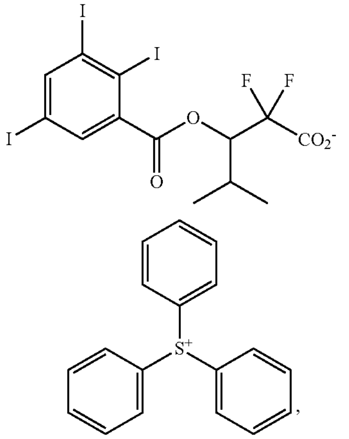

,

Q-2

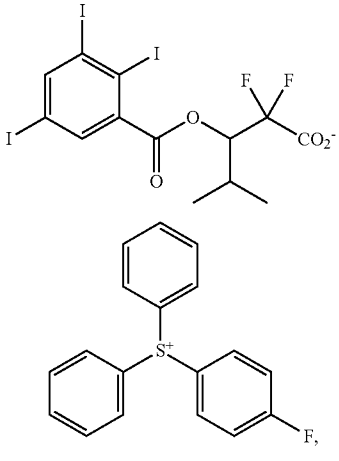

-continued

Q-24

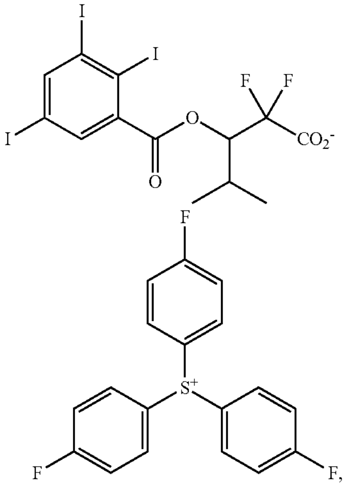

(D) an organic solvent, and optionally at least one selected from the group consisting of a surfactant, an acid amplifier compound, an organic acid derivative, a fluorinated alcohol, a crosslinker, a dissolution inhibitor and an acetylene alcohol, wherein the base polymer comprises recurring units having the formula (a), and the recurring units having a function of generating an acid upon exposure to light are units of at least one type selected from the formulae (d1) to (d4):

(a)

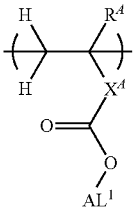

wherein $R^A$ is hydrogen or methyl, $X^A$ is a single bond, phenylene group, naphthylene group or (backbone)-C(=O)—O—$X^{A1}$—, $X^{A1}$ is a $C_1$-$C_{15}$ hydrocarbylene group which may contain a hydroxyl moiety, ether bond, ester bond or lactone ring, $AL^1$ is an acid labile group having the formula (L1):

(L1)

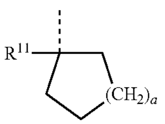

wherein $R^{11}$ is a $C_1$-$C_7$ hydrocarbyl group in which —$CH_2$— may be replaced by —O—, a is 1 or 2, and the broken line designates a valence bond, (d1)

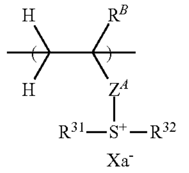

(d2)

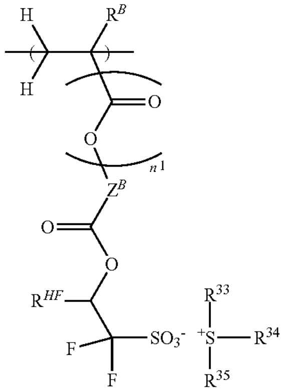

(d3)

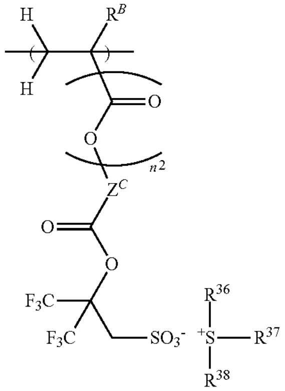

(d4)

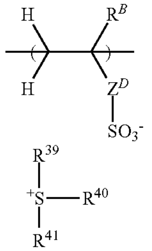

wherein $R^B$ is hydrogen, fluorine, methyl or trifluoromethyl, $Z^A$ is a single bond, phenylene group, —O—$Z^{A1}$—, —C(═O)—O—$Z^{A1}$— or —C(═O)—NH—$Z^{A1}$—, $Z^{A1}$ is a $C_1$-$C_{20}$ hydrocarbylene group which may contain a heteroatom, $Z^B$ and $Z^C$ are each independently a single bond or a $C_1$-$C_{20}$ hydrocarbylene group which may contain a heteroatom, $Z^D$ is a single bond, methylene, ethylene, phenylene, fluorinated phenylene, —O—$Z^{D1}$—, —C(═O)—O—$Z^{D1}$— or —C(═O)—NH—$Z^{D1}$—, $Z^{D1}$ is an optionally substituted phenylene group, $R^{31}$ to $R^{41}$ are each independently a $C_1$-$C_{20}$ hydrocarbyl group which may contain a heteroatom, any two of $Z^A$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, and any two of $R^{39}$, $R^{40}$ and $R^{41}$ may bond together to form a ring with the sulfur atom to which they are attached, $R^{HF}$ is hydrogen or trifluoromethyl, $n^1$ is 0 or 1, $n^1$ is 0 when $Z^B$ is a single bond, $n^2$ is 0 or 1, $n^2$ is 0 when $Z^C$ is a single bond, and $Xa^-$ is a non-nucleophilic counter ion.

3. The resist composition of claim 1 wherein the base polymer comprises recurring units having the formula (c):

(c)

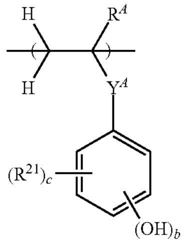

wherein $R^A$ is hydrogen or methyl, $Y^A$ is a single bond or ester bond, $R^{21}$ is fluorine, iodine or a $C_1$-$C_{10}$ hydrocarbyl group in which —$CH_2$— may be replaced by —O— or —C(═O)—, b is an integer of 1 to 5, c is an integer of 0 to 4, and b+c is from 1 to 5.

4. A pattern forming process comprising the steps of applying the chemically amplified resist composition of claim 1 to form a resist film on a substrate, exposing a selected region of the resist film to KrF excimer laser, ArF excimer laser, EB or EUV, and developing the exposed resist film in a developer.

5. The pattern forming process of claim 4 wherein the developing step uses an alkaline aqueous solution as the developer, thereby forming a positive pattern in which an exposed region of the resist film is dissolved away and an unexposed region of the resist film is not dissolved.

6. The pattern forming process of claim 4 wherein the developing step uses an organic solvent as the developer, thereby forming a negative pattern in which an unexposed region of the resist film is dissolved away and an exposed region of the resist film is not dissolved.

7. The pattern forming process of claim 6 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

* * * * *